United States Patent
Fangrow

(10) Patent No.: US 10,799,692 B2
(45) Date of Patent: *Oct. 13, 2020

(54) MEDICAL CONNECTORS AND METHODS OF USE

(71) Applicant: ICU Medical, Inc., San Clemente, CA (US)

(72) Inventor: Thomas F. Fangrow, Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 204 days.

This patent is subject to a terminal disclaimer.

(21) Appl. No.: 16/125,567

(22) Filed: Sep. 7, 2018

(65) Prior Publication Data

US 2019/0001114 A1   Jan. 3, 2019

Related U.S. Application Data

(63) Continuation of application No. 14/977,550, filed on Dec. 21, 2015, now Pat. No. 10,086,188, which is a
(Continued)

(51) Int. Cl.
*A61M 39/10* (2006.01)
*A61M 39/26* (2006.01)
(Continued)

(52) U.S. Cl.
CPC ........ *A61M 39/1011* (2013.01); *A61M 39/10* (2013.01); *A61M 39/22* (2013.01); *A61M 39/221* (2013.01); *A61M 39/24* (2013.01); *A61M 39/26* (2013.01); *A61M 2039/2406* (2013.01); *A61M 2039/2433* (2013.01); *A61M 2039/263* (2013.01); *A61M 2039/266* (2013.01); *A61M 2039/267* (2013.01);
(Continued)

(58) Field of Classification Search
CPC .. A61M 39/1011; A61M 39/10; A61M 39/22; A61M 39/26; A61M 2039/2433
See application file for complete search history.

(56) References Cited

U.S. PATENT DOCUMENTS 274,447 A    3/1883   Kennish
1,578,517 A  3/1926   Hein
(Continued)

FOREIGN PATENT DOCUMENTS

CA   1 105 959    7/1981
CA   2 149 725    11/1995
(Continued)

OTHER PUBLICATIONS

U.S. Appl. No. 15/887,777, filed Feb. 2, 2018, Fangrow.
(Continued)

*Primary Examiner* — Bradley J Osinski
(74) *Attorney, Agent, or Firm* — Knobbe Martens Olson & Bear LLP

(57) ABSTRACT

Some embodiments disclosed herein relate to a medical connector with an internal cavity with an internal closure system having a dome valve configured to resist retrograde fluid flow caused by various sources, including patient activity and fluid administration activity. A proximal closure system with a seal member and a moveable plug are also located within the internal cavity.

22 Claims, 81 Drawing Sheets

Related U.S. Application Data continuation of application No. 13/857,019, filed on Apr. 4, 2013, now Pat. No. 9,278,206, which is a continuation of application No. 12/730,074, filed on Mar. 23, 2010, now Pat. No. 8,454,579.

(60) Provisional application No. 61/163,367, filed on Mar. 25, 2009, provisional application No. 61/251,232, filed on Oct. 13, 2009.

(51) Int. Cl.
    *A61M 39/24*      (2006.01)
    *A61M 39/22*      (2006.01)

(52) U.S. Cl.
    CPC ... *A61M 2207/00* (2013.01); *A61M 2230/005* (2013.01); *A61M 2230/30* (2013.01); *A61M 2230/40* (2013.01); *Y10T 29/494* (2015.01); *Y10T 137/87917* (2015.04)

(56) References Cited

U.S. PATENT DOCUMENTS

| | | |
|---|---|---|
| 1,923,501 A | 8/1933 | Perry |
| 2,210,098 A | 8/1940 | Ravenscroft |
| 2,289,677 A | 7/1942 | Perelson |
| 2,347,988 A | 10/1943 | Burke |
| 2,577,780 A | 12/1951 | Lockhart |
| 2,688,979 A | 9/1954 | Kendrick |
| 2,756,282 A | 7/1956 | Deane |
| 2,756,740 A | 7/1956 | Deane |
| 2,809,665 A | 10/1957 | Crowe |
| 2,847,995 A | 8/1958 | Adams |
| 2,999,499 A | 9/1961 | Willet |
| 3,134,380 A | 5/1964 | Armao |
| 3,135,261 A | 6/1964 | Carroll |
| 3,171,412 A | 3/1965 | Braun |
| 3,176,021 A | 3/1965 | Volungis et al. |
| 3,191,655 A | 6/1965 | McCord |
| 3,193,154 A | 7/1965 | Bross et al. |
| 3,334,860 A | 8/1967 | Bolton, Jr. |
| 3,352,531 A | 11/1967 | Kilmarx |
| 3,354,881 A | 11/1967 | Bloch |
| 3,385,301 A | 5/1968 | Harautuneian |
| 3,502,097 A | 3/1970 | Muller |
| 3,534,771 A | 10/1970 | Eyerdam et al. |
| 3,570,484 A | 3/1971 | Steer et al. |
| 3,630,199 A | 12/1971 | Gangarosa |
| 3,648,684 A | 3/1972 | Barnwell et al. |
| 3,659,602 A | 5/1972 | Cloyd |
| 3,717,174 A | 2/1973 | Dewall |
| 3,726,282 A | 4/1973 | Patel |
| 3,788,519 A | 1/1974 | Mengel |
| 3,830,241 A | 8/1974 | Dye et al. |
| 3,831,629 A | 8/1974 | Mackal et al. |
| 3,852,385 A | 12/1974 | Huggins |
| 3,861,388 A | 1/1975 | Vaughn |
| 3,889,675 A | 6/1975 | Stewart |
| 3,896,853 A | 7/1975 | Bernhard |
| 3,965,910 A | 6/1976 | Fisher |
| 3,974,832 A | 8/1976 | Kruck |
| 3,976,063 A | 8/1976 | Henneman et al. |
| 3,976,073 A | 8/1976 | Quick et al. |
| 3,977,403 A | 8/1976 | Patel |
| 3,986,508 A | 10/1976 | Barrington |
| 3,993,063 A | 11/1976 | Larrabee |
| 3,994,293 A | 11/1976 | Ferro |
| 4,005,710 A | 2/1977 | Zeddies et al. |
| 4,019,512 A | 4/1977 | Tenczar |
| 4,022,205 A | 5/1977 | Tenczar |
| 4,040,420 A | 8/1977 | Speer |
| 4,076,285 A | 2/1978 | Martinez |
| 4,079,738 A | 3/1978 | Dunn et al. |
| 4,080,965 A | 3/1978 | Phillips |
| 4,121,585 A | 10/1978 | Becker, Jr. |
| 4,128,098 A | 12/1978 | Bloom et al. |
| 4,133,441 A | 1/1979 | Mittleman et al. |
| 4,143,853 A | 3/1979 | Abramson |
| 4,149,535 A | 4/1979 | Volder |
| 4,161,949 A | 7/1979 | Thanawalla |
| 4,186,775 A | 2/1980 | Muroi |
| 4,187,846 A | 2/1980 | Lolachi et al. |
| 4,191,183 A | 3/1980 | Mendelson |
| 4,198,983 A | 4/1980 | Becker et al. |
| 4,200,096 A | 4/1980 | Charvin |
| 4,214,779 A | 7/1980 | Losell |
| 4,219,912 A | 9/1980 | Adams |
| 4,243,034 A | 1/1981 | Brandt |
| 4,257,416 A | 3/1981 | Prager |
| D259,278 S | 5/1981 | McCaw et al. |
| 4,294,249 A | 10/1981 | Sheehan et al. |
| 4,294,250 A | 10/1981 | Dennehey |
| 4,296,949 A | 10/1981 | Muetterties et al. |
| 4,306,705 A | 12/1981 | Svensson |
| 4,324,239 A | 4/1982 | Gordon et al. |
| 4,328,802 A | 5/1982 | Curley et al. |
| 4,329,987 A | 5/1982 | Rogers et al. |
| 4,334,551 A | 6/1982 | Pfister |
| 4,338,933 A | 7/1982 | Bayard et al. |
| 4,342,315 A | 8/1982 | Jackson |
| 4,346,703 A | 8/1982 | Dennehey et al. |
| 4,362,156 A | 12/1982 | Feller et al. |
| 4,387,879 A | 6/1983 | Tauschinski |
| RE31,315 E | 7/1983 | Jenkins et al. |
| 4,392,851 A | 7/1983 | Elias |
| 4,405,163 A | 9/1983 | Voges et al. |
| 4,405,312 A | 9/1983 | Gross et al. |
| 4,411,662 A | 10/1983 | Pearson |
| 4,417,890 A | 11/1983 | Dennehey et al. |
| 4,421,296 A | 12/1983 | Stephens |
| 4,429,856 A | 2/1984 | Jackson |
| 4,432,759 A | 2/1984 | Gross et al. |
| 4,432,765 A | 2/1984 | Oscarsson |
| 4,434,810 A | 3/1984 | Atkinson |
| 4,439,188 A | 3/1984 | Dennehey et al. |
| 4,439,193 A | 3/1984 | Larkin |
| 4,449,693 A | 5/1984 | Gerea |
| 4,457,749 A | 7/1984 | Bellotti et al. |
| 4,483,368 A | 11/1984 | Panthafer |
| 4,508,367 A | 4/1985 | Oreopoulos et al. |
| 4,511,359 A | 4/1985 | Vaillancourt |
| 4,512,766 A | 4/1985 | Vaillancourt |
| 4,535,818 A | 8/1985 | Duncan et al. |
| 4,564,054 A | 1/1986 | Gustaysson |
| 4,592,356 A | 6/1986 | Guiterrez |
| 4,607,868 A | 8/1986 | Harvey et al. |
| 4,610,469 A | 9/1986 | Wolff-Mooij |
| 4,617,012 A | 10/1986 | Vaillancourt |
| 4,619,640 A | 10/1986 | Poholshy et al. |
| 4,621,654 A | 11/1986 | Holter |
| 4,623,068 A | 11/1986 | Brown et al. |
| 4,645,494 A | 2/1987 | Lee et al. |
| 4,666,429 A | 5/1987 | Stone |
| 4,673,400 A | 6/1987 | Martin |
| 4,676,228 A | 6/1987 | Krasner et al. |
| 4,683,916 A | 8/1987 | Raines |
| 4,706,487 A | 11/1987 | Bandou et al. |
| 4,710,168 A | 12/1987 | Schwab et al. |
| 4,725,267 A | 2/1988 | Vaillancourt |
| 4,730,635 A | 3/1988 | Linden |
| 4,752,292 A | 6/1988 | Lopez et al. |
| D296,592 S | 7/1988 | Wellenstam |
| 4,758,224 A | 7/1988 | Siposs |
| 4,759,756 A | 7/1988 | Forman et al. |
| 4,775,369 A | 10/1988 | Schwartz |
| 4,778,447 A | 10/1988 | Velde et al. |
| 4,778,453 A | 10/1988 | Lopez |
| 4,781,702 A | 11/1988 | Herrli |
| 4,804,015 A | 2/1989 | Albinsson |
| D300,177 S | 3/1989 | Bellotti et al. |
| 4,810,241 A | 3/1989 | Rogers et al. |
| 4,813,938 A | 3/1989 | Raulerson |
| 4,819,684 A | 4/1989 | Zaugg et al. |
| 4,832,214 A | 5/1989 | Schrader et al. |

(56) References Cited

U.S. PATENT DOCUMENTS

| | | |
|---|---|---|
| 4,834,664 A | 5/1989 | Lin |
| 4,834,716 A | 5/1989 | Ogle, II |
| D303,013 S | 8/1989 | Konopka |
| 4,874,377 A | 10/1989 | Newgard et al. |
| 4,878,897 A | 11/1989 | Katzin |
| 4,880,414 A | 11/1989 | Whipple |
| 4,883,456 A | 11/1989 | Holter |
| 4,889,527 A | 12/1989 | Herrli |
| 4,915,687 A | 4/1990 | Sivert |
| 4,917,668 A | 4/1990 | Haindl |
| 4,919,167 A | 4/1990 | Manska |
| 4,928,212 A | 5/1990 | Benavides |
| 4,934,657 A | 6/1990 | Dodson |
| 4,943,896 A | 7/1990 | Johnson |
| 4,946,445 A | 8/1990 | Lynn |
| 4,963,133 A | 10/1990 | Whipple |
| 4,964,855 A | 10/1990 | Todd et al. |
| 4,966,199 A | 10/1990 | Ruschke |
| 4,969,883 A | 11/1990 | Gilbert et al. |
| D314,050 S | 1/1991 | Sone |
| 4,985,399 A | 1/1991 | Matsuda et al. |
| 4,987,181 A | 1/1991 | Bichon et al. |
| 4,991,413 A | 2/1991 | Arnalda |
| 4,991,629 A | 2/1991 | Ernesto et al. |
| 4,991,745 A | 2/1991 | Brown |
| 4,995,863 A | 2/1991 | Nichols et al. |
| 4,998,713 A | 3/1991 | Vaillancourt |
| 4,998,927 A | 3/1991 | Vaillancourt |
| 5,006,114 A | 4/1991 | Rogers et al. |
| 5,009,490 A | 4/1991 | Kuono et al. |
| 5,018,532 A | 5/1991 | Ethridge III |
| 5,024,657 A | 6/1991 | Needham et al. |
| 5,030,210 A | 7/1991 | Alchas |
| 5,031,675 A | 7/1991 | Lindgren |
| 5,041,087 A | 8/1991 | Loo et al. |
| 5,046,456 A | 9/1991 | Heyman et al. |
| 5,049,128 A | 9/1991 | Duquette |
| D321,250 S | 10/1991 | Jepson et al. |
| D321,251 S | 10/1991 | Jepson et al. |
| 5,061,253 A | 10/1991 | Yoshida |
| 5,064,416 A | 11/1991 | Newgard |
| 5,065,783 A | 11/1991 | Ogle, II |
| 5,071,411 A | 12/1991 | Hillstead |
| 5,098,385 A | 3/1992 | Walsh |
| 5,098,405 A | 3/1992 | Peterson et al. |
| 5,098,406 A | 3/1992 | Sawyer |
| 5,100,394 A | 3/1992 | Dudar et al. |
| 5,108,380 A | 4/1992 | Heritze et al. |
| 5,114,408 A | 5/1992 | Fleischhaker et al. |
| 5,116,361 A | 5/1992 | Kim et al. |
| 5,122,123 A | 6/1992 | Vaillancourt |
| 5,125,915 A | 6/1992 | Berry et al. |
| 5,135,489 A | 8/1992 | Jepson et al. |
| 5,137,524 A | 8/1992 | Lynn et al. |
| 5,147,333 A | 9/1992 | Raines |
| 5,154,703 A | 10/1992 | Bonaldo |
| 5,156,600 A | 10/1992 | Young |
| 5,158,554 A | 10/1992 | Jepson et al. |
| 5,163,922 A | 11/1992 | McElveen, Jr. et al. |
| 5,167,238 A | 12/1992 | Newman |
| 5,167,636 A | 12/1992 | Clement |
| 5,171,234 A | 12/1992 | Jepson et al. |
| 5,180,761 A | 1/1993 | Shiao |
| 5,188,620 A | 2/1993 | Jepson et al. |
| 5,190,067 A | 3/1993 | Paradis et al. |
| 5,199,947 A | 4/1993 | Lopez et al. |
| 5,201,717 A | 4/1993 | Wyatt et al. |
| 5,201,722 A | 4/1993 | Moorehead et al. |
| 5,203,775 A | 4/1993 | Frank et al. |
| 5,211,638 A | 5/1993 | Dudar et al. |
| 5,215,538 A | 6/1993 | Larkin |
| 5,221,271 A | 6/1993 | Nicholson et al. |
| 5,224,515 A | 7/1993 | Foster et al. |
| 5,242,393 A | 9/1993 | Brimhall et al. |
| 5,242,423 A | 9/1993 | Goodsir et al. |
| 5,242,425 A | 9/1993 | Whine et al. |
| 5,242,432 A | 9/1993 | DeFrank |
| 5,249,598 A | 10/1993 | Schmidt |
| 5,251,873 A | 10/1993 | Atkinson et al. |
| 5,253,842 A | 10/1993 | Huebscher et al. |
| 5,255,676 A | 10/1993 | Russo |
| 5,256,155 A | 10/1993 | Yerlikaya et al. |
| 5,267,966 A | 12/1993 | Paul |
| 5,269,771 A | 12/1993 | Thomas et al. |
| 5,273,533 A | 12/1993 | Bonaldo |
| 5,280,876 A | 1/1994 | Atkins |
| 5,284,475 A | 2/1994 | Mackal |
| 5,290,254 A | 3/1994 | Vaillancourt |
| 5,292,308 A | 3/1994 | Ryan |
| 5,293,902 A | 3/1994 | Lapierie |
| 5,295,657 A | 3/1994 | Atkinson |
| 5,295,658 A | 3/1994 | Atkinson et al. |
| 5,301,686 A | 4/1994 | Newman |
| 5,306,265 A | 4/1994 | Ragazzi |
| 5,312,083 A | 5/1994 | Ekman |
| 5,312,377 A | 5/1994 | Dalhon |
| 5,322,518 A | 6/1994 | Schneider |
| 5,324,270 A | 6/1994 | Kayon et al. |
| 5,336,192 A | 8/1994 | Palestrant |
| 5,342,316 A | 8/1994 | Wallace |
| 5,342,326 A | 8/1994 | Peppel et al. |
| 5,344,414 A | 9/1994 | Lopez et al. |
| 5,348,542 A | 9/1994 | Ellis |
| 5,353,837 A | 10/1994 | Faust |
| 5,356,396 A | 10/1994 | Wyatt et al. |
| 5,360,413 A | 11/1994 | Leason et al. |
| 5,380,306 A | 1/1995 | Brinon |
| 5,389,086 A | 2/1995 | Attermeier et al. |
| 5,398,530 A | 3/1995 | Derman |
| 5,401,245 A | 3/1995 | Haining |
| 5,402,826 A | 4/1995 | Molnar et al. |
| 5,402,982 A | 4/1995 | Atkinson et al. |
| 5,407,437 A | 4/1995 | Heimreid |
| 5,409,471 A | 4/1995 | Atkinson et al. |
| 5,395,348 A | 5/1995 | Ryan |
| 5,411,483 A | 5/1995 | Loomas et al. |
| 5,411,499 A | 5/1995 | Dudar et al. |
| 5,417,673 A | 5/1995 | Gordon |
| 5,439,451 A | 8/1995 | Collinson et al. |
| 5,439,452 A | 8/1995 | McCarty |
| 5,441,487 A | 8/1995 | Vedder |
| 5,442,941 A | 8/1995 | Kahonen et al. |
| 5,456,676 A | 10/1995 | Nelson |
| 5,462,255 A | 10/1995 | Rosen et al. |
| 5,470,319 A | 11/1995 | Mayer |
| 5,474,544 A | 12/1995 | Lynn |
| 5,480,393 A | 1/1996 | Bommarito |
| 5,487,731 A | 1/1996 | Denton |
| 5,501,426 A | 3/1996 | Atkinson |
| 5,501,526 A | 3/1996 | Asai et al. |
| 5,509,433 A | 4/1996 | Paradis |
| 5,514,116 A | 5/1996 | Vaillancourt et al. |
| 5,520,665 A | 5/1996 | Fleetwood |
| 5,522,804 A | 6/1996 | Lynn |
| 5,533,708 A | 7/1996 | Atkinson et al. |
| 5,533,996 A | 7/1996 | Murphey et al. |
| 5,535,771 A | 7/1996 | Purdy et al. |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,554,136 A | 9/1996 | Luther |
| 5,555,908 A | 9/1996 | Edwards et al. |
| 5,556,388 A | 9/1996 | Johlin, Jr. |
| 5,562,632 A | 10/1996 | Davila et al. |
| 5,569,235 A | 10/1996 | Ross et al. |
| 5,573,516 A | 11/1996 | Tyner |
| 5,577,706 A | 11/1996 | King |
| 5,578,059 A | 11/1996 | Patzer |
| 5,597,536 A | 1/1997 | Mayer |
| 5,674,206 A | 1/1997 | Allton et al. |
| 5,603,706 A | 2/1997 | Wyatt et al. |
| 5,609,584 A | 3/1997 | Gettig et al. |

(56) References Cited

U.S. PATENT DOCUMENTS

| | | |
|---|---|---|
| 5,616,129 A | 4/1997 | Mayer |
| 5,616,130 A | 4/1997 | Mayer |
| 5,617,897 A | 4/1997 | Myers |
| 5,620,424 A | 4/1997 | Abramson |
| 5,620,434 A | 4/1997 | Brony |
| 5,624,414 A | 4/1997 | Boettger |
| 5,632,735 A | 5/1997 | Wyatt et al. |
| 5,639,810 A | 6/1997 | Smith, III et al. |
| 5,660,205 A | 8/1997 | Epstein |
| 5,667,500 A | 9/1997 | Palmer et al. |
| 5,669,891 A | 9/1997 | Vaillancourt |
| 5,676,346 A | 10/1997 | Leinsing |
| 5,685,866 A | 11/1997 | Lopez |
| 5,690,612 A | 11/1997 | Lopez et al. |
| 5,690,865 A | 11/1997 | Kindt-Larsen et al. |
| 5,694,686 A | 12/1997 | Lopez |
| 5,695,466 A | 12/1997 | Lopez et al. |
| 5,699,821 A | 12/1997 | Paradis |
| 5,700,248 A | 12/1997 | Lopez |
| 5,707,357 A | 1/1998 | Mikhail et al. |
| 5,728,751 A | 3/1998 | Patnaik |
| 5,730,418 A | 3/1998 | Feith et al. |
| 5,738,663 A | 4/1998 | Lopez |
| 5,749,861 A | 5/1998 | Guala et al. |
| 5,769,825 A | 6/1998 | Lynn |
| 5,775,671 A | 7/1998 | Cote, Sr. |
| 5,776,113 A | 7/1998 | Daugherty et al. |
| 5,782,816 A | 7/1998 | Werschmidt |
| 5,785,693 A | 7/1998 | Haining |
| 5,788,215 A | 8/1998 | Ryan |
| 5,797,897 A | 8/1998 | Jepson et al. |
| 5,806,551 A | 9/1998 | Meloul et al. |
| 5,806,831 A | 9/1998 | Paradis |
| 5,807,348 A | 9/1998 | Zinger et al. |
| 5,807,349 A | 9/1998 | Person et al. |
| 5,810,789 A | 9/1998 | Powers et al. |
| 5,817,069 A | 10/1998 | Arnett |
| 5,820,601 A | 10/1998 | Mayer |
| 5,833,213 A | 11/1998 | Ryan |
| 5,836,923 A | 11/1998 | Mayer |
| 5,839,715 A | 11/1998 | Leinsing |
| 5,843,044 A | 12/1998 | Moorehead |
| 5,843,046 A | 12/1998 | Motisi et al. |
| 5,846,233 A | 12/1998 | Lilley et al. |
| 5,865,807 A | 2/1999 | Blake, III |
| 5,873,862 A | 2/1999 | Lopez |
| 5,882,348 A | 3/1999 | Winterton et al. |
| 5,899,888 A | 5/1999 | Jepson et al. |
| 5,901,942 A | 5/1999 | Lopez |
| 5,911,710 A | 6/1999 | Barry et al. |
| 5,928,204 A | 7/1999 | Lopez |
| 5,935,620 A | 8/1999 | Baudin |
| 5,947,954 A | 9/1999 | Bonaldo |
| 5,954,313 A | 9/1999 | Ryan |
| 5,957,898 A | 9/1999 | Jepson et al. |
| 5,967,490 A | 10/1999 | Pike |
| 5,979,868 A | 11/1999 | Wu et al. |
| 5,984,903 A | 11/1999 | Nadal |
| 6,009,902 A | 1/2000 | Troiani et al. |
| 6,019,748 A | 2/2000 | Lopez |
| 6,029,946 A | 2/2000 | Doyle |
| 6,036,171 A | 3/2000 | Weinheimer et al. |
| 6,039,302 A | 3/2000 | Cote, Sr. et al. |
| 6,048,335 A | 4/2000 | Mayer |
| 6,050,978 A | 4/2000 | Orr et al. |
| 6,063,062 A | 5/2000 | Paradis |
| 6,079,432 A | 6/2000 | Paradis |
| 6,089,541 A | 7/2000 | Weinheier et al. |
| 6,113,068 A | 9/2000 | Ryan |
| 6,116,571 A | 9/2000 | Hettinger |
| 6,117,114 A | 9/2000 | Paradis |
| 6,132,403 A | 10/2000 | Lopez |
| 6,132,404 A | 10/2000 | Lopez |
| 6,142,446 A | 11/2000 | Leinsing |
| 6,152,900 A | 11/2000 | Mayer |
| 6,162,206 A | 12/2000 | Bindokas et al. |
| 6,162,251 A | 12/2000 | Kredovski |
| 6,168,137 B1 | 1/2001 | Paradis |
| 6,170,800 B1 | 1/2001 | Meloul et al. |
| 6,171,287 B1 | 1/2001 | Lynn |
| 6,177,037 B1 | 1/2001 | Mayer |
| 6,183,448 B1 | 2/2001 | Mayer |
| 6,189,859 B1 | 2/2001 | Rohrbough et al. |
| 6,206,861 B1 | 3/2001 | Mayer |
| 6,210,624 B1 | 4/2001 | Mayer |
| 6,213,996 B1 | 4/2001 | Jepson et al. |
| 6,228,065 B1 | 5/2001 | Lynn |
| 6,228,069 B1 | 5/2001 | Barth et al. |
| 6,245,048 B1 | 6/2001 | Fangrow et al. |
| 6,254,579 B1 | 7/2001 | Cogger et al. |
| 6,261,282 B1 | 7/2001 | Jepson et al. |
| 6,261,630 B1 | 7/2001 | Nazarova et al. |
| 6,279,783 B1 | 8/2001 | Brown et al. |
| 6,290,206 B1 | 9/2001 | Doyle |
| 6,299,131 B1 | 10/2001 | Ryan |
| 6,299,132 B1 | 10/2001 | Wienheimer |
| 6,325,782 B1 | 12/2001 | Lopez |
| 6,364,869 B1 | 4/2002 | Bonaldo |
| 6,428,520 B1 | 8/2002 | Lopez et al. |
| 6,444,324 B1 | 9/2002 | Yang et al. |
| 6,482,188 B1 | 11/2002 | Rogers et al. |
| D468,016 S | 12/2002 | Mosler et al. |
| 6,530,504 B2 | 3/2003 | Socier |
| 6,541,802 B2 | 4/2003 | Doyle |
| 6,543,745 B1 | 4/2003 | Enerson |
| 6,572,592 B1 | 6/2003 | Lopez |
| 6,585,229 B2 | 7/2003 | Cote, Sr. et al. |
| 6,595,964 B2 | 7/2003 | Finley et al. |
| 6,595,981 B2 | 7/2003 | Huet |
| 6,599,273 B1 | 7/2003 | Lopez |
| 6,605,076 B1 | 8/2003 | Jepson et al. |
| 6,609,696 B2 | 8/2003 | Enerson |
| 6,635,044 B2 | 10/2003 | Lopez |
| 6,651,956 B2 | 11/2003 | Miller |
| 6,656,517 B2 | 12/2003 | Michal et al. |
| 6,669,673 B2 | 12/2003 | Lopez |
| 6,669,681 B2 | 12/2003 | Jepson et al. |
| 6,673,053 B2 | 1/2004 | Wang et al. |
| 6,682,509 B2 | 1/2004 | Lopez |
| 6,689,109 B2 | 2/2004 | Lynn |
| 6,695,817 B1 | 2/2004 | Fangrow, Jr. |
| 6,706,022 B1 | 3/2004 | Leinsing et al. |
| 6,712,791 B2 | 3/2004 | Lui et al. |
| 6,727,294 B2 | 4/2004 | Kanayama et al. |
| 6,740,063 B2 | 5/2004 | Lynn |
| 6,745,998 B2 | 6/2004 | Doyle |
| 6,755,391 B2 | 6/2004 | Newton et al. |
| 6,758,833 B2 | 7/2004 | Lopez |
| 6,783,709 B2 | 8/2004 | Harreld et al. |
| 6,802,490 B2 | 10/2004 | Leinsing |
| 6,808,161 B1 | 10/2004 | Hishikawa |
| 6,840,501 B2 | 1/2005 | Doyle |
| 6,848,139 B2 | 2/2005 | Simon et al. |
| 6,866,656 B2 | 3/2005 | Tingey et al. |
| 6,869,426 B2 | 3/2005 | Ganem |
| 6,871,838 B2 | 3/2005 | Raines et al. |
| 6,883,778 B1 | 4/2005 | Newton et al. |
| 6,892,998 B2 | 5/2005 | Newton |
| 6,908,459 B2 | 6/2005 | Harding et al. |
| 6,916,309 B2 | 7/2005 | Fangrow, Jr. |
| 6,932,795 B2 | 8/2005 | Lopez et al. |
| 6,964,406 B2 | 11/2005 | Doyle |
| 6,991,215 B2 | 1/2006 | Kiehne |
| 6,994,315 B2 | 2/2006 | Ryan et al. |
| 6,997,917 B2 | 2/2006 | Niedospial, Jr. et al. |
| 7,014,169 B2 | 3/2006 | Newton et al. |
| 7,025,744 B2 | 4/2006 | Utterberg et al. |
| 7,033,339 B1 | 4/2006 | Lynn |
| 7,037,302 B2 | 5/2006 | Vaillancourt |
| 7,044,441 B2 | 5/2006 | Doyle |
| 7,074,216 B2 | 7/2006 | Fowles et al. |
| 7,100,890 B2 | 9/2006 | Cote et al. |
| 7,104,520 B2 | 9/2006 | Leinsing et al. |
| 7,114,701 B2 | 10/2006 | Peppel |

(56) References Cited

U.S. PATENT DOCUMENTS

| | | |
|---|---|---|
| 7,125,396 B2 | 10/2006 | Leinsing et al. |
| 7,140,592 B2 | 11/2006 | Phillips et al. |
| 7,184,825 B2 | 2/2007 | Leinsing et al. |
| D547,862 S | 7/2007 | Dikeman et al. |
| 7,244,249 B2 | 7/2007 | Leinsing et al. |
| 7,252,652 B2 | 8/2007 | Moorehead et al. |
| 7,264,859 B2 | 9/2007 | Souns et al. |
| 7,306,197 B2 | 12/2007 | Parrino et al. |
| 7,306,199 B2 | 12/2007 | Leinsing et al. |
| 7,314,061 B2 | 1/2008 | Peppel |
| 7,329,249 B2 | 2/2008 | Bonaldo |
| 7,335,182 B1 | 2/2008 | Hilaire |
| D567,941 S | 4/2008 | Dikeman et al. |
| 7,357,792 B2 | 4/2008 | Newton et al. |
| D568,466 S | 5/2008 | Dikeman et al. |
| D569,506 S | 5/2008 | Dikeman et al. |
| 7,396,348 B2 | 7/2008 | Newton et al. |
| 7,422,369 B2 | 9/2008 | Bergman et al. |
| 7,470,261 B2 | 12/2008 | Lynn |
| 7,470,262 B2 | 12/2008 | Hiejima et al. |
| 7,497,848 B2 | 3/2009 | Leinsing et al. |
| 7,497,849 B2 | 3/2009 | Fangrow, Jr. |
| 7,510,545 B2 | 3/2009 | Peppel |
| 7,520,489 B2 | 4/2009 | Rushke |
| 7,530,546 B2 | 5/2009 | Ryan et al. |
| 7,556,060 B2 | 7/2009 | Guala |
| 7,559,530 B2 | 7/2009 | Korogi et al. |
| 7,563,243 B2 | 7/2009 | Mendels |
| 7,581,561 B2 | 9/2009 | Funamura et al. |
| 7,584,767 B2 | 9/2009 | Funamura et al. |
| 7,588,563 B2 | 9/2009 | Guala |
| 7,591,449 B2 | 9/2009 | Raines et al. |
| 7,601,141 B2 | 10/2009 | Dikeman et al. |
| 7,615,035 B2 | 11/2009 | Peppel |
| 7,624,749 B2 | 12/2009 | Guala |
| 7,628,774 B2 | 12/2009 | Fangrow, Jr. |
| 7,645,274 B2 | 1/2010 | Whitley |
| 7,651,481 B2 | 1/2010 | Raybuck |
| 7,666,170 B2 | 2/2010 | Guala |
| 7,673,653 B2 | 3/2010 | Mijers et al. |
| 7,703,486 B2 | 4/2010 | Costanzo |
| 7,713,250 B2 | 5/2010 | Harding et al. |
| 7,717,882 B2 | 5/2010 | Harding |
| 7,717,886 B2 | 5/2010 | Lopez |
| 7,743,799 B2 | 6/2010 | Mosler et al. |
| 7,753,338 B2 | 7/2010 | Desecki |
| 7,753,892 B2 | 7/2010 | Newton et al. |
| 7,758,566 B2 | 7/2010 | Simpson et al. |
| 7,763,013 B2 | 7/2010 | Baldwin et al. |
| 7,763,199 B2 | 7/2010 | Fangrow |
| 7,771,383 B2 | 8/2010 | Truitt et al. |
| 7,784,766 B2 | 8/2010 | Guala |
| 7,806,873 B2 | 10/2010 | Dikeman et al. |
| 7,815,168 B2 | 10/2010 | Vangsness et al. |
| 7,824,393 B2 | 11/2010 | Fangrow, Jr. |
| 7,837,658 B2 | 11/2010 | Cote, Sr. et al. |
| 7,841,581 B2 | 11/2010 | Thorne, Jr. et al. |
| 7,842,026 B2 | 11/2010 | Cahill et al. |
| 7,857,284 B2 | 12/2010 | Kimball et al. |
| 7,857,285 B2 | 12/2010 | Lee et al. |
| 7,857,802 B2 | 12/2010 | Brandenburger et al. |
| 7,857,805 B2 | 12/2010 | Raines |
| 7,862,537 B2 | 1/2011 | Zinger et al. |
| 7,867,204 B2 | 1/2011 | Bartholomew et al. |
| 7,879,012 B2 | 2/2011 | Kane et al. |
| 7,879,013 B2 | 2/2011 | Smith et al. |
| 7,900,659 B2 | 3/2011 | Whitley et al. |
| 7,905,873 B2 | 3/2011 | Rondeau |
| 7,909,056 B2 | 3/2011 | Truitt et al. |
| 7,914,502 B2 | 3/2011 | Newton et al. |
| 7,954,515 B2 | 6/2011 | Gerst |
| 7,959,614 B2 | 6/2011 | Dikeman et al. |
| 7,967,797 B2 | 6/2011 | Winsor et al. |
| 7,975,722 B2 | 7/2011 | Kiehne |
| 7,981,090 B2 | 7/2011 | Plishka et al. |
| 7,981,381 B2 | 7/2011 | Lurvey et al. |
| 7,984,730 B2 | 7/2011 | Ziv et al. |
| 7,985,206 B2 | 7/2011 | Dikeman et al. |
| 7,988,128 B2 | 8/2011 | Wentling |
| 7,998,134 B2 | 8/2011 | Fangrow |
| 8,006,953 B2 | 8/2011 | Bennett |
| D644,731 S | 9/2011 | Fangrow, Jr. |
| 8,015,990 B2 | 9/2011 | Pascal et al. |
| 8,021,354 B2 | 9/2011 | Huang |
| 8,034,035 B2 | 10/2011 | Weaver et al. |
| 8,038,663 B2 | 10/2011 | Miner |
| 8,042,838 B2 | 10/2011 | Buckler et al. |
| 8,048,038 B2 | 11/2011 | Guala |
| 8,052,648 B2 | 11/2011 | Dikeman et al. |
| 8,057,442 B2 | 11/2011 | Dikeman et al. |
| 8,062,266 B2 | 11/2011 | McKinnon et al. |
| 8,062,267 B2 | 11/2011 | McKinnon et al. |
| 8,062,280 B2 | 11/2011 | Jepson et al. |
| 8,066,648 B1 | 11/2011 | Mark |
| 8,066,669 B2 | 11/2011 | Christensen et al. |
| 8,066,670 B2 | 11/2011 | Cluff et al. |
| 8,070,189 B2 | 12/2011 | Yow et al. |
| 8,070,725 B2 | 12/2011 | Christensen |
| 8,074,964 B2 | 12/2011 | Mansour et al. |
| 8,092,432 B2 | 1/2012 | Nordgren |
| 8,100,868 B2 | 1/2012 | Newton et al. |
| 8,100,869 B2 | 1/2012 | Vangsness et al. |
| 8,105,314 B2 | 1/2012 | Fangrow |
| 8,123,738 B2 | 2/2012 | Vaillancourt |
| 8,133,209 B2 | 3/2012 | Guala |
| 8,136,330 B2 | 3/2012 | Ostler et al. |
| 8,137,303 B2 | 3/2012 | Stout et al. |
| 8,142,403 B2 | 3/2012 | Carlyon |
| 8,152,790 B2 | 4/2012 | Lopez et al. |
| 8,162,006 B2 | 4/2012 | Guala |
| 8,162,013 B2 | 4/2012 | Rosenquist et al. |
| 8,162,914 B2 | 4/2012 | Kraushaar et al. |
| 8,167,863 B2 | 5/2012 | Yow |
| 8,172,823 B2 | 5/2012 | Rondeau et al. |
| 8,177,760 B2 | 5/2012 | Rome et al. |
| 8,177,768 B2 | 5/2012 | Leinsing |
| 8,177,772 B2 | 5/2012 | Christensen et al. |
| 8,182,452 B2 | 5/2012 | Mansour et al. |
| 8,197,452 B2 | 6/2012 | Harding et al. |
| 8,197,466 B2 | 6/2012 | Yokota et al. |
| 8,211,089 B2 | 7/2012 | Winsor et al. |
| 8,221,363 B2 | 7/2012 | Jepson |
| 8,221,391 B2 | 7/2012 | Fangrow, Jr. |
| 8,277,424 B2 | 10/2012 | Pan |
| 8,286,657 B2 | 10/2012 | Belley et al. |
| 8,287,518 B2 | 10/2012 | Kitani et al. |
| 8,298,195 B2 | 10/2012 | Peppel |
| 8,298,196 B1 | 10/2012 | Mansour |
| 8,328,769 B2 | 12/2012 | Dikeman et al. |
| 8,337,483 B2 | 12/2012 | Harding et al. |
| 8,361,408 B2 | 1/2013 | Lynn |
| 8,366,658 B2 | 2/2013 | Davis et al. |
| 8,366,676 B2 | 2/2013 | Harding et al. |
| 8,372,043 B2 | 2/2013 | Grimm et al. |
| 8,377,010 B2 | 2/2013 | Harding et al. |
| 8,382,741 B2 | 2/2013 | Chelak |
| 8,398,598 B2 | 3/2013 | Carlyon et al. |
| 8,398,607 B2 | 3/2013 | Fangrow, Jr. |
| 8,403,886 B2 | 3/2013 | Bialecki et al. |
| 8,403,894 B2 | 3/2013 | Lynn et al. |
| 8,403,905 B2 | 3/2013 | Yow |
| 8,408,226 B2 | 4/2013 | Raines et al. |
| 8,409,164 B2 | 4/2013 | Fangrow |
| 8,409,165 B2 | 4/2013 | Niedospial, Jr. et al. |
| 8,414,542 B2 | 4/2013 | Stroup |
| 8,439,880 B2 | 5/2013 | Rondeau |
| 8,444,628 B2 | 5/2013 | Fangrow, Jr. |
| 8,454,579 B2 | 6/2013 | Fangrow, Jr. |
| 8,512,307 B2 | 8/2013 | Fangrow |
| 8,529,524 B2 | 9/2013 | Newton et al. |
| 8,540,692 B2 | 9/2013 | Fangrow |
| 8,551,037 B2 | 10/2013 | Suchecki et al. |
| 8,591,476 B2 | 11/2013 | Winsor et al. |
| 8,628,515 B2 | 1/2014 | Fangrow, Jr. et al. |

(56) References Cited

U.S. PATENT DOCUMENTS

| | | |
|---|---|---|
| 8,636,720 B2 | 1/2014 | Truitt et al. |
| 8,671,964 B2 | 3/2014 | Py |
| 8,679,090 B2 | 3/2014 | Anderson et al. |
| 8,684,994 B2 | 4/2014 | Lev et al. |
| 8,702,675 B2 | 4/2014 | Imai |
| 8,715,222 B2 | 5/2014 | Truitt et al. |
| 8,715,247 B2 | 5/2014 | Mansour et al. |
| 8,721,627 B2 | 5/2014 | Albert |
| 8,758,306 B2 | 6/2014 | Lopez et al. |
| 8,814,849 B1 | 8/2014 | Winsor |
| 8,834,432 B2 | 9/2014 | Winsor et al. |
| 8,864,725 B2 | 10/2014 | Ranalletta et al. |
| 8,870,846 B2 | 10/2014 | Davis et al. |
| 8,870,850 B2 | 10/2014 | Fangrow, Jr. |
| 8,876,784 B2 | 11/2014 | Cote, Sr. et al. |
| 8,882,742 B2 | 11/2014 | Dikeman et al. |
| 8,910,919 B2 | 12/2014 | Bonnal et al. |
| 8,945,084 B2 | 2/2015 | Warren et al. |
| 8,951,233 B2 | 2/2015 | Mansour |
| 8,968,261 B2 | 3/2015 | Kimball et al. |
| 8,974,425 B2 | 3/2015 | Tachizaki et al. |
| 8,974,433 B2 | 3/2015 | Fangrow |
| 8,992,501 B2 | 3/2015 | Seifert et al. |
| 9,005,179 B2 | 4/2015 | Fangrow et al. |
| 9,005,180 B2 | 4/2015 | Seifert et al. |
| 9,017,295 B2 | 4/2015 | Pan |
| 9,039,047 B2 | 5/2015 | Imai |
| 9,044,585 B2 | 6/2015 | Masuda et al. |
| 9,060,921 B2 | 6/2015 | Seifert et al. |
| 9,061,130 B2 | 6/2015 | Truitt et al. |
| 9,067,049 B2 | 6/2015 | Panian et al. |
| 9,072,657 B2 | 7/2015 | Seifert et al. |
| 9,119,950 B2 | 9/2015 | Mansour et al. |
| 9,138,572 B2 | 9/2015 | Zeytoonian et al. |
| 9,186,494 B2 | 11/2015 | Fangrow et al. |
| 9,192,753 B2 | 11/2015 | Lopez et al. |
| 9,198,831 B2 | 12/2015 | Rogers |
| 9,205,243 B2 | 12/2015 | Lopez et al. |
| 9,205,248 B2 | 12/2015 | Wu et al. |
| 9,220,882 B2 | 12/2015 | Belley et al. |
| 9,238,129 B2 | 1/2016 | Fangrow et al. |
| 9,278,206 B2 | 3/2016 | Fangrow et al. |
| 9,314,604 B2 | 4/2016 | Bonnal et al. |
| 9,345,641 B2 | 5/2016 | Kraus et al. |
| 9,370,466 B2 | 6/2016 | Garfield et al. |
| 9,381,339 B2 | 7/2016 | Wu et al. |
| 9,393,398 B2 | 7/2016 | Truitt et al. |
| 9,415,200 B2 | 8/2016 | Fangrow |
| 9,440,060 B2 | 9/2016 | Fangrow |
| 9,533,137 B2 | 1/2017 | Fangrow |
| 9,750,926 B2 | 9/2017 | Lopez et al. |
| 9,884,176 B2 | 2/2018 | Fangrow et al. |
| 10,086,188 B2 | 10/2018 | Fangrow |
| 10,195,413 B2 | 2/2019 | Lopez et al. |
| 10,391,293 B2 | 8/2019 | Fangrow |
| 2002/0024036 A1 | 2/2002 | Rohrbough et al. |
| 2002/0120333 A1 | 8/2002 | Keogh et al. |
| 2002/0156430 A1 | 10/2002 | Haarala et al. |
| 2004/0102738 A1 | 5/2004 | Dikeman et al. |
| 2004/0201216 A1 | 10/2004 | Segal et al. |
| 2005/0010176 A1 | 1/2005 | Dikeman et al. |
| 2005/0020981 A1 | 1/2005 | Kurth |
| 2005/0038397 A1 | 2/2005 | Newton et al. |
| 2005/0059952 A1 | 3/2005 | Giuliano et al. |
| 2005/0121638 A1 | 6/2005 | Doyle |
| 2005/0234405 A1 | 10/2005 | Dikeman et al. |
| 2006/0161115 A1 | 7/2006 | Fangrow, Jr. |
| 2007/0100284 A1 | 5/2007 | Leinsing et al. |
| 2007/0106205 A1 | 5/2007 | Connell et al. |
| 2007/0224865 A1 | 9/2007 | Fangrow, Jr. |
| 2007/0225425 A1 | 9/2007 | Nash et al. |
| 2007/0225648 A1 | 9/2007 | Winsor |
| 2007/0235676 A1 | 10/2007 | Vangsness et al. |
| 2007/0254000 A1 | 11/2007 | Guo et al. |
| 2007/0270756 A1 | 11/2007 | Peppel et al. |
| 2008/0039802 A1 | 2/2008 | Vangsness |
| 2008/0086095 A1 | 4/2008 | Dikeman et al. |
| 2008/0086097 A1 | 4/2008 | Rasmussen et al. |
| 2008/0086099 A1 | 4/2008 | McKinnon et al. |
| 2008/0097407 A1 | 4/2008 | Plishka |
| 2008/0169444 A1 | 7/2008 | Guala |
| 2008/0249508 A1 | 10/2008 | Lopez et al. |
| 2009/0005761 A1 | 1/2009 | Guala |
| 2009/0209922 A1 | 8/2009 | Boisjoly |
| 2009/0292252 A1 | 11/2009 | Lareau et al. |
| 2009/0292274 A1 | 11/2009 | Guala |
| 2010/0030163 A1 | 2/2010 | Carrez et al. |
| 2010/0030164 A1 | 2/2010 | Kimball et al. |
| 2010/0036328 A1 | 2/2010 | Dikeman et al. |
| 2010/0036330 A1 | 2/2010 | Plishka et al. |
| 2010/0059474 A1 | 3/2010 | Brandenburger et al. |
| 2010/0059702 A1 | 3/2010 | Mansour et al. |
| 2010/0063456 A1 | 3/2010 | Rahlmy et al. |
| 2010/0063482 A1 | 3/2010 | Mansour |
| 2010/0108681 A1 | 5/2010 | Jepson et al. |
| 2010/0152680 A1 | 6/2010 | Memahon |
| 2010/0174242 A1 | 7/2010 | Anderson et al. |
| 2010/0179514 A1 | 7/2010 | Guala |
| 2010/0241088 A1 | 9/2010 | Ranalletta et al. |
| 2010/0249724 A1 | 9/2010 | Cote, Sr. et al. |
| 2010/0249725 A1 | 9/2010 | Cote, Sr. et al. |
| 2010/0264343 A1 | 10/2010 | Jeory |
| 2010/0270792 A1 | 10/2010 | Lauer |
| 2010/0283238 A1 | 11/2010 | Deighan et al. |
| 2010/0292673 A1 | 11/2010 | Korogi et al. |
| 2010/0292674 A1 | 11/2010 | Jepson et al. |
| 2010/0300556 A1 | 12/2010 | Carmody et al. |
| 2010/0324502 A1 | 12/2010 | Guala |
| 2011/0004183 A1 | 1/2011 | Carrez et al. |
| 2011/0024664 A1 | 2/2011 | Burnard et al. |
| 2011/0028914 A1 | 2/2011 | Mansour et al. |
| 2011/0028915 A1 | 2/2011 | Siopes et al. |
| 2011/0048540 A1 | 3/2011 | Stroup |
| 2011/0054440 A1 | 3/2011 | Lewis |
| 2011/0060293 A1 | 3/2011 | Guala |
| 2011/0087164 A1 | 4/2011 | Mosler et al. |
| 2011/0106046 A1 | 5/2011 | Hiranuma et al. |
| 2011/0125104 A1 | 5/2011 | Lynn |
| 2011/0130717 A1 | 6/2011 | David et al. |
| 2011/0130724 A1 | 6/2011 | Mansour et al. |
| 2011/0130726 A1 | 6/2011 | Crawford et al. |
| 2011/0130727 A1 | 6/2011 | Crawford et al. |
| 2011/0130728 A1 | 6/2011 | McKinnon |
| 2011/0152832 A1 | 6/2011 | Foshee et al. |
| 2011/0166532 A1 | 7/2011 | Brandenburger et al. |
| 2011/0178493 A1 | 7/2011 | Okiyama |
| 2011/0257590 A1 | 10/2011 | Winsor et al. |
| 2011/0264037 A1 | 10/2011 | Foshee et al. |
| 2011/0266477 A1 | 11/2011 | Stroup |
| 2011/0275988 A1 | 11/2011 | Davis et al. |
| 2011/0276010 A1 | 11/2011 | Davis et al. |
| 2011/0276031 A1 | 11/2011 | Hoang et al. |
| 2011/0295235 A1 | 12/2011 | Fangrow |
| 2011/0306940 A1 | 12/2011 | Miyasaka |
| 2011/0319821 A1 | 12/2011 | Kitani et al. |
| 2011/0319859 A1 | 12/2011 | Zeytoonian et al. |
| 2012/0013121 A1 | 1/2012 | Weckstrom |
| 2012/0022469 A1 | 1/2012 | Alpert |
| 2012/0042971 A1 | 2/2012 | Py |
| 2012/0046636 A1 | 2/2012 | Kriheli |
| 2012/0053529 A1 | 3/2012 | Imai |
| 2012/0059314 A1 | 3/2012 | Eichhorst |
| 2012/0059334 A1 | 3/2012 | Pan |
| 2012/0059346 A1 | 3/2012 | Sheppard et al. |
| 2012/0065626 A1 | 3/2012 | Naftalovitz et al. |
| 2012/0095407 A1 | 4/2012 | Chebator et al. |
| 2012/0109077 A1 | 5/2012 | Ryan |
| 2012/0130305 A1 | 5/2012 | Bonnal et al. |
| 2012/0130352 A1 | 5/2012 | Naftalovitz et al. |
| 2012/0150129 A1 | 6/2012 | Jin et al. |
| 2012/0153201 A1 | 6/2012 | Larose et al. |
| 2012/0157928 A1 | 6/2012 | Mermet |
| 2012/0157933 A1 | 6/2012 | Newton et al. |
| 2012/0179108 A1 | 7/2012 | Delabie |

(56) References Cited

U.S. PATENT DOCUMENTS

| | | |
|---|---|---|
| 2012/0192968 A1 | 8/2012 | Bonnal et al. |
| 2012/0209238 A1 | 8/2012 | Rosenquist et al. |
| 2012/0215182 A1 | 8/2012 | Mansour et al. |
| 2012/0220955 A1 | 8/2012 | Maseda et al. |
| 2012/0220977 A1 | 8/2012 | Yow |
| 2012/0220984 A1 | 8/2012 | Christensen et al. |
| 2012/0245564 A1 | 9/2012 | Tekeste et al. |
| 2012/0259292 A1 | 10/2012 | Koehler |
| 2012/0316514 A1 | 12/2012 | Mansour |
| 2012/0316536 A1 | 12/2012 | Carrez et al. |
| 2012/0323063 A1 | 12/2012 | Costanzo |
| 2012/0330277 A1 | 12/2012 | Winsor et al. |
| 2013/0012870 A1 | 1/2013 | Dikeman et al. |
| 2013/0030386 A1 | 1/2013 | Panian et al. |
| 2013/0035668 A1 | 2/2013 | Kitani et al. |
| 2013/0046315 A1 | 2/2013 | Woehr et al. |
| 2013/0053815 A1 | 2/2013 | Mucientes et al. |
| 2013/0060205 A1 | 3/2013 | Mansour et al. |
| 2013/0066293 A1 | 3/2013 | Garfield et al. |
| 2013/0079730 A1 | 3/2013 | Mosler et al. |
| 2013/0138075 A1 | 5/2013 | Lambert |
| 2013/0226099 A1 | 8/2013 | Fangrow, Jr. |
| 2013/0253478 A1 | 9/2013 | Fangrow, Jr. |
| 2013/0289534 A1 | 10/2013 | Fangrow, Jr. |
| 2013/0331800 A1 | 12/2013 | Newton et al. |
| 2014/0031765 A1 | 1/2014 | Siopes et al. |
| 2014/0107588 A1 | 4/2014 | Fangrow |
| 2014/0142519 A1 | 5/2014 | Truitt et al. |
| 2014/0155836 A1 | 6/2014 | Truitt et al. |
| 2014/0174578 A1 | 6/2014 | Bonnel et al. |
| 2014/0188088 A1 | 7/2014 | Fangrow |
| 2014/0209197 A1 | 7/2014 | Carrez et al. |
| 2014/0257198 A1 | 9/2014 | Truitt et al. |
| 2014/0303602 A1 | 10/2014 | Mansour et al. |
| 2014/0316350 A1 | 10/2014 | Yamaguchi et al. |
| 2014/0358033 A1 | 12/2014 | Lynn |
| 2014/0371686 A1 | 12/2014 | Sano et al. |
| 2015/0008664 A1 | 1/2015 | Tachizaki |
| 2015/0011979 A1 | 1/2015 | Fangrow |
| 2015/0148756 A1 | 5/2015 | Lynn |
| 2015/0151100 A1 | 6/2015 | Mansour |
| 2015/0157848 A1 | 6/2015 | Wu et al. |
| 2015/0190627 A1 | 7/2015 | Ueda et al. |
| 2015/0196749 A1 | 7/2015 | Ziv et al. |
| 2015/0265829 A1 | 9/2015 | Truitt et al. |
| 2015/0320992 A1 | 11/2015 | Bonnet et al. |
| 2016/0106970 A1 | 4/2016 | Fangrow |
| 2016/0263369 A1 | 9/2016 | Naftalovitz et al. |
| 2018/0050184 A1 | 2/2018 | Lopez et al. |
| 2018/0099137 A1 | 4/2018 | Fangrow |
| 2018/0289942 A1 | 10/2018 | Fangrow |
| 2019/0001114 A1 | 1/2019 | Fangrow |
| 2019/0269900 A1 | 9/2019 | Fangrow |
| 2019/0358443 A1 | 11/2019 | Lopez |

FOREIGN PATENT DOCUMENTS

| | | |
|---|---|---|
| CA | 2 176 021 | 11/1996 |
| CA | 2 476 075 | 10/2003 |
| CH | 636526 | 6/1983 |
| CH | 670955 | 7/1989 |
| DE | 856 319 | 9/1952 |
| DE | 84 25 197 | 9/1985 |
| DE | 37 40 269 | 6/1989 |
| EP | 0 263 789 | 4/1988 |
| EP | 0 309 771 | 4/1989 |
| EP | 0 399 119 | 11/1990 |
| EP | 0 446 463 | 9/1991 |
| EP | 0 805 930 | 6/2002 |
| EP | 1 466 644 | 10/2004 |
| EP | 1 547 646 | 6/2005 |
| EP | 1 563 867 | 8/2005 |
| EP | 1 685 872 | 8/2006 |
| EP | 1 854 502 | 11/2007 |
| EP | 1 857 137 | 11/2007 |
| EP | 1 669 101 | 7/2008 |
| EP | 2 004 274 | 12/2008 |
| FR | 2 707 505 | 1/1995 |
| GB | 2 000 685 | 1/1979 |
| GB | 2 001 146 | 1/1979 |
| GB | 2 034 185 | 6/1980 |
| NZ | 333508 A | 8/2005 |
| WO | WO 1992/20736 | 11/1992 |
| WO | WO 1994/22523 | 10/1994 |
| WO | WO 1996/23158 | 1/1996 |
| WO | WO 1999/59672 | 11/1999 |
| WO | WO 1999/61093 | 12/1999 |
| WO | WO 2000/20070 | 4/2000 |
| WO | WO 2003/018104 | 3/2003 |
| WO | WO 2005/115521 | 8/2005 |
| WO | WO 2006/013433 | 2/2006 |
| WO | WO 2006/062912 | 6/2006 |
| WO | WO 2007/112278 | 10/2007 |
| WO | WO 2008/048777 | 4/2008 |
| WO | WO 2009/052433 | 4/2009 |
| WO | WO 2009/111596 | 9/2009 |
| WO | WO 2010/135080 | 11/2010 |
| WO | WO 2011/064738 | 6/2011 |
| WO | WO 2011/101389 | 8/2011 |

OTHER PUBLICATIONS

International Preliminary Report on Patentability dated Sep. 27, 2011 re PCT Application No. PCT/2010/028743.
International Search Report dated Oct. 5, 2010 to international application No. PCT/2010/028743.
"Faulding Inc. receives FDA permission to market patented Safe-Connect Valve", dated Dec. 2, 1996.
BD Medical: Needleless IV Access Devices, one page, 2007.
Capless Backcheck Valve, dated Sep. 3, 1993.
CareFusion, Medegen Introduces MaxPlus® Clear, First and Only Clear Positive Displacement Connector for Use in Infusion Therapy, MaxGuard News, one page article, dated Mar. 10, 2008—Ontario, CA.
Caresite™ Luer Access Device, dated 2010.
Clearlink, needleless IV access system, Baxter 2007 brochure in 2 pages.
F.D.A. 510(k) Summary of Safety and Effectiveness, dated Nov. 17, 1997.
LifeShield TKO Anti-Reflux Device Brochure, appears to contain a date of Feb. 8.
MEDI-4955 Liquid Silicone Rubber from NuSil Silicone Technology, dated Dec. 17, 2010.
MicroClave Connector Brochure. The MicroClave was available before Mar. 25, 2008.
MicroClave Neutral Displacement Connector A Neddlefree Closed System Device. Brochure Sep. 24, 2008.
MicroClave Product Page Video Shots. Sep. 24, 2008.
Nexus Medical Nexus TKO, appears to contain a date of Mar. 2006.
PASV Valve Connector Brochure, which appears to be at least as early as Feb. 20, 2001.
Photographs of LifeShield Clave®& TKO-4S product, consisting of a needleless valve essentially as illustrated in Lopez (U.S. Pat. No. 5,685,866) and a flow control valve essentially as illustrated in Dikeman (U.S. Pat. No. 7,601,141), sold in the U.S. at least as early as May 2008.
Saechtling Tworzywa Sztuczne, WN-T Warszawa, 1999, V edition, pp. 224-225.
European Examination Report, re EP Application No. 19150262.4, dated Sep. 9, 2019.

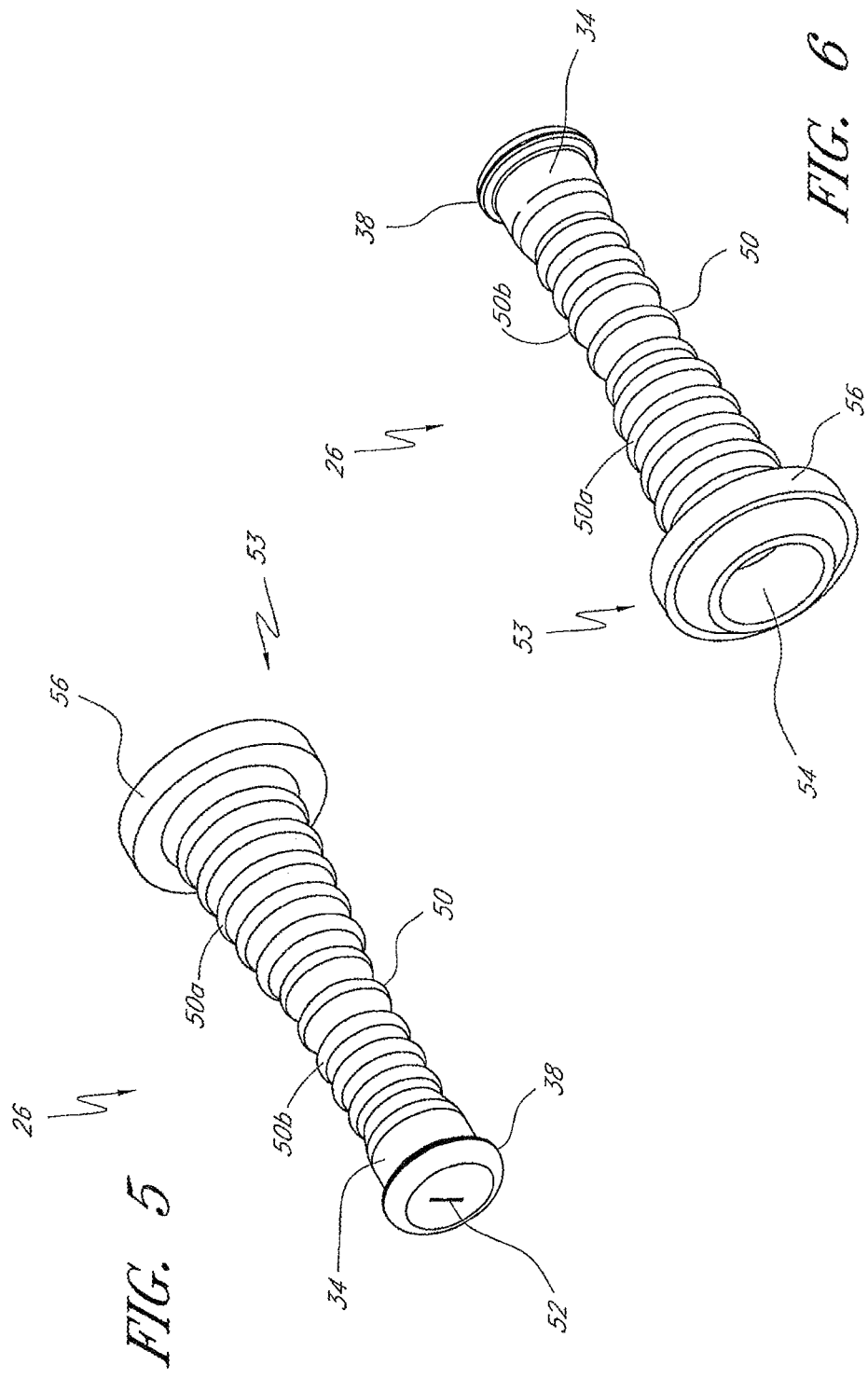

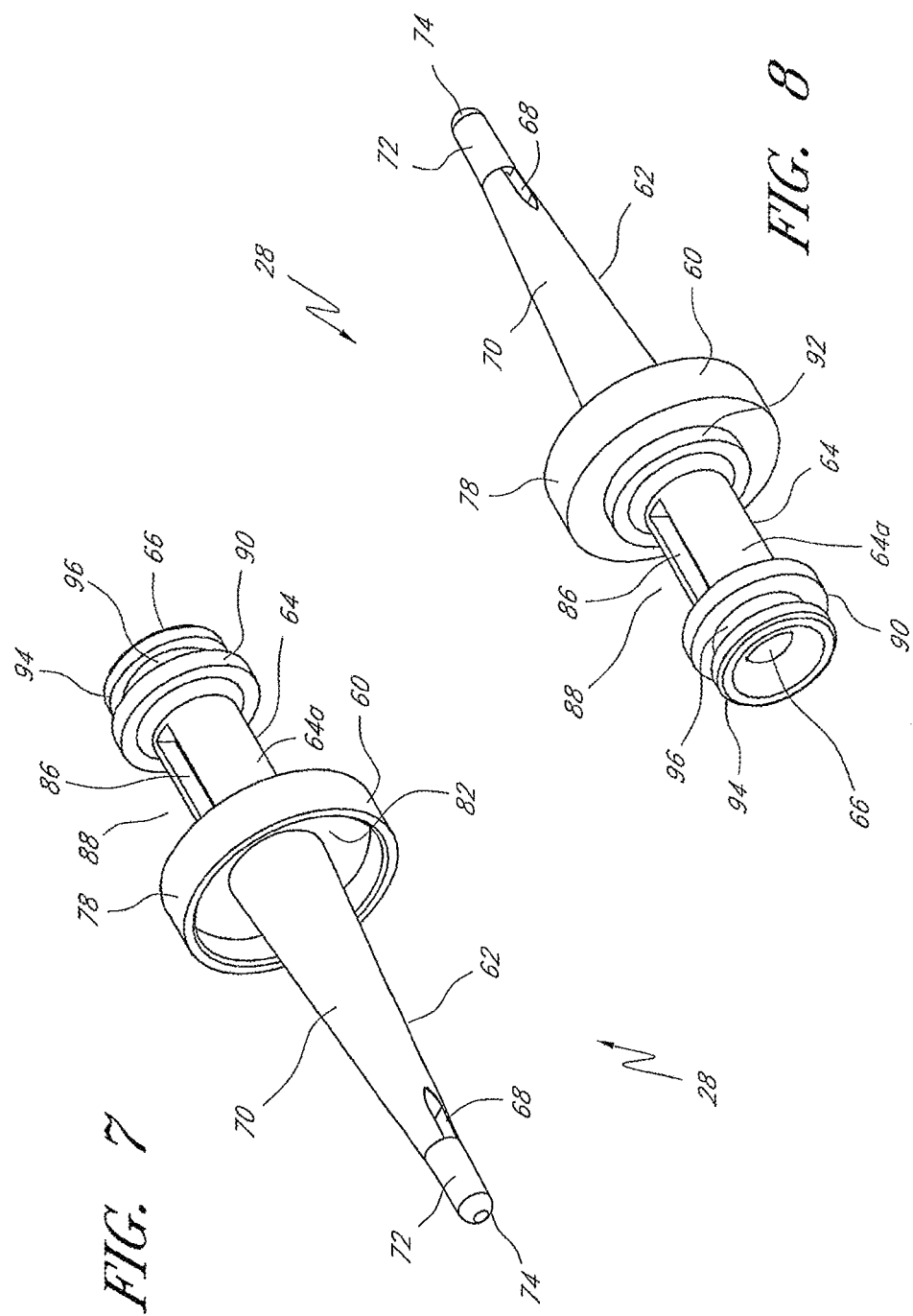

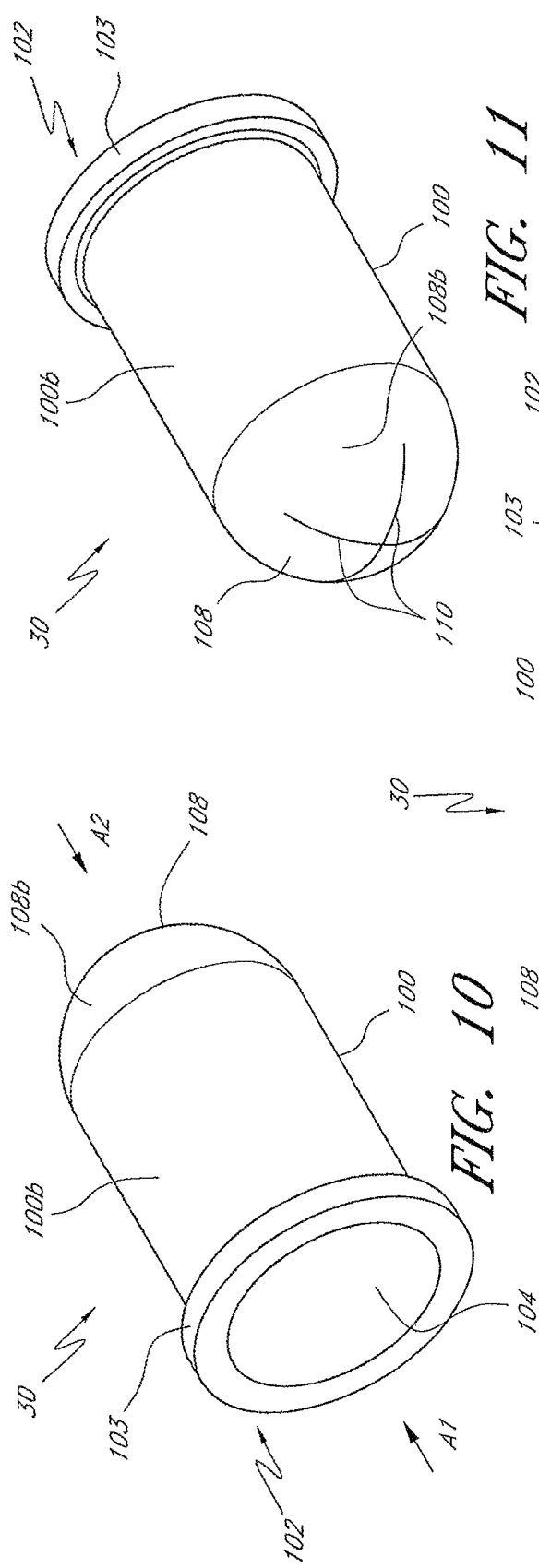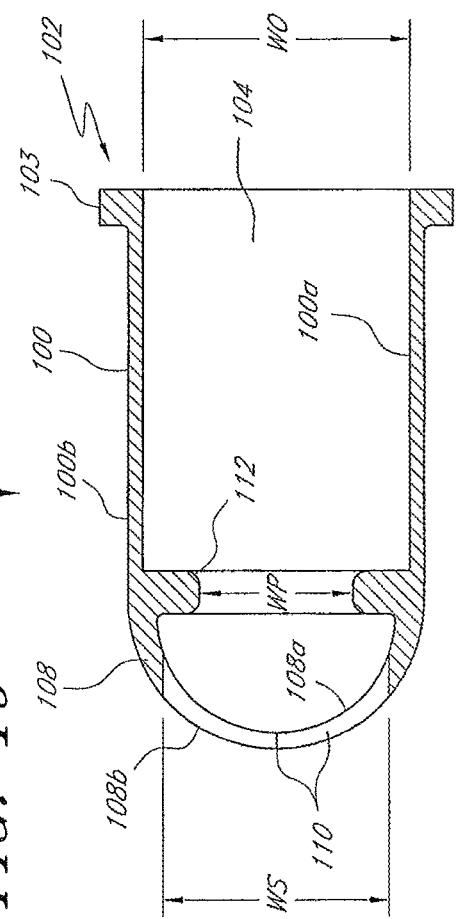

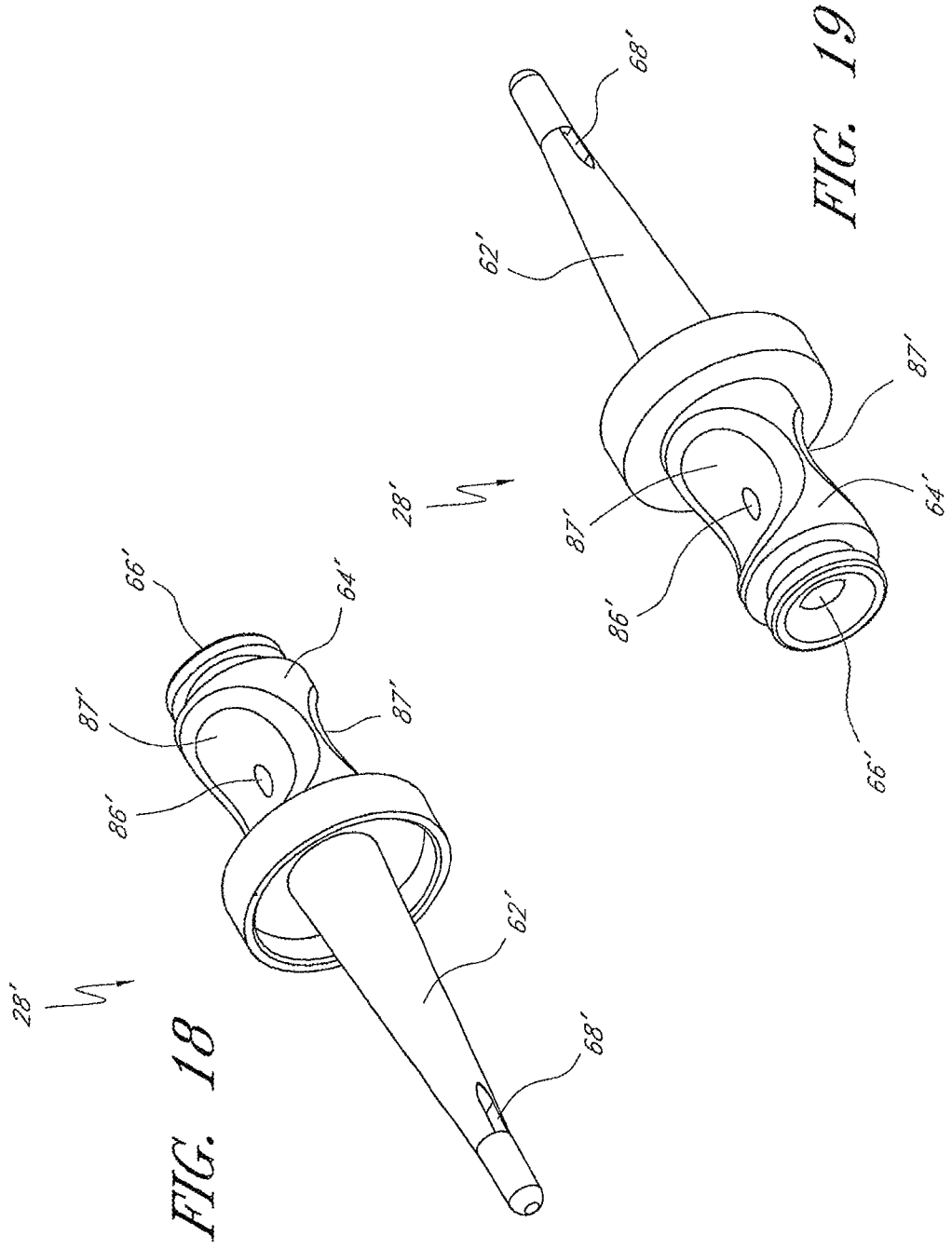

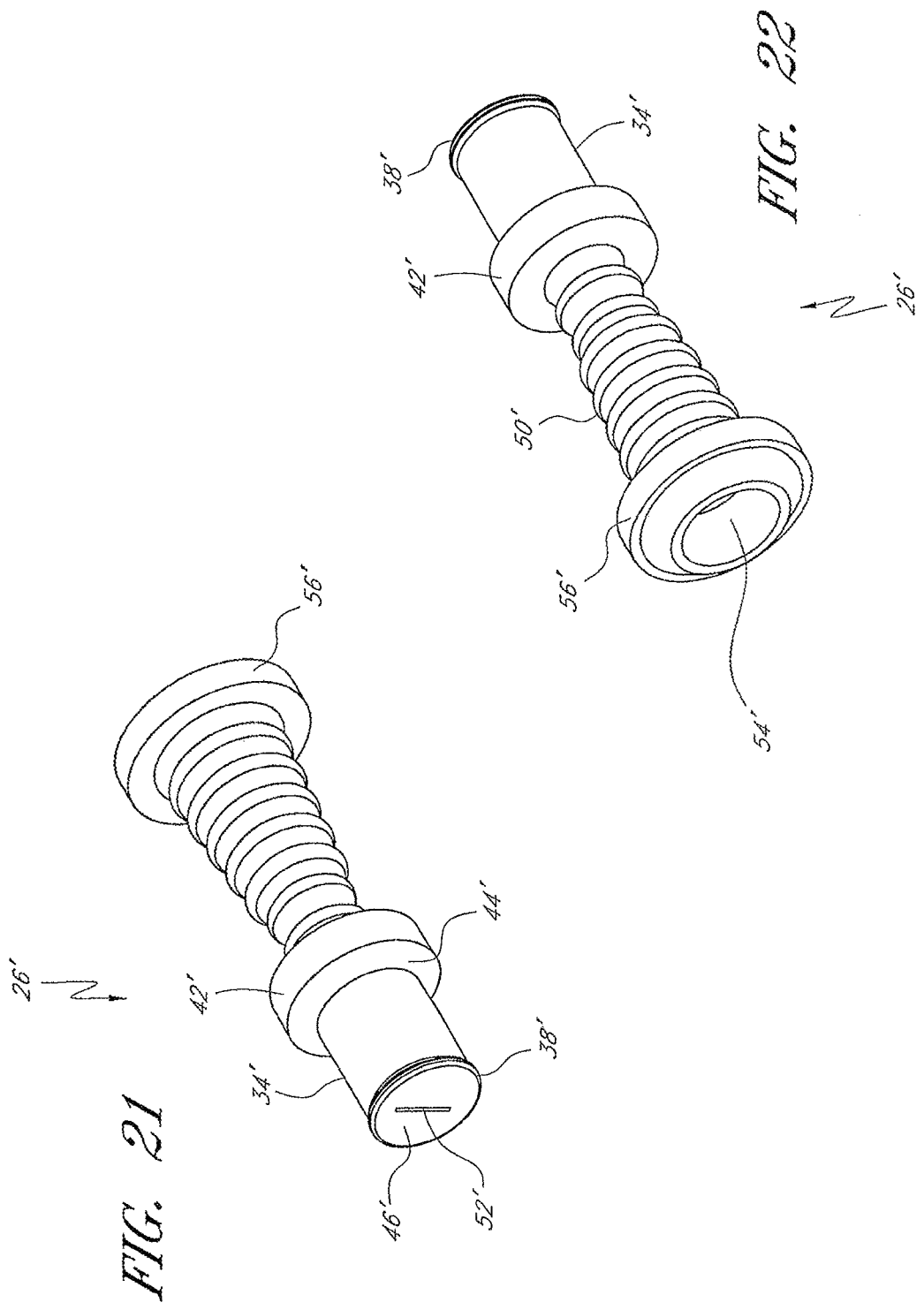

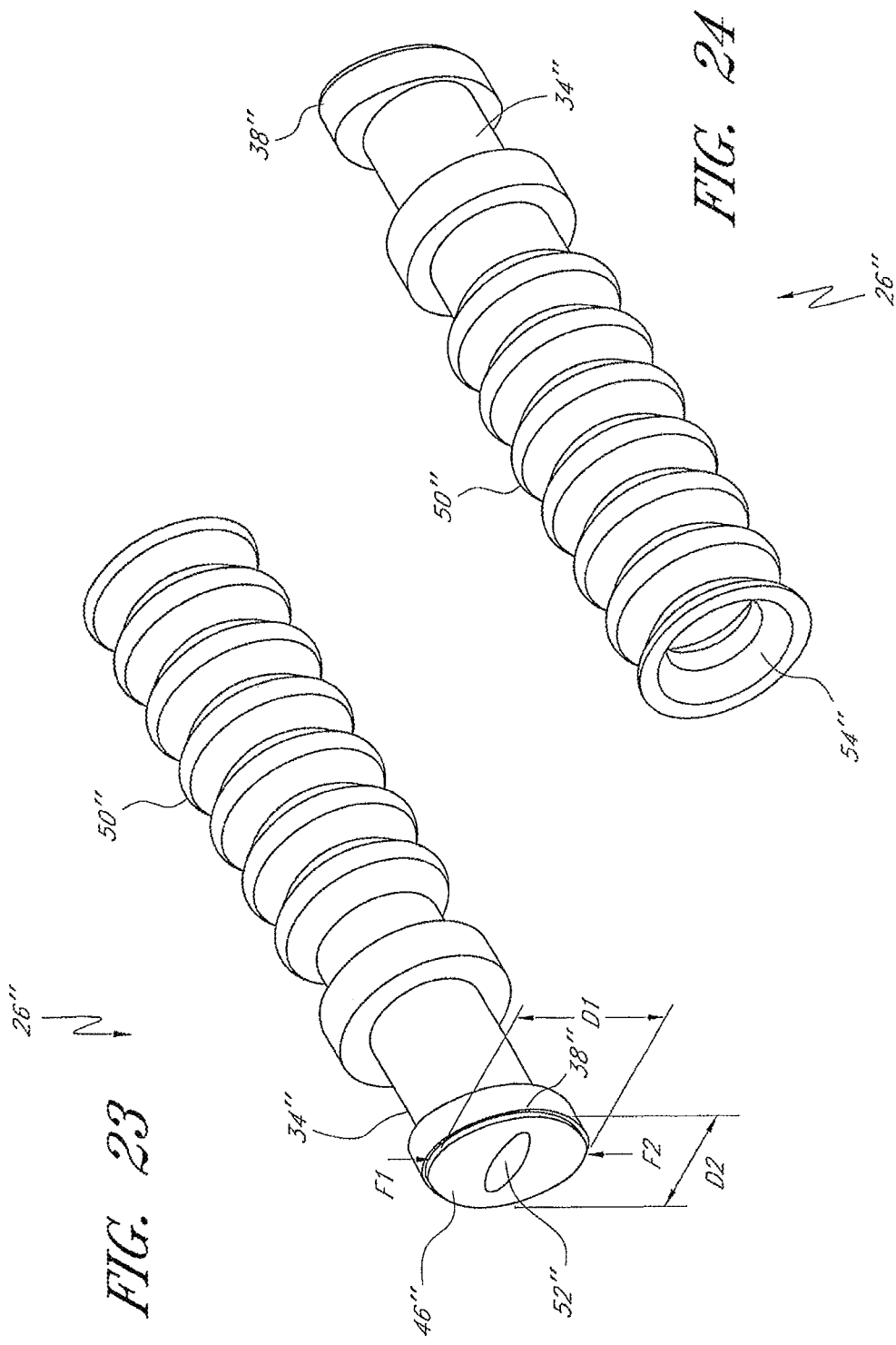

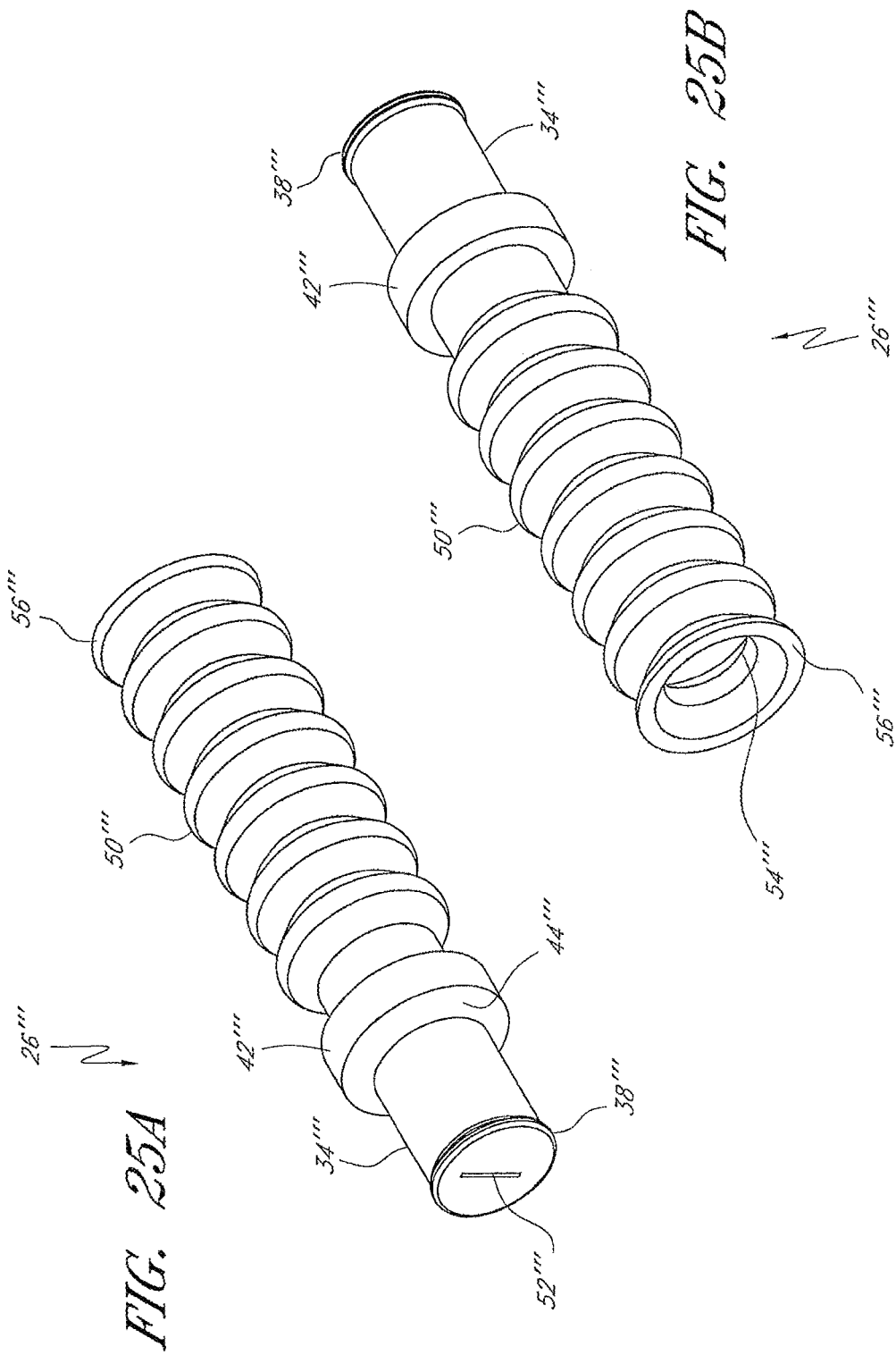

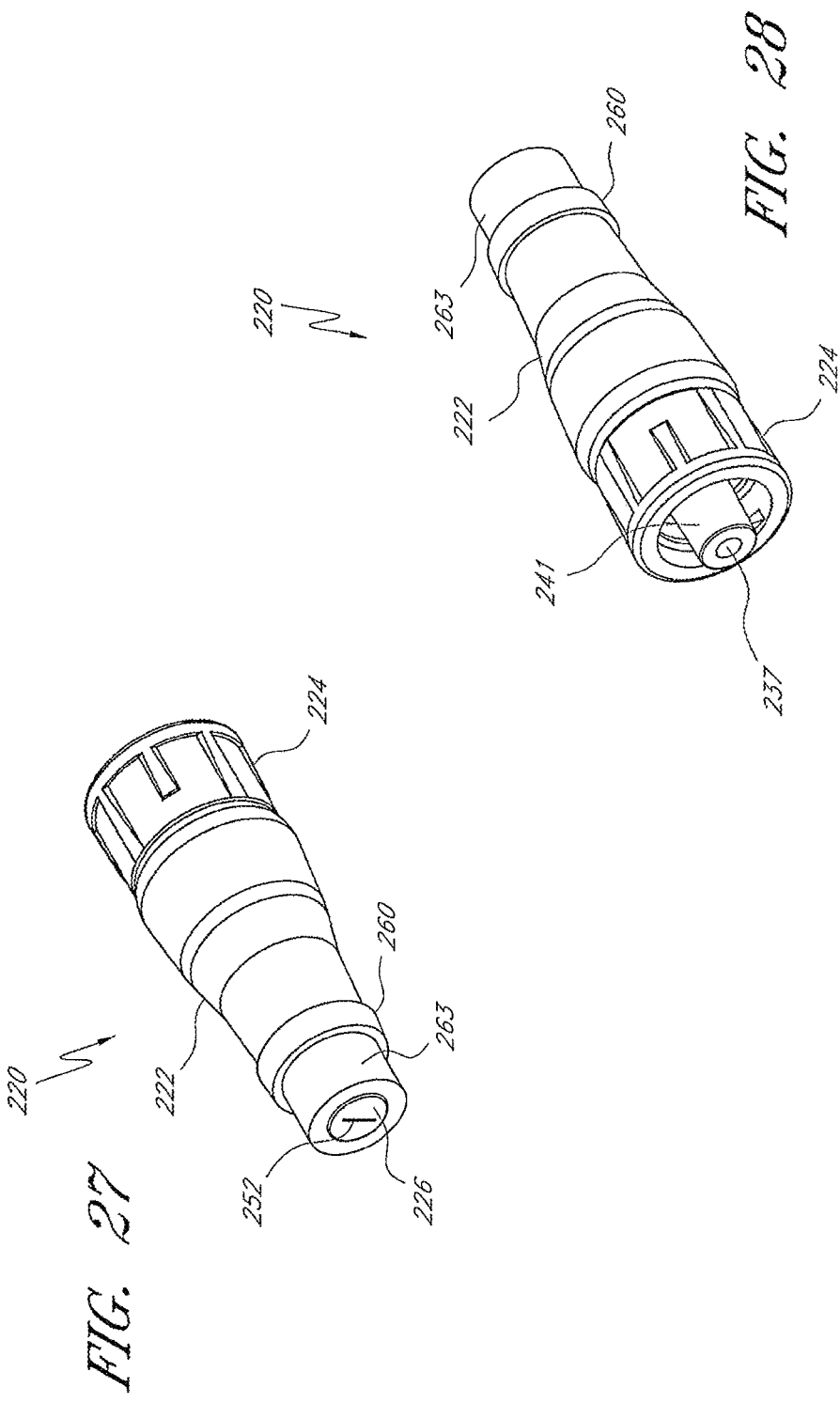

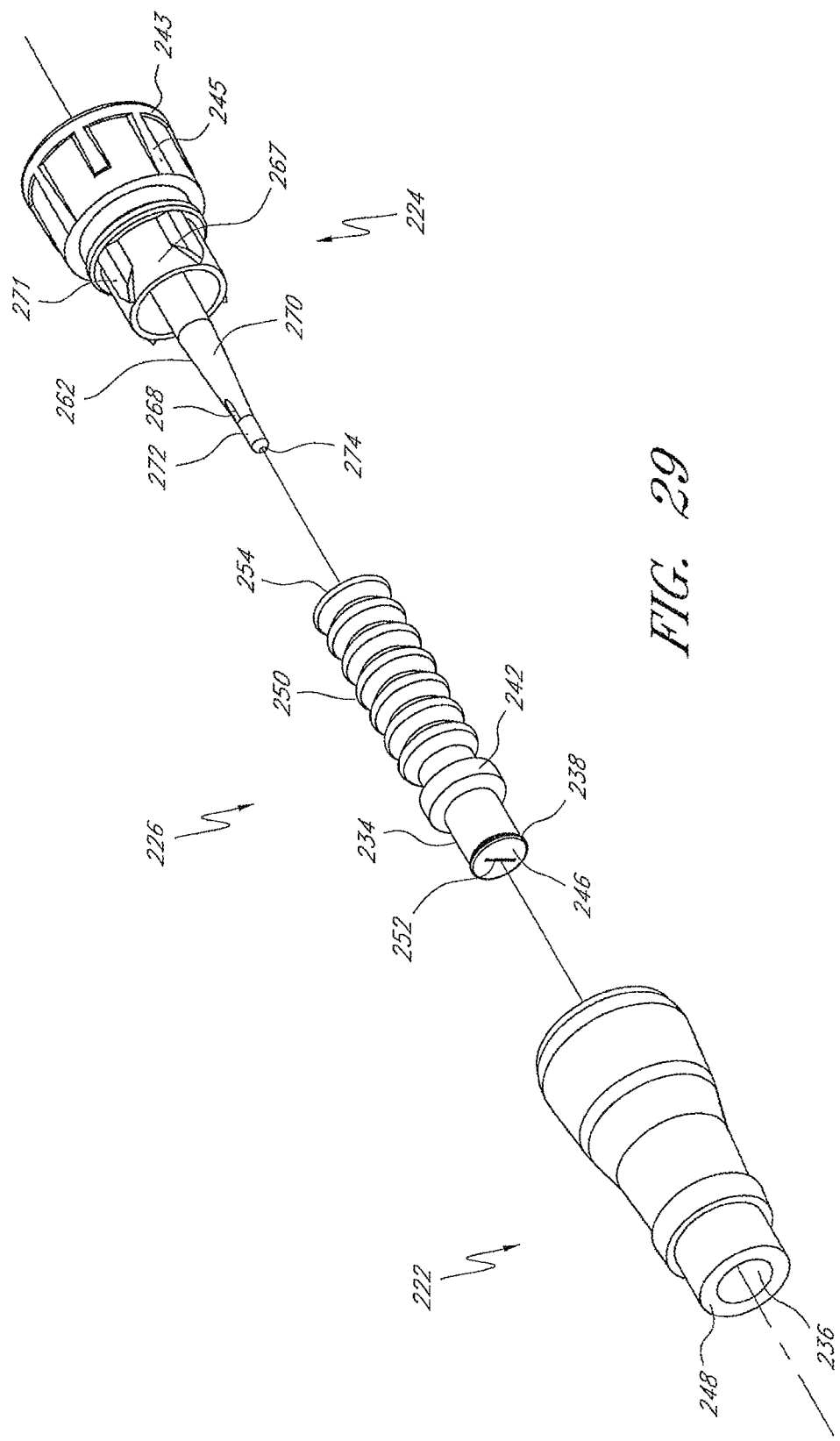

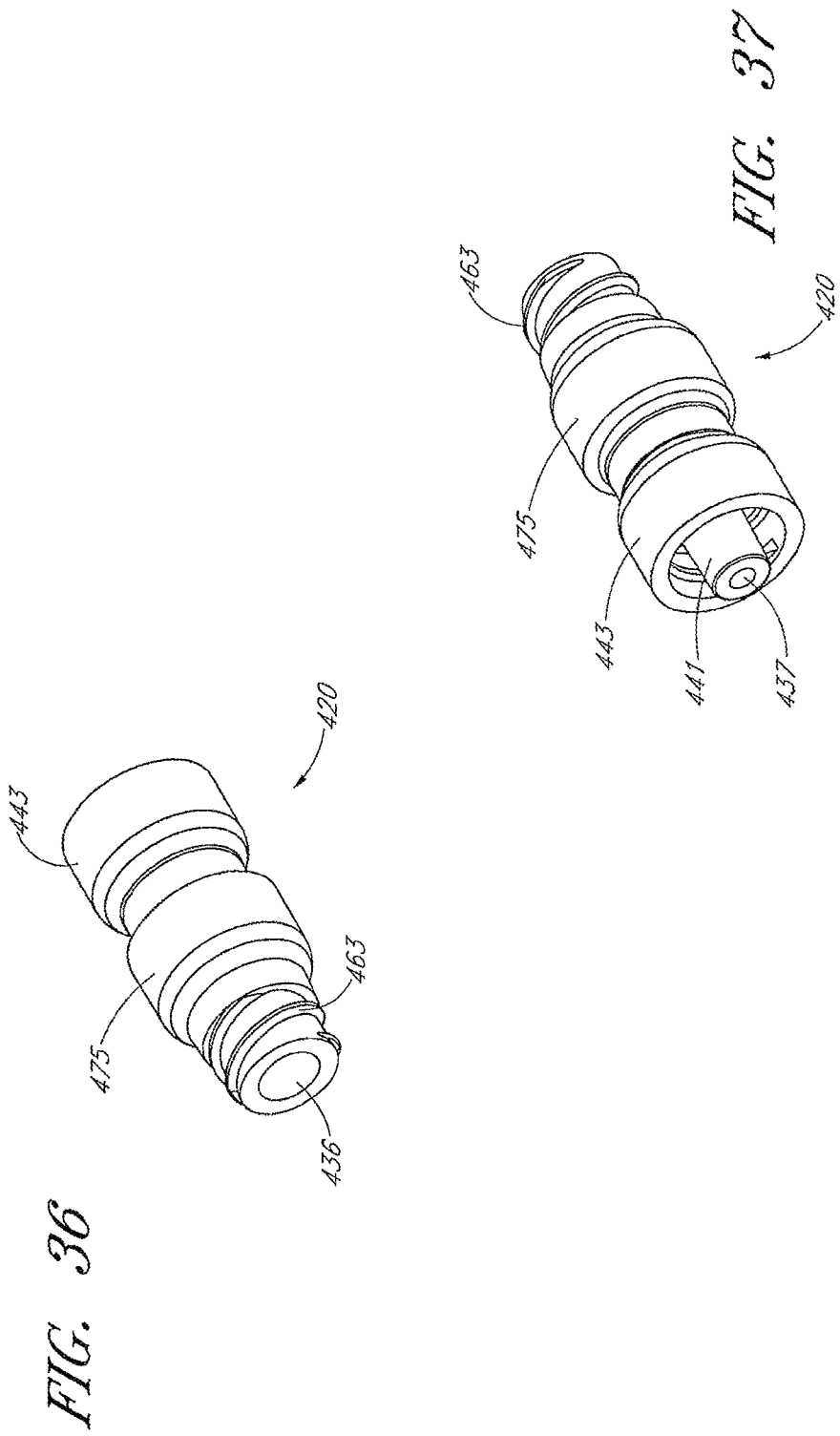

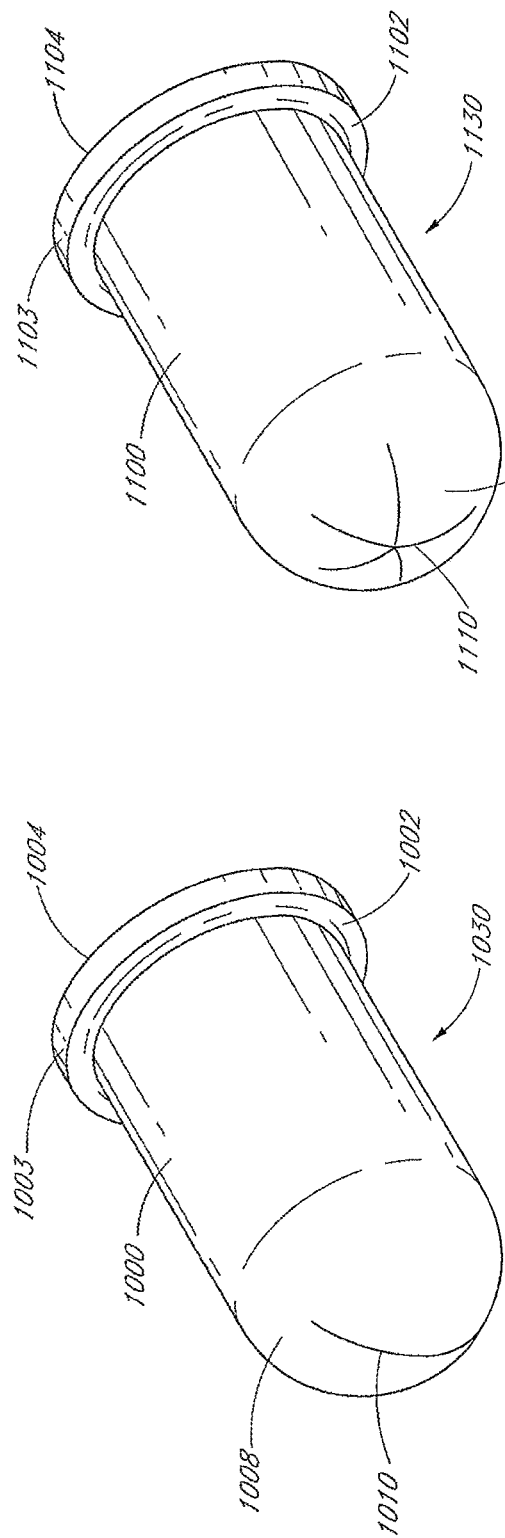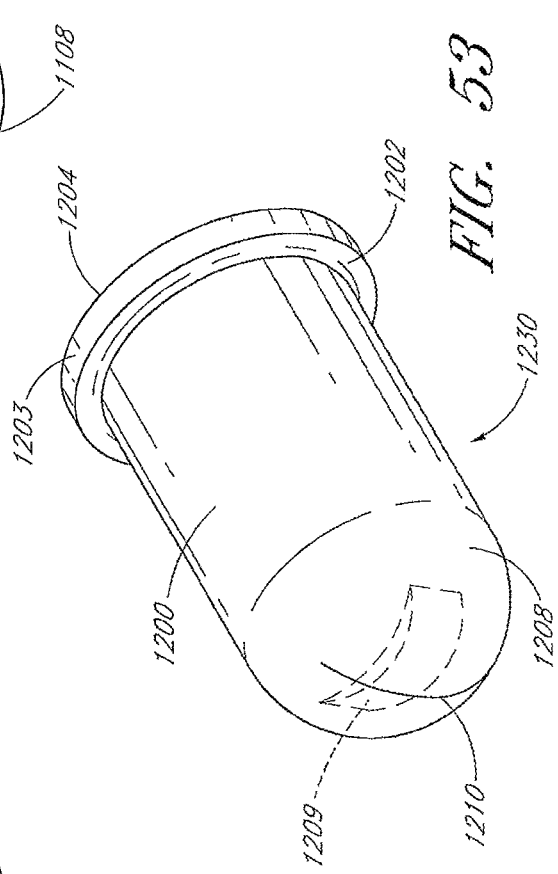
FIG. 51
FIG. 52
FIG. 53

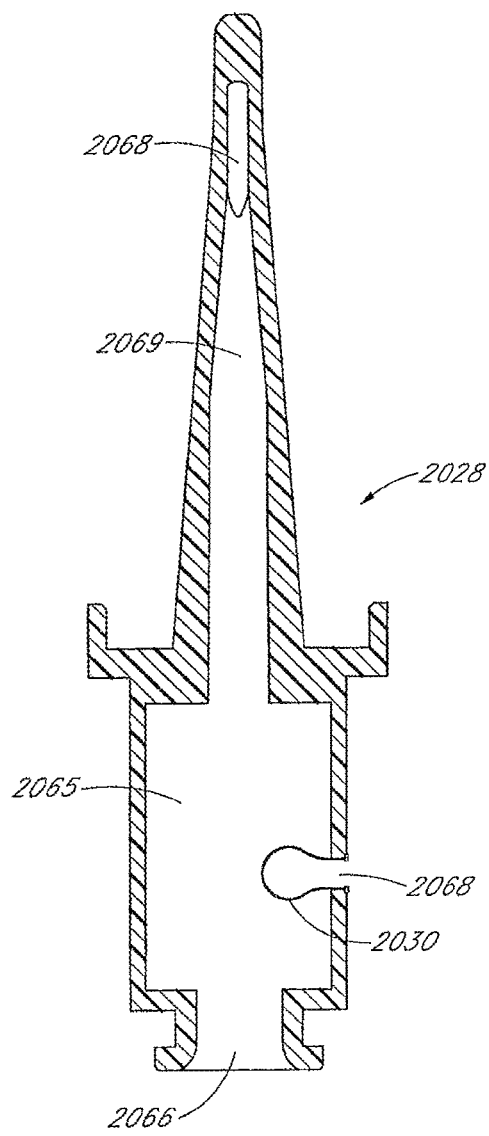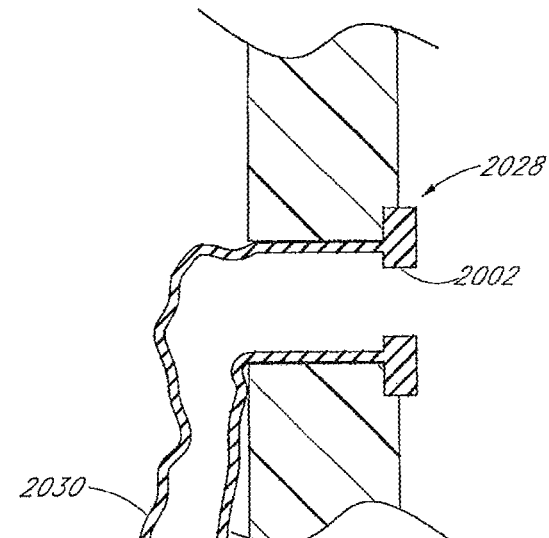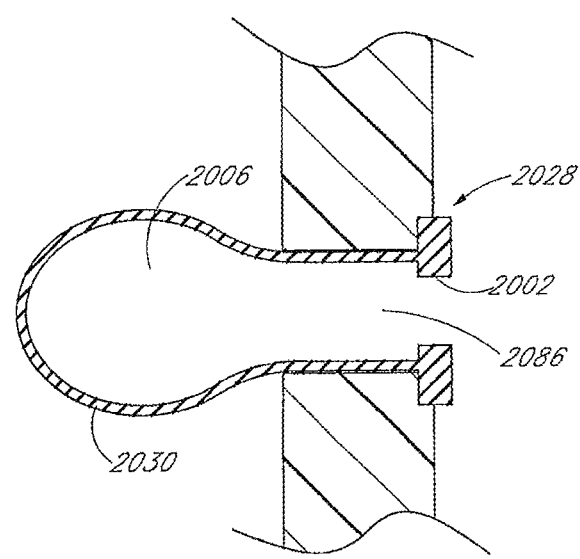
FIG. 75
FIG. 76
FIG. 77

MEDICAL CONNECTORS AND METHODS OF USE

RELATED APPLICATIONS

This is a continuation of U.S. patent application Ser. No. 14/977,550, filed on Dec. 21, 2015, which is a continuation of U.S. patent application Ser. No. 13/857,019, filed on Apr. 4, 2013, now U.S. Pat. No. 9,278,206, which is a continuation of U.S. patent application Ser. No. 12/730,074, filed on Mar. 23, 2010, now U.S. Pat. No. 8,454,579, which claims the benefit under 35 U.S.C. § 119(e) of U.S. Provisional Patent Application No. 61/163,367, filed on Mar. 25, 2009, and entitled "Medical Connectors And Methods Of Use," and U.S. Provisional Patent Application No. 61/251,232, filed on Oct. 13, 2009, and entitled "Medical Connectors And Methods Of Use," the entire contents of all of which are hereby incorporated by reference herein and made part of this specification for all that, they disclose.

BACKGROUND OF THE DISCLOSURE

Field of the Disclosure

Embodiments of the invention relate generally to medical connectors through which fluids flow, and in particular, to self-sealing medical connectors.

Background of the Disclosure

Closeable medical connectors or valves are useful in the administration of fluids in hospital and medical settings. Such closeable medical connectors can be repeatedly connectable with a range of other medical implements and can be self-sealing when disconnected from other medical implements.

SUMMARY OF SOME EMBODIMENTS

Some embodiments disclosed herein relate to a closed, patient access system which can automatically reseal after administering fluid, medicaments, or other suitable substances (hereinafter, collectively referred to as "fluid") using a medical implement that connects or communicates with the system. A two-way valve can be employed, utilizing a reusable seal that may be repeatedly opened. The valve can facilitate the transfer of fluid, particularly liquid, while maintaining sterility. After use, the valve can be swabbed in a conventional manner with a suitable substance to maintain sterility.

Some embodiments disclosed herein relate to a medical connector having a backflow resistance module configured to prevent fluid from being drawn into the connector when a backflow inducing event occurs (e.g., a syringe rebound, a syringe disconnection, etc.). In some embodiments, the backflow resistance module can include a variable volume chamber configured to change in volume in response to a backflow-inducing event and a check valve configured to resist backflow. In some embodiments, the medical connector can include a fluid diverter configured to direct fluid flowing through the medical connector into the variable volume chamber to prevent fluid stagnation therein. In some embodiments, the medical connector includes a body member, a base member, a seal member, a support member, and a valve member.

BRIEF DESCRIPTION OF THE DRAWINGS

Certain embodiments of the inventions will now be discussed, in detail with reference to the following figures. These figures are provided for illustrative purposes only, and the inventions are not limited to the subject matter illustrated in the figures.

FIG. 5 is a perspective view of an embodiment of a seal member of the embodiment of the connector shown in FIG. 2A.

FIG. 6 is another perspective view of the embodiment of the seal member shown in FIG. 5.

FIG. 7 is a proximal perspective view of an embodiment of a support member of the embodiment of the connector shown in FIG. 2A.

FIG. 8 is a distal perspective view of the embodiment of the support member shown in FIG. 7.

FIG. 10 is a proximal perspective view of an embodiment of a regulator of the embodiment of the connector shown in FIG. 2A.

FIG. 11 is a distal perspective view of the embodiment of the regulator shown in FIG. 10.

FIG. 12 is a section view of the embodiment of the regulator shown in FIG. 10, taken through the axial centerline of the regulator.

FIG. 18 is a proximal perspective view of another embodiment of a support member that can be used with the connector shown in FIG. 2A or any other connector disclosed herein.

FIG. 19 is a distal perspective view of the embodiment of the support member shown in FIG. 18.

FIG. 21 is a proximal perspective view of another embodiment of a seal member that can be used with the connector shown in FIG. 2A or any other connector disclosed herein.

FIG. 22 is a distal perspective view of the embodiment of the seal member shown in FIG. 21.

FIG. 23 is a proximal perspective view of another embodiment of a seal member that can be used with the connector shown in FIG. 2A or any other connector disclosed herein.

FIG. 24 is a distal perspective view of the embodiment of the seal member shown in FIG. 23.

FIG. 25A is a proximal perspective view of another embodiment of a seal member that can be used with the connector shown in FIG. 2A or any other connector disclosed herein.

FIG. 25B is a distal perspective view of the embodiment of the seal member shown in FIG. 25A.

FIG. 27 is a proximal perspective view of another embodiment of a valve or needleless connector.

FIG. 28 is a distal perspective view of the embodiment of the connector shown in FIG. 27.

FIG. 29 is a proximal exploded view of the embodiment of the connector shown in FIG. 27.

FIG. 36 is a proximal perspective view of another embodiment of a valve or needleless connector.

FIG. 37 is a distal perspective view of the connector shown in FIG. 36.

FIG. 51 is a distal perspective view of an embodiment of a regulator having a single slit formed therein.

FIG. 52 is a distal perspective view of an embodiment of a regulator having five slits formed therein.

FIG. 53 is a distal perspective view of another embodiment of a regulator.

FIG. 75 is a section view of another embodiment of a support member that includes a bag member.

FIG. 76 is a partial section view of the support member shown in FIG. 75, with the bag member in a generally collapsed configuration.

FIG. 77 is another partial section view of the support member shown in FIG. 75, with the bag member in an inflated configuration.

DETAILED DESCRIPTION OF SOME EXAMPLES OF EMBODIMENTS

Figure 1:
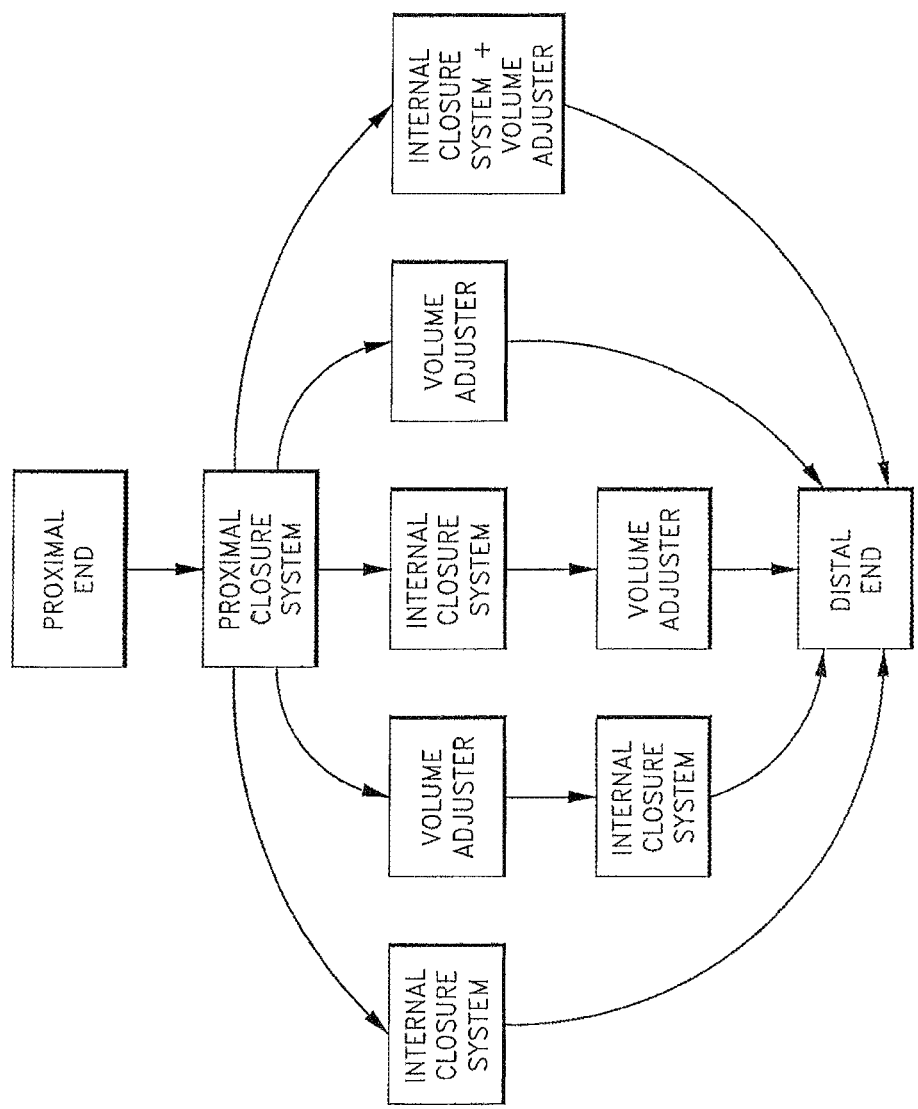
FIG. 1 is a schematic illustration of certain components of some embodiments of medical connectors.

The following detailed description is now directed to certain specific embodiments of the disclosure. In this description, reference is made to the drawings wherein like parts are designated with like numerals throughout the description and the drawings.

In some aspects of the embodiments described herein, a variety of means are shown for closing one or more end portions of the connectors described herein. These closing mechanisms can function to substantially prevent and/or substantially impede fluid from passing through the end portions of the connector when the closing mechanisms or valves are in a closed position. When the closing mechanisms are in an open position, such as when the connector is engaged with a needleless syringe or other medical connector, fluid is permitted to pass through one or more end portions of the connectors. As used herein, terms such as "closed" or "sealed" and variants thereof should be understood to refer to obstructions or barriers to fluid flow. These terms should not be understood to require that a particular structure or configuration achieves a complete fluid closure in all circumstances.

In some aspects of embodiments disclosed herein, a variety of means are shown for controlling the flow of fluid inside a connector. These fluid control valves or mechanisms can facilitate the control of potentially undesirable fluid movement out of or into the connector. For example, it may be desirable to prevent, inhibit, or diminish negative flow or fluid ingress into the connector. As used herein, negative flow, retrograde flow, backflow, ingress flow, and related terms are used in accordance with their customary meanings in the medical connector field. In some cases, these terms refer to the flow of fluid into the connector due to an increase or effective increase in the internal volume of the fluid space within the connector, or due to an external draw or removal of fluid (such as by withdrawal of a portion of a medical implement previously inserted into the connector), or due to an external source of fluid pressure in a general retrograde direction, such as that caused by a patient's cough, or by an increase in a patient's blood pressure, or by disturbances in a fluid source (e.g., fluid volume in an IV bag diminishing or "running dry"), etc. Negative flow generally occurs in a direction generally opposite from or opposed to an intended flow of fluid.

As used herein, the terms "neutral," "neutral displacement," "neutral flow," and other related terms are also used in accordance with their customary meanings in the medical connector field. In some cases, these terms refer to medical connectors or valves that generally do not exhibit negative flow in most clinical situations in which the particular connectors or valves are intended to be used or that generally exhibit negative flow at a sufficiently low level in most clinical situations in which the particular connectors or valves are intended to be used that the risk of harm to a patient or the likelihood of needing to replace the connector, valve, or catheter due to negative flow is extremely low. Also, a neutral connector or valve generally does not exhibit a clinically significant positive flow of fluid emanating from the distal end of the connector or valve automatically upon connection or disconnection of another medical implement to the proximal end of the connector or valve. In some embodiments disclosed herein, the connectors or valves can be neutral or can achieve neutral flow.

There are many sources of negative flow. These include negative flow that occurs when a medical implement, such as a syringe, is removed from the proximal end, also referred to herein as the first or female end of the connector. As the syringe is removed, the fluid holding space inside the connector may increase. When that fluid space is in communication with a patient's fluid line catheter, the increase in fluid space inside the connector may draw fluid from the catheter into the connector from the distal end, also referred to herein as second or male end of the connector. This can be disadvantageous in that such negative flow can thereby draw blood from the patient into the opposite end of the catheter line. Such blood in the line can clot or otherwise fowl the line, possibly requiring premature replacement and reinsertion of the catheter line, the connector, and other medical implements.

Negative flow can also come from an implement coupled to the proximal side of the connector. An example of this type of negative flow can be caused by a pump machine or by a manual syringe. For example, when the medical implement connected to the connector is a syringe, it generally includes an elastic plunger head connected to a plunger arm configured to be pressed by a user or a machine. When the fluid in the syringe is expelled, the plunger may be compressed against the end of the syringe internal cavity. Upon release of the pressure on the plunger arm, the compressed plunger head generally rebounds or expands slightly in the proximal direction away from the end of the cavity and, likewise, the connector. A small void may thereby be formed between the end of the cavity and the distal surface of the plunger head. Because there is still fluid communication with the syringe and the catheter connecting the patient, the void can be filled with fluid pulled from the connector which, in turn, can pull fluid from the catheter into the connector. This fluid drawback can also cause clotting or otherwise fowl the line.

Negative flow can occur in other ways during use, such as when an IV bag that is used to infuse fluid through the catheter runs dry, or the blood pressure in the patient changes, or a patient moves, etc. Negative flow can also be produced by the momentum of fluid flow. A syringe or machine may inject fluid into a connector. The user or machine generally dispels as much fluid as possible into the connector, such as by pressing the plunger head all the way to the end of the internal cavity of the syringe. Even before the pressure on the plunger is released, some negative flow can occur into the connector. The fluid molecules are connected by intermolecular forces and have momentum. As the final amount of fluid is displaced from the source, it pushes fluid out of the connector and thereby out of the catheter. As the force pushing the fluid in the distal direction ends, the fluid at the end of the catheter may continue out of the catheter while the fluid further from the end of the catheter remains in the catheter. The void between the end of the catheter and the end of the fluid column in the catheter can fill with blood which can lead to clotting.

Some embodiments of the present invention can generally eliminate, diminish, minimize, or control the effect of some or all sources of negative flow. Although the functionality of some of the embodiments disclosed herein is discussed in connection with a single source of negative flow (e.g., syringe rebound), it should be understood that many sources of negative flow can be eliminated, diminished, minimized, or controlled in similar or identical ways.

FIG. 1 illustrates examples of a variety of different components and configurations thereof that can be included in some embodiments of the needleless connectors disclosed herein. FIG. 1 should not be construed to illustrate all possible combinations and/or components that can be used. Some embodiments can include a proximal end, a proximal closure system, an internal closure system, and a distal end, arranged in series with each other, as illustrated by the first series of boxes on the left side of FIG. 1. Some embodiments can include a proximal end, a proximal closure system, a volume adjuster, an internal closure system, and a distal end, arranged in series with each other, as illustrated by the second series of boxes of FIG. 1. Some embodiments can include a proximal end, a proximal closure system, an internal closure system, a volume adjuster, and a distal end, arranged in series with each other, as illustrated by the third series of boxes of FIG. 1. Some embodiments can include a proximal end, a proximal closure system, a volume adjuster, and a distal end, arranged in series with each other, as illustrated by the fourth series of boxes of FIG. 1. Some embodiments can include a proximal end, a proximal closure system, a combined internal closure system and volume adjuster, and a distal end, arranged in series with each other, as illustrated by the fifth series of boxes of FIG. 1. Any of these components can be omitted in certain embodiments, and components can be included in between the illustrated components arranged in series with each other.

Many other combinations and other types of components can be used instead of or in addition to the configurations illustrated in FIG. 1. For example, some embodiments can include a proximal end, a combined proximal closure system and volume adjuster and/or a combined proximal closure system and internal closure system, and a distal end. In some embodiments, there can be multiple sets of the components illustrated in FIG. 1. For example, a pair of volume adjusters can be provided on both sides of an internal closure system. In some embodiments, the distal end can include a closure system. Any component, feature, or step illustrated or described herein can be omitted in some embodiments. No component, feature, or step is essential or indispensable.

Several examples of proximal closure systems are illustrated, including the seal member 26 and support member 28 (see, e.g., FIG. 3), the seal member 26' (see, e.g., FIG. 21), the seal member 26" (see, e.g., FIG. 23), the seal member 326 (see, e.g., FIG. 34), the cap 491 (see, e.g., FIG. 38), and the seal members 2126, 2226, 2326, 2426, 2526, 2626, 2726, 2826, 2926, and 3026 (see, e.g., FIGS. 79, 81, 83, 85, 86B, 87B, 88B, 89B, 90B, and 91B). Other types of proximal closure systems can also be used. The proximal closure systems of each embodiment can be interchanged with those of other embodiments with appropriate modifications (if needed). The proximal closure system can be omitted from some embodiments.

Several examples of volume adjusters are illustrated, including the regulators 30, 330, 630, 1030, 1130, 1230, 1430, 1530, 1730, 1930, 2130, 2230, 2330, 2430, 2530, 2630, 2730, 2830, 2930, 3030 (see, e.g., FIGS. 10-12, 34, 43-44, 51-53, 59-60, 63, 67-68, 74, 79, 81, 83, 85, 86B, 87B, 88B, 89B, 90B, 91B), the balloon member 1830 (see, e.g., FIG. 72), and the bag member 2030 (see, e.g., FIGS. 75-77). Other types of volume adjusters can also be used, including others that are illustrated and/or described herein. The volume adjusters of each embodiment can be interchanged with those of other embodiments with appropriate modifications (if needed). The volume adjuster can be omitted from some embodiments.

Several examples of internal closure systems are illustrated, including valve members 108, 308, 408, 730, 1008, 1108, 1208, 1330, 1408, 1508, 1708 (see, e.g., FIGS. 10-12, 34, 40, 46-47, 51-53, 57, 59-60, 63, 67-68), and similar valve members illustrated in FIGS. 79, 81, 83, 85, 86B, 87B, 88B, 89B, 90B, and 91B). Other types of internal closure systems can also be used, including others that are illustrated and/or described herein. The internal closure systems of each embodiment can be interchanged with those of other embodiments with appropriate modifications (if needed). The internal closure systems can be omitted from some embodiments.

Figure 2:
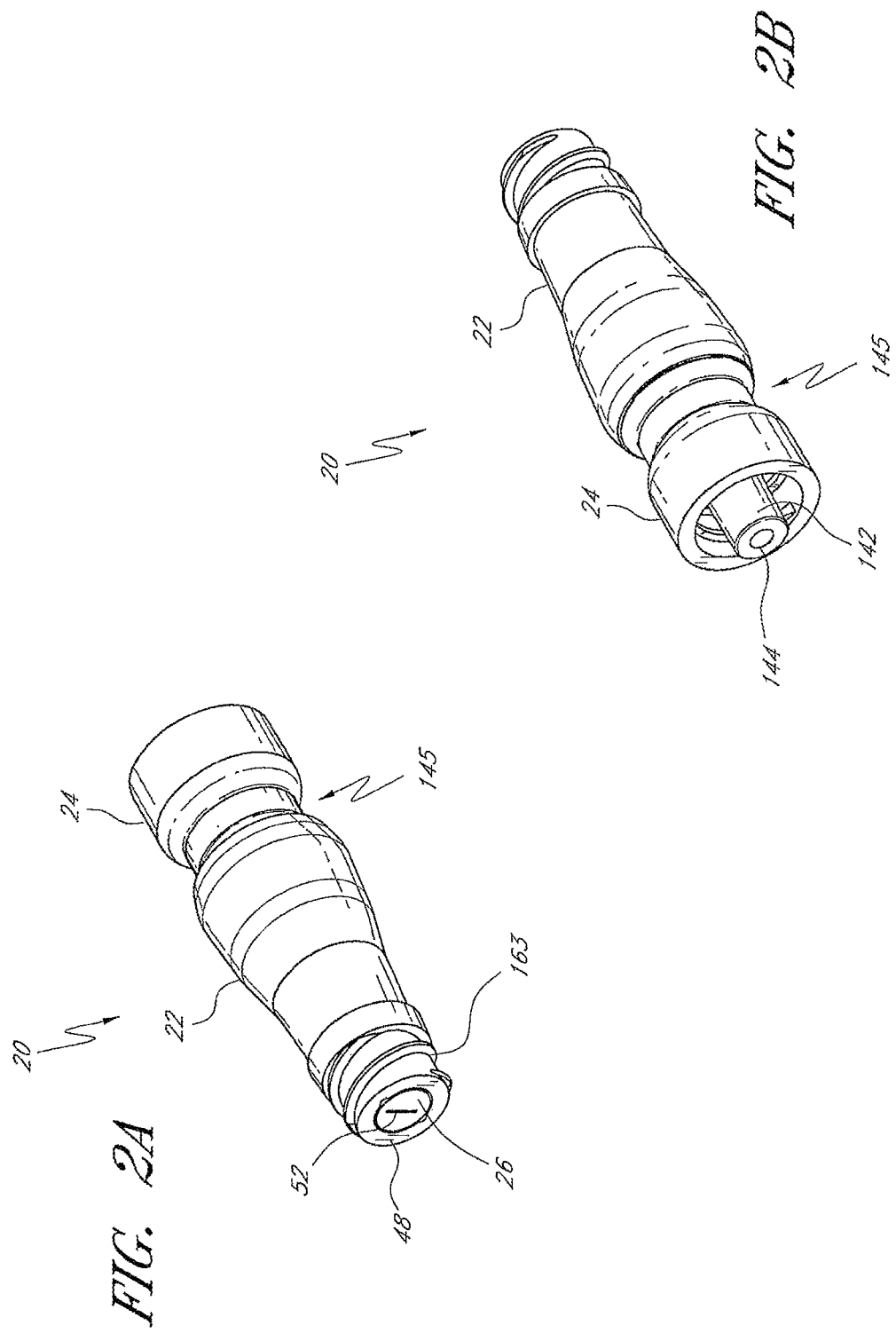
FIG. 2A is a proximal perspective view of an embodiment of a valve or needleless connector.
FIG. 2B is a distal perspective view of the embodiment of the connector shown in FIG. 2A.
Figure 3:
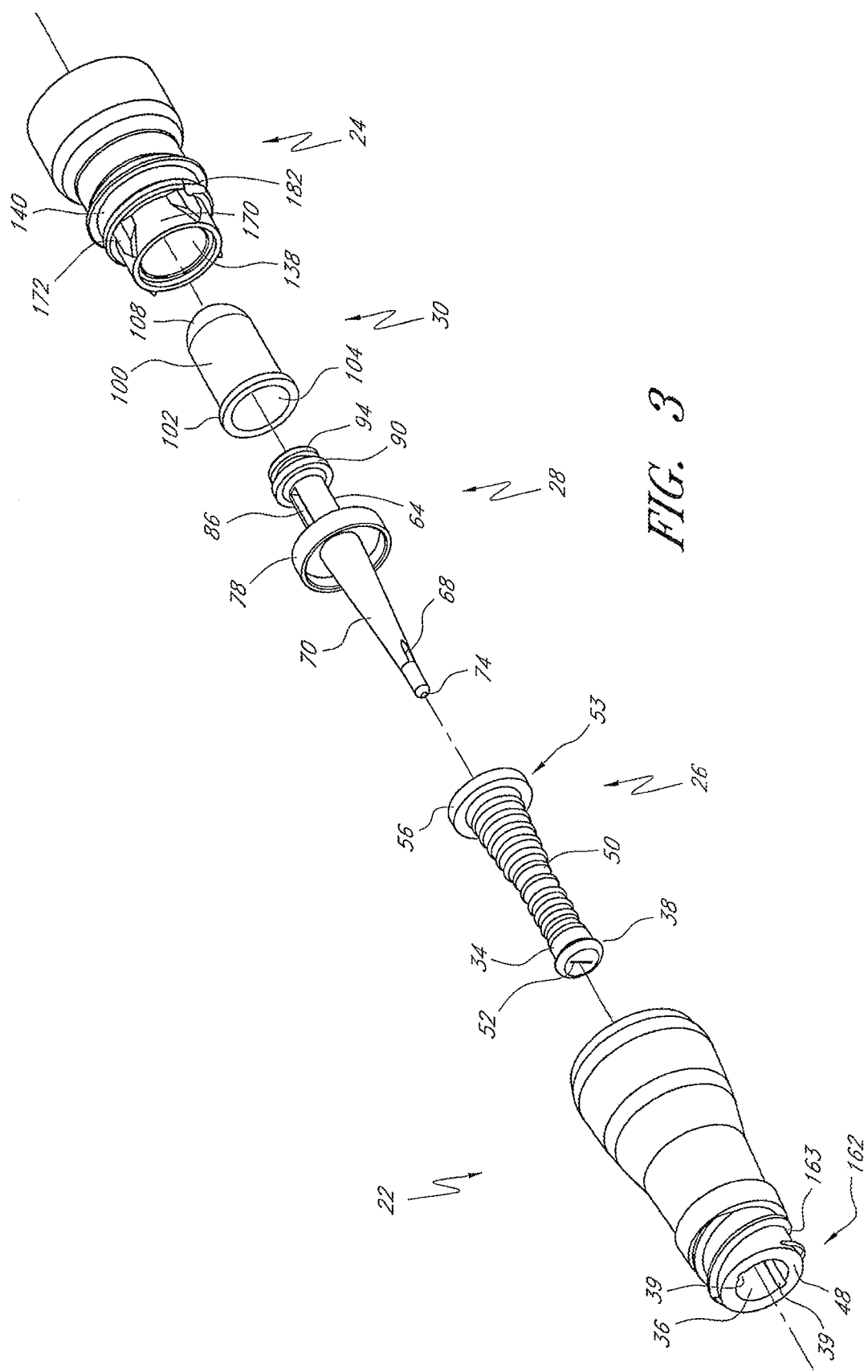
FIG. 3 is a proximal exploded view of the embodiment of the connector shown in FIG. 2A.
Figure 4:
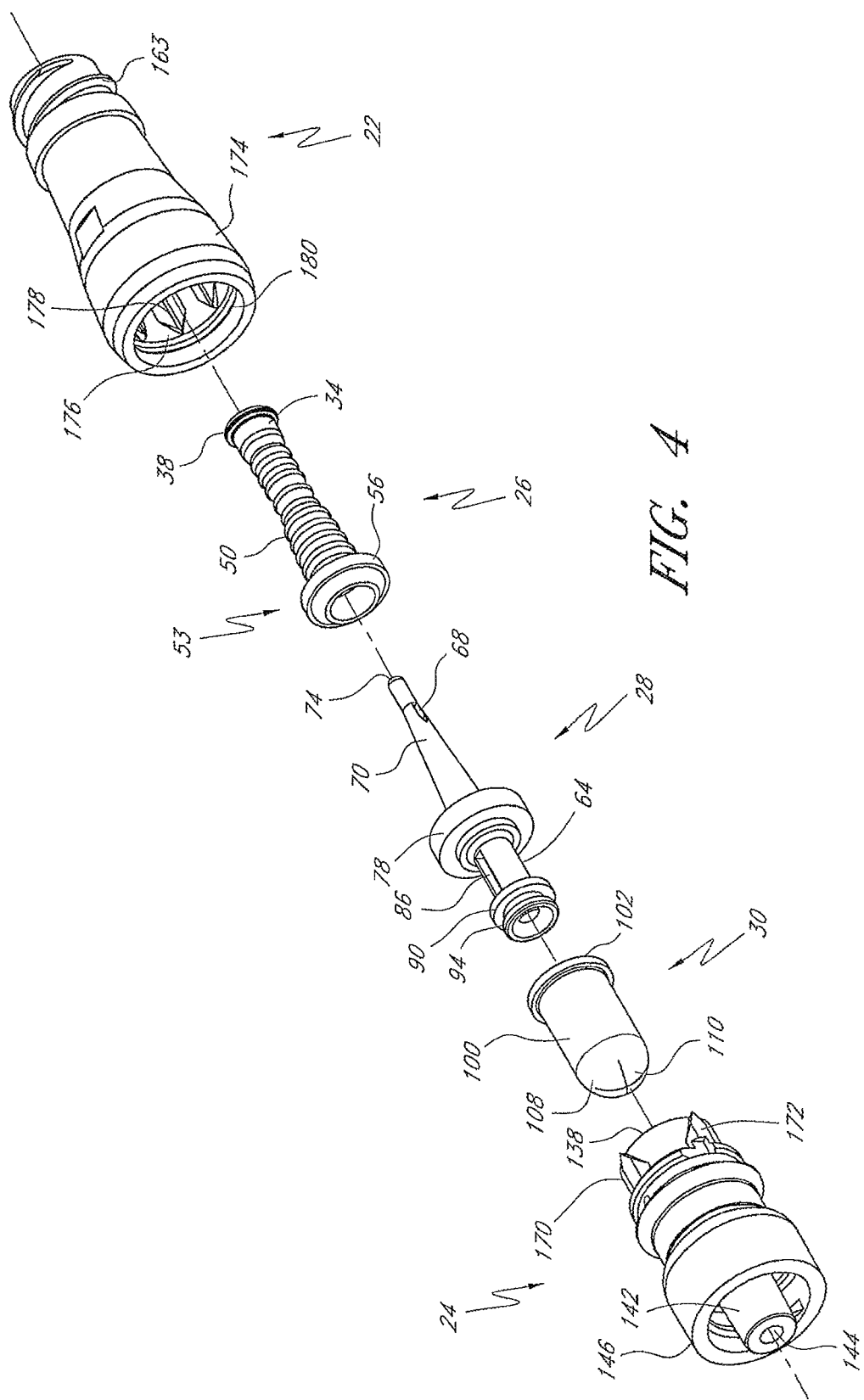
FIG. 4 is a distal exploded view of the embodiment of the connector shown in FIG. 2A.
Figure 4A:
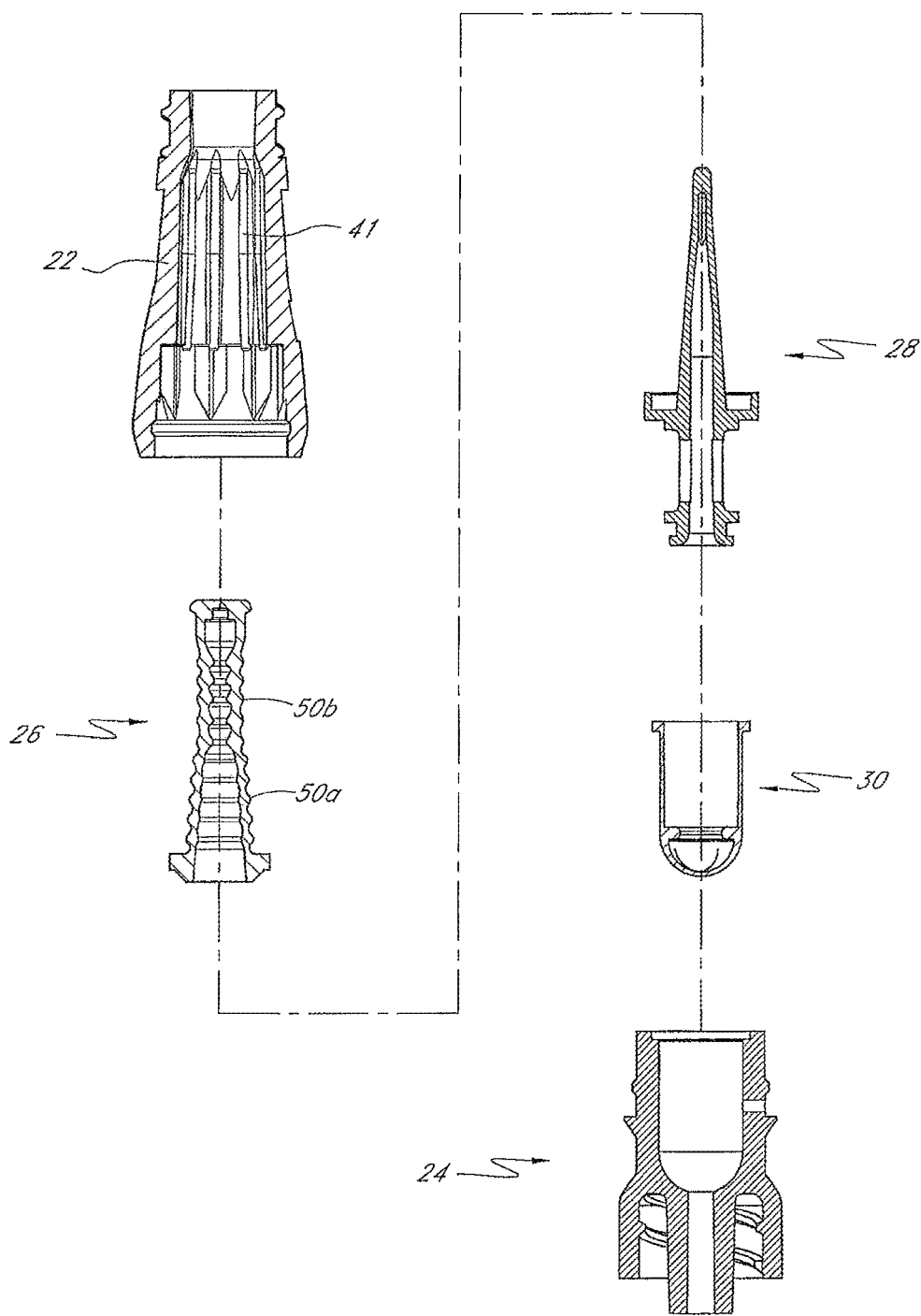
FIG. 4A is an exploded section view of the embodiment of the connector shown in FIG. 2A, taken through the axial centerline of the connector.

FIGS. 2A and 2B are perspective views of an embodiment of a valve or needleless connector 20. FIGS. 3 and 4 are exploded views of the embodiment of the connector 20 shown in FIG. 2A. FIG. 4A is an exploded sectional view of the connector 20 shown in FIG. 2A. With reference to FIGS. 2A-4A, some embodiments of the needleless connector 20 can include, inter alia, a body member 22, base member 24, a seal member 26, a support member 28, and a regulator 30.

In the illustrated embodiment, the body member 22 and the base member 24 can be assembled together to form a housing that substantially encloses the seal member 26 (also referred to herein as a first valve member), the support member 28, and the regulator 30 (also referred to herein as a second valve member). The body member 22 and the base member 24 can be coupled together with adhesive, plastic or sonic welds, snap, interference, or press-fit features, or by using any other suitable features or methods. In some embodiments, the body member 22 and the base member 24 can be coupled together using sonic welds having a substantially triangular shape, although other shapes may also be suitable.

The body member 22, base member 24, support member 28, and any other components or features of the connector 20 can be constructed from any of a number of suitable materials. For example, the body member 22, base member 24, support member 28, or any other suitable components or features of the connector 20 can be constructed from a relatively rigid material, such as polycarbonate, glassed-filled GE Valox 420, polypropylene, or other polymeric material. The body member 22, base member 24, support member 28, and any other suitable components or features of the connector 20 can also be constructed of a hydrophobic material, such as Bayer Makrolon, or any other similar or suitable material. One or more components of the connector 20 or any other connector disclosed herein can include a suitable antimicrobial agent in any appropriate form, such as a component coating, as a part of the component matrix, or in any other suitable manner. In some embodiments, the antimicrobial agent may leach from or off one or more of the components during use or over time. In some embodiments, the antimicrobial again can include a silver ion.

As mentioned, the support member 28 can be formed from the same type of rigid materials as can be used to form the body member 22 or the base member 24. In some embodiments, for example, the support member 28 can be formed from a semi-rigid or even more flexible material than used for the body member 22, the base member 24, or other components of the connector 20. In some embodiments, the support member 28 (and any other embodiment of a support member of any other connector disclosed herein) can be formed integrally with the base member 24 (or any other embodiment of a base member of any other connector disclosed herein), or can be formed separately and thereafter joined with the base member.

In some embodiments, the body member 22 may include one or more recesses or grooves 41 extending generally along the longitudinal direction of the connector 20 to facilitate the movement of the seal member 26 therein. Such groves 41 can provide an area for the seal member 26 to collapse into and can reduce the surface area in contact with the seal member 26 when it moves within the housing.

FIGS. 5 and 6 are perspective views of the embodiment of the seal member 26 in the connector 20 shown in FIG. 2A. With reference to FIGS. 1-6, the seal member 26 can be configured such that the proximal end portion 34 of the seal number 26 can be sealingly received by an opening 36 formed in the proximal end 162 of the body member 22. In some embodiments, as in the illustrated embodiment, the proximal end portion 34 of the seal member 26 can have lip portion 38 (which can be an annular protrusion) formed thereon that is configured to contact the inside surface of the opening 36 of the body member 22 to provide a seal therewith. The distal end 53 of the seal member 26 can include an opening 54. In some embodiments, a support member 28 can be received within the opening 54. In some embodiments, the distal end 53 further includes an outwardly extending flange 56 extending around or substantially around the seal member 26. The flange 56 can facilitate placement of the seal member 26 within the internal cavity of the body member 22 in some embodiments.

The term "proximal" is used herein to denote the end of the connector 20 at or near the end of the body member 22. The term "distal" is used to denote the opposite end of the connector, e.g., the end of the connector 20 at or near the end of the base member 24. In the illustrated embodiment, the proximal end is configured as a female end and the distal end is configured as a male end. Any of the end portions, fittings, or other aspects of the connector 20 can be configured to accommodate any standard medical connector or implement, and can be configured to conform with ANSI (American National Standards Institute, Washington, D.C.) or other applicable standards. The term "medical implement" is used herein to denote any medical device commonly used in the medical field that can be connected or joined with any embodiments of the connectors disclosed herein. Examples of medical implements that are contemplated include, without limitation, tubing, luers, conduits, syringes, intravenous devices (both peripheral and central lines), closable male luer connectors (both integrally formed with a syringe or independent connectors), pumps, piggyback lines, and other components which can be used in connection with a medical valve or connector.

The seal member 26, the proximal end portion 34 of the seal member 26, and the lip portion 38 can be integrally formed or can be separately formed and adhered or otherwise joined together using adhesive or any suitable material or method. In some embodiments, the seal member 26 or any other embodiment of a seal or seal member disclosed herein and any of the components or features thereof can be constructed from a number of different suitable materials, including silicone-based deformable materials, rubbers, or other suitable materials. Silicone-based deformable materials are among those that form fluid-tight closures with plastics and other rigid polymeric materials.

The seal member 26 or any other seal member disclosed herein can be formed from one, two, or more different materials. In some embodiments, different portions of the seal member 26 can be formed from different materials. For example, the seal member 26 can have a spring formed therein (not shown) to provide some or all of the restoring force desired to bias the seal member 26 to the closed position. The spring can be formed from a metal such as steel, plastic, or any other suitable rigid or pliable material, and can form the core of the seal member 26 such that the silicone rubber or other pliable sealing material encapsulates the spring. In some embodiments, the seal member 26 can be constructed just from a resilient or elastomeric material. Also by way of example, seal member 26 may include a resilient main body portion and a separately formed resilient proximal end portion. The separate pieces may configured to engage each other, such as for example, by coupling to a guide member with a first end configured for attachment to the proximal end portion and a second end configured for attachment to the main body portion. The guide member may be manufactured from a more rigid material than used in either or both of the main body portion and the proximal end portion.

The seal member 26 can have a tapered resilient body portion 50 having a generally accordion, generally wave-like, generally alternating, or generally undulating contour shape configured to facilitate resilient compression and expansion of the seal member 26 as axial forces are applied to and removed from, respectively, the proximal end portion 34 of the seal member 26. In some embodiments, the body portion 50 can include a series of generally circular or o-ring shaped structures integrally formed together or separately formed and bonded together, or one or more groove structures oriented generally transverse to the direction of compression and expansion. These structures and contours can vary in diameter or cross-sectional shape and/or size. In some embodiments, the structures or contours can extend alternately generally inwardly and outwardly in a direction substantially perpendicular to the longitudinal axis of the seal member 26 (as shown, for example, in FIGS. 3-6). The structure or contours can be formed in many configurations, such as in a helical configuration.

In some embodiments, the inside surface of the body portion 50 can approximately match the outside surface of the body portion 50 such that the inside surface of the body portion 50 also can have the structure or contour described elsewhere herein. In some embodiments, the inside surface of the body portion 50 can generally extend radially inward when the corresponding portion of the outer surface of the body portion 50 extends radially outward, and the inside surface of the body portion 50 can generally extend radially outward when the corresponding portion of the outer surface extends radially inward. Thus, the body portion 50 can comprise a series of bulges, wherein the thickness of the wall of the body portion 50 alternates between thick and thin regions, as shown, for example, in FIG. 4A. In some embodiments, the inside surface of the body portion 50 can generally extend radially inward when the corresponding portion of the outer surface of the body portion 50 extends radially inward, and the inside surface of the body portion 50 can generally extend radially outward when the corresponding portion of the outer surface extends radially outward. Thus, the body portion 50 can comprise a series of curved segments, wherein the wall of the body portion 50 has a more uniform thickness. In some embodiments, the inside surface of the body portion 50 can have a relatively smooth or flat surface contour.

The body portion 50 can have a generally consistent cross-sectional shape or size along the length thereof, or the cross-sectional shape or size of the body portion 50 can vary along at least a portion of the length thereof. In some embodiments, the shape of the inside of the body portion 50 can approximately match the outside surface of the elongated portion 62 of the support member 28. In some embodiments, the body portion 50 comprises a lower section 50a having a generally conical shape, and an upper section 50b having a generally cylindrical shape. Many variations are possible.

The seal member 26 can be configured so that the body portion 50 is biased to an initial or expanded position, as illustrated in FIG. 5. When an axial force is exerted on the seal member 26, the proximal end portion 34 and/or the body portion 50 can be caused to compress to a second position and, hence, axially retract so as to shorten the overall length of the seal member 26. When the axial force is removed from the seal member 26, the proximal end portion 34 and/or the body portion 50 can extend again as a result of the bias so as to return the seal member 26 to its initial or relaxed state. Although the seal member 26 can return to its relaxed state in the first or closed position, the seal member 26 can remain under some level of compression in this state, such as, for example, where the lip 38 of the proximal end portion 34 engages an inner surface or surfaces of the body member 22 under some degree of axial tension.

The seal member 26 can be configured such that the proximal end portion 34 of the seal member 26 can be received by an opening 36 formed in the body member 22. In some embodiments, as in the illustrated embodiment, the proximal end portion 34 of the seal member 26 can have a lip portion 38 (which can be an annular protrusion) formed thereon that is configured to contact the inside surface of the opening 36 of the body member 22 to provide a seal therewith which generally resists the ingress of particulates or fluids into the connector. As shown in FIG. 3, the proximal end 162 of the body member 22 may include one or more grooves or recesses 39 configured to permit air or fluid to flow around the proximal end portion 34 of the seal member 26.

Additionally, as shown in FIG. 5, a slit or opening 52 can be formed in the proximal end portion 34 of the seal member 26. The seal member 26 can be configured so that the slit 52 is biased to a closed position, so as to substantially prevent or inhibit liquid from flowing through the slit 52 formed in the seal member 26. Additionally, in some embodiments, as will be described in greater detail below, the slit 52 can be opened by retracting the seal member 26 in the distal direction over the support member 28, causing at least a portion of the proximal end portion of the support member 28 to penetrate and pass through the slit 52. In some embodiments, the slit 52 can be configured to open without the support member 28 penetrating therethrough.

Figure 9:
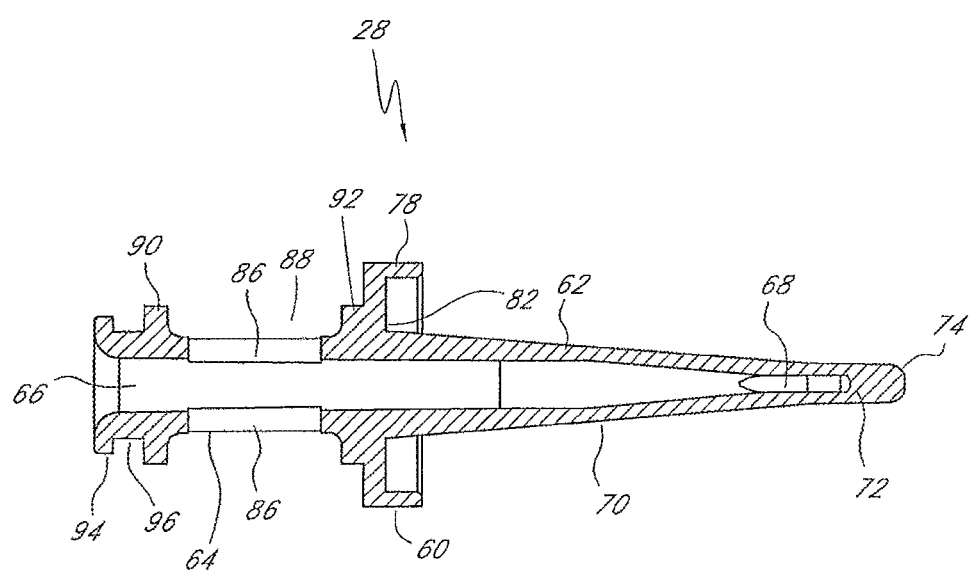
FIG. 9 is a section view of the embodiment of a support member shown in FIG. 7, taken through the axial centerline of the support member.

FIGS. 7 and 8 are perspective views of the embodiment of the support member 28 of the embodiment of the connector 20 shown in FIG. 2A. FIG. 9 is a section view of the embodiment of the support member 28 shown in FIG. 7, taken through the axial centerline of the support member 28. With reference to FIGS. 7-9, in some but not all embodiments, support member 28 can comprise a base portion 60, an elongated portion 62 projecting from the base portion 60 in the proximal direction, and a distal portion 64 projecting from the base portion 60 in the distal direction. In some embodiments, one or more of these components of the illustrated support member 28 can be omitted or replaced with a different component. For example, a support member need not include an elongated portion 62. In some embodiments, the support member may be substantially shorter, such that it does not extend into, through and/or near the proximal end of the seal. In some embodiments of the connector 20, there is no support member at all. A seal member can be configured to open without a penetrating support member or without a support member at all, such as when a seal member is made in a naturally open position that is forced to close by a smaller-diameter housing, or when a seal member is attached to the proximal region of the housing, etc. A regulator also can be secured or positioned within the housing and can function without a support member. For example, in some embodiments, the regulator 30 can be attached to the seal member and/or can be suspended from another structure, or the regulator 30 can be unattached and free-floating, without requiring the distal portion 64 or internal support illustrated in FIG. 13.

In some embodiments, the one or more components of the illustrated support member 28 can be separately formed and attached to one another via an adhesive, sonic welding, snap fit, or other manner. For example, the elongated portion 62 and the base portion 60 can be separately formed and attached by, for example, sonic welding. In some embodiments, the entire support member 28 can be integrally formed as a one-piece unit. In some embodiments, fluid can flow through one or more holes within the cavity of the connector 20, such as holes positioned at or near the distal end of the cavity, either within or outside of a seal member or other fluid-flow impediment. Though shown as a unitary member, in some embodiments the components of the support member 28 can be separately formed. For example, the elongated portion 62 may be separately formed from the base member and the distal portion 64, and the elongated portion 62 and/or any other portion can be configured to move within the connector during use.

In some embodiments, the distal portion 64 can comprise a generally cylindrical outer surface 64a. The longitudinal length of the distal portion 64 can be substantially shorter than the longitudinal length of the elongated portion 62, as illustrated. The transverse cross-sectional distance generally across the distal portion 64 can be less than the transverse cross-sectional distance generally across the regulator 30 (see, e.g., FIG. 12). Additionally, in some embodiments, an opening 66 can be formed axially through at least a portion of the support member 28. In the illustrated embodiment, the opening 66 can be in fluid communication with a fluid passageway 69 extending generally axially through the support member 28. The fluid passageway can extend through the distal portion 64, base portion 60, and a substantial portion of the elongated portion 62 so that the one or more lateral or radial openings 68 formed in the proximal end of the elongated portion 62 can be in communication with the opening 66.

As illustrated in FIGS. 7-9, the elongated portion 62 can have a tapered outer surface 70 and a proximal tip portion 72. The proximal tip portion 72 can have a generally tapered (or generally conical) outer surface, or can be generally cylindrical. The elongated portion 62 can be configured so that the proximal tip portion comprises a cross-sectional area that is significantly less than the cross-sectional area of the base portion 60 of the support member 28. In some embodiments, the proximal tip portion 72 can be configured so that the proximal end portion 34 of the seal member 26 can be retracted (e.g., from the compressed to the expanded or initial positions) relative to the proximal tip portion 72 of the support member 28 without significant drag or resistance from the support member 28. In some embodiments, the proximal tip portion 72 has a sharp or rounded tip 74 configured to penetrate through the slit 52 formed in the seal member 26. In some embodiments, the tip 74 is integrally formed with the tip portion 72 and the rest of the elongated portion 62. In some embodiments, the proximal end of the elongated portion 62 includes a hole positioned at its proximal tip and the passageway 69 may extend from the opening 66 to the opening at the tip.

The base portion 60 can have an outer annular wall 78 cooperating with the distal end of the support member 28 to form an annular channel 82. The channel 82 can be configured to receive a portion of the distal end portion 56 of the seal member 26. In some embodiments, the base portion 60 can be configured to secure the distal end portion 56 relative to the base portion 60 of the support member 28 so as to prevent the distal end portion 56 from translating in a distal axial direction relative to the base portion 60. Additionally, the channel 82 can be configured to secure the distal end portion 56 relative to the base portion 60 of the support member 28 so as to prevent the distal end portion 56 from translating in a radial direction relative to the base portion 60. The seal member 26 can be assembled with the support member 28 with or without adhering or otherwise fixing the distal end portion 56 of the seal member 26 to the base portion 60 support member 28. Indeed, in some embodiments, the distal end of the seal member 26 can "float" in the internal cavity of the body member 22 and can translated axially as the seal member 26 moves from a closed position to an open position.

The distal portion 64 of the support member 28 can have one or more openings 86 formed laterally or radially through the distal portion 64. In the illustrated embodiment, two openings 86 are formed in the distal portion 64 and are configured as generally rectangular slots with their long axis extending generally along the axis of the connector. However, in some embodiments, only one opening, or three, four, or more openings can be formed in the distal portion 64 and can be formed as slots or other shaped holes. In some embodiments, the one or more openings 86 can extend along at least a majority of the longitudinal length of the distal portion 64, as illustrated. The one or more openings 86 can be formed so as to be in communication with the axial opening 66 formed in the support member 28.

A generally annular cavity or space 88 can be formed in the distal portion 64 of the support member 28. The annular cavity 88 can be formed between two annular protrusions 90, 92 formed on the distal portion 64. As will be described in greater detail below, the cavity 88 can be filled with fluid flowing through the openings 66, 86 formed in the support member 28. An annular protrusion 94 can also be formed at a distal end portion of the support member 28, so that a channel 96 can be formed between the annular protrusions 90, 94.

FIGS. 10 and 11 are perspective views of the embodiment of the regulator 30 of the connector shown in FIG. 2A. FIG. 12 is a section view of an embodiment of a regulator 30 shown in FIG. 10, taken through the axial centerline of the regulator 30. As illustrated in FIGS. 10-12, the regulator 30 can have a body portion 100 and a proximal end portion 102. In some embodiments, as in the illustrated embodiment, the body portion 100 can be generally cylindrically shaped, and the proximal end portion 102 can have an annular raised portion or lip 103 and an opening 104 therethrough. In some embodiments, as illustrated, the connector includes a plurality of valving structures, such as the seal member 26 and regulator 30, that can control fluid flow through and/or within the connector 20.

The regulator 30 or any other embodiment of a regulator, valve, or valve member disclosed herein and any of the components or features thereof can be constructed from a number of different materials, including silicone-based deformable materials, rubbers, or other suitable materials.

Silicone-based deformable materials are among those that form fluid-tight closures with plastics and other rigid polymeric or metallic materials. In some embodiments, the regulator 30 can be flexible, elastomeric, and/or resilient. In some embodiments, the regulator 30 can be made from the same material as the seal member 26. As shown in the illustrated example, a variable-volume or dynamic regulator portion of the regulator 30 can have a very thin, extremely flexible and/or compliant side wall or side walls, which in some embodiments is substantially thinner than the side wall of at least a portion of, or virtually all of, the side wall of the seal member 26 to enable the regulator 30 to be highly responsive to fluid pressure changes.

Additionally, the regulator 30 can include a valve member at the distal end portion 108 having one or more apertures or slits 110 formed therein, two slits 110 being shown in the illustrated embodiment. In some embodiments, as in the illustrated embodiment, the end portion 108 can comprise a valve member with a generally arcuate, generally domed, or generally spherical shape. The distal end portion 108 can be configured such that the distal end portion 108 is biased to a closed position (e.g., such that the slits 110 are biased to a closed configuration). Therefore, in some embodiments, the distal end portion 108 can be configured so as to be generally closed when the magnitude of the pressure differential between the fluid inside of the regulator 30 and the fluid acting on the outside surface of the regulator 30 is below a predetermined level (e.g., where the difference between the pressure exerted on the inside surface 108a of the end portion 108 and the pressure exerted on the outside surface 108b of the end portion 108 is below a predetermined level).

As illustrated, the shape of the valve member on the distal end portion 108 can assist in closing the valve member more tightly as fluid pressure on the distal side of the valve member increases up to a certain level. Beyond this fluid-pressure resistance level, the valve member can buckle or otherwise move inwardly (e.g., in the proximal direction) to permit retrograde flow. The valve member can be configured (e.g., by selection of appropriate shape, positioning, and use of materials) so that this fluid resistance level is above the pressure differentials normally produced by syringe rebound, proximal-end luer withdrawal, and/or externally induced negative flow (e.g., patient coughing, sneezing, movement, and blood pressure increases, or IV bag fluid decreases), but below the pressure differentials normally produced by intentional withdrawal of fluid from the proximal end of the connector 20. In some embodiments, as illustrated, the valve member can be configured to essentially retain the same initial shape as pressure differentials increase or build-up toward its cracking pressure to avoid or diminish communication of negative flow forces through the valve member at pressure differentials below the cracking pressure.

In some embodiments, retrograde or negative flow can be caused by external effects (which are sometimes upstream from the connector 20), such as a diminished level of fluid within an IV bag, and/or jostling or other movement of a fluid line by a patient or caregiver. When the fluid in an IV bag diminishes to a low level or runs dry (or the IV bag is positioned too low in comparison with the patient), the head pressure previously supplied by the IV bag also diminishes. In some circumstances, this decrease in head, pressure can render the fluid line vulnerable to "sloshing" or alternating movement of the column of fluid upstream and downstream from a connector as the patient moves around, creating periodic negative flow. In some embodiments, an internal or distal valve member such as the valve member at the distal end 108 of the regulator can be configured to close when the upstream head pressure from a dwindling level of fluid in an IV bag falls below a threshold level at which sloshing or alternating fluid movement may otherwise begin.

In some embodiments, the valve member can be a bi-stable valve that is configured to open in a first direction (e.g., in the proximal-to-distal direction) under the influence of a fluid force above a certain threshold that is applied in the first direction and to remain open to fluid flow in that direction until a fluid force above a desired threshold is applied in a second direction (e.g., in the distal-to-proximal direction), which causes the valve to open and remain open to flow in the second direction. The bistable valve can be switched back again from flow in the second direction to the first direction upon application of a force above the desired threshold in the first direction.

In some embodiments, one or more of the slits 110 can have a width (represented by "WS" in FIG. 12) that can be approximately equal in length to the width of the opening 104 (represented by "WO" in FIG. 12). In some embodiments, as in the illustrated embodiment, the width WS of one or more of the slits 110 can be smaller than the width WO of the opening 104. In some embodiments, as illustrated, the width WS, or the width of the transverse cross-sectional distance across the variable volume chamber, can be substantially smaller than the longitudinal length of the variable volume chamber or substantially smaller than the longitudinal length of the overall regulator 30. In some embodiments, as illustrated, the thickness of the wall of the regulator 30 on at least a portion of the region of the valve member at the distal end portion 108 can be substantially larger than the thickness of the wall of the regulator 30 in the variable volume chamber or body portion 100 to provide increased flexibility and compliance in the body portion 100 and increased resistance to backflow by the valve member. In some embodiments, as illustrated, the longitudinal length of the valve member at the distal end portion 108 can be substantially shorter than the longitudinal length of the variable volume chamber in the body portion 100 of the regulator 30 (both in embodiments in which these portions are connected or separated).

In some embodiments, the regulator 30 can be configured such that the distal end portion 108 of the regulator 30 will open so as to permit fluid to flow through the regulator 30 in a first direction (e.g., in the direction from the proximal end 102 to the closure end or distal end 108, represented by arrow A1 in FIG. 10) when the pressure differential between the inside of the regulator 30 and the outside surface of the regulator 30 reaches a first magnitude. Similarly, the regulator 30 can be configured such that the distal end portion 108 of the regulator 30 will open so as to permit fluid to flow through the regulator 30 in a second direction (e.g., in the direction from the closure end or distal end 108 to the proximal end 102, represented by arrow A2 in FIG. 10) when the pressure differential between the inside of the regulator 30 and the outside surface of the regulator 30 reaches a second magnitude.

The valve member in the internal or distal closure system can have many different shapes and configurations. For example, in some embodiments, the valve member and related attachment and positioning structure can be the same as or similar to the valves 2200, 2250 illustrated and described in at least FIGS. 50-56 and paragraphs 309-325 of U.S. Patent Application Publication No. 2010/0049157 A1, which publication is incorporated herein in its entirety (including the cited portions) for all that it discloses.

In some embodiments, the first magnitude of the pressure differential can be approximately equal to the second magnitude of the pressure differential. In some embodiments, as in the illustrated embodiment, the first magnitude of the pressure differential can be less than the second magnitude of the pressure differential so that the regulator 30 is more resistant to opening up to fluid flow in the second direction A2 than in the first direction A1. In other words, the regulator 30 can be configured such that the end portion 108 is biased to permit flow through the end portion 108 in a first direction A1 at a lower pressure differential magnitude than in a second direction A2. In this arrangement, the regulator 30 can inhibit backflow (e.g., flow in the direction A2) from downstream of the regulator 30 until the magnitude of the pressure differential overcomes the threshold value required to open the slits 110.

For example, without limitation, the embodiment of the regulator 30 illustrated in FIGS. 10-12 can be configured so that the spherical shape of the distal end portion 108 of the regulator 30 provides less rigidity to the end portion 108 in the first direction (represented by arrow A1) than in the second direction (represented by arrow A2). In this configuration, a greater force can be required to deflect the closure end or distal end portion 108 of the regulator in the A2 direction so as to cause the slits 110 to open in the A2 direction as compared to the force required to deflect the distal end portion 108 of the regulator in the A1 direction so as to cause the slits 110 to open in the A1 direction.

In some embodiments, the pressure of the fluid (liquid or gas) acting on the inside surface 108a of the regulator 30 can be approximately 0.5 atmosphere greater than the pressure of the fluid (liquid or gas) acting on the outside surface 108b of the regulator 30 for the distal end portion 108 of the regulator 30 to open in the A1 direction. In some embodiments, the pressure of the fluid acting on the inside surface 108a of the regulator 30 can be between approximately 0.1 atmosphere and approximately 1.0 atmosphere, or between approximately 0.2 atmosphere and approximately 0.8 atmosphere, or between approximately 0.4 atmosphere and approximately 0.6 atmosphere, greater than the pressure of the fluid acting on the outside surface 108b of the regulator 30 for the closure end or distal end portion 108 of the regulator 30 to open in the A1 direction so as to permit fluid to flow in the A1 direction.

In some embodiments, the pressure of the fluid acting on the outside surface 108b of the regulator 30 can be approximately 1 atmosphere greater than the pressure of the fluid acting on the inside surface 108a of the regulator 30 for the distal end portion 108 of the regulator 30 to open in the A2 direction. In some embodiments, the pressure of the fluid acting on the outside surface 108b of the regulator 30 can be between approximately 0.5 atmosphere and approximately 1.5 atmospheres, or between approximately 0.7 atmosphere and approximately 1.3 atmospheres, or between approximately 0.9 atmosphere and approximately 1.1 atmospheres greater than the pressure of the fluid acting on the inside surface 108a of the regulator 30 for the distal end portion 108 of the regulator 30 to open in the A2 direction so as to permit fluid to flow in the A2 direction.

In some embodiments, the magnitude of the pressure differential required to open the distal end portion 108 of the regulator 30 in the A2 direction is approximately at least twice as large as the pressure required to open the distal end portion 108 of the regulator 30 in the A1 direction. In some embodiments, the magnitude of the pressure differential required to open the distal end portion 108 of the regulator 30 in the A2 direction is substantially larger than in the A1 direction, such as at least approximately 40% greater than the pressure required to open the distal end portion 108 of the regulator 30 in the A1 direction. In some embodiments, including some of those illustrated herein, the magnitude of the pressure differential required to open the distal end portion 108 of the regulator 30 in the A2 direction is less than approximately twice or thrice the pressure in the A1 direction required to open the distal end portion. In some embodiments, the regulator 30 will permit fluid flow in the A1 direction when a standard syringe 15 is attached to the proximal end of the connector and the stein of the syringe is advanced with the amount of force normally applied for fluid transfer, but the regulator 30 will permit fluid flow in the A2 direction when substantially greater retraction force is applied to the syringe stein.

In some embodiments, at least a portion of the distal end portion 108 of the regulator 30 can be substantially flat, rather than being generally spherically shaped. In some embodiments, the magnitude of the pressure differential required to open the regulator 30 in the A1 direction is substantially the same as, or similar to, the magnitude of the pressure differential required to open the regulator 30 in the A2 direction. In some embodiments, a flow-impeding portion, such as the distal end portion 108, of the regulator 30 can include a portion with an increased thickness, or an indentation, on either the proximal or distal surface of the distal end portion 108, which can act to raise or lower the magnitude of the pressure differential required to open the regulator 30 in either the A1 or A2 direction, depending on the placement thereof. Thus, in some embodiments, the regulator 30 can provide greater resistance to fluid flow in one direction than another, such as greater resistance in the A2 direction than the A1 direction, even if the distal end portion is substantially flat, rather than spherically shaped.

In some embodiments, the distal end portion 108 of the regulator 30 can flex inwardly, in the proximal direction, before the slits 110 crack open to allow fluid flow in the A2 (proximal) direction. In some circumstances, this pre-opening movement can result in a slight backflow of fluid into the distal end of the connector 20, and it can be advantageous to reduce or eliminate this pre-opening movement of the regulator 30. In some embodiments, the spherical shape of the distal end portion 108 of the regulator can be configured to diminish or minimize the amount that the regulator 30 moves prior to opening to allow fluid flow in the A2 direction. In some embodiments, the regulator 30 can be configured so that only a small volume, such as less than or equal to about than about 0.10 ml of fluid, is displaced before the regulator 30 opens for fluid flow.

Additionally, with reference to FIG. 12, the regulator 30 can further comprise an inner annular protrusion 112 formed on an inside surface 100a of the body portion 100. In some embodiments, the inner annular protrusion 112 can be configured to be received within the channel 96 formed between the annular protrusions 90, 94 of the support member 28. In this arrangement, the inner annular protrusion 112 can be used to secure or support the regulator 30 in the desired axial position relative to the support member 28, so as to prevent or inhibit the regulator 30 from translating axially relative to the support member 28. In some embodiments, the regulator 30 is positioned within a cavity in a distal region of the connector 20 and generally or completely surrounds an internal component such as the distal end 64 of the support member 28.

With reference to FIG. 12, in some embodiments, the annular protrusion 112 can have a width therebetween (represented by "WP" in FIG. 12) that can be less than, such as about half of, the width WO of the opening 104. As illustrated, the interior of the regulator 30 can include a first cross-sectional area (e.g., in a proximal region), a second cross-sectional area (e.g., in a mid-region), and a third cross-sectional area (e.g., in a distal region), wherein the second cross-sectional area is less than each of the first and third cross-sectional areas. Also, an interior volume of a first or proximal region can be substantially larger than an internal volume of a second or distal region. In some embodiments, as in the illustrated embodiment, the width WP can be defined by the protrusion 112, which can be at least about one-quarter or one-half of the width WO of the opening 104. Additional features regarding the regulator 30 will be described below with reference to FIGS. 13-16.

Figure 13:
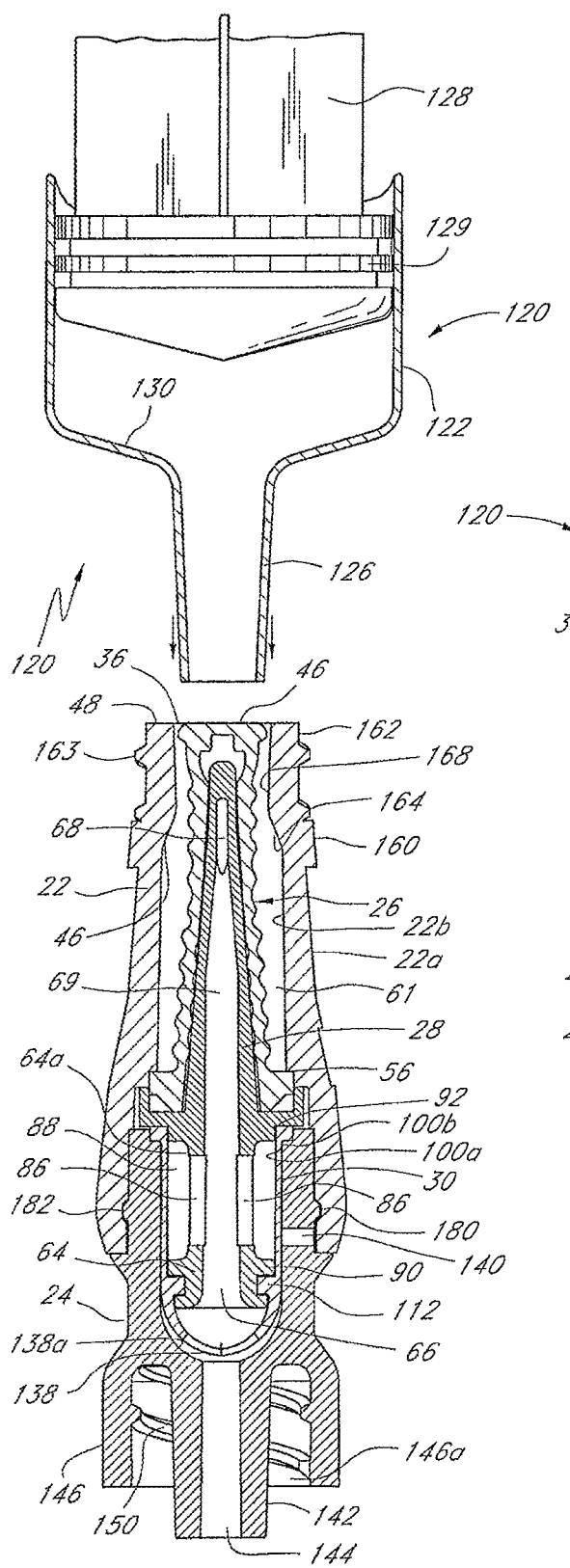
FIG. 13 is a section view of the embodiment of the connector shown in FIG. 2A, showing the seal member in a first or closed position before the seal member has been contacted and opened by a medical implement, such as the illustrated example of a syringe.
Figure 14:
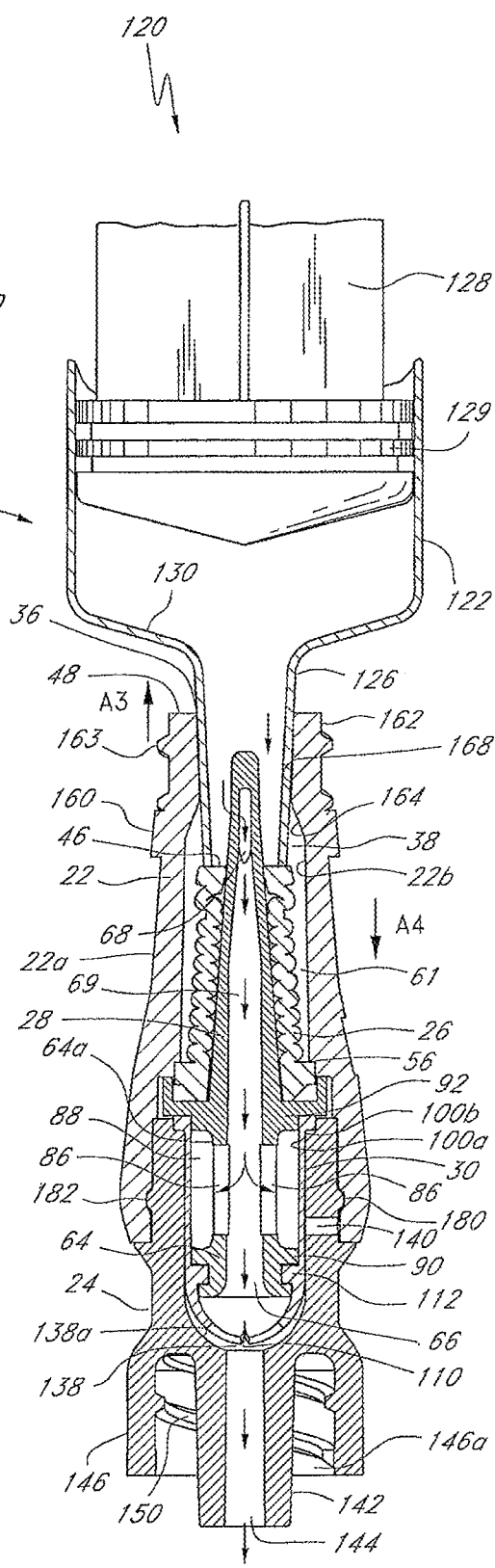
FIG. 14 is a section view of the embodiment of the connector shown in FIG. 2A, showing the seal member in a second or open position after the seal member has been contacted and opened by the syringe.

FIG. 13 is a section view of the embodiment of the connector 20 shown in FIG. 2A, showing the seal member 26 in a first or closed position (e.g., before the seal member 26 has been contacted and opened by insertion of a luer, such as a luer on a syringe 120). FIG. 14 is a section view of the embodiment of the connector 20 shown in FIG. 2A, showing the seal member 26 in a second or open position (e.g., after the seal member 26 has been contacted and opened by insertion of a luer, such as a luer on the syringe 120). In progressing between the closed and opened positions, the seal member 26 can be configured to move. In some embodiments, as illustrated, the seal member 26 can be compressed in the open position and expanded or allowed to return to its initial position in the closed position. In some embodiments, the seal member 26 has a smaller longitudinal length in the open position than in the closed position. Many other types of seal members can be used to open and close the fluid passage within the connector in many different ways. The seal member 26 can be positioned within the connector 20 so that a proximal end surface 46 of the seal member 26 is generally flush or generally even with a proximal end opening of the connector 20 to permit effective antiseptic wiping across the proximal end surface 46.

The syringe 120 illustrated in FIGS. 13-16 (and elsewhere in this disclosure) is an example of one type of medical implement that can be used with the connector 20. However, the connector 20 can be configured for use with a wide range of medical implements and is not limited to use with the example of the syringe 120 illustrated. The syringe 120 can be any suitable or common medical syringe used in the medical field. As illustrated, the syringe 120 can have a cylindrical body portion 122 defining an opening 124 therein, a hollow cannula 126 projecting from the body portion 122, and a plunger 128 configured to be received and axially translate within the opening 124 formed in the body portion 122. The plunger 128 can have an elastomeric or rubber seal 129 supported on the end of the plunger 128. As is commonly done with such medical syringes, fluid can be expelled from the syringe 120 by forcing the plunger 128 toward the bottom surface 130 of the body portion 122, thus causing the fluid to exit through the hollow cannula 126. In this manner, the fluid is typically expelled from the syringe 120 until the rubber seal 129 of the plunger 128 reaches the bottom surface 130 of the syringe 120.

Figure 15:
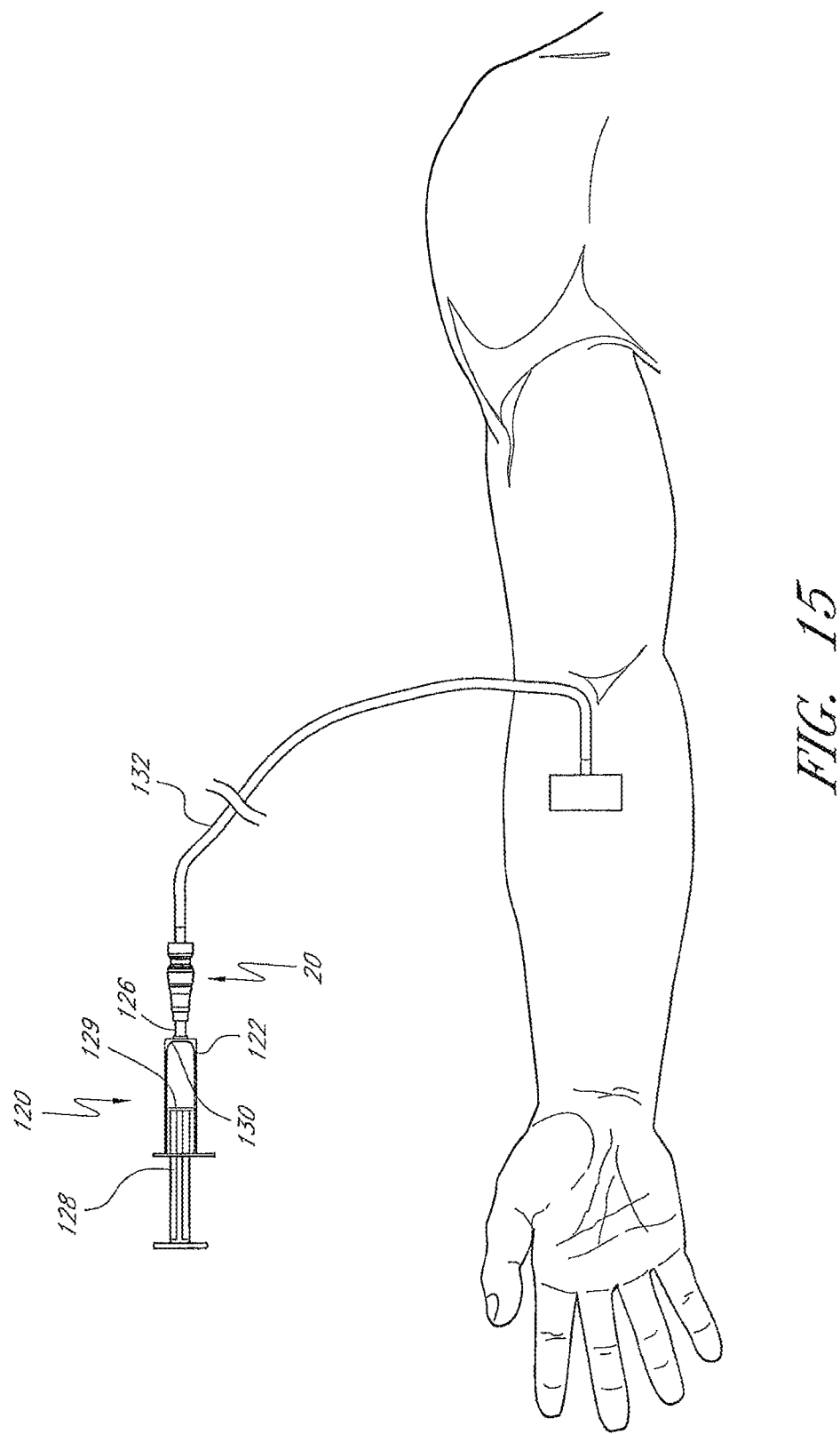
FIG. 15 is a schematic illustration showing the embodiment of the connector of FIG. 2A being used to inject fluids into the blood stream of a patient's arm.

FIG. 15 is a schematic illustration showing the embodiment of the connector 20 illustrated in FIG. 2A being used to inject a fluid into the blood stream of a patient's arm. The connector 20 (or any other embodiment of a connector disclosed herein) can be configured for a wide range of medical applications, and is not meant to be limited to the use illustrated in FIG. 15. As illustrated in FIG. 15, the connector 20 can be joined with the conduit 132 with the other end of the conduit being in communication with a patient's bloodstream. In this configuration, the syringe 120 can be inserted into the connector 20 so as to open the seal member 26 of the connector 20. When the seal member 26 is in an open position, as illustrated in FIG. 14, the fluid from the syringe 120 can be transferred through the connector 20 and conduit 132 and into the patient's vasculature.

In order to inject all or substantially all of the fluid held within the syringe 120 into the patient's vasculature, a caregiver or automated machine will typically depress the plunger 128 of the syringe 120 or other mechanism all the way into the body member 122 until the plunger 128 and the rubber seal 129 bottoms out against the bottom surface 130 of the syringe 120, which can cause the typically resilient rubber seal 129 to be compressed between the generally rigid plunger 128 and the bottom surface 130 of the syringe. When this occurs, the seal 129 on the end of the plunger 128, which is typically made from a rubber or other resilient material, can rebound when the force exerted by a caregiver on the plunger 128 is removed.

In a conventional system (e.g., in a system not having a connector 20 configured to offset the effects of the syringe rebound), when the plunger 128 and seal 129 rebound away from the bottom surface 130 of the syringe 120, a vacuum or source of suction can be created within the syringe 120. In some instances, the rebound effect of the plunger 128 within the syringe 120 can be significant enough to allow fluids to be drawn from within the conduit 132 and even within the patient's own vasculature back toward the syringe 120. For example, the syringe rebound can create a vacuum that can decrease the pressure within the syringe and the connector by up to approximately 1 atmosphere. Additionally, in some cases, removal of the syringe or other medical implement from the connector can cause a vacuum or source of suction within the connector. As used herein, the term "backflow" is used interchangeably with "negative flow" in some contexts to describe the inadvertent or detrimental flow of blood and/or other fluids from the patient's vasculature into the conduit 132 and/or other components in fluid communication with the conduit 132.

The connector 20 can include a backflow resistance module that can be configured to prevent, substantially prevent, diminish, or inhibit backflow, retrograde flow, negative flow, ingress flow, or other pressure differential that could otherwise result from many different types of sources, such as the rebound effect of the syringe 120, the removal of at least a portion of a medical implement (such as the luer of the syringe 120) from the connector, the running dry of an IV bag, etc. In some embodiments, the backflow phenomenon can be prevented, substantially prevented, diminished, or inhibited by configuring the backflow resistance module of the connector 20 to have a regulator, such as a variable volume internal chamber, a volume adjuster, a dynamic volume adjuster, or a dynamic regulator, that is configured to collapse, move, or otherwise reduce in volume to offset the vacuum effect generated by the syringe rebound or various other effects, and/or a valve member that is configured to prevent fluid flow in at least one direction until a particular pressure differential threshold is surpassed. In some embodiments, as illustrated, the regulator can also be configured to expand, move, or otherwise increase in volume to offset a pressure differential. In some embodiments, for example, the regulator 30 can be configured to perform a diaphragm-like function. In particular, the regulator 30 can comprise resilient, flexible, or elastomeric walls with interior surfaces that are in fluid communication with the fluid pathway inside the connector 20, such walls being configured to buckle, flex inwardly, or otherwise move in response to the suction or other fluid forces so as to reduce or otherwise change the volume of space within the regulator 30 and, consequently, to permit all or a portion of the gas, liquid, or other fluid contained within the regulator 30 to flow into or out of the syringe 120 or other medical implement to offset a vacuum effect. As illustrated, the regulator 30 can form a portion of the fluid pathway through the valve (e.g., fluid can enter into a first end of the regulator 30 and exit from a second end of the regulator 30). The moving wall or walls of the regulator 30 can have many different configurations. For example, the wall or walls can be resilient (as illustrated), or rigid, and/or the wall or walls can flex or bend (as illustrated), or slide, rotate, etc. In some embodiments, the desired dynamic change in volume can be accomplished by the interaction of generally rigid and/or generally tubular structures in the flow path with different interior volumes. For example, such structures can be configured to slide in a generally co-axially, telescoping manner with respect to each other to accomplish a change in fluid volume.

In some embodiments, the backflow resistance module can also include a valve configured to resist fluid flow in the proximal direction. The valve can be a check valve or one-way valve that diminishes or substantially entirely prevents fluid flow in the proximal direction, such that the connector 20 can be a one-way connector under most fluid pressures commonly present in medical valves. In some embodiments, the valve can be configured to allow fluid flow in the proximal direction if a sufficient force is applied, such that the connector 20 can be a two-way connector. In some embodiments, the valve can be positioned downstream from, or distal to, the variable volume chamber. In some embodiments, for example, the distal end portion 108 of the regulator 30 and the one or more slits 110 formed therein can be configured to resist fluid flow in the proximal direction, as discussed in greater detail elsewhere herein.

In some embodiments, the valve can be configured so that the force required to open the valve for fluid flow in the proximal direction can be greater than the force required to reduce the volume of the variable volume chamber from a first volume to a second volume. For example, if a pressure differential is unintentionally created (e.g., by the syringe rebound effect), the variable volume chamber can shrink to offset the pressure differential while the valve can remain closed. Thus, in some embodiments, the pressure differential caused by the syringe rebound or other effect is not transferred or communicated to the fluid on the distal side of the valve or on the distal end of the connector 20, and the backflow of fluid is prevented.

In some embodiments, the force required to further reduce the volume of the variable volume chamber beyond the second volume is greater than the force required to open the valve for fluid flow in the proximal direction. Therefore, if a pressure differential is intentionally created (e.g., by a medical practitioner retracting the syringe plunger 128 to draw fluid into the syringe 120), the variable volume chamber can shrink to the second volume after which the valve can open to allow fluid to flow in the proximal direction. Thus, in some embodiments, if a sufficient force is applied, the backflow resistance module can be overridden.

In the illustrated embodiment, the backflow resistance module can include various components of the connector 20 such as, but not limited to, the regulator 30, the distal portion 64 of the support member 28, the inner surface of the base member 24, and the one or more openings 140 formed in the base member. Many other variations are possible. For example, in some embodiments, the regulator 30 by itself, or an independent flow-impeding portion 108 by itself, can be the backflow resistance module.

With reference to FIG. 13, the regulator 30 can be positioned over the distal portion 64 of the support member 28 so as to seal the annular cavity 88 formed between the two annular protrusions 90, 92 on the distal portion 64 of the support member 28. In this configuration, the annular cavity 88 can be sealingly bound by the annular protrusions 90, 92, the outside surface 64a of the distal end portion 64 of the support member 28, and the inside surface 100a of the volume adjuster or body portion 100 of the regulator 30. As will be described in greater detail below, the volume adjuster or body portion 100 of the regulator 30 can be configured to buckle, flex, or deform inwardly, or otherwise move, in response to the rebound of the plunger 128 within the syringe 120 when a portion of the gas or fluid within the cavity 88 can be drawn into the syringe 120, or in response to a variety of other effects that may otherwise induce an undesired level of negative pressure. A regulator or volume adjuster can be positioned and/or oriented in many other ways within a connector. For example, in some embodiments, the regulator or volume adjuster can be positioned inside of, or structured as an integrated or unitary part of, the elongated portion 62 of the support member 28. In some embodiments, at least a portion of the sides of the elongated portion 62 can be flexible or otherwise moveable to produce changes in volume within the connector. In this way, the overall length of the connector can be diminished as compared to some of the embodiments illustrated herein.

One or more openings 86 can be formed through the distal end portion 64 of the support member 28 to allow fluid to flow between the cavity 88 and the opening 66 in the support member 28. In the illustrated embodiment, two openings 86 are formed through the distal end portion 64 of the support member 28. Any number of any suitable or desired numbers of openings 86 can be formed in a portion 64 of the support member 28 to allow fluid to flow between the cavity 88 and the opening 66 formed in the support member 28. In the illustrated embodiment, the openings 86 are generally shaped as slots, but in other embodiments, the openings 86 can have any suitable cross-sectional shape and/or size. For example, in some embodiments, the openings can have a generally circular cross-section.

Additionally, with reference to FIGS. 3, 4, and 13, the connector 20 can be configured such that the regulator 30 is positioned in a second cavity in the connector 20 such as the cavity 138 formed in the base member 24. In some embodiments, the regulator 30 in an initial position can be tightly received within the cavity 138 formed in the base member 24 so that there is very little air space, if any, between the outer surface 100b of the body portion 100 of the regulator 30 and the inside surface 138a of the cavity 138.

As illustrated in FIGS. 3 and 13, one or more openings 140 can be formed through a portion of the base member 24 to provide an airway between the ambient atmosphere and the outside surface 100b of the body portion 100 of the regulator 30. The connector 20 can be configured such that the body member 22 does not significantly restrict the flow of air through the one or more openings 140. Although one opening 140 is illustrated, any suitable number of openings 140 can be formed in the base member 24. As will be described in greater detail below, the opening or openings 140 can be configured to permit air to substantially freely flow into the space between the outside surface 100b of the regulator 30 and the inside surface 138a of the cavity 138. In some embodiments, air can travel between at least a portion of the interface between the body member 122 and the base member 124 (e.g., the portion of the interface below the annular protrusion 182 and the annular channel 180) to reach the hole 140. In some embodiments, the body member 122 can include a hole (not shown) that allows air to reach the hole 140 in the base member 124. In some embodiments, the hole 140 in the base member can be positioned so that is it not covered by the body member 122, but opens directly to the outside of the connector 20. In some embodiments, air can leach through at least a portion of the body member 122 to reach the hole 140. In some embodiments, the base member 124 can be formed without a hole 140, but can be configured to allow air to leach through at least a portion of the base member 124 to reach the space between the outside surface 100b of the regulator 30 and the inside surface 138a of the cavity 138.

The regulator 30 and/or the base member 24 can be configured to seal the connector 20 such that air flowing through the opening 140 is not able to flow around the outside surface 100b of the regulator 30 and into the cavity 138 formed in the base member 24. For example, projection 90 can be configured to cooperate with the resilient wall of regulator 30 and the inner wall 138a of cavity 138 to form an air tight seal to keep air that moves into the connector 20 through hole 140 effectively contained between inner wall surface 138a and outer surface 100b between projections 90 and 92. As will be described in greater detail below, the openings 140 can be configured to permit air to flow against the outside surface 100b of the body portion 100 of the regulator 30 so that the regulator 30 can substantially freely deform inwardly in response to the syringe rebound effect or other retrograde-flow inducing effect, such as those described herein.

With reference to FIGS. 3, 4, and 13, additional features of the body member 22 and the base member 24 will now be described. In the assembled configuration, the seal member 26 can be supported by the support member 28 so that the elongated portion 62 is received within the opening 54 formed within the seal member 26. Additionally, the regulator 30 can be supported by the support member 28 so that the distal end portion 64 of the support member 28 is received within the opening 104 formed in the regulator 30. The seal member 26, support member 28, and the regulator 30 can thus be assembled together and can be supported within the body member 22 and the base member 24. The body member 22 and the base member 24 can be joined together to provide a rigid housing that substantially encapsulates the seal member 26, the support member 28, and the regulator 30 in an internal cavity 61.

The base member 24 can have a male tip protrusion 142 projecting therefrom, the male tip protrusion 142 defining an opening 144 therethrough that can be in fluid communication with the chamber 138 formed inside the base portion 24. In some embodiments, as illustrated, the male tip protrusion 142 can be substantially open to fluid communication in both the open and closed positions of the valve. Additionally, a shroud 146 may include protrusions or other features (not shown) thereon designed to enhance the grip of the connector 20 and internal threads 150 formed on the inside surface 146a of the shroud 146. The base member 24 can include a circumferential slot or groove 145 extending around or substantially around the base member 24 to provide an area of traction to be grasped by an operator. Such a groove also permits a more uniform wall thickness in the area of the base member 24 to enhance the efficiency of manufacture. The base member 24 can be configured to conform with ANSI standards for medical connectors.

The body member 22 can have an annular ridge or protrusion 160 formed around an outside surface 22a of the body member 22 adjacent to a proximal end portion 162 of the body member 22. The proximal end portion 162 can be smooth and generally cylindrical, or can have external threads or thread features 163 formed thereon so that the connector 20 can be threadedly joined with other suitable medical implements. The protrusion 160 can be configured to engage a threaded collar or shroud (not shown) that may be included on a luer lock type syringe to prevent or inhibit over insertion of the syringe into the connector. Additionally, with reference to FIG. 14, the inside surface 22b of the body member 22 can be generally smooth (as illustrated in FIGS. 13, 14). In some embodiments, the inside surface 22b of the body member 22 can comprise linearly arranged ridges or channels, or other such features. The channels or depressions created by the ridges can be configured to receive portions of the seal member 26 as the seal member 26 is compressed and expanded outwardly against such ridges or channels when the seal member 26 is opened. In addition, such ridges can reduce the amount of surface area in contact with the seal member as it moves in the housing of the connector.

As illustrated in FIGS. 3 and 4, the base member 24 can comprise a proximal end portion 170 having one or more protrusions 172 positioned around an outside surface of the proximal end portion 170 of the base member 24. Additionally, the body member 22 can comprise a distal end portion 174 with an opening 176 extending through the entire body member 22, and one or more channels or notches 178 formed in the distal end portion 174. The one or more channels or notches 178 can be configured to receive the one or more protrusions 172 formed on the proximal end portion 170 of the base member 24. The protrusions 172 and the notches 178 can be configured to substantially prevent the body member 22 from rotating relative to the base member 24, thereby providing a more secure joint between the body member 22 and the base member 24.

Additionally, the body member 22 can include an annular channel 180 formed inside the distal end portion 174 thereof, configured to receive an annular protrusion 182 formed on the proximal end portion 170 of the base member 24. The annular channel 180 and the annular protrusion 182 can be configured to provide a snap-fit type connection between the body member 22 and the base member 24. In this configuration, when the body member 22 has been joined with the base member 24 (as is illustrated in FIG. 13), the annular channel 180 and the annular protrusion 182 substantially prevent the body member 22 from becoming disconnected from the base member 24. Many other structures and methods of attachment of these components can also be used.

The operation of an example of connector 20 will now be described. FIG. 13 illustrates the position of the components comprising the connector 20 when the seal member 26 is in the closed position (e.g., before a syringe or other medical implement has been joined with the connector 20). In this configuration, the seal member 26 can be biased to the closed position, as illustrated in FIG. 13. Additionally, the slits 110 formed in the regulator 30 can be biased in the closed position as illustrated in FIG. 13.

FIG. 14 illustrates the seal member 26 in an open position in response to the insertion of the syringe 120 being joined with the connector 20. As illustrated in FIG. 14, the luer or cannula 126 of the syringe 120 or other medical implement has been pushed in the direction represented by arrow A4 in FIG. 14 against the seal member 26 with sufficient force to overcome the bias of the seal member 26 so as to cause the seal member 26 to compress or otherwise move within the body member 22. When the seal member 26 is compressed within the body member 22 to a sufficient distance such that the end surface 46 of the seal member 26 has passed the openings 68 formed in the support member 28, the opening 66 and/or passageway 69 is in fluid communication with the inside of the syringe 120. The force that the cannula 126 exerts on the end surface 46 of the seal member 26 can be sufficient to cause a substantially fluid-tight seal between the cannula 126 and the end surface 46 of the seal member 26, so that all or substantially all of the fluid within the syringe 120 is caused to flow into the opening 68 when the syringe 120 is joined with the connector 20 in this manner.

Thus, when the seal member 26 is in the open position, as illustrated in FIG. 14, the plunger 128 of the syringe 120 can be depressed so as to force fluid into the connector 20. Flow arrows in FIG. 14 illustrate that, in some embodiments, when fluid is forced from the syringe 120, fluid can flow into the opening or openings 68 formed in the support member 28, through the passageway 69, and through the opening 66 formed in the support member 28. In some embodiments, some of the fluid can flow through the one or more openings 86 formed in the support member 28, and into the chamber 88 formed between the support member 28 and the regulator 30. Additionally, if the pressure exerted on the plunger 128 within the syringe 120 is sufficient to overcome the threshold pressure differential to open the slit or slits 110 formed in the regulator 30, fluid will also flow through the opening 144 formed in the base member 24 and into another medical implement, if any, joined with the base member 24. As illustrated, the volume capacity within the regulator 30 in the stage illustrated in FIG. 14 can be approximately the same as in the stage illustrated in FIG. 13. As discussed, when the syringe 120 or other medical implement is removed from connector 20, the connector 20 can be configured such that the seal member 26 can return to the closed position due to the bias force within the seal member 26.

Figure 16:
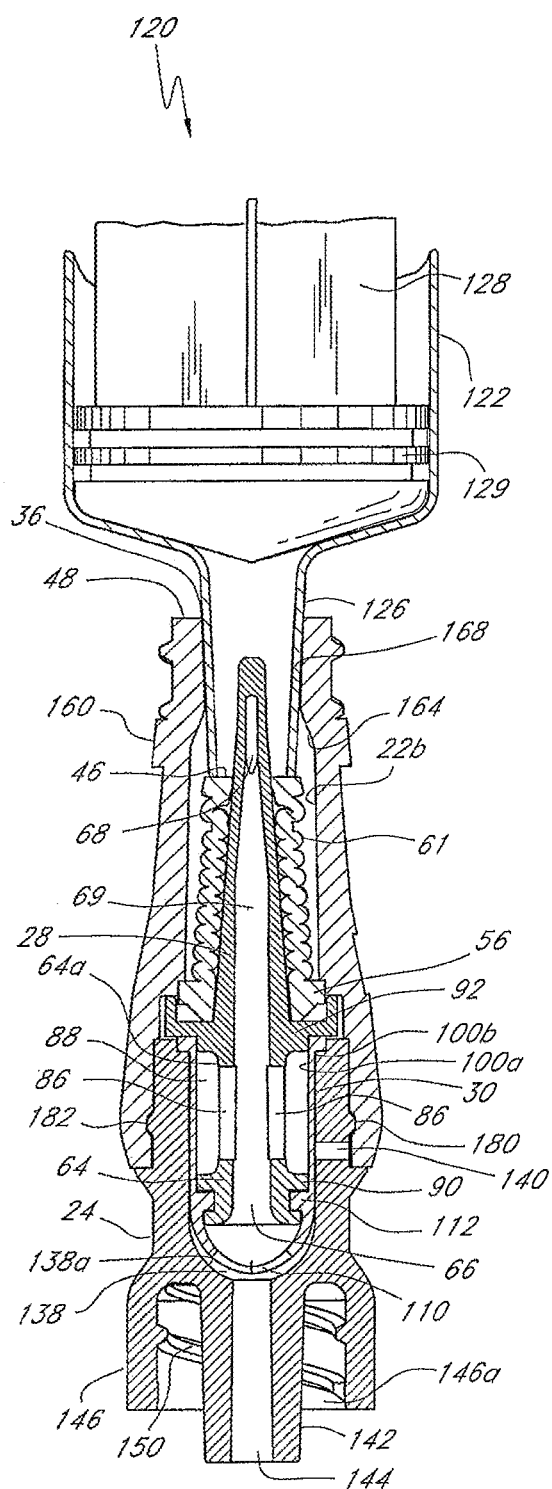
FIG. 16 is a section view of the embodiment of the connector shown in FIG. 2A, showing the seal member in an open position and the plunger of the syringe advanced to the bottom surface of the syringe.

FIG. 16 is a section view of the embodiment of the connector 20 shown in FIG. 2A, showing the seal member 26 in an open position and the plunger 128 of the syringe 120 compressed against the bottom surface 130 of the syringe 120. As illustrated in FIG. 16, medical practitioners or caregivers that administer the fluid in the syringe 120 to a patient typically depress the plunger 128 against the bottom surface 130 of the syringe so as to expel substantially all of the fluid from the syringe into the connector, causing the commonly resilient seal 129 on the end of the plunger 128 to compress between the substantially rigid plunger 128 and the substantially rigid bottom surface 130 of the syringe. As illustrated, the volume capacity within the regulator 30 in the stage illustrated in FIG. 16 can be approximately the same as in the stage illustrated in FIGS. 13 and 14.

In this position, when the plunger 128 has been completely depressed relative to the syringe 120 such that no additional fluid is being forced from the syringe 120, the fluid flow within the syringe 120 and, hence, the connector 20, stops. With no fluid flowing through the connector 20, the fluid pressure differential between the fluid within the connector 20 and the fluid outside of the connector 20 (e.g., in a catheter that is in fluid communication with the distal end of the connector 20) falls below the threshold value required to open or keep open the slit or slits 110 in the regulator 30, and the slit or slits 110 close so that no additional fluid passes through the regulator 30, until the pressure differential again exceeds the threshold required to open the slit or slits 110.

Figure 17:
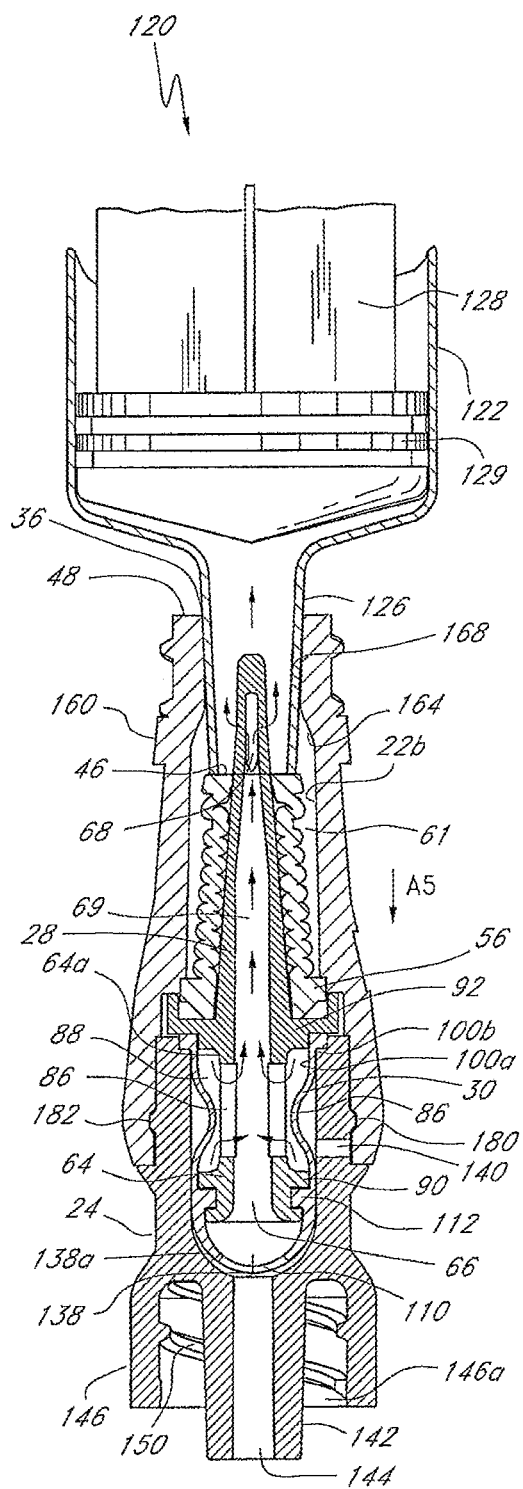
FIG. 17 is a section view of the embodiment of the connector shown in FIG. 2A, showing the seal member in an open position and the syringe after the plunger of the syringe has rebounded away from the bottom surface of the syringe.

FIG. 17 is a section view of the embodiment of the connector 20 shown in FIG. 2A, showing the seal member 26 in an open position and the syringe 120 after the plunger 128 of the syringe 120 has rebounded away from the bottom surface 130 of the syringe 120. After the rubber seal 129 on the end of the plunger 128 has been depressed against the bottom surface 130 of the syringe 120 such that substantially all of the fluid has been expelled from the syringe 120 and the caregiver releases the plunger 128, the resilient seal 129 on the end of the plunger 128 typically causes the plunger 128 to rebound away (as illustrated) or expand upward from the bottom surface 130 of the syringe. When this occurs, a volume of space is created between the seal 129 and the bottom surface 130 of the syringe 120, causing a vacuum to be created in the syringe 120.

With reference to FIG. 17, the connector 20 can be configured to compensate for the syringe rebound effect so that the pressure differential between the fluid inside the connector 20 relative to the fluid outside of the connector 20 can be less than the threshold pressure differential required to open the slit or slits 110 formed in the regulator 30.

For example, after the plunger 128 has moved away from the bottom surface 130 of the syringe 120 or expanded in the direction represented by arrow A5 (e.g., after the plunger 128 has rebounded), the connector 20 can compensate for the vacuum created within the syringe 120. As illustrated in FIG. 17, the regulator 30 can be configured such that the volume adjuster or body portion 100 of the regulator 30 can deflect inwardly into the one or more chambers 88 in response to the vacuum created within the syringe 120, so as to reduce the volume of the chamber 88, and hence reduce the volume of space within the connector 20. As illustrated, the volume capacity within the regulator 30 in the stage illustrated in FIG. 17 can be less than the volume capacity within the regulator 30 in the stages illustrated in FIGS. 13, 14, and 16 (e.g., by approximately the amount of fluid that has re-entered the syringe 120 as a result of the rebound of the plunger 128).

In some embodiments, as illustrated, a regulator, such as a dynamic regulator, variable volume chamber, or volume adjuster, can move to diminish, generally eliminate, or generally counteract a vacuum or pressure differential by inducing a corresponding and opposing change in volume that has substantially the same magnitude or size as, and/or that occurs at substantially the same time as, the vacuum or pressure differential that would otherwise produce a negative or retrograde flow. In some embodiments, as illustrated, the regulator 30 can be configured to provide a plurality of different volume adjustments (e.g., a continuously variable volume adjustment within a clinically relevant range) to enable the regulator to respond to a plurality of different effects that may otherwise cause varying amounts of vacuum or pressure differential that would produce negative or retrograde flow. The volume adjustment of the regulator 30 can be enabled or configured to occur automatically and independently of the movement of other components of the valve. For example, as illustrated, the volume change in the regulator 30 between the stages illustrated in FIGS. 16 and 17 does not necessarily depend on or require the connector 20 to be moving between the closed and opened positions; rather, the position of the proximal closure system (e.g., the seal 26 in relation to the support member 28) can be essentially the same in these stages. As illustrated, in some embodiments, the seal member 26 can be spaced from and disconnected from the regulator 30 in either or both of the open and closed positions.

As the regulator 30 changes its volume, the volume of fluid (gas or liquid) within the chamber 88 that is displaced by the change in volume of the chamber 88 can flow into the syringe 120 or other medical implement attached to the connector 20. In some embodiments, the closure end portion 108 of the regulator 30 can remain closed while the regulator 30 adjusts the fluid volume capacity inside of the connector 20. In some embodiments, the body portion 100 of the regulator 30 can be configured to move independent of the movement of the seal member 26. As shown, for example, in FIGS. 16 and 17, the body portion 100 of the regulator 30 can deflect inwardly while the seal member 26 remains substantially still in the collapsed configuration. In some embodiments, the seal member 26 and the regulator 30 can be combined in an integral or unity component, and/or the seal member 26 can be appropriately configured to include some or all of the features of the regulator 30.

In some embodiments, as illustrated, the regulator 30 can primarily expand and contract, or otherwise move, in a direction that is generally transverse to the fluid flow axis through the connector 20, without generally expanding or contracting by a significant amount (or at all) in a direction that is generally parallel with the fluid flow axis through the connector 20. In some embodiments, as illustrated, the diameter and/or cross-sectional area of the variable volume portion or body portion 100 of the regulator 30 can be generally constant between proximal and distal ends thereof in an initial position.

Thus, the connector 20 and, in particular, the regulator 30, can be configured such that, when the syringe 120 rebounds, the pressure differential between the fluid within the connector 20 and the fluid outside of the connector 20 can be dynamically maintained below the threshold pressure differential required to open the slit or slits 110 in the regulator 30 by reducing the volume within the connector 20 even before the seal member 26 closes, thus mitigating the vacuum suction or retrograde fluid flow within the syringe. Additionally, in some embodiments, the end portion 108 of the regulator 30 can be configured to deflect inwardly slightly without the slit or slits 110 opening, to account for the vacuum generated by the syringe rebound.

In some embodiments, the connector 20 and the regulator 30 can be configured to compensate for a vacuum of at least approximately 1 atmosphere within the syringe 120 without the regulator 30 opening. In some embodiments, the connector 20 and the regulator 30 can be configured to compensate for a vacuum of between approximately 0.5 atmospheres and approximately 3 atmospheres, or between approximately 1 atmosphere and approximately 2 atmospheres within the syringe 120 without the regulator 30 opening.

After the desired amount of fluid has been dispensed from the syringe 120 or other medical implement, the syringe 120 or other medical implement can be removed from the connector 20. When the syringe 120 or other medical implement is removed from connector 20, the connector 20 can be configured such that the seal member 26 can return to the closed position due to the bias force within the seal member 26. This reversibility of the seal member 26 makes the connector 20 particularly attractive as a connector valve to provide fluid communication between two fluid lines. Since the connector 20 can be sealed closed and can be disinfected, various syringes or medical implements can be easily joined with the connector 20 multiple times without requiring removal of the connector 20 from communication with the patient's vasculature.

Figure 17A:
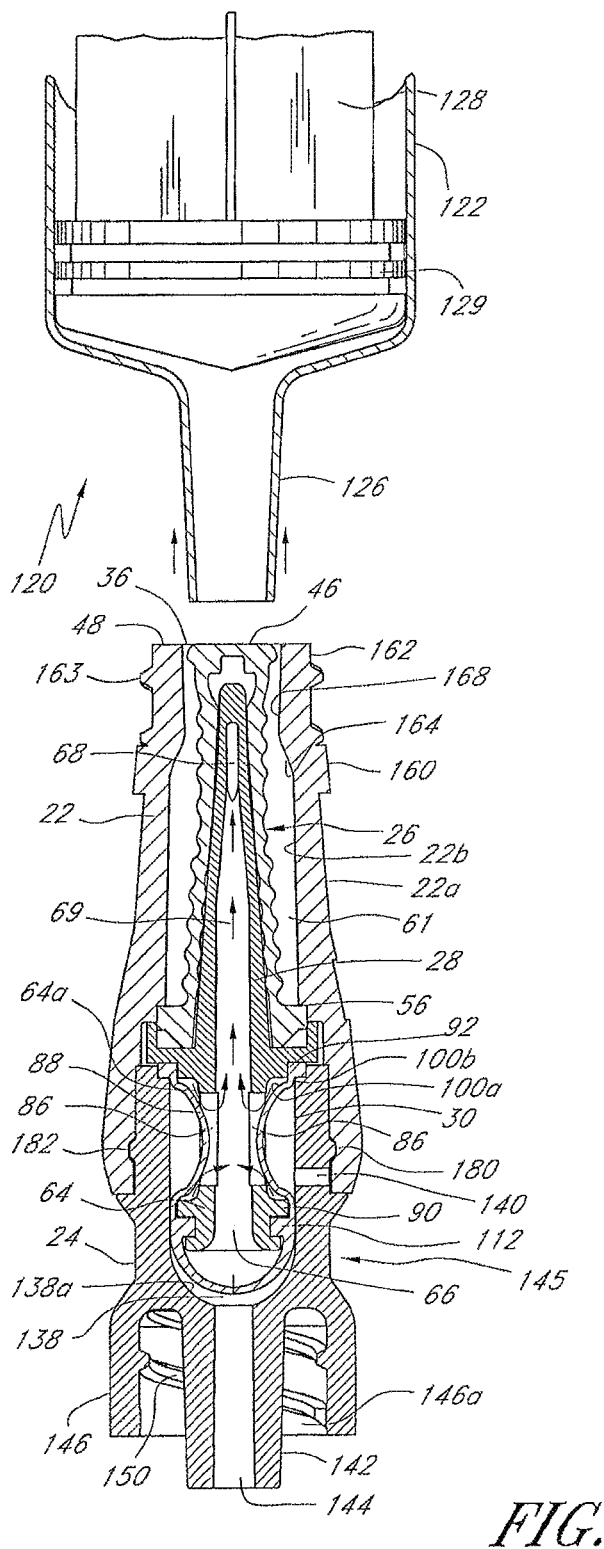
FIG. 17A is a section view of the embodiment of the connector shown in FIG. 2A, showing the seal member in the first position after the syringe has been removed from the connector.

The removal of the luer of a medical implement, such as the syringe 120 can also cause backflow or negative flow into the connector 20. As shown in FIG. 17A, regulator 30 can be configured to inhibit or prevent this negative flow as well. As shown, the regulator 30 may be sized to accommodate additional inward flex or other movement even after the syringe rebound effect shown in FIG. 17. Thus, the side wall 100 of the regulator 30 continues to collapse inwardly as the syringe 120 is removed from the connector 20 to maintain a pressure differential less than the cracking pressure needed to open the slits 110 and therefore the regulator 30. As illustrated, the volume capacity within the regulator 30 in the stage illustrated in FIG. 17 can be less than the volume capacities within the regulator 30 in the stages illustrated in FIGS. 13, 14, 16, and 17A. Since the regulator 30 remains closed, essentially no fluid is drawn into the distal end of the connector 20, essentially no fluid is drawn into the catheter or other medical implement attached to the distal end of the connector, and therefore, essentially no negative flow is created. In some embodiments, the variable volume within the regulator 30 can vary by at least about 0.01 ml and/or less than or equal to about 0.10 ml, although in many embodiments, the volume can vary by amounts outside this range, depending on the configuration (e.g., amount of dead space) within the connector. In some embodiments, the variable volume of the variable volume chamber is at least about 0.02 cc and/or less than or equal to about 0.06 cc. In some embodiments, the variable volume of the variable volume chamber is about 0.04 cc.

In some embodiments, as illustrated in FIGS. 17 and 17A, even after the regulator 30 moves to compensate or respond to a change in pressure or fluid volume, some amount of fluid can still remain within the regulator 30, including within the fluid cavity 88 between the outer surface of the distal portion 64 of the support member 28 and the inner surface of the volume adjuster of the body portion 100 of the regulator 30

In some embodiments, as illustrated in FIG. 17A, the volume adjustment of the regulator 30 can be permitted to occur independently of the movement of other components of the valve (such as the proximal closure system). For example, the volume change in the regulator 30 between the stages illustrated in FIGS. 17A and 17B does not necessarily depend on or require that the connector 20 is moving between the closed and opened positions; rather, the change in volume in the regulator 30 can occur because the regulator 30 automatically responds to pressure differentials communicated through the fluid, but not necessarily because the regulator is mechanically or directly linked to other components within the connector 20. In some embodiments, there can be a direct or mechanical connection between the regulator 30 and other components, including the proximal closure system.

In some embodiments (not shown), the regulator 30 can be configured to include a rigid chamber instead of the flexible, resilient body portion 100 described elsewhere herein. For example, the regulator 30 can be configured to have a resilient end portion defining one or more slits or openings in the end thereof, similar to the regulator 30, but having a body portion that is not configured to buckle or deflect inwardly in response to the syringe rebound or other retrograde-inducing event. Rather, in some embodiments, a regulator (not shown) could be configured to slide axially within the chamber 138 formed within the base member 24, but to be biased by a spring member away from the support member. In these and other embodiments, the support member can be formed without the distal end portion 64. In such configurations, when the vacuum is formed within the syringe, the regulator can be configured to slide toward the syringe, against the force of the bias, so as to reduce the volume within the connector and prevent the slit or slits in the regulator from opening. In some embodiments, the variable volume cavity or dynamic volume adjuster of the regulator 30 can comprise a flaccid bag or other flaccid fluid container that is generally not resilient and generally not stretchable. The container can be made of very soft polyethylene or other materials, and can be configured to selectively permit fluid ingress and/or egress by filling up without necessarily causing a stretching of the walls of the container.

In some embodiments (not illustrated), the regulator can be positioned adjacent to the inside surface of the opening 66 formed in the distal end portion 64 of the support member 28 so as to line or be positioned generally within at least a portion of the inside surface of the opening 66 and the passageway 69 extending inside the distal end portion 64 of the support member 28, or adjacent to the inside surface of another member having an internal opening in fluid communication with the opening 66. For example, in some embodiments, the regulator can cover a portion of the inside surface of a hollow, cylindrical member wherein the opening through the cylindrical member is in communication with the opening 66. In some embodiments, at least a portion of the regulator (e.g., a middle portion) can be unrestrained so as to be permitted to buckle inwardly or otherwise move in response to the vacuum from the syringe, disconnection of the syringe or other medical implement from the connector, or otherwise. The size or diameter of the opening 66 formed in the distal end portion 64 of the support member 28 can be increased to accommodate the regulator positioned adjacent to the inside surface thereof. As mentioned, in some embodiments (not illustrated), the regulator can comprise cylindrical sidewalls configured to buckle inwardly to reduce the internal volume, and hence the internal pressure within the connector so as to compensate for the vacuum created by the syringe rebound or disconnection of the medical implement. As with the other embodiments described herein, the connector can have an air port therein that is sealed from the opening 66 and the fluid passing through the connector, but which permits the regulator to freely slide axially, or buckle or collapse inwardly. When a medical implement, such as the luer tip 120 of the syringe 120, is reinserted into the proximal end of the connector 20 in the closed state after the introduction of fluid (e.g., the state illustrated in FIG. 17A), the fluid volume within the connector 20 may again change. In this situation, the fluid volume within the connector 20 may increase, causing the variable volume within the regulator 30 to increase by forcing the sidewalls to expand outwardly or otherwise move. Since the regulator 30 can thus absorb the volume differential, the valve member 138 can remain closed during reinsertion, and fluid flow toward the patient upon reinsertion of the luer tip 126 can be substantially or entirely eliminated. In some cases, the positive flow of fluid that would otherwise be caused by the reinsertion of a medical implement is not desirable and can be avoided, especially for patients with a comparatively small blood volume, such as neonatal patients. After reinsertion of the medical implement, the connector 20 can progress to one or more states with variable internal volumes that are different from that illustrated in FIG. 17A, such as states similar to those illustrated in FIGS. 16 and 17.

In some embodiments, as illustrated in FIGS. 13-17A, the valve member on the distal end portion 108 of the regulator 30 can generally prevent many forms of internally or externally generated negative flow or fluid ingress. The dynamically adjusting volume of the body 100 of the regulator 30 can permit the valve member on the distal end portion 108 to remain closed even when fluid volume is withdrawn or changes, and can allow usage of a valve member on the distal end portion 108 that is configured to permit a substantially lower threshold for fluid flow in the proximal direction. In some embodiments, as illustrated, the threshold pressure differential required to open the valve member to fluid flow in the proximal-to-distal direction is substantially lower than the threshold pressure differential required to open the valve member to fluid flow in the distal-to-proximal direction. Also, the valve member on the distal end portion 108 can be configured to generally prevent negative flow or retrograde flow caused by external sources on the distal side of the connector 20.

Figure 20:
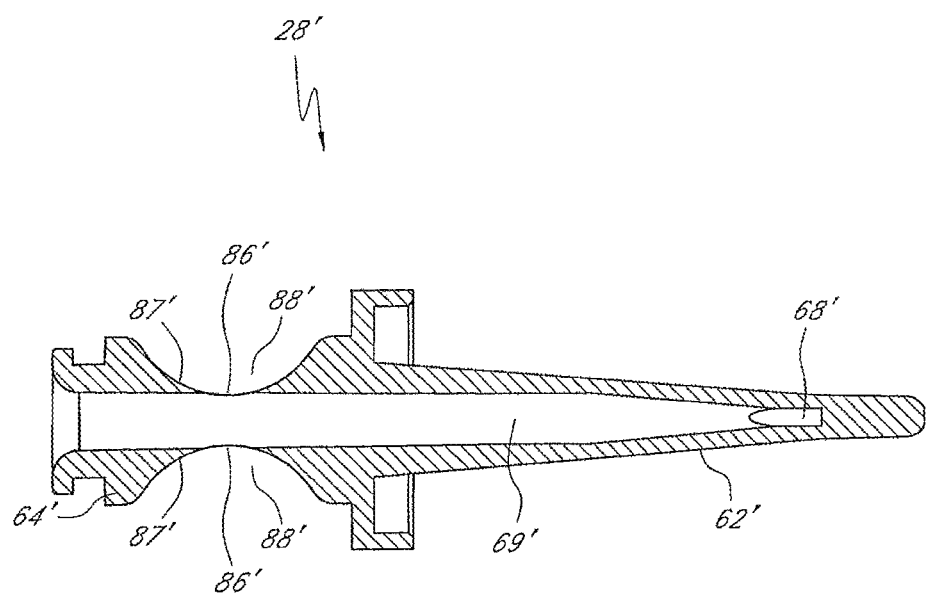
FIG. 20 is a section view of the embodiment of the support member shown in FIG. 18, taken through the axial centerline of the support member.

FIGS. 18 and 19 are perspective views of another embodiment of a support member 28' that can be used with the connector 20 shown in FIG. 2A or any other connector disclosed herein. FIG. 20 is a section view of the embodiment of the support member 28' shown in FIG. 18, taken through the axial centerline of the support member 28'. In some embodiments, the support member 28' can have any of the features or other details or configurations of the support member 28. Additionally, the support member 28' can be configured to operate with the body member 22, the base member 24, the seal member 26, or the regulator 30. Thus, in some embodiments, the support member 28' can be interchanged with the support member 28. Many features of the support member 28' illustrated in FIGS. 18-20 can be the same as or similar to the corresponding features of the support member 28.

As illustrated in FIGS. 18-20, the distal portion 64' of the support member 28' can have one or more openings 86' formed laterally or radially through the distal portion 64'. In the illustrated embodiment, two openings 86' are formed in the distal portion 64'. However, in some embodiments, only one opening, or three, four, or more openings can be formed in the distal portion 64'. The openings 86' can be formed so as to be in communication with the axial opening 66' and the fluid passageway 69' formed in the support member 28'. Similar to the support member 28, the opening 66' can be in communication with the one or more openings 68' formed in the proximal tip portion 62' of the support member 28.

Additionally, the support member 28' can have one or more depressions 87' formed in the distal end portion 64' of the support member 28', the one or more depressions 87' being formed so as to be in fluid communication with the one or more openings 86' formed in the distal end portion 64'. The one or more smoothly contoured depressions 87' can include one or more generally round, generally parabolically shaped cavities 88' that can be filled with fluid flowing through the openings 66', 86' formed in the support member 28' in a manner similar to the cavities 88 of the support member 28. Similar to the support member 28, the distal end portion 64' of the support member 28' can be configured to be received within the opening 104 formed within the regulator 30, and hence support the regulator 30 in a similar fashion as has been described with reference to the connector 20.

The support member 28' can function in the same or similar manner as compared to the support member 28. In particular, when syringe rebound, or other force, generates a vacuum within the syringe, the body portion 100 of the regulator 30 can deflect inwardly into the cavities 88' in response to the vacuum created within the syringe 120. This can cause a reduction in the volume of the chamber 88', and hence reduce the volume of space within the connector 20.

As this occurs, the volume of fluid (gas or liquid) within the chamber or chambers 88' that is displaced by the change in volume of the chamber or chambers 88' can flow into the syringe 120, thereby mitigating the effects of the vacuum within the syringe as described herein.

FIGS. 21 and 22 are perspective views of another embodiment of a seal member 26' that can be used with the connector 20 shown in FIG. 2A or any other connector disclosed herein. In some embodiments, the seal member 26' can have any of the features or other details or configurations of the seal member 26 or any other seal member described herein. The seal member 26' can be configured to operate with the body member 22, the base member 24, the support member 28, or the regulator 30. Thus, in some embodiments, the seal member 26' can be interchanged with the seal member 26. In some embodiments, the internal wall structure of the body member 22, (including but not limited to the inside abutment surface 164), can be slightly modified to accommodate the different configuration of the seal member 26'. For example, the inside abutment surface 264 of the body member illustrated in FIGS. 27-32 can be oriented at a generally shallow angle (e.g., less than about 45°) from the horizontal plane.

The seal member 26' can include an annular collar portion 42' having a proximal face 44'. In some embodiments, as will be described in greater detail below, the collar portion 42' can be configured to interact with an inside surface of the body member 22 (which can be an annular protrusion, one or more tabs, or other protruding feature) so as to limit the axial movement of the proximal end portion 34' of the seal member 26' in the proximal direction. In some embodiments, the body member 22 and the seal member 26' can be configured so that the end surface 46' (which can be planar) of the seal member 26' can be adjacent to or approximately coplanar with the end surface 48 of the body member 22, when the seal member 26' is in the closed position. The first or closed position of the seal member 26' relative to the body member 22 is illustrated in FIG. 2A. This approximate alignment of the proximal surfaces can make it easier to clean and disinfect the seal member and other components of the connector 20. The seal member 26' and body member 22 can thus be configured so that the end surface 46' can be consistently aligned generally with the end surface 48 of the body member 22 when the seal member 26' is in the closed position.

As with seal member 26, seal member 26' can have a resilient body portion 50' having a shape as previously described configured to permit the seal member 26' to resiliently compress and expand as axial forces are applied to and removed from, respectively, the proximal end portion 34' of the seal member 26'. In some embodiments, the body portion 50' can include a series of o-ring shaped structures integrally formed together or separately formed and bonded together. The o-rings can vary in diameter or cross-sectional shape and/or size.

In some embodiments, the inside surface of the body portion 50' can approximately match the outside surface of the body portion 50'. In some embodiments, the inside surface of the body portion 50' can have a relatively smooth or flat surface contour. The body portion 50' can have a generally consistent cross-sectional shape or size along the length thereof, or the cross-sectional shape or size of the body portion 50' can vary along at least a portion of the length thereof. In some embodiments, the shape of the inside of the body portion 50' can approximately match the outside surface of the elongated portion 62 of the support member 28. Seal member 26' can move from the first to second position in a similar manner to the seal member 26. In the closed position, seal member 26' can remain under some additional level of compression, such as, for example, where the proximal face 44' of the collar portion 42' engages an inner surface or surfaces of the body member 22

The body member 22 can comprise an inside abutment surface 164 that can be configured to interact with the corresponding annular collar portion 42' formed on the seal member 26'. The abutment surface 164 and annular collar portion 42' formed on the body member 22 and the seal member 26', respectively, can be configured to limit the motion of the seal member 26' relative to the body member 22 in the proximal direction (e.g., the direction represented by arrow A3 shown in FIG. 14). In some embodiments, the abutment surface 164 and the annular collar portion 42' formed on the body member 22' and the seal member 26', respectively, can be configured to stop the seal member 26' at the approximate position where the end surface 46' of the seal member 26' can be adjacent to or approximately coplanar with the end surface 48 of the body member 22. The end surface 46' of the seal member 26' can thereby be prevented from protruding past the end surface 48 of the body member 22, or protruding past the end surface 48 in a consistent manner, e.g. to a consistent distance beyond the end surface 48 during various valve activations.

The seal member 26' can be configured such that the proximal end portion 34' of the seal number 26' can be sealingly received by an opening 36 formed in the body member 22. In some embodiments, as in the illustrated embodiment, the proximal end portion 34' of the seal member 26' can have a lip portion 38' (which can be an annular protrusion) formed thereon that is configured to contact the inside surface of the opening 36 of the body member 22 to provide a seal therewith.

The seal member 26', the proximal end portion 34' of the seal member 26', and the lip portion 38' can be integrally formed or can be separately formed and adhered or otherwise joined together using adhesive or any suitable material or method. In some embodiments, the seal member 26' or any other embodiment of a seal or seal member disclosed herein and any of the components or features thereof can be constructed from a number of different suitable materials, including silicone-based deformable materials, rubbers, or other suitable materials. Silicone-based deformable materials are among those that form fluid-tight closures with plastics and other rigid polymeric materials.

Similar to the seal member 26, the seal member 26' can be configured so that the body portion 50' is biased to an expanded or initial position. When an axial force is exerted on the seal member 26', the body portion 50' can be caused to compress and, hence, axially retract so as to shorten the overall length of the seal member 26'. When the axial force is removed from the seal member 26', the body portion 50' can expand as a result of the bias so as to return the seal member 26' to its initial or relaxed state.

Additionally, as shown in FIG. 21, a slit or opening 52' can be formed in the proximal end portion 34' of the seal member 26'. The seal member 26 can be configured so that the slit 52' is biased to a closed position, so as to substantially prevent or inhibit any liquid from flowing through the slit 52' or the opening 54' formed in the seal member 26'. Additionally, as will be described in greater detail below, in some embodiments, the slit 52' can be opened by retracting the seal member 26' in the distal direction over the support member 28, causing at least a portion of the proximal end portion of the support member 28 to penetrate and pass through the slit 52'.

FIGS. 23, 24 are perspective views of another embodiment of a seal member 26" that can be used with the connector 20 shown in FIG. 2A or any other connector disclosed herein. In some embodiments, the seal member 26" can have any of the features or other details or configurations of the seal member 26 or the seal member 26'. The seal member 26" can be configured to operate with the body member 22, the base member 24, the support member 28, or the regulator 30. Further, as will be described, the seal member 26" can be configured to operate with the body member 22, the base member 24, an embodiment of a support member 28 not having the elongated portion 62 (not illustrated), and the regulator 30. In particular, because the seal member 26" can be configured to open and close without the use of the elongated portion 62 of the support member 28, in some embodiments of the connector 20 (not illustrated), the seal member 26" can operate without the inclusion of the elongated portion 62.

Thus, in some embodiments, the seal member 26" can be interchanged with the seal member 26 or the seal member 26'. In some embodiments, the internal wall structure of the body member 22, including but not limited to the inside abutment surface 164, may need to be slightly modified to accommodate the different configuration of the seal member 26". Many features of the seal member 26" illustrated in FIG. 23 can be the same as or similar to the corresponding features of the seal member 26.

As illustrated in FIG. 23, the seal member 26" can be configured such that the proximal end portion 34" of the seal member 26" can be sealingly received by an opening 36 formed in the body member 22. The seal member 26" can be configured such that the proximal end portion 34" and/or the end surface 46" of the seal number 26" can have a generally ovular or elliptical shape. In some embodiments, the end surface 46" of the seal number 26" can have a first length or dimension (represented by length D1 in FIG. 23) and a second length or dimension (represented by length D2 in FIG. 23), the second length D2 being less than the first length D1. In some embodiments, the length D1 can be at least approximately one-quarter or at least approximately one-third greater than length D2. As mentioned, in some embodiments, the shape of the cross-section of the proximal end portion 34" can be similar to the shape of the end surface 46" of the seal number 26".

Additionally, as shown in FIG. 23, a slit or opening 52" can be formed in the proximal end portion 34" of the seal member 26". The seal member 26" can be configured so that the opening 52" is biased to an open position (as illustrated) when the seal member 26" is in a relaxed state, so as to permit liquid to flow through the opening 52" and, hence, the opening 54" formed in the seal member 26". The opening 52" can be configured such that, when generally mutually opposing such as, but not limited to, forces F1 and F2 shown in FIG. 23, are applied to the proximal end portion 34" of the seal member 26", the opening 52" will be sealingly closed so as to substantially inhibit or prevent any fluid flow therethrough.

Therefore, the opening 36 in the body member 22 can be configured to have a substantially circular cross-section so that, as the proximal end portion 34" of the seal member 26" is inserted into the opening 36 of the body member 22, the substantially rigid and circular opening 36 can exert a force on the proximal end portion 34" of the seal member 26" that can close the opening 52" so as to substantially inhibit the flow of fluid through the opening 52". The body member 22 can also be configured such that, as the proximal end portion 34" of the seal member 26" is compressed and, hence, retracted away from the opening 36 (such as by the insertion of a syringe or other medical implement), the proximal end portion 34" of the seal member 26" will no longer be restrained by the openings 36 of the body member 22, such that the bias of the proximal end portion 34" will cause the opening 52" to open and permit fluid flow therethrough.

Therefore, in this configuration, the connector can operate as desired without the use of the elongated portion 62 of the support member 28. However, in some embodiments, the seal member 26" can be used with a support member 28 having an elongated portion 62, wherein the slit or opening 52" can also be opened by retracting the seal member 26" in the distal direction over the support member 28, causing at least a portion of the proximal end portion of the support member 28 to penetrate and pass through the slit 52". In some embodiments, as with other embodiments of the seal member, the proximal end portion 34" of the seal member 26 can have a lip portion 38" (which can be an annular protrusion) formed thereon that is configured to contact the inside surface of the opening 36 of the body member 22 to provide a seal therewith.

The seal member 26", the proximal end portion 34" of the seal member 26", and the lip portion 38" can be integrally formed or can be separately formed and adhered or otherwise joined together using adhesive or any suitable material or method. In some embodiments, the seal member 26" or any other embodiment of a seal or seal member disclosed herein and any of the components or features thereof can be constructed from a number of different suitable materials, including silicone-based deformable materials, rubbers, or other suitable materials. Silicone-based deformable materials are among those that form fluid-tight closures with plastics and other rigid polymeric materials.

The seal member 26" can have a resilient body portion 50" having a plurality of accordion-like structures configured to permit the seal member 26" to resiliently compress and expand as axial forces are applied to the proximal end portion 34" of the seal member 26". The body portion 50" can have a generally consistent cross-sectional shape throughout the length thereof (as illustrated), or the cross-section of the body portion 50" can vary along a portion of the length thereof (not illustrated), similar to the seal member 26'. In some embodiments, the shape of the inside of the body portion 50" can approximately match the outside surface of the elongated portion 62 of the support member 28, if such elongated portion 62 is present.

Similar to the seal member 26, the seal member 26" can be configured so that the body portion 50" is biased to an expanded or initial position. When an axial force is exerted on the seal member 26", the body portion 50" can be caused to compress and, hence, axially retract so as to shorten the overall length of the seal member 26". When the axial force is removed from the seal member 26", the body portion 50" can expand as a result of the bias so as to return the seal member 26" to its relaxed state.

FIGS. 25A and 25B are perspective views of another embodiment of a seal member 26''' that can be used with the connector shown in FIG. 2A or any other connector disclosed herein. In some embodiments, the seal member 26''' can have any of the features or other details or configurations of the seal member 26 or any other seal member described herein. The seal member 26''' can be configured to operate with the body member 22, the base member 24, the support member 28, or the regulator 30. Thus, in some embodiments, the seal member 26''' can be interchanged with the seal member 26. Many features of the seal member 26''' illustrated in FIGS. 25A and 25B can be the same as or similar to the corresponding features of the seal member 26.

The seal member 26''' can be configured such that the proximal end portion 34''' of the seal number 26''' can be sealingly received by an opening 36 formed in the body member 22. The proximal end portion 34''' can be generally cylindrical with a generally smooth sidewall. In some embodiments, as in the illustrated embodiment, the proximal end portion 34''' of the seal member 26 can have a lip portion 38''' (which can be an annular protrusion) formed thereon that is configured to contact the inside surface of the opening 36 of the body member 22 to provide a seal therewith.

The seal member 26 can also comprise an annular collar portion 42''' having a proximal face 44'''. In some embodiments, the collar portion 42' can be configured to interact with an inside surface of the body member 22 (which can be an annular protrusion, one or more tabs, or other protruding feature) so as to limit the axial movement of the proximal end portion 34''' of the seal member 26''' in the proximal direction. In some embodiments, the body member 22''' and the seal member 26''' can be configured so that the end surface 46''' (which can be planar) of the seal member 26''' can be adjacent to or approximately coplanar with the end surface 48''' of the body member 22, when the seal member 26''' is in the closed position. This approximate alignment can make it easier to clean and disinfect the seal member and other components of the connector 20. The seal member 26''' and body member 22 can thus be configured so that the end surface 46''' can be consistently aligned generally with the end surface 48 of the body member 22 when the seal member 26''' is in the closed position.

The seal member 26''', the proximal end portion 34''' of the seal member 26''', and the lip portion 38''' can be integrally formed or can be separately formed and adhered or otherwise joined together using adhesive or any suitable material or method. In some embodiments, the seal member 26''' or any other embodiment of a seal or seal member disclosed herein and any of the components or features thereof can be constructed from a number of different suitable materials, including silicone-based deformable materials, rubbers, or other suitable materials. Silicone-based deformable materials are among those that form fluid-tight closures with plastics and other rigid polymeric materials.

The seal member 26''' can have a resilient body portion 50''' having a contour as described in other seal embodiments that is configured to permit the seal member 26''' to resiliently compress and expand as axial forces are applied to and removed from, respectively, the proximal end portion 34 of the seal member 26'''. In some embodiments, the inside surface of the body portion 50''' can approximately match the outside surface of the body portion 50'''. In some embodiments, the inside surface of the body portion 50''' can have a relatively smooth or flat surface contour. In some embodiments, the body portion 50''' can have a generally consistent cross-sectional shape or size along the length thereof, or the cross-sectional shape or size of the body portion 50''' can vary along at least a portion of the length thereof. In some embodiments, the shape of the inside of the body portion 50''' can approximately match the outside surface of the elongated portion 62 of the support member 28.

Similar to the seal member 26, the seal member 26''' can be configured so that the body portion 50''' is biased to an expanded or initial position. When an axial force is exerted on the seal member 26''', the body portion 50''' can be caused to compress and, hence, axially retract so as to shorten the overall length of the seal member 26'''. When the axial force is removed from the seal member 26''', the body portion 50''' can expand as a result of the bias so as to return the seal member 26''' to its relaxed state.

Additionally, as shown in FIG. 25A, a slit or opening 52''' can be formed in the proximal end portion 34''' of the seal member 26'''. The seal member 26 can be configured so that the slit 52''' is biased to a closed position, so as to substantially prevent or inhibit any liquid from flowing through the slit 52''' or the opening 54''' formed in the seal member 26'''. Additionally, as will be described in greater detail below, the slit 52''' can be opened by retracting the seal member 26''' in the distal direction over the support member 28, causing at least a portion of the proximal end portion of the support member 28 to penetrate and pass through the slit 52'''.

Figure 26A:
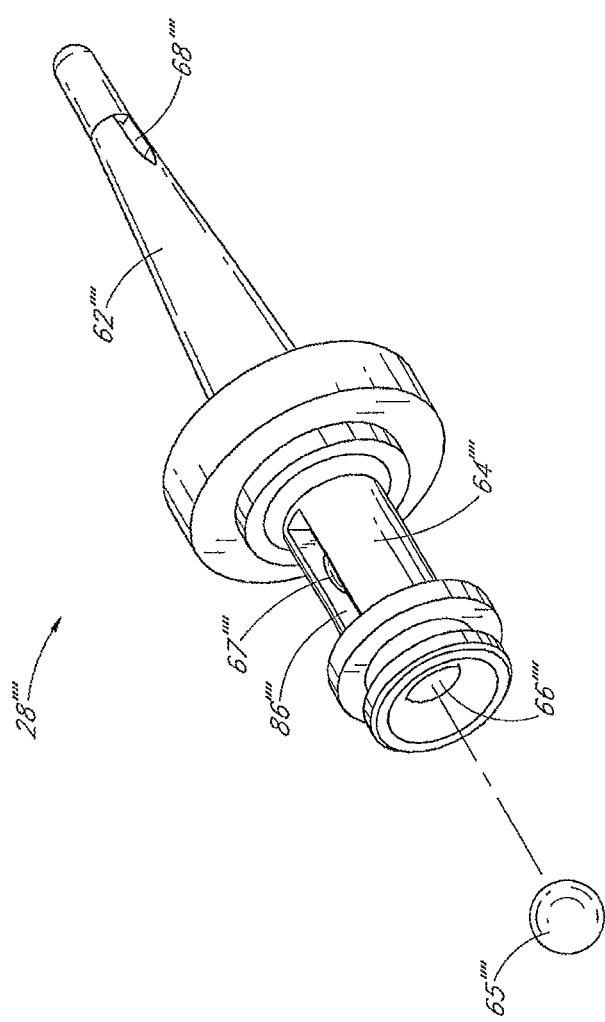
FIG. 26A is a perspective view of another embodiment of a support member that can be used with the connector shown in FIG. 2A or any other connector disclosed herein.
Figure 26B:
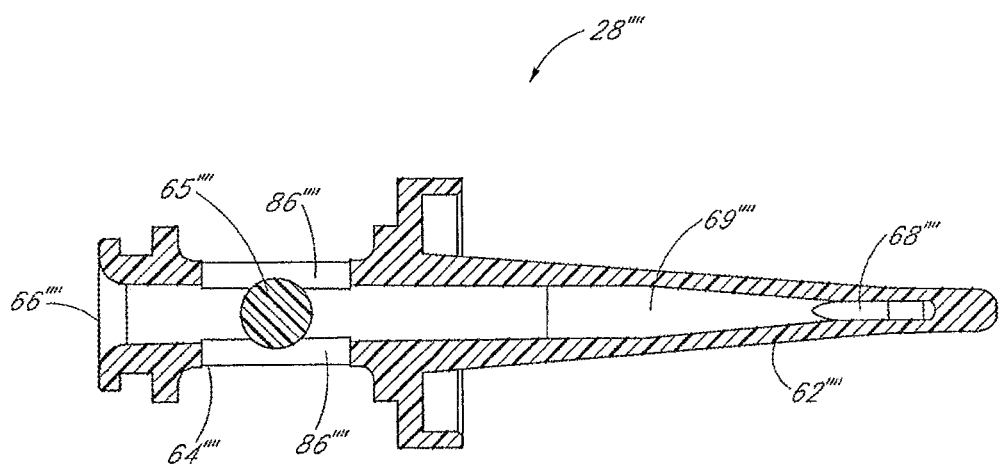
FIG. 26B is a section view of the embodiment of the support member shown in FIG. 26A.
Figure 26C:
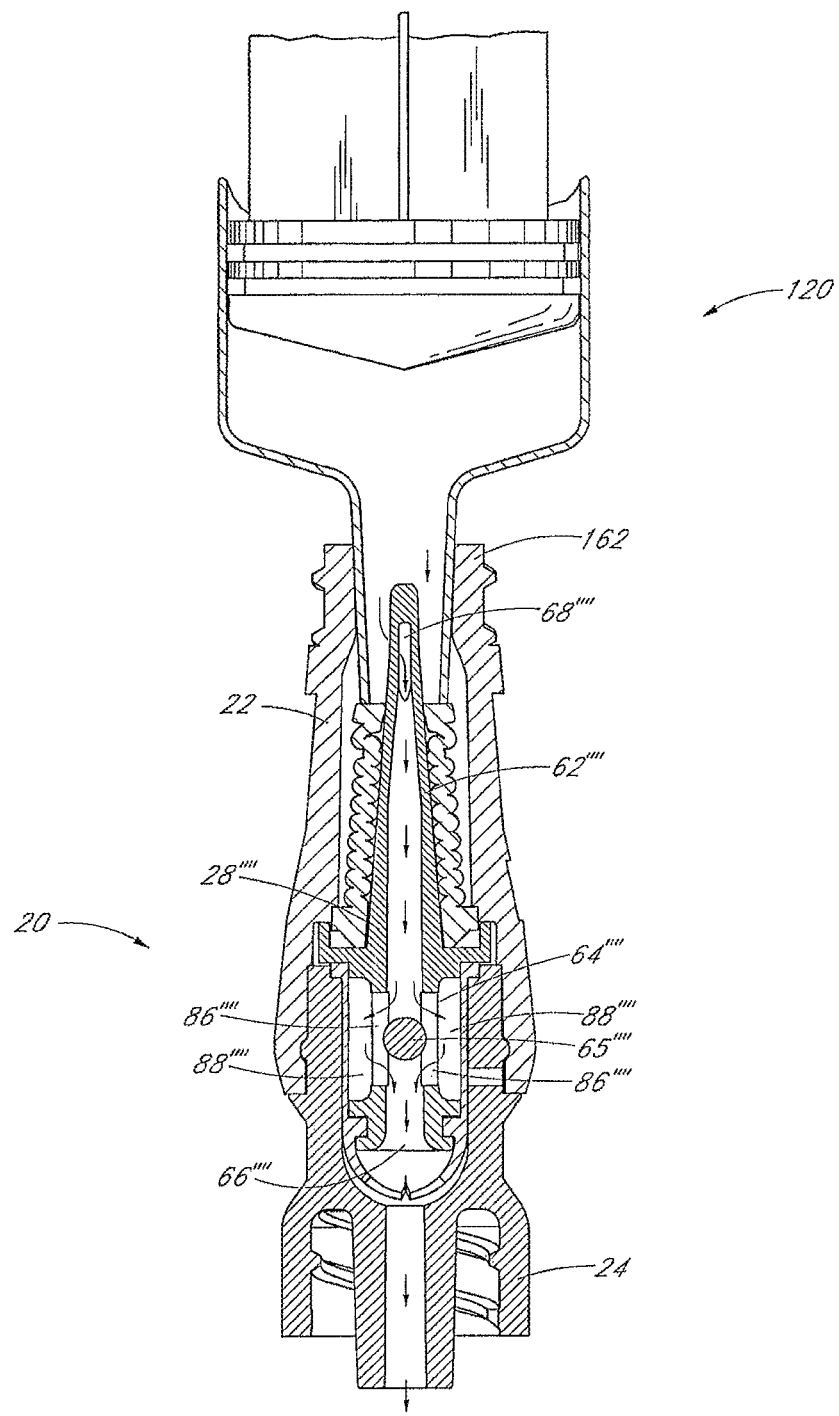
FIG. 26C is a section view of a connector comprising the embodiment of the support member shown in FIG. 26A.

FIG. 26A is a perspective view of another embodiment of a support member 28'''' that can be used with the connector 20 shown in FIG. 2A or any other connector disclosed herein. FIG. 26B is a section view of the embodiment of the support member 28'''' shown in FIG. 26A, taken through the axial centerline of the support member 28''''. FIG. 26C is a section view of a connector 20 comprising the support member 28''''. In some embodiments, the support member 28'''' can have any of the feature or other details or configurations of the support member 28. Additionally, the support member 28'''' can be configured to operate with the body member 22, the base member 24, the seal member 26, the regulator 30, and their components described herein. Thus, in some embodiments, the support member 28'''' can be interchangeable with the support member 28. Many features of the support member 28'''' illustrated in FIG. 26A-26B can be the same as or similar to the corresponding features of the support member 28.

As illustrated in FIGS. 26A-26C, the support member 28'''' can include a fluid diverter 65''' configured to divert at least a portion of the flowing fluid out of the fluid passageway 69'''', through the openings 86'''' formed in the distal portion 64'''' of the support member 28'''', and into the chamber or chambers 88'''' formed between the support member 28'''' and the body portion 100 of the regulator 30.

In some embodiments, the fluid diverter can be a ball 65''''. The ball 65'''' can be formed from a generally rigid material such as nylon, or a semi-rigid or flexible material. In some embodiments, the ball 65'''' can be lodged in the fluid passageway 69'''' at a position such that a portion of the openings 86'''' is located proximal to the ball 65'''' and a portion of the openings 86'''' is located distal to the ball 65''', as shown in FIG. 26B. In some embodiments, the ball 65'''' can be formed separately from the remainder of the support member 28'''' (as shown in FIG. 26A), and can be inserted into the fluid passageway, for example, through the opening 66''''. In some embodiments, the ball 65'''' can be formed from a more rigid material than the distal end portion 64'''' of the support member 28'''' such that the walls of the opening 66'''' and of the fluid passageway 69'''' can temporarily flex outwardly by a small amount as the ball 65'''' is inserted therethrough. In some embodiments, the ball 65'''' can be formed from a less rigid material than the distal end portion 64''' of the support member 28'''' such that the ball 65'''' can compress and deform as it is inserted through the opening 66''' and up through the fluid passageway 69''''. In some embodiments, the walls of the opening 66'''' and of the fluid passageway 69'''' can expand while the ball simultaneously compresses and deforms during insertion. In some embodiments, the ball 65'''' can be formed from the same material (e.g., polycarbonate) as the rest of the support member 28''''.

In some embodiments, the ball 65"" can have a diameter larger than the fluid passageway 69"", such that the ball 65"" can be secured in place during operation by the friction generated by the walls of the fluid passageway 69'" pressing against the outer surface of the ball 65"". Depending on the materials selected, the ball 65"" and/or the walls of the fluid passageway 69"" can be compressed or flexed or otherwise configured to maintain a friction fit to hold the ball 65"" in place. In some embodiments, the fluid passageway 69"" can include a groove 67"" configured to receive the ball 65"". The groove 67"" can be, for example, shaped similar to at least a portion of the surface of the ball 65"" and can have a diameter that is equal to or slightly smaller than the ball 65'". The ball 65"" can be generally maintained in place once it has been inserted to the point where it "snaps" into the groove 67"". The fluid diverter 65"" can have a smooth, rounded, curved, and/or gradually changing shape configured to substantially avoid or diminish abrupt, angular shifts in the fluid flow and accompanying turbulence therein and/or damage to the transported fluid (especially blood cells).

As can be seen in FIG. 26C, during operation, fluid can flow from a syringe or other medical implement connected to the proximal end 162 of the body portion 22 of the connector 20 into the fluid passageway 69"" of the support member 28"" via one or more openings 68'" in the elongate portion 62"". The fluid can flow distally through the fluid passageway 69"" until it reaches the fluid diverter (e.g., the ball 65""). The fluid diverter can cause the fluid to flow out of the fluid passageway 69"" and into the one or more chambers 88"" via the openings 86"". The fluid can reenter the fluid passageway 69"" via the openings 86"" at a location distal to the fluid diverter. The fluid can then flow out of the support member 28"" via the opening 66"" and through the slits 110 of the regulator 30 and out the distal end of the base member 24. Thus, the fluid diverter can interrupt the substantially linear or laminar flow path of fluid between the proximal and distal ends that can otherwise occur inside of the support member 28"" and can increase the lateral fluid flow through the chamber or chambers 88"", thereby preventing or diminishing fluid stagnation in the chamber or chambers 88"". In some embodiments, the increased fluid flow through the chamber or chambers 88"" can prevent or diminish the risk of clotting (in the event that blood is transported through the connector 20), bacteria development, or other adverse affects that can result from stagnant fluid inside the connector 20. It will be understood that although the operation of the connector 20 with the support member 28"" was described above with respect to fluid flowing from the proximal end to the distal end of the connector 20, the fluid diverter can also divert fluid into the chamber or chambers 88"" to increase fluid flow therein if fluid is drawn from the distal to proximal ends of the connector 20 (e.g., when drawing blood from a patient into the syringe 120). A fluid diverter can also be used independent of a support member, such as when no support member is present, in which case some embodiments can include a diverter that is attached to or configured to move within the housing or another structure.

It will be understood that although the fluid diverter is shown in FIGS. 26A-26C as being a ball 65"" having a substantially spherical shape, many other shapes of fluid diverters can be inserted into the fluid passageway 69"" to direct fluid into the chamber or chambers 88"", such as a substantially flat plate, a pyramid, diamond, or teardrop-shaped insert, etc. Many variations are possible.

Figure 26D:
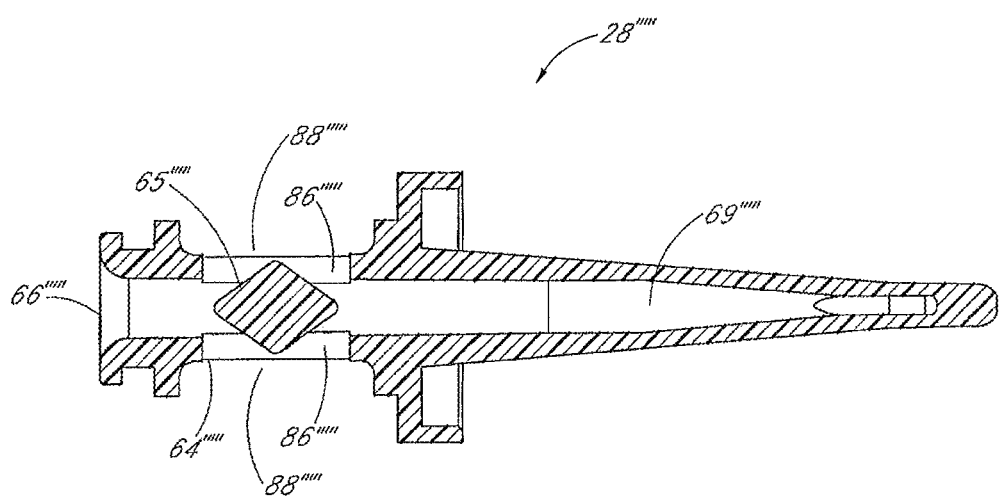
FIG. 26D is a section view of another embodiment of a support member that can be used with the connector shown in FIG. 2A or any other connector disclosed herein.

FIG. 26D is a section view of another embodiment of a support member 28""'. In some embodiments, the support member 28""' can have any of the feature or other details or configurations of the support member 28. Additionally, the support member 28""' can be configured to operate with the body member 22, the base member 24, the seal member 26, or the regulator 30 with little or no modification to those components. Thus, in some embodiments, the support member 28""' can be interchangeable with the support member 28 with little or no modification to the other components of comprising the connector 20. Many features of the support member 28""' illustrated in FIG. 26D can be the same as or similar to the corresponding features of the support member 28.

In some embodiments, the support member 28""' can include a flow diverter 65""' that is integrally formed as part of the support member 28""'. In some embodiments, the flow diverter 65""' can be injection molded as part of the distal portion 64""' of the support member 28""'. The flow diverter 65""' can be positioned in the fluid passageway 69""' such that a portion of the openings 86""' are positioned proximal to the fluid diverter 65""' and a portion of the openings 86""' are positioned distal to the fluid diverter 65'"". Thus, the fluid diverter 65""' can operate in a manner similar to the ball 65"", directing fluid out if the fluid passageway 69""' and into the chamber or chambers 88""' and then from the chamber or chambers 88""' back into the fluid passageway 69""' via the openings 86""'. In some embodiments, as illustrated, the flow diverter can be narrower on its proximal and/or distal ends (where it initially contacts the flowing fluid, depending on the flow direction) than in its intermediate region to assist in more gradually changing the direction of at least a portion of the flowing fluid from a generally vertical flow direction to an increased lateral flow direction. The increased flow of fluid through the chamber or chambers 88""' caused by the fluid diverter 65""' can prevent fluid stagnation in the chamber or chambers 88""'. In some embodiments, the fluid diverter 65""' can be a substantially diamond-shaped piece having rounded corners to divide the flow of fluid without abrupt turns.

Figure 30:
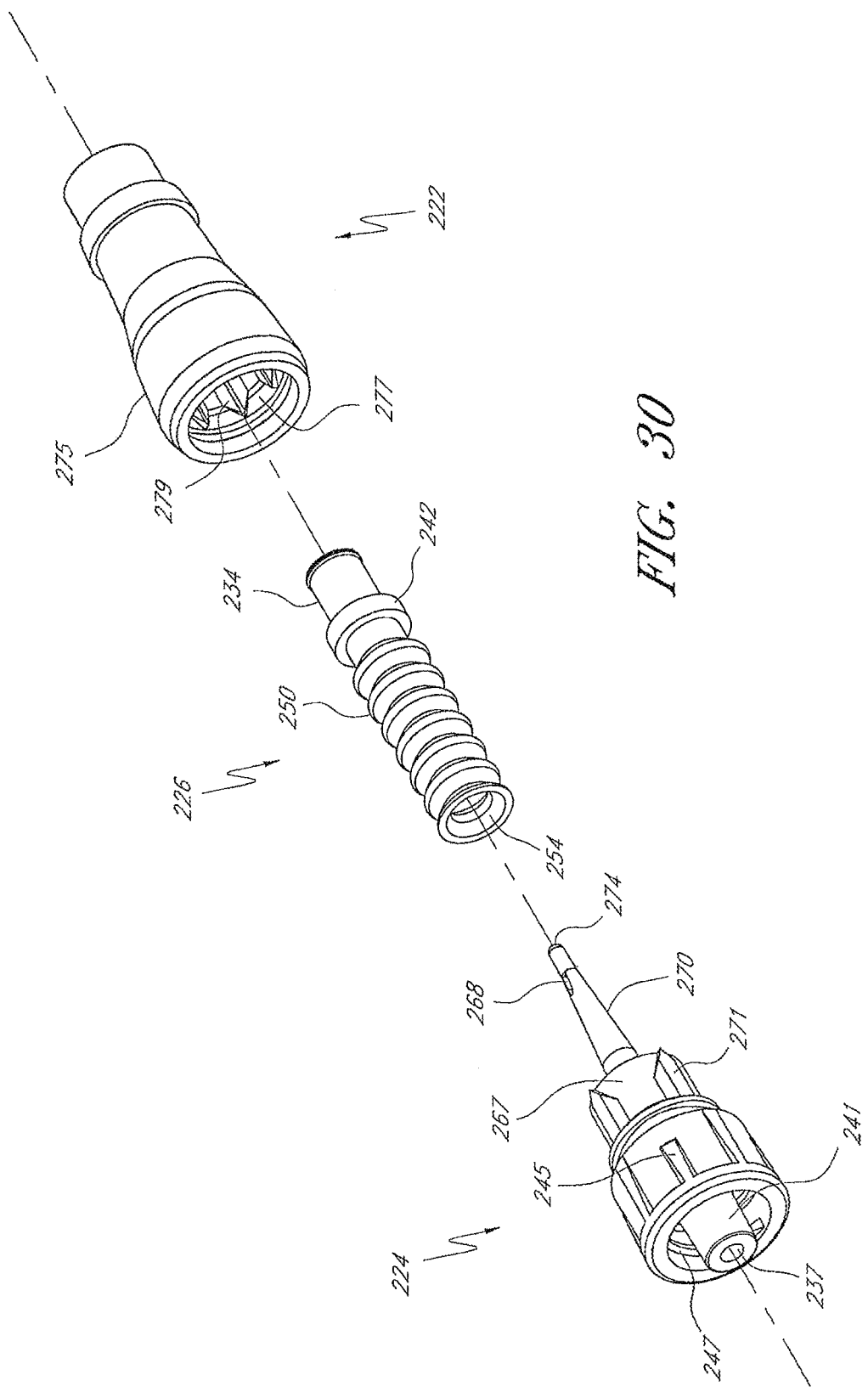
FIG. 30 is a distal exploded view of the embodiment of the connector shown in FIG. 27.

FIGS. 27 and 28 are perspective views of another embodiment of a valve or needleless connector 220. FIGS. 29 and 30 are exploded views of the embodiment of the connector 220 shown in FIG. 27. In some embodiments, the connector 220 can have any of the features or other details or configurations of any other connector described herein, including but not limited to connector 20.

Some embodiments of the connector 220 can be formed so that there is very little dead space volume within the connector 220 as compared to the volume range of a typical bolus of fluid administered to a target patient population. Thus, the volume of fluid entering into the connector 220 can be substantially equivalent to the volume of fluid leaving the connector 220. Further, the total equivalent fluid volume of the connector 220 can be very small such that the volume of fluid flowing through the system in order to place the valve in fluid communication with a medical implement such as a syringe can be very close or equal to zero. Even in embodiments including an internal valve mechanism, such as the embodiment illustrated in FIGS. 1-6, the valve mechanism can be configured to achieve the negative flow compensation effects while reducing dead space.

As will be described, the body member 222 and the base member 224 can be joined together to provide a rigid housing that substantially encapsulates the seal member 226. The body member 222 and the base member 224 can be joined together using any suitable method or features, including but not limited to the features described elsewhere herein for joining the body member 22 with the base member 24.

With reference to FIGS. 27-30, in some embodiments, the connector 220 can comprise a body member 222, a base member 224, and a seal member 226. In some embodiments, the body member 222 and the seal member 226 can be the same or similar to the embodiments of the body member 22 and the seal member 26 or any other body member or seal member described herein. As illustrated, the seal member 226 can be configured such that the proximal end portion 234 of the seal number 226 can be sealingly received by an opening 236 formed in the body member 222. In some embodiments, as in the illustrated embodiment, the proximal end portion 234 of the seal member 226 can have a lip portion 238 (which can be an annular protrusion) formed thereon that is configured to contact the inside surface of the opening 236 of the body member 222 to provide a seal therewith.

The seal member 226 can also comprise an annular collar portion 242, similarly configured as compared to the collar portion 42' of the seal member 26'. In some embodiments, the collar portion 242 can be configured to interact with an inside surface of the body member 222 (which can be an annular protrusion, one or more tabs, or other protruding feature) so as to limit the axial movement of the proximal end portion 234 of the seal member 226 in the proximal direction. In some embodiments, the body member 222 and the seal member 226 can be configured so that the end surface 246 (which can be planar) of the seal member 226 can be adjacent to or approximately coplanar with the end surface 248 of the body member 222, when the seal member 226 is in the closed position. The closed position of the seal member 226 is illustrated in FIG. 27. The seal member 226 and body member 222 can thus be configured so that the end surface 246 can be consistently aligned with the end surface 248 of the body member 222 when the seal member 226 is in the closed position as described in connection with other embodiments herein.

The seal member 226 can have a resilient body portion 250 having a plurality of accordion-like structures configured to permit the seal member 226 to resiliently compress and expand as axial forces are applied to the proximal end portion 234 of the seal member 226. The body portion 250 can have a generally consistent cross-sectional shape throughout the length thereof (as illustrated), or the cross-section of the body portion 250 can vary along at least a portion of the length thereof, such as with the body portion 50' of the seal member 26'. The seal member 226 can have any of features, sizes, or other configuration details of any other seal member disclosed herein.

Additionally, as shown in FIG. 29, a slit or opening 252 can be formed in the proximal end portion 234 of the seal member 226. The seal member 226 can be configured so that the slit 252 is biased to a closed position, so as to substantially prevent or inhibit any liquid from flowing through the slit 252 or the opening 254 formed in the seal member 226. The opening 254 can be configured such that the elongated portion 262 can be received therein. Additionally, as will be described in greater detail below, the slit 252 can be opened by retracting the seal member 226 in the distal direction over the elongated portion 262, causing at least a portion of the proximal end portion of the elongated portion 262 to penetrate and pass through the slit 252.

With reference to FIG. 29, the elongated portion 262 can project from the base member 224. In some embodiments, the elongated portion 262 can have the same features or configurations of any of the other elongated portions described herein, including but not limited to the elongated portion 62. As illustrated, the elongated portion 262 can have one or more openings 268 therethrough. Additionally, the elongated portion 262 can have a tapered (or cylindrical) outer surface 270 and a proximal tip portion 272. The proximal tip portion 272 can have a tapered outer surface, or can be generally cylindrical.

The proximal tip portion 272 can be configured so that the proximal end portion 234 of the seal member 226 in some embodiments can be retracted relative to the proximal tip portion 272 of the elongated portion 262 without significant drag or resistance from the elongated portion 262. In some embodiments, the proximal tip portion 272 can have a sharp or rounded tip 274 configured to penetrate through the slit 252 formed in the seal member 226.

The base member 224 can have a male tip protrusion 241 projecting therefrom, the male tip protrusion 241 defining an opening 237 therethrough that can be in fluid communication with the passageway 269 extending axially through the elongated portion 262 and the one or more openings 268 formed in the elongated portion 262. Additionally, a shroud 243 having protrusions 245 or other features designed to enhance the grip of the connector 220 thereon and internal threads 247 formed on the inside surface of the shroud 243. The base member 224 can be configured to conform with ANSI standards for medical connectors.

Figures 31, 32:
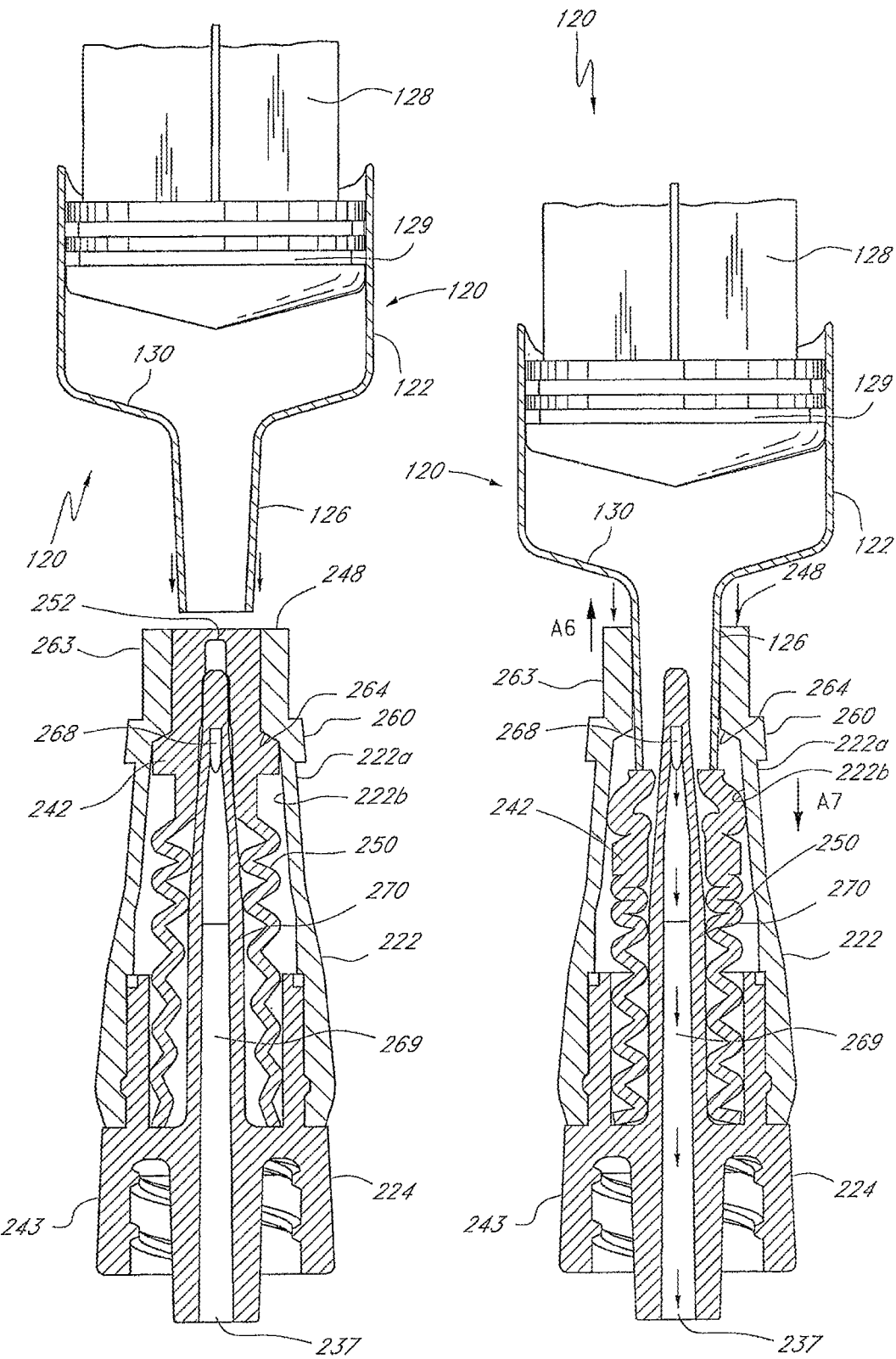
FIG. 31 is a section view of the embodiment of the connector shown in FIG. 27, showing the seal member in a first or closed position before the seal member has been contacted and opened by the syringe.
FIG. 32 is a section view of the embodiment of the connector shown in FIG. 27, showing the seal member in a second or open position after the seal member has been contacted and opened by the syringe.

FIG. 31 is a section view of the embodiment of the connector 220 shown in FIG. 27, showing the seal member 226 in a first or closed position before the seal member 226 has been contacted and opened by the syringe 120. FIG. 32 is a section view of the embodiment of the connector 220 shown in FIG. 27, showing the seal member 226 in a second or open position after the seal member 226 has been contacted and opened by the syringe 120.

The syringe 120 illustrated in FIGS. 31 and 32 (and elsewhere in this disclosure) is an example of one type of medical implements that can be used with the connector 220. However, the connector 220 can be configured for use with a wide range of medical implements and is not limited to use with the syringe 120. The syringe 120 can be any suitable or common syringe used in the medical field.

With reference to FIG. 31, the body member 222 can have an annular ridge or protrusion 260 formed around an outside surface 222a of the body member 222 adjacent to a proximal end portion 263 of the body member 222. The proximal end portion 263 can be smooth and generally cylindrical, or can have external threads or thread features formed thereon so that the connector 220 can be threadedly joined with other suitable medical implements. The inside surface 222b of the body member 222 can be generally smooth (as illustrated in FIGS. 31 and 32). In some embodiments, the inside surface 222b of the body member 222 can include generally axially oriented, generally linearly arranged ridges or channels, or other such features configured to receive portions of the seal member 226 as the seal member 226 is compressed and expanded outwardly against such ridges or channels when the seal member 226 is opened.

Additionally, the body member 222 can include an inside abutment surface 264 that can be configured to interact with the corresponding annular collar portion 242 formed on the seal member 226. The abutment surface 264 and annular collar portion 242 formed on the body member 222 and the seal member 226, respectively, can be configured to limit the motion of the seal member 226 relative to the body member 222 in the proximal direction (e.g., the direction represented by arrow A6 shown in FIG. 32). In some embodiments, the abutment surface 264 and the annular collar portion 242 formed on the body member 222 and the seal member 226, respectively, can be configured to stop the seal member 226 at the approximate position where the end surface 246 of the seal member 226 can be generally adjacent to or approximately coplanar with the end surface 248 of the body member 222 so that the end surface 246 of the seal member 226 cannot protrude past a certain point, such as the region at or near the end surface 248 of the body member 222.

Similar to the base member 24, as illustrated in FIGS. 29 and 30, the base member 224 can include a proximal end portion 267 having one or more protrusions 271 positioned around an outside surface of the proximal end portion 267 of the base member 224. Additionally, the body member 222 can comprise a distal end portion 275 defining an opening 277 extending through the entire body member 222, and one or more channels or notches 279 formed in the distal end portion 275 of the body member 222. The one or more channels or notches 275 can be configured to receive the one or more protrusions 271 formed on the proximal end portion 267 of the base member 224. The protrusions 271 and the notches 275 can be configured to substantially prevent the body member 222 from rotating relative to the base member 224, thereby providing a more secure joint between the body member 222 and the base member 224.

As shown in FIGS. 31 and 32, the body portion 250 of the seal member 226 can extend into the base member 224. The force with which a resilient seal member rebounds to the first or closed position is determined by a number of factors, including the resiliency of the material, the shape of the seal member walls, and the length of the seal member. In some embodiments, the increased length of the body portion 250 of the seal member 226 as compared to certain other seal members disclosed herein can reduce the force with which the seal member 226 returns to the first position upon withdrawal of a syringe or other medical implement, making it easier to disconnect and connect the medical implements. In some embodiments, the body portion 250 in a relaxed state is between approximately 1 and approximately 4 times as long as the proximal portion 234 (including any annular projection) of the seal member 226. In some embodiments, the body portion 250 is between approximately 1.5 and approximately 3 times as long as the proximal portion 234 of the seal member 226. In some embodiments, the body portion 250 is approximately at least 2.5 times as long as the proximal portion 234 of the seal member 226.

The operation of the connector 220 will now be described. FIG. 31 illustrates the position of the components comprising the connector 220 when the seal member 226 is in the closed position (e.g., before a syringe or other medical implement has been joined with the connector 220). In this configuration, the seal member 226 can be biased to the closed position, as illustrated in FIG. 31.

FIG. 32 illustrates the seal member 226 in an open position in response to the insertion of the syringe 120 being joined with the connector 220. As illustrated in FIG. 32, the cannula 126 of the syringe 120 has been pushed in the direction represented by arrow A7 in FIG. 32 against the seal member 226 with sufficient force to overcome the bias of the seal member. 226 so as to cause the seal member 226 to compress within the body member 222. When the seal member 226 has been compressed within the body member 222 to a sufficient distance such that the end surface 246 of the seal member 226 has passed the openings 268 formed in the support member 228, the passageway 269 will be in fluid communication with the inside of the syringe 120. The force that the cannula 126 exerts on the end surface 246 of the seal member 226 can be sufficient to cause a substantially fluid-tight seal between the cannula 126 and the end surface 246 of the seal member 226, so that all or substantially all of the fluid within and/or leaving the syringe 120 is caused to flow into the passageway 269 when the syringe 120 is so joined with the connector 220.

Thus, when the seal member 226 is in the open position, as illustrated in FIG. 32, the plunger 128 of the syringe 120 can be depressed so as to force fluid into the connector 220. Flow arrows in FIG. 32 illustrate that, when fluid is forced from the syringe 120, fluid can flow into the opening or openings 268 formed in the support member 228, through the passageway 269 formed in the support member 228, through the opening 237 formed in the base member 224, and into any other medical implement, if any, joined with the base member 224. As discussed, when the syringe 120 or other medical implement is removed from connector 220, the connector 220 can be configured such that the seal member 226 can return to the closed position due to the bias force within the seal member 226.

In the illustrated embodiment, the connector 220 does not include a backflow prevention module but the connector 220 can be configured to include a backflow resistance module, which can be the same as or similar to the backflow resistance module in connection with the connector 20. For example, the connector 220 can include a variable volume chamber and a valve configured to resist backflow of fluid. In some embodiments, the backflow resistance module can include a regulator similar to the regulator 30.

Figure 33:
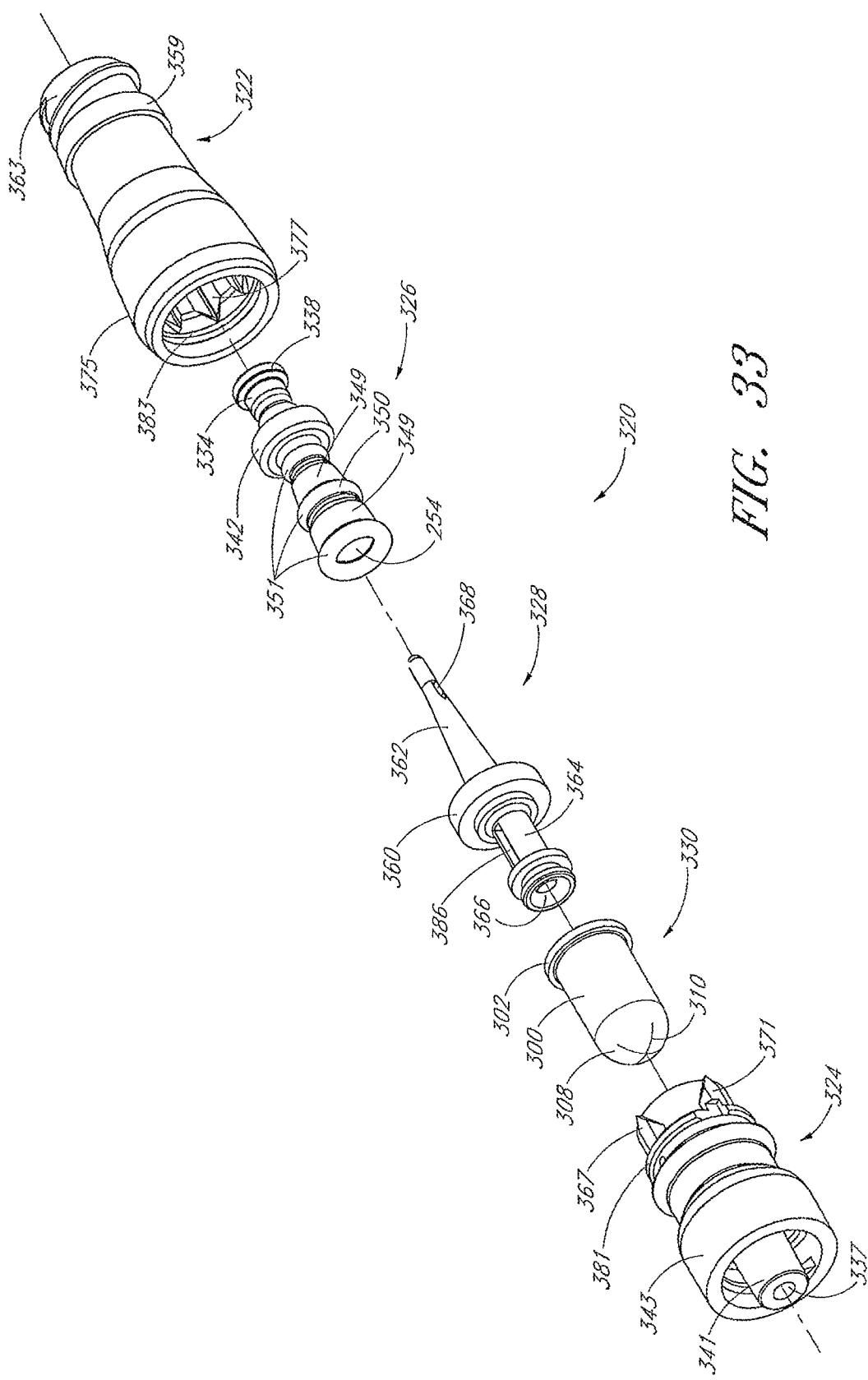
FIG. 33 is a distal exploded perspective view of another embodiment of a connector.
Figure 34:
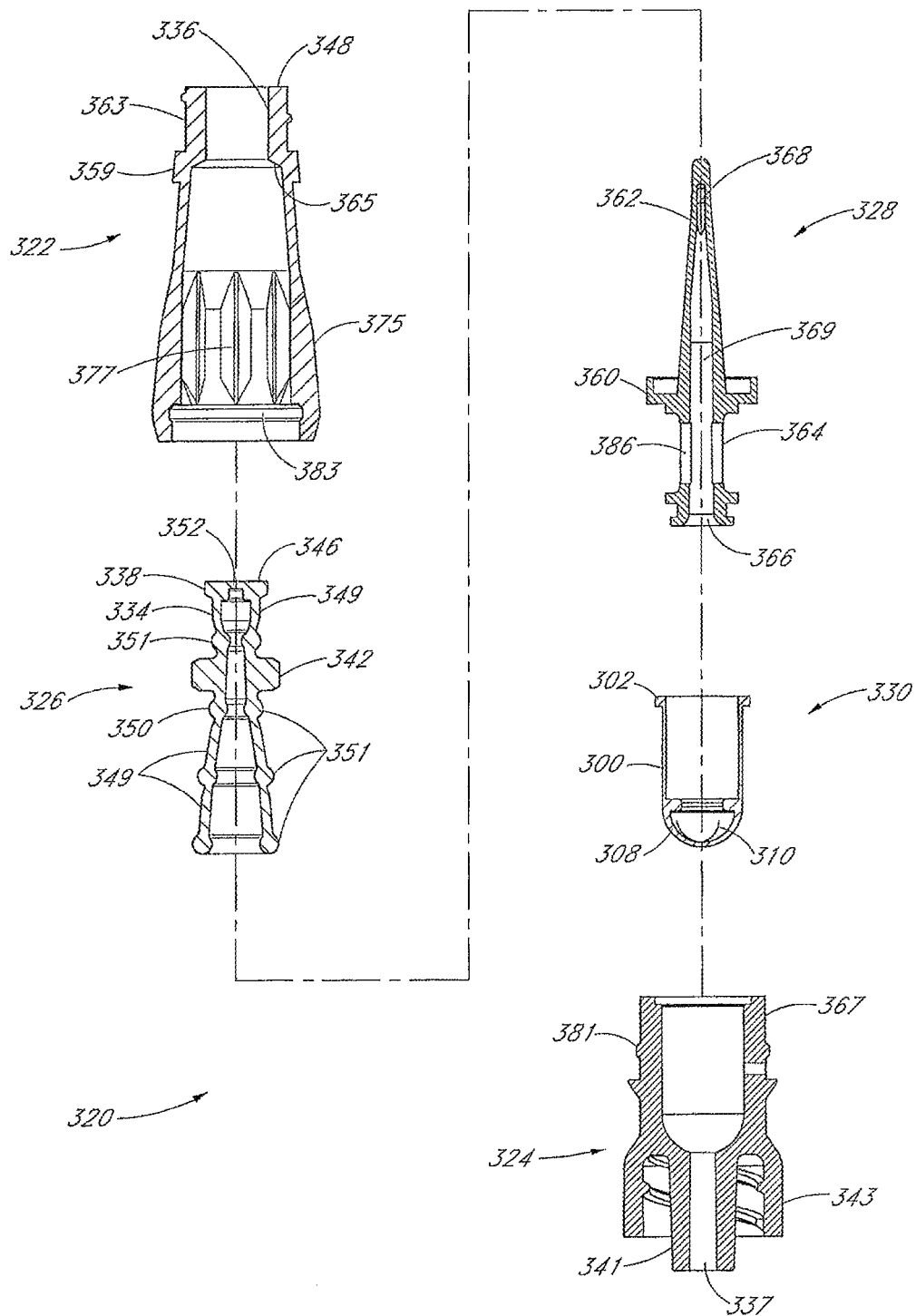
FIG. 34 is an exploded section view of the embodiment of the connector shown in FIG. 33, taken along the axial centerline of the connector.

FIG. 33 is a distal exploded view of another valve or needleless connector 320. FIG. 34 is a exploded section view of connector 320 shown in FIG. 33, taken along the axial centerline of the connector 320. In some embodiments, the connector 320 can have any of the features or other details or configurations of any other connector described herein, including but not limited to connector 20.

With reference to FIGS. 33 and 34, in some embodiments, the connector 320 can comprise a body member 322, a base member 324, a seal member 326, support member 328, and regulator 330, which can be the same as or similar to the body member 22, base member 24, seal member 26, support member 28, and regulator 30 or any other of such components described herein. The body member 322 and base member 324 can be coupled together to form a rigid housing that generally encapsulates the seal member 326, the support member 328, and the regulator 330. The body member 322 can be coupled to the base member 324 using an adhesive, snaps, sonic welding, or any other suitable method of feature, including but not limited to the method and features described herein.

In the illustrated embodiment, the seal 326 can be configured such that the proximal end region 334 thereof can be received by an opening 336 formed in the body member 322. The fitting between the proximal end region 334 and the opening 336 can produce a substantially fluid-tight seal. In some embodiments, the proximal end portion 334 of the seal member 326 can have a lip portion 338 (which can be an annular protrusion) formed thereon that is configured to contact the inside surface of the opening 336 of the body member 322 to provide a moving seal therewith.

The seal member 326 can also have an annular collar portion 342, which can be similar to the collar portion 42' of the seal member 26'. In some embodiments, the collar portion 342 can be spaced distally from the proximal end portion 334 and can be larger in diameter than any other portion of the proximal end portion 334 or any other portion of the seal member 326. The collar portion 342 can be configured to interact with an inside surface of the body member 322 (which can be an annular protrusion, one or more tabs, or other protruding feature) so as to limit the axial movement of the proximal end portion 334 of the seal member 326 in the proximal direction. In some embodiments, the vertical thickness of the collar portion 342 can be at least as large as, or substantially larger than, the thickness of the wall of the seal member 326 in other nearby or adjacent regions, as illustrated, to diminish bending or contortion of the collar portion 342. In some embodiments, the body member 322 and the seal member 326 can be configured so that the end surface 346 (which can be planar) of the seal member 326 can be adjacent to or approximately coplanar with the end surface 348 of the body member 322, when the seal member 326 is in the closed position. The seal member 326 and body member 322 can thus be configured so that the end surface 346 can be consistently aligned generally with the end surface 348 of the body member 322 when the seal member 326 is in the closed position.

The seal member 326 can have a resilient body portion 350 having a plurality of stiffer segments, regions, or o-rings 351 separated by one or more resilient collapsible sections 349 configured to permit the seal member 326 to resiliently compress and expand as axial forces are applied to the proximal end portion 334 of the seal member 326. The body portion 350 can have a generally consistent cross-sectional shape throughout the length thereof, or the cross-section of the body portion 350 can vary along at least a portion of the length thereof (as illustrated). In some embodiments, as illustrated, the proximal region of the seal member 326 can comprise a proximal end region 334 that generally tapers radially inwardly in a downward or distal direction, and a distal region of the seal member 326 that can generally taper radially outwardly in a downward or distal direction. The seal member 326 can have any of the features, sizes, or other configuration details of any other seal member disclosed herein.

Figure 35:
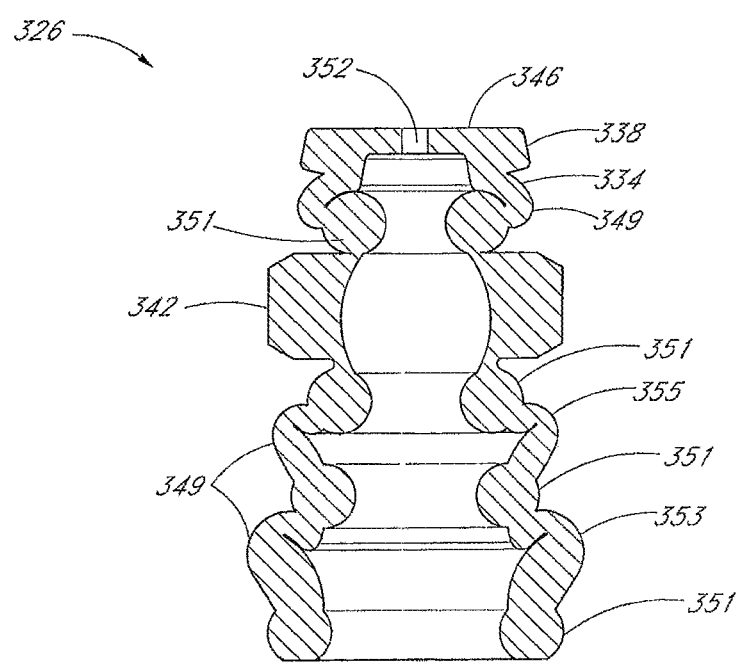
FIG. 35 is a section view of the seal member of the embodiment of the connector shown in FIG. 33 when the seal element is in a second or open configuration, taken along the axial centerline of the seal element.

The seal member 326 is illustrated in the open (e.g., compressed) position in FIG. 35. In an open and/or closed state, the seal member 326 can have collapsible regions with walls that are less than about one-third or less than about one-quarter as thick as the walls of nearby stiffer regions. The collapsible sections 349 can be configured to buckle radially outwardly away from the elongate portion 362 of the support member 328 when the seal member 326 is compressed. The collapsible sections 349 can be horizontally spaced from, and/or generally otherwise configured so that they do not slidingly contact, the elongate portion 362 when the seal member 326 is in the collapsed or open state and/or as the seal member 326 progresses from the closed to the open state. In some embodiments, at least one, some, or all of the stiffer regions, segments, or o-rings 351 are configured to contact the elongate portion 362 as the seal member 326 slides axially thereon. In some embodiments, substantially less than half of the surface area of the inner surface of the seal member 326 contacts the elongate portion 362 when the seal member 326 is in the open or compressed state, and/or as it progresses from the closed to the open state. In some embodiments, the inner surface of the collar portion 342 (e.g., inside of the seal) can be configured to bow radially outwardly when the seal member 326 is compressed. In some embodiments, the proximal portion 334 of the seal member 326 can also include one or more o-rings 351 and/or one or more collapsible sections 349. In some embodiments, the o-rings 351 can protrude radially inwardly so that the collapsible sections 349 and/or the inner surface of the collar portion 342 do not contact the elongate portion 362 when the seal member 326 is in the closed state. The seal member 326 is shown in the closed state, for example, in FIG. 34.

In the open position, as illustrated in FIG. 35, the seal member 326 can include at least one radially outwardly extending portion 349 on its proximal side (for example, between the collar 342, if present, and the proximal end surface 346) that is larger in cross-sectional area (e.g., defined by the outer perimeter) than the surface area of the proximal end portion 346. The seal member 326 can include at least a first radially outwardly extending portion 353 on the distal side (for example, between the collar 342, if present, and the distal end portion) that is larger in cross-sectional area than the collar 342 and/or the surface area of the proximal end portion 346. The seal member 326 can include at least a second radially outwardly extending portion 355 on the distal side that is larger in cross-sectional area than the cross-sectional area of nearby or contiguous portions of the collapsible wall of seal member 326, and smaller in cross-sectional area than the first radially outwardly extending portion 353 on the distal side. In some embodiments, the seal member 326 is free to slide axially on the elongate support member with relatively little frictional resistance because much of the inner surface of the seal member 326 does not contact the elongate portion 362, Thus, the seal member 326 can be configured to reduce the likelihood that the seal member 326 will become stuck in or move slowly away from the open (e.g., compressed) state.

The seal member 326 can be configured in a variety of other manners. For example, in the embodiment illustrated, the seal member 326 includes a plurality (e.g., four) of stiffer regions or segments, such as o-rings, and a plurality (e.g., three) of collapsible sections 349, but other numbers of stiffer regions, segments, or o-rings 351 and/or collapsible sections 349 can be used. Also, in some embodiments, the collapsible sections 349 can be configured to collapse radially inwardly so that a portion of the collapsible sections 349 contacts the elongate portion 362 while other portions of the inner surface of the seal member 326 are maintained out of contact with the elongate portion 362.

A slit or opening 352 can be formed in the proximal end portion 334 of the seal member 326. The seal member 326 can be configured so that the slit 352 is biased to a closed position, so as to substantially prevent or inhibit any liquid from flowing through the slit 352 or the opening 354 formed in the seal member 326. The opening 354 can be configured such that the elongated portion 362 can be received therein. The slit 352 can be opened by retracting the seal member 326 in the distal direction over the elongated portion 362, causing at least a portion of the proximal end portion of the elongated portion 362 to penetrate and pass through the slit 352.

The support member 328 can be the same as or similar to the support member 28, and can include, for example, an elongate portion 362 projecting from a base portion 360 in the proximal direction, and a distal portion 364 projection from the base portion 360 in the distal direction. The distal portion 364 can include an opening 366 that can be in fluid communication with a fluid passageway 369 extending axially through the distal portion 364, the base portion 360 and at least a portion of the elongate portion 362. The elongate portion 362 can include one or more openings 368 in fluid communication with the fluid passageway 369 and the opening 366. The distal portion 364 can include one or more openings 386 in fluid communication with the fluid passageway 369. The support member 328 can have any of features, sizes, or other configuration details of any other support member disclosed herein.

The regulator 330 can be the same as or similar to the regulator 30, and can include, for example, a cylindrical body portion 300, an annular raised proximal portion 302, and a distal end portion 308. The distal end portion 308 can be substantially dome shaped or hemispherically shaped. The distal end portion 308 can have one or more slits 310 formed therein. In some embodiments, the slits 310 can be biased to a closed state, but can open to allow fluid to flow through the regulator 330 if a sufficient pressure differential is applied, as discussed elsewhere herein.

The base member 324 can have a male tip protrusion 341 projecting therefrom, the male tip protrusion 341 defining an opening 337 therethrough that can be in fluid communication with the passageway 369 extending axially through the support member 328 and the one or more openings 368 formed in the elongated portion 362. The base member 324 can also include a shroud 343 having internal threads formed on the inside surface thereof. The base member can include one or more protrusions 371 positioned around an outside surface of the proximal end portion 367 of the base member 324. Additionally, the body member 322 can have one or more channels or notches 377 formed in the distal portion 375 thereof. The one or more channels or notches 377 can be configured to receive the one or more protrusions 371 to substantially prevent the body member 322 from rotating relative to the base member 324. Additionally, the body member 322 can comprise an annular channel 383 configured to receive an annular protrusion 381 formed on the proximal end portion 367 of the base member 324 to provide a snap-fit type connection between the body member 322 and the base member 324.

The body member 322 can have an annular ridge or protrusion 359 formed around an outside surface of the body member 322 adjacent to a proximal end portion 363 of the body member 322. The proximal end portion 363 can be smooth and generally cylindrical, or can have external threads or thread features formed thereon so that the connector 320 can be threadedly joined with other suitable medical implements. Additionally, the body member 322 can comprise an inside abutment surface 365 that can be configured to interact with the corresponding annular collar portion 342 formed on the seal member 326. The abutment surface 36 and annular collar portion 342 formed on the body member 322 and the seal member 326, respectively, can be configured to limit the motion of the seal member 326 relative to the body member 322 in the proximal direction. In some embodiments, the abutment surface 364 and the annular collar portion 342 formed on the body member 322 and the seal member 326, respectively, can be configured to stop the seal member 326 at the approximate position where the end surface 346 of the seal member 326 can be generally adjacent to or approximately coplanar with the end surface 348 of the body member 322 so that the end surface 346 of the seal member 326 cannot protrude past a certain point, such as the region at or near the end surface 348 of the body member 322, or so that the end surface 346 of the seal member 326 cannot protrude past the end surface 348 of the body member 322 by more than a predetermined amount (e.g., at least about 1 mm).

Figure 38:
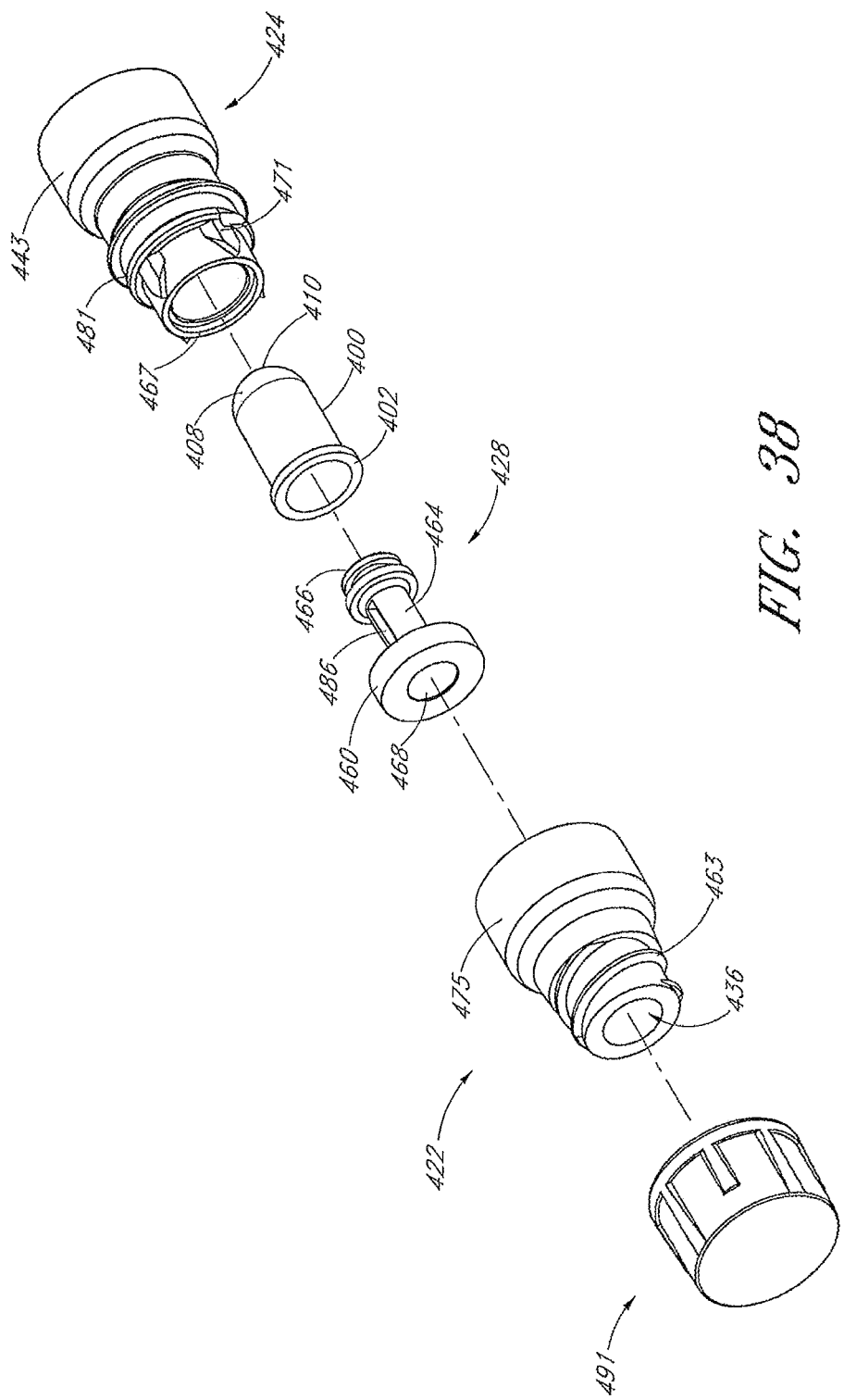
FIG. 38 is a proximal exploded perspective view of the connector shown in FIG. 36.
Figure 39:
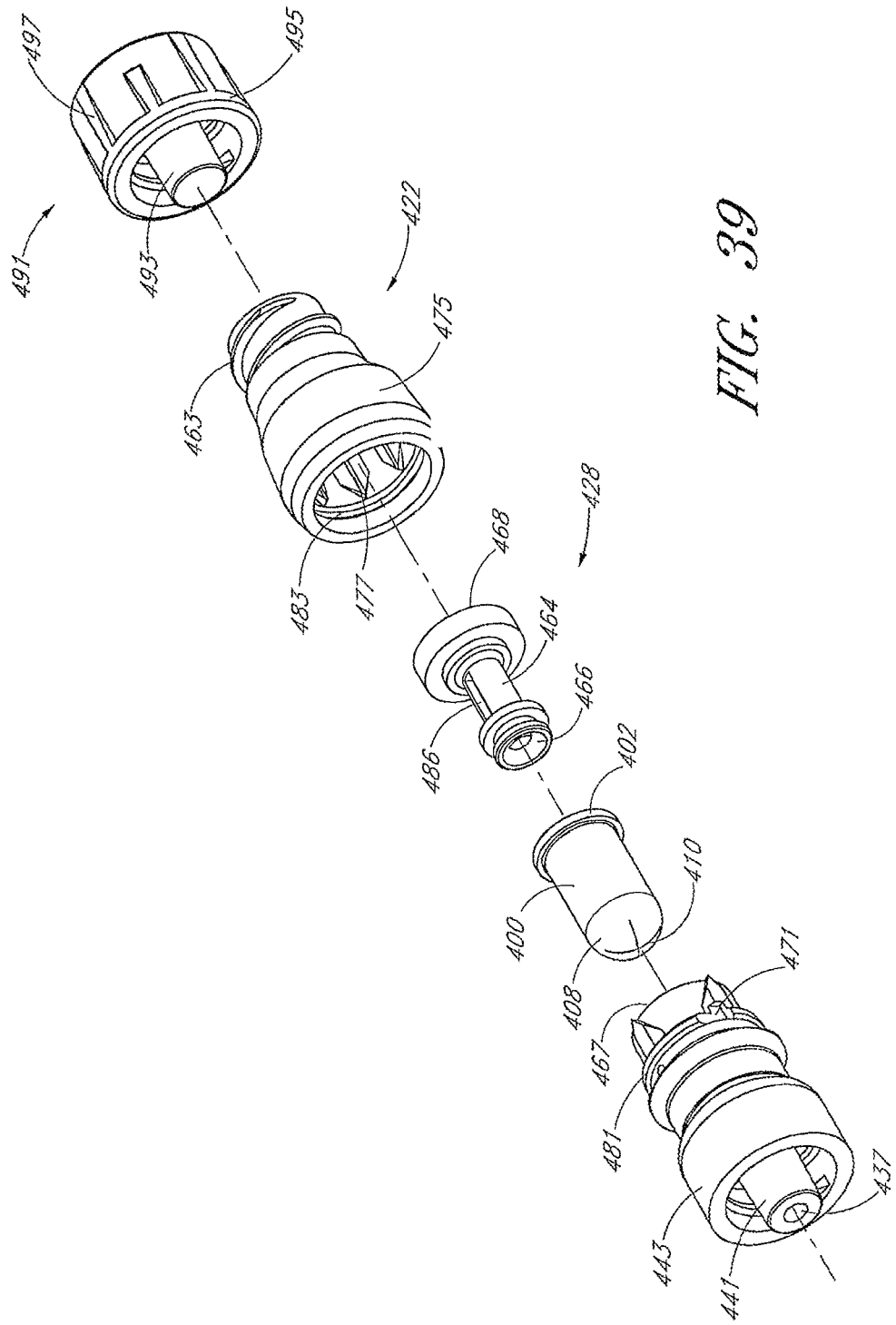
FIG. 39 is a distal exploded perspective view of the connector shown in FIG. 36.
Figure 40:
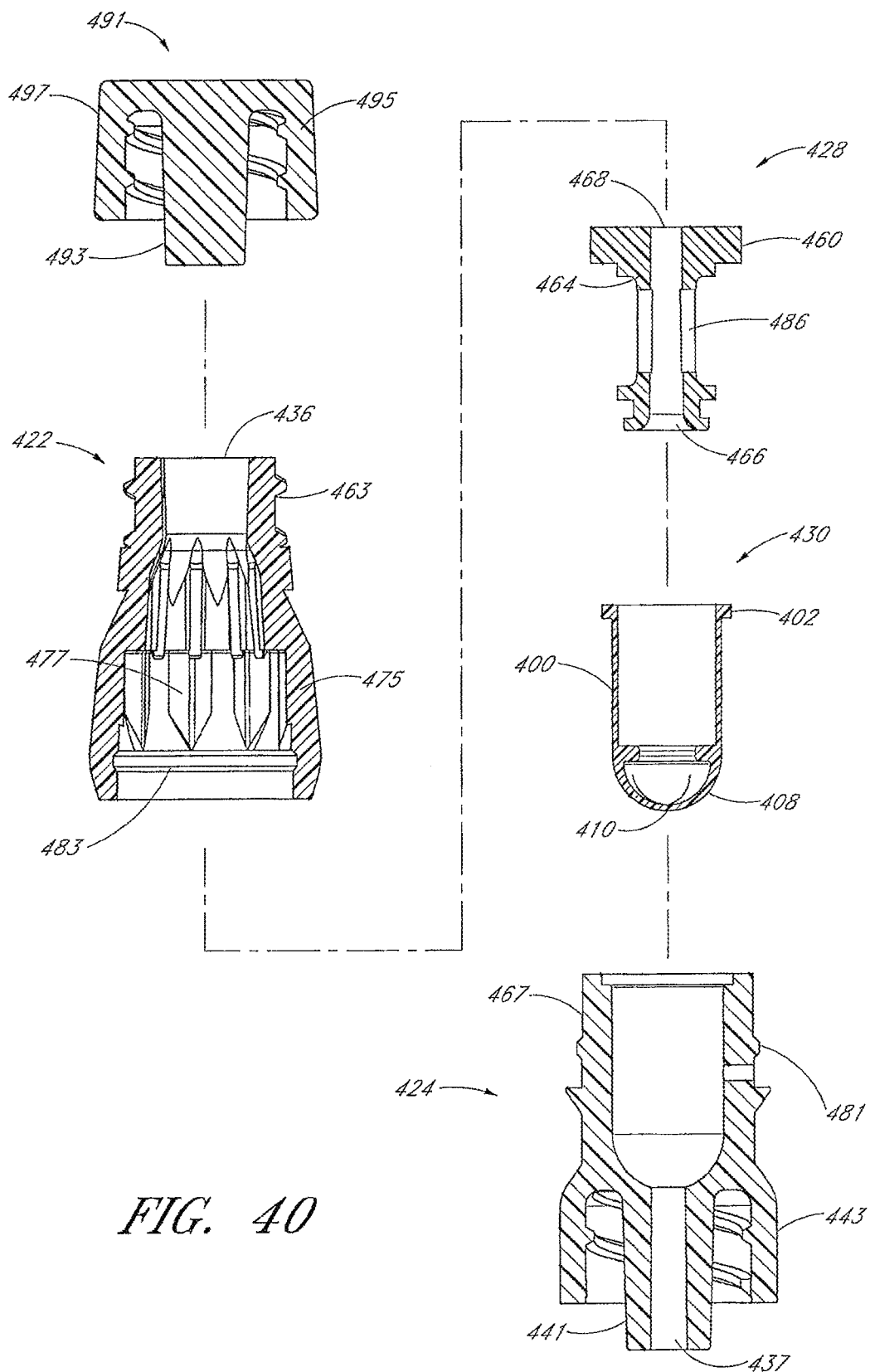
FIG. 40 is an exploded section view of the connector shown in FIG. 36, taken along the axial centerline of the connector.

FIGS. 36 and 37 are perspective views of an embodiment of a valve or needleless connector 420. FIGS. 38 and 39 are exploded perspective views of the connector 420. FIG. 40 is an exploded sectional view of the connector 420. In some embodiments, the connector 420 can have any of the features or other details or configurations of any other connector described herein including but not limited to the connector 20. The connector 420 can be especially suited for use as an intermediate connector in a fluid flow path between two portions of a patient fluid line or catheter, although may other uses are also possible, as illustrated herein.

Referring to FIGS. 36-40, in the illustrated embodiment, the connector 420 can include a body member 422, a base member 424, a support member 428, and a regulator 430, which can be the same as, or similar to, the body member 22, base member 24, support member 28, and regulator 30 in connection with the connector 20. In some embodiments, the connector 420 can include a backflow resistance module, while omitting some of the other features of the connector 20. Notably, the illustrated embodiment can be formed without the seal member. As will be discussed in greater detail below, in some embodiments, the connector 420 can be configured to attach to a connector that does not include backflow prevention (e.g., the illustrated embodiment of connectors 220) to add backflow prevention functionality to the connector. In some embodiments, the connector 420 can be configured to be used directly with a medical implement (e.g., syringe 120).

The body member 422 can be coupled to the base member 424 to form a housing that generally encapsulates the support member 428 and regulator 430. The body member 422 can be coupled to the base member 424 using an adhesive, snaps, sonic welding, or any other suitable method of feature, including but not limited to the method and features described herein.

The support member 428 can be the same as or similar to any of the support members disclosed herein and can include, for example, a base portion 460, and a distal portion 464 projecting from the base portion 460 in the distal direction. The distal portion 464 can include an opening 466 that can be in fluid communication with a fluid passageway 469 extending axially through the distal portion 364 and the base portion 460. The base portion 460 can include an opening 468 in fluid communication with the fluid passageway 469 and the opening 466. The distal portion 464 can include one or more openings 486 in fluid communication with the fluid passageway 469. In some embodiments, as illustrated, the support member 428 can be formed without the elongate portion.

The regulator 430 can be the same as or similar to any of the other regulators, valves, or valve members or components thereof disclosed herein. The regulator 430 can include, for example, a cylindrical body portion 400, an annular raised proximal portion 402, and a distal end portion 408. The distal end portion 408 can be substantially dome shaped or hemispherically shaped. The distal end portion 408 can have one or more slits 410 formed therein. In some embodiments, the slits 410 can be biased to a closed state, but can open to allow fluid to flow through the regulator 430 if a sufficient pressure differential is applied.

The base member 424 can have a male tip protrusion 441 projecting therefrom, the male tip protrusion 441 defining an opening 437 therethrough that can be in fluid communication with the passageway 469 extending axially through the support member 428. The base member 424 can also include a shroud 443 having internal threads formed on the inside surface thereof. The base member 424 can include one or more protrusions 471 positioned around an outside surface of the proximal end portion 467 of the base member 424. Additionally, the body member 422 can have one or more channels or notches 477 formed in the distal end portion 475 thereof. The one or more channels or notches 477 can be configured to receive the one or more protrusions 471 to substantially prevent the body member 422 from rotating relative to the base member 424. Additionally, the body member 422 can include an annular channel 483 configured to receive an annular protrusion 481 formed on the proximal end portion 467 of the base member 424 to provide a snap-fit type connection between the body member 422 and the base member 424.

The body member 422 can have a proximal end portion 463 which can be smooth and generally cylindrical, or can have external threads or thread features formed thereon so that the connector 420 can be threadedly joined with other suitable medical implements such as, for example, a connector that lacks backflow prevention functionality (e.g., the illustrated embodiment of connector 220). An opening 436 can be formed in the proximal end portion 463 of the body member 422. In some embodiments, the connector 420 can be formed without a seal member configured to close the opening 436.

In some embodiments, the connector 420 can also include a cap 491. The cap can include a closed male protrusion 493, and a shroud 495 surrounding the closed male protrusion 493. The shroud 495 can have internal threads formed on the inside surface thereof configured to threadedly mate with the external threads on the proximal end portion 463 of the body member 422. The cap 491 can include gripping features 497 formed on the outside surface of the shroud 495 to facilitate securing or removal of the cap 491. Many variations are possible. For example, in some embodiments, the cap 491 can be formed without the closed male protrusion 493.

Figure 41:
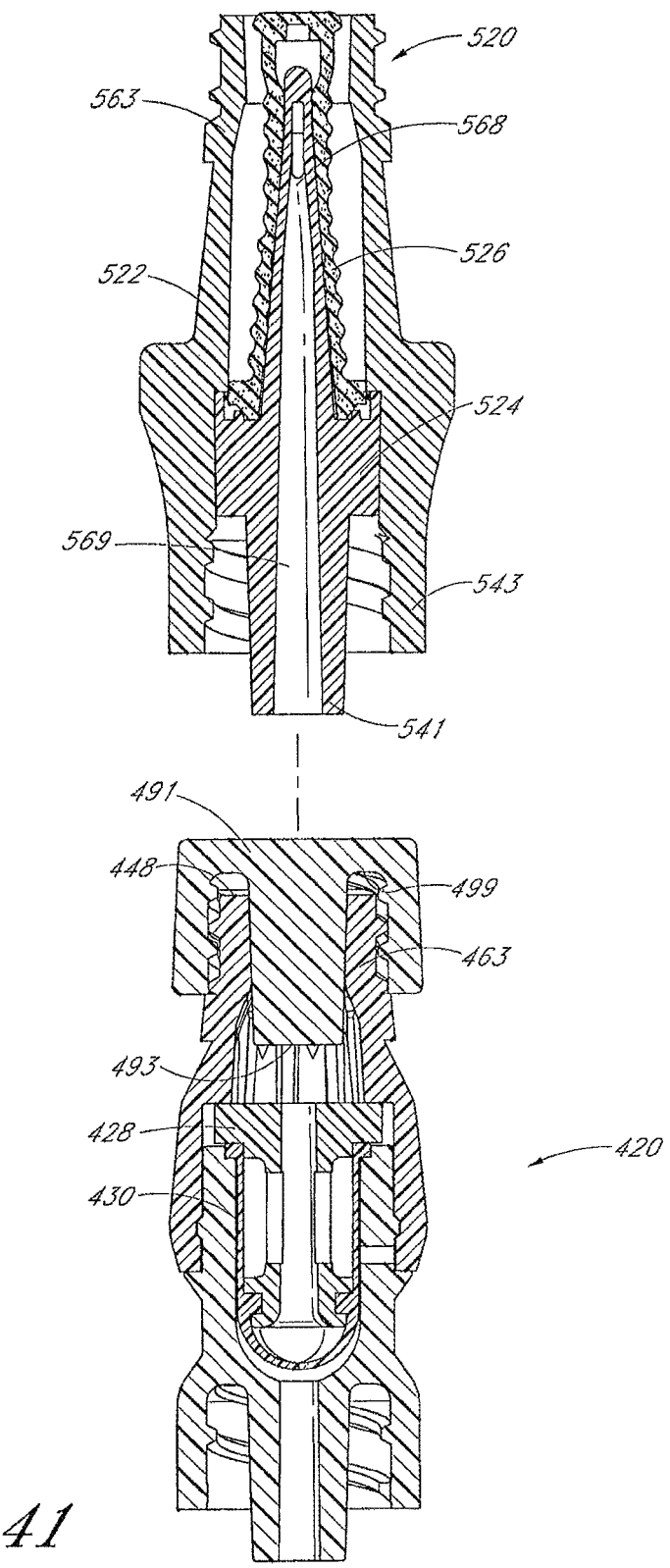
FIG. 41 is a section view of the connector shown in FIG. 36 and an additional needleless connector in an unengaged configuration.
Figure 42:
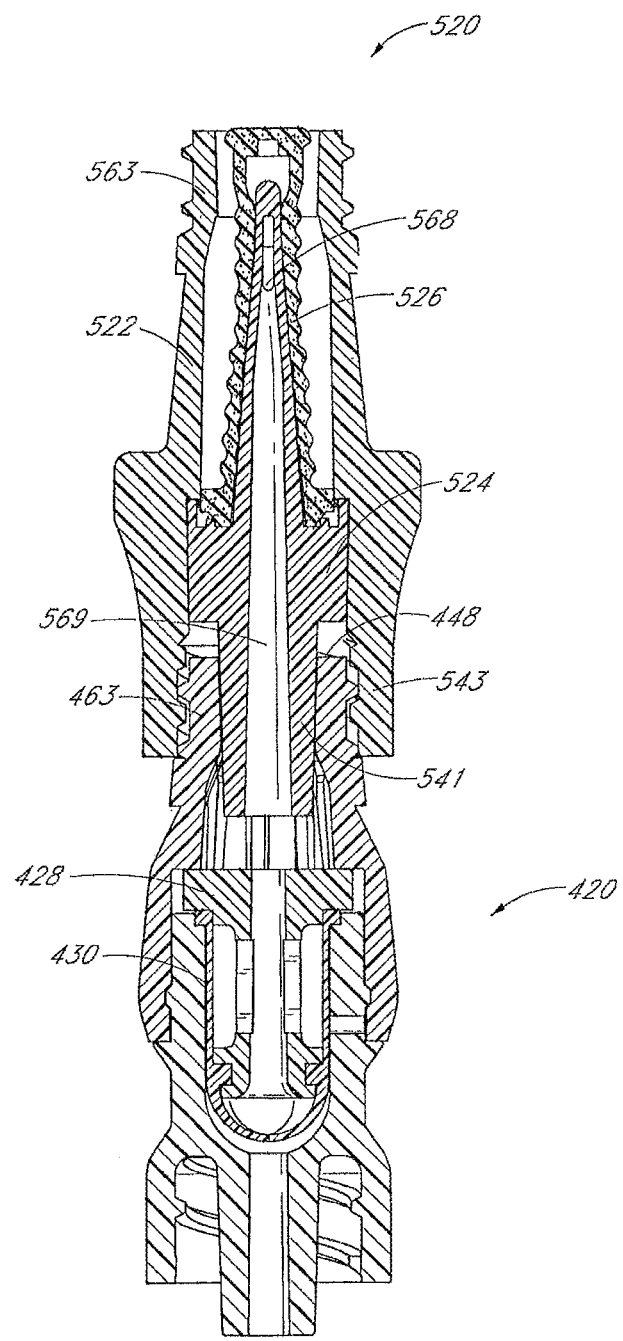
FIG. 42 is a section view of the connector shown in FIG. 36 and the additional connector shown in FIG. 41 in an engaged configuration.

[0282] FIG. 41 is a sectional view of the connector 420 and a connector 520 without backflow prevention functionality 520 in an unengaged configuration. FIG. 42 is a sectional view of the connector 420 and the connector 520 in an engaged configuration. With reference now to FIGS. 41 and 42, the cap 491 can be configured to seal the opening 436 when secured to the proximal end 463 of the body member 422, as shown in FIG. 41. In some embodiments, some portion of the cap (such as closed male protrusion 493, the annular surface 499 surrounding the base of the closed male protrusion 493), can include a seal (e.g., an o-ring) configured to seal against the end surface 448, or other portion, of the body member 422. In some embodiments, the closed male protrusion 493 can extend into the opening 436, and can be configured to seal against the inside surface of the body member 422.

The connector 520 can be, for example, a version of the Clave® connector manufactured by ICU Medical, Inc., of San Clemente, Calif. Various embodiments of a connector of this type are described in U.S. Pat. No. 5,685,866 (the "'866 patent"), the entirety of which is incorporated herein by reference. The connector 520 can include for example, a body member 522, a base member 524, and a seal member 526. The body member 522 can be coupled to the base member 524 to form a housing. The base member 524 can include a male tip protrusion 541 and an elongate. portion 562. A fluid passageway 569 can extend through the male tip protrusion 541 and through at least a portion of the elongate portion 562 to one or more holes 568 formed near the proximal end of the elongate portion 562. The body member 522 can include a shroud 543 configured to surround the male tip protrusion when the body member 522 and base member 524 are coupled to each another. The shroud can have internal threads formed on the inside surface thereof configured to mate with the external threads formed on the proximal end portion 463 of the connector 420. The body member 522 can also include a proximal end 563 that can include external threads so that the connector 520 can be threadedly joined with other suitable medical implements (e.g., a syringe).

The seal member 526 can be positioned so that it surrounds at least a portion of the elongate portion 562. The seal member 526 can be the same as or similar to the seal member 26 or any other seal member described herein. In some embodiments, the seal member 562 can be configured to resiliently compress when a medical implement is attached to the proximal end 563 of the connector 520, exposing the one or more holes 568 on the elongate portion 562 and opening a fluid connection between the fluid passageway 569 and the medical implement.

In some embodiments, the connector 520 does not include backflow prevention functionality, such that if the connector 520 where used without having the connector 420 attached thereto, the connector 520 may experience a degree of fluid backflow upon the occurrence of a syringe rebound, medical implement disconnect, or other backflow inducing event. The connector 420 can include a backflow resistance module, which can be made up of various components of the connector 420 such as the regulator 430, the support member 428, etc. Under some circumstances, the connector 420 can be coupled to the connector 520 (as shown in FIG. 42) to add backflow prevention functionality to the connector 520. Thus, when the connector 520 is coupled to the connector 420, the backflow resistance module can function substantially as described elsewhere herein to prevent fluid backflow out of the connector 520 in the event of a syringe rebound, or other backflow inducing event. It will be understood that the connector 520 can be any of a variety of other connector types. Thus, the connector 420 can be used to add backflow prevention functionality to a variety of connector types that provide a variety of different features.

Under some circumstances, the connector 420 can remain coupled to the connector 520 throughout the period of use of the connector 520, such that, once connected, the connectors 420 and 520 can be treated as a single connector. In some embodiments, the connector 420 can be coupled to the connector 520 prior to being packaged or sold to the user. In some embodiments, the connector 420 can be permanently coupled to the connector 520 (e.g., using plastic welding or the like) prior to being packaged or sold to the user. In some embodiments, the connector 420 can be used without the cap 491. For example, if the connector 420 is sold pre-attached to the connector 520, no cap 491 is used. Also, the connector 420 without a cap 491 can be enclosed in sterile packaging designed to be opened immediately prior to connecting the connector 420 to the connector 520.

Under some circumstances, a medical implement such as a syringe can be connected directly to the proximal end portion 463 of the connector 420 without the connector 520 being positioned therebetween. However, in some embodiments, the connector 420 does not include a resilient seal member (e.g., the seal member 526) to reseal the opening 436 each time the medical implement is removed. Thus, the use of the connector 420 without the connector 520 attached thereto can be advantageous, for example, in circumstances when the medical implement is to be connected to the connector 420 only once, or a relatively few number of times. In some embodiments, the cap 491 can be used to seal the proximal end portion 463 after the medical implement has been removed. In some embodiments, a fresh, sterilized cap can be used.

Figure 43:
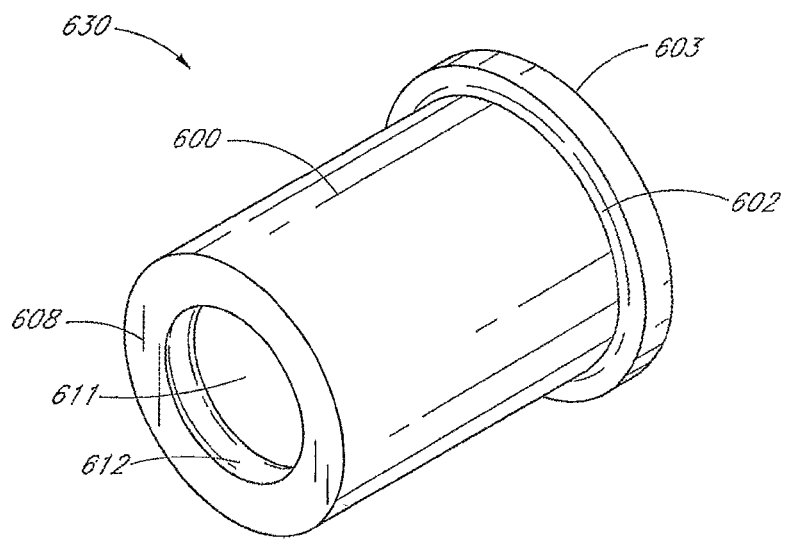
FIG. 43 is a distal perspective view of an embodiment of a dynamic volume adjuster.
Figure 44:
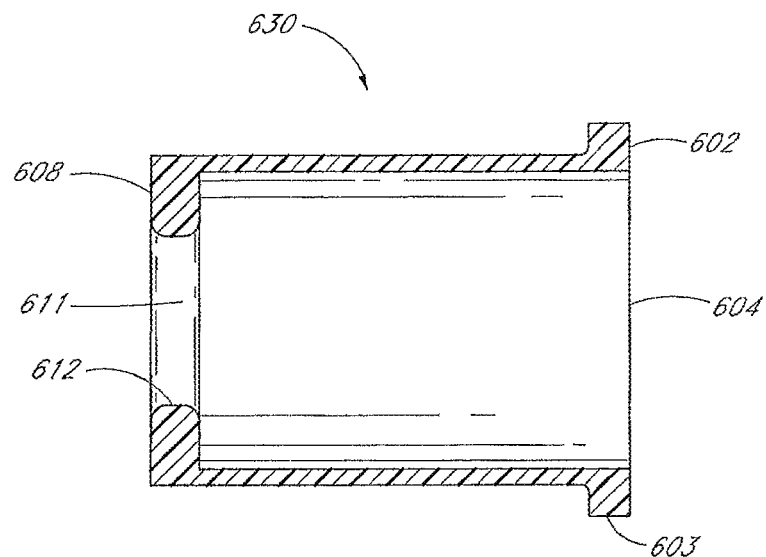
FIG. 44 is a section view of the dynamic volume adjuster shown in FIG. 43 taken along the axial centerline of the dynamic volume adjuster.

FIG. 43 is a perspective view of an embodiment of a regulator 630. FIG. 44 is a section view of the regulator 630 shown in FIG. 43 taken through the axial centerline of the regulator 630. The regulator 630 can include a body portion 600, which can be, for example, substantially cylindrical. The proximal end portion 602 of the regulator 630 can include an annular raised lip 603 and an opening 604 therethrough. The distal end portion 608 can include an inner annular protrusion 612 and an opening formed therethrough. In some embodiments, as illustrated, the regulator 630 can be formed without a closure portion (such as the distal end portion 108 and slits 110 in connection with the regulator 30). Thus, in some embodiments a fluid passageway is constantly open through the regulator 630.

Figure 45:
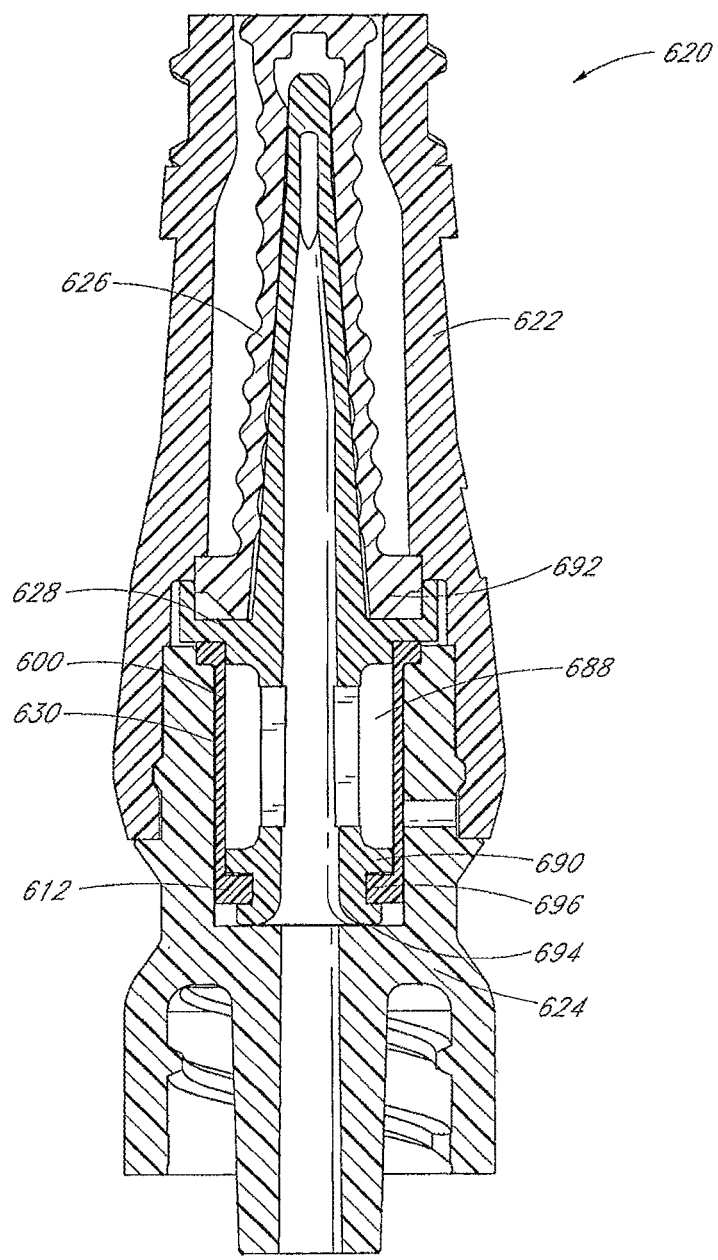
FIG. 45 is a section view of a valve or needleless connector that includes the dynamic volume adjuster shown in FIG. 43.

FIG. 45 is a sectional view of a valve or needleless connector 620 configured to use the regulator 630 shown in FIG. 43. In some embodiments, the connector 620 can have any of the features or other details or configurations of any other connector described herein. In some embodiments, the connector 620 can include a body member 622, a base member 624, a seal member 626, a support member 628, and the regulator 630, which can be, for example, the same as, or similar to, the body member 22, base member 24, seal member 26, support member 28, and regulator 30 in connection with the connector 20.

The regulator 630 can be positioned over the distal portion 664 of the support member 628, defining an annular cavity 688 between two annular protrusions 690, 692 on the support member 628. The inner annular protrusion 612 can be received within the channel 696 formed between the annular protrusions 690, 694 to secure the regulator 630 to the support member 628. In some embodiments, as illustrated, the regulator is in constant fluid communication with the distal end of the fluid path inside the valve.

The regulator 630, or at least a portion thereof, can be formed from one, or a combination, of various suitable materials including, but not limited to, rubber, silicone-based deformable materials, and the like, such that the body portion 600 of the regulator 630 can deflect inwardly, reducing the volume of the annular cavity 688 to compensate for a syringe rebound or other backflow inducing event. In some embodiments, the regulator 630 can be configured such that less force is required to deflect the body portion 600 of the regulator 630 inwardly to reduce the volume of the annular cavity 688 than to draw a similar volume of fluid from the patient toward the connector 620 (e.g., against gravity). Thus, if a syringe rebound, or other backflow inducing event, occurs, the body portion 600 of the regulator 630 can collapse, reducing the volume of the annular cavity 688 and expelling fluid to compensate for the vacuum and prevent or delay backflow.

Figure 46:
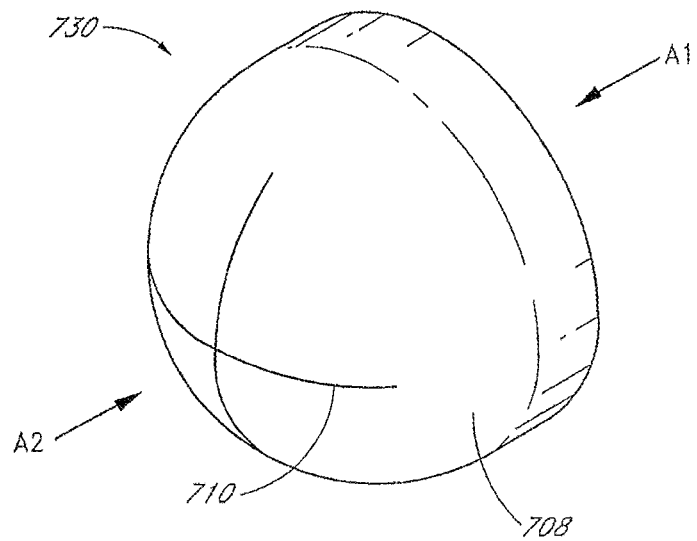
FIG. 46 is a distal perspective view of an embodiment of a valve member.
Figure 47:
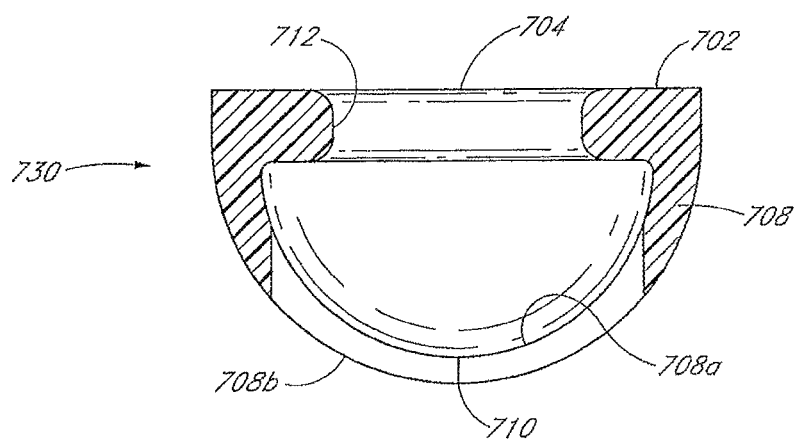
FIG. 47 is a section view of the valve member shown in FIG. 46, taken along the axial centerline of the valve member.

FIG. 46 is a perspective view of an example of a valve member 730. FIG. 47 is a section view of the valve member 730 shown in FIG. 46. The valve member 730 can include a proximal end portion 702 that includes an inner annular protrusion 712 and an opening therethrough 704. The valve member 730 can also include a distal end portion 708 that can be substantially dome or hemispherically shaped, and can include one or more slits 710. Similarly to the regulator 30, the valve member 730 can be configured to remain closed and resist fluid flow until a pressure threshold is reached, at which point the slits 710 on the valve member 730 can open to allow fluid to flow therethrough. In some embodiments, the valve member 730 can be configured such that greater force is required to open the valve member 730 in a first direction (e.g., in the A2 direction) than in a second direction (e.g., in the A1 direction).

Figure 48:
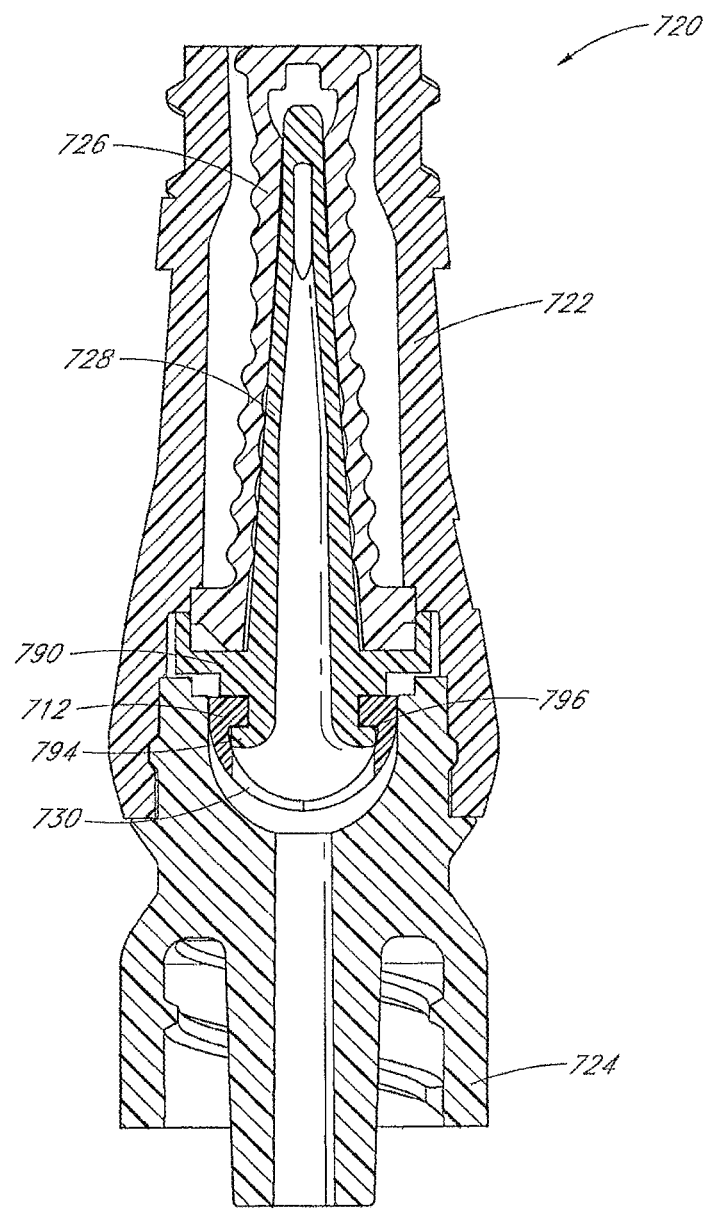
FIG. 48 is a section view of a valve or needleless connector that includes the dynamic volume adjuster shown in FIG. 46.

FIG. 48 is a section view of a valve or needleless connector 720 configured to use the valve member 730 shown in FIG. 46. In some embodiments, the connector 720 can have any of the features or other details or configurations, of any other connector described herein. In some embodiments, the connector 720 can include a body member 722, a base member 724, a seal member 726, a support member 728, and the valve member 730, which can be, for example, the same as, or similar to, the body member 22, base member 24, seal member 26, support member 28, and regulator 30 in connection with the connector 20.

The valve member 730 can be positioned over the distal portion 764 of the support member 728 so that the inner annular protrusion 712 is received within the channel 796 formed between the annular protrusions 790, 794 to secure the valve member 730 to the support member 728.

In some embodiments as illustrated, the connector 720 can be formed without a variable volume chamber (e.g., the annular cavity 88). In these embodiments, because no variable volume chamber is present to alleviate the pressure caused by a syringe rebound, or other backflow inducing event, the valve member 730 may be configured to more rigorously resist backflow. For example, in some embodiments, the pressure of the fluid acting on the outside surface 708b of the valve member 730 can be between approximately 1.0 atmosphere and approximately 2.0 atmospheres greater than the pressure of the fluid acting on the inside surface 708a of the valve member 730 for the valve member 730 to open in allow fluid flow in the A2 direction. The valve member 730 can be modified in various ways to increase the threshold pressure required to open the valve member for fluid flow in the A2 direction. For example, the curvature, or thickness, or materials of the domed distal end portion 708 can be modified to adjust the backflow threshold pressure. Also, the number or orientation of the slits 710 can be modified to adjust the backflow threshold pressure.

Figure 49:
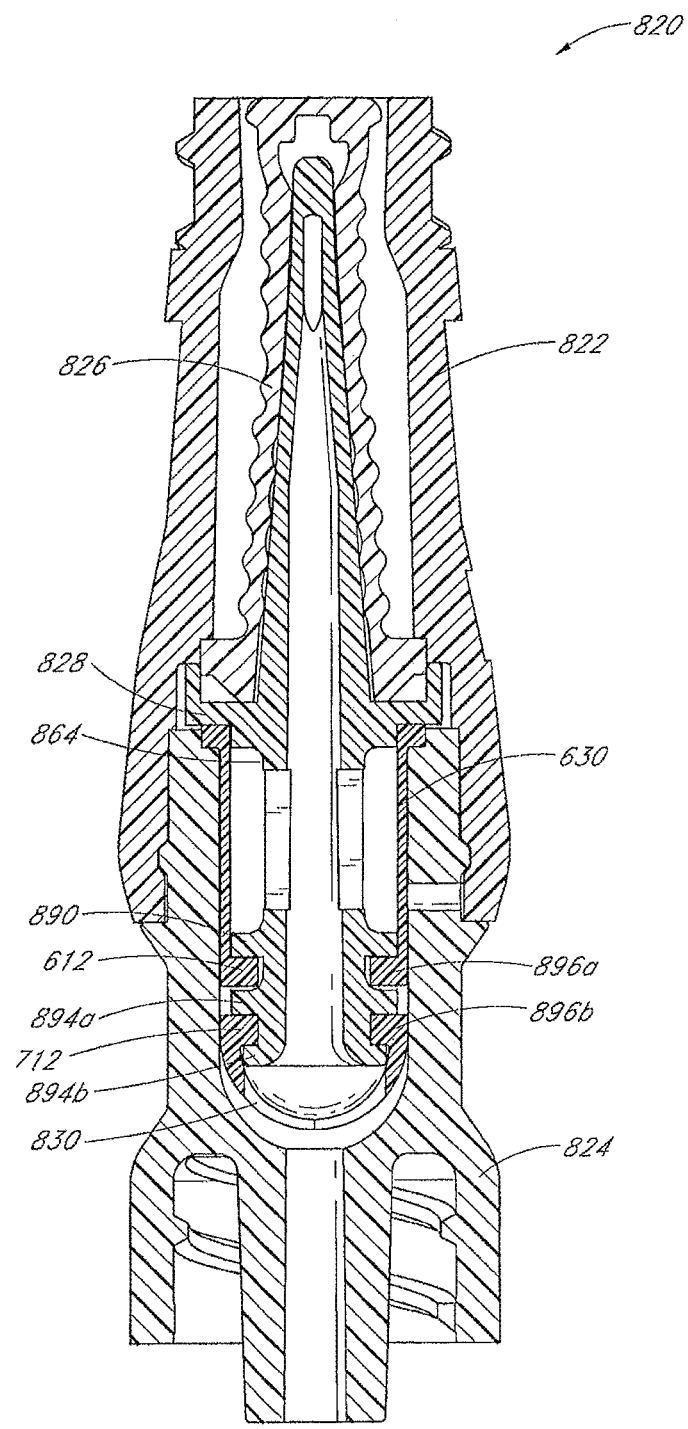
FIG. 49 is a section view of a valve or needleless connector that includes both the dynamic volume adjuster shown in FIG. 43 and the valve member shown in FIG. 46.

FIG. 49 shows a section view of an embodiment of a valve or needleless connector 820 configured to use both the regulator 630 shown in FIG. 43 and the valve member 730 shown in FIG. 46. In some embodiments, the connector 820 can have any of the features or other details or configurations of any other connector described herein. In some embodiments, the connector 820 can include a body member 822, a base member 824, a seal member 826, a support member 828, the regulator 630, and the valve member 730, which can be, for example, the same as, or similar to, the body member 22, base member 24, seal member 26, support member 28, and regulator 30 in connection with the connector 20.

In some embodiments, the support member 828 can include a first channel 896a formed between the annular protrusions 890, 894a, and a second channel 896b formed between the annular protrusions 894a, 894b. When assembled, the regulator 630 and valve member 730 can be positioned over the distal portion 864 of the support member 828. The inner annular protrusion 612 of the regulator 630 can be received within the channel 896a and the inner annular protrusion of the valve member 730 can be received within the channel 896b, to prevent the regulator 630 and the valve member 730 from moving axially with respect to the support member 828. In some embodiments, the connector 820 can function similarly to the connector 20, except that the variable volume chamber and backflow resist valve are provided by a separate regulator 630 and valve member 730.

Figure 50A:
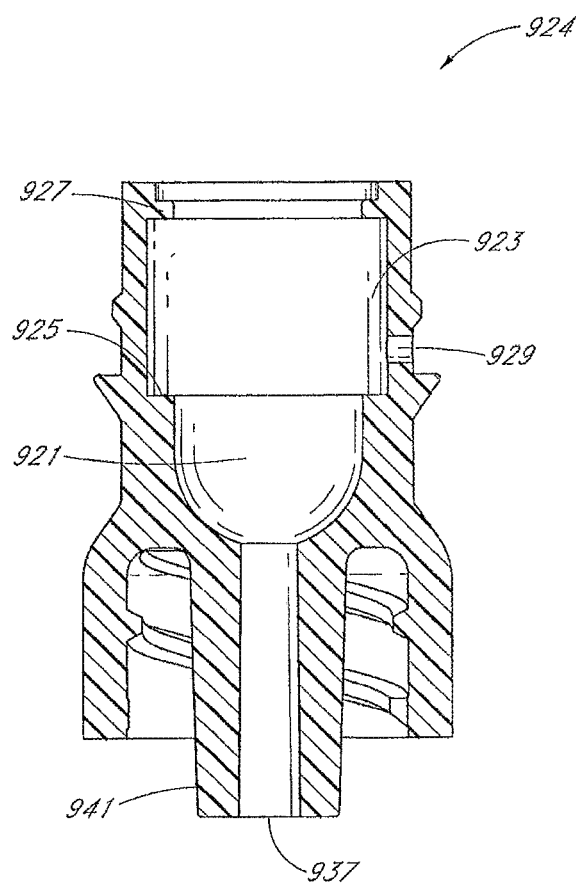
FIG. 50A is a section view of an embodiment of a base member.

FIG. 50A is a section view of a base member 924. The base member 924 can be similar in some regards to the base member 24. The base member 924 can include a male tip protrusion 941 that includes an opening 937 therethrough that can be in fluid communication with a cavity 921 formed in the base member 924. The cavity 921 can have an annular recess 923 between an annular step 925 and an annular protrusion 927. A hole 929 extending through the wall of the base member 924 can provide access to the annular recess 923 so that air from outside the base member 924 can flow into and out of the annular recess 923 through the hole 929.

Figure 50B:
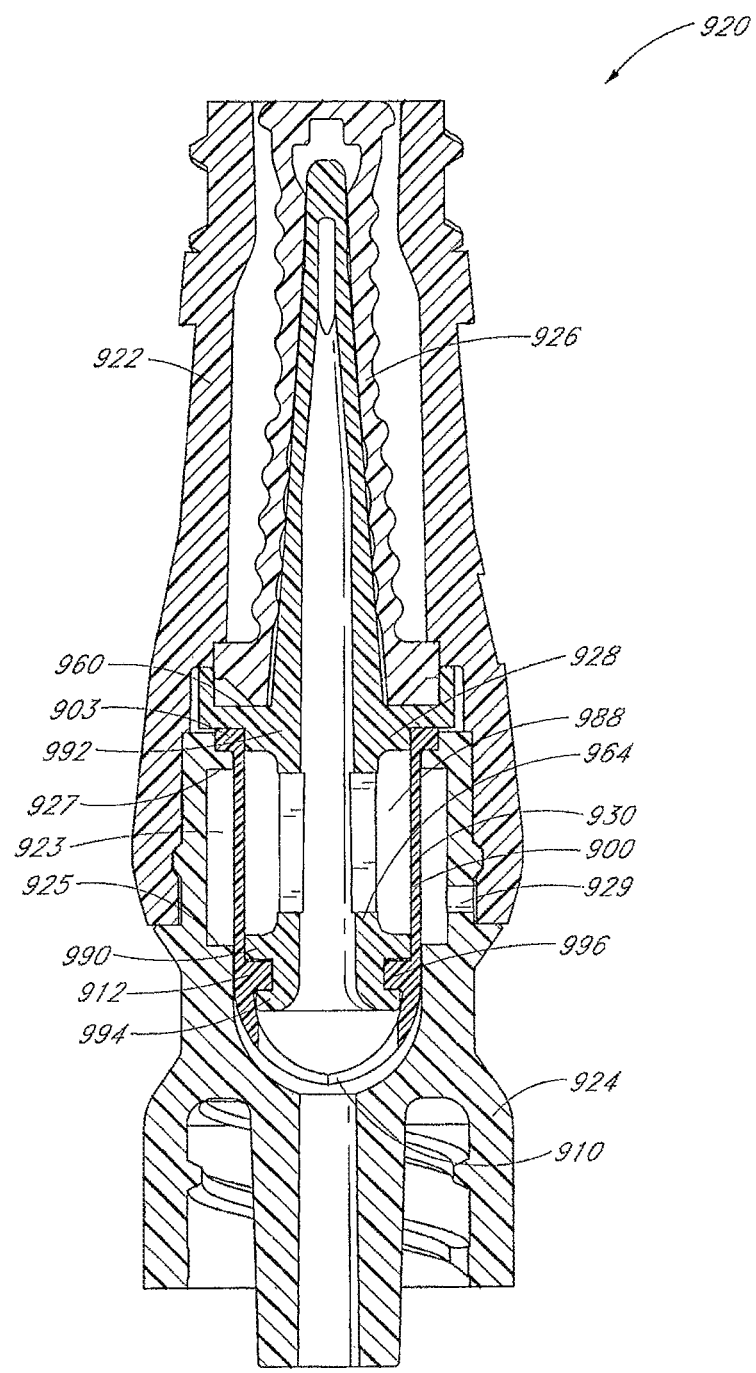
FIG. 50B is a section view of a valve or needleless connector that includes the base member shown in FIG. 50A.

FIG. 50B shows a section view of an embodiment of a valve or needleless connector 920 that uses the base member 924 shown in FIG. 50A. In some embodiments, the connector 920 can have any of the features or other details or configurations of any other connector described herein. In some embodiments, the connector 920 can include a body member 922, the base member 924, a seal member 926, a support member 928, and a regulator 930 which can be, for example, the same as, or similar to, the body member 22, base member 24, seal member 26, support member 28, and regulator 30 in connection with the connector 20.

In some embodiments of the connector 920, the variable volume chamber can be configured to expand when fluid is infused from a medical implement (e.g., a syringe) into the connector 920. The variable volume chamber can be configured to return to its natural, unexpanded volume, or shrink to a volume that is less than its natural volume, to compensate for syringe rebound, or other backflow inducing events, and prevent backflow.

The regulator 930 can be positioned over the distal portion 964 of the support member 928, defining an annular cavity 988 between the two annular protrusions 990, 992 on the support member 928. The inner annular protrusion 912 of the regulator 930 can be received within the channel 996 formed between the annular protrusions 990, 994 to secure the regulator 930 to the support member 928. The annular raised portion 903 of the regulator 930 can be secured between the base portion 960 of the support member 928 and the top surface of the annular protrusion 927 of the base member 924, sealing the top of the annular recess 923. In some embodiments, the annular protrusion 90 can press the wall of the regulator 930 against the inside wall of the cavity 921 below the annular step 925 to form an airtight seal. Thus, air that enters the annular recess 923 through the hole 929 can be prevented from traveling to other parts of the connector 920 or from entering the fluid stream as a bubble, which can cause a serious health risk to the patient.

In some embodiments, the body portion 900 of the regulator 930 can be configured to flex outwardly into the annular recess 923, thereby increasing the volume of the annular cavity 988, when pressure is applied to the inside surface of the body portion 900, such as when infusing fluids from a medical implement (e.g., a syringe) into the connector 920. In some embodiments, the force required to expand the volume of the annular cavity 988 is less than the force required to open the slits 910 on the regulator 930 to allow fluid flow in the distal direction. Thus, when fluid is infused into connector 920 from a medical implement (e.g., a syringe), the annular cavity 988 expands until the force required to further expand the annular cavity 988 is greater than the force required to open the regulator 930 for fluid flow in the distal direction, at which point the regulator 930 opens and fluid is pushed out the distal end of the connector 920. When a syringe rebounds, or other backflow inducing event occurs, the body portion 900 of the regulator 930 can return to its unexpanded position, reducing the volume of the annular cavity 988, compensating for the vacuum, and preventing backflow from occurring. In some circumstances, the volume of the annular cavity 988 can be reduced beyond its natural, unexpanded volume by the body portion 900 of the regulator 930 flexing inwardly into the annular cavity 988, thereby providing additional vacuum compensation. In some embodiments, the body portion 900 of the regulator 930 can stretch as it expands so that the body portion 900 contains an amount of potential energy in its expanded state. In some embodiments, the amount of potential energy is not enough to produce adverse effects, such as raising the plunger of the syringe, or opening the slits in the regulator 930.

In some embodiments, the connector 920 can be configured so that the body portion 900 of the valve body 930 is positioned substantially flush against the distal portion 964 of the support member 928 when in the unexpanded state. In this embodiment, no annular cavity 988 is present when the body portion 900 is in the unexpanded state. The body portion 900 can expand outwardly into the annular recess 923 when fluid is infused into the connector 920. To prevent backflow, the body portion 900 can return to the unexpanded state, but does not flex inwardly to further reduce the volume in the connector 920. In some embodiments, the distal portion 964 of the support member 928 can be thicker than as shown in FIG. 50B, so that no annular cavity 988 is formed between the annular protrusions 990, 992, and the body portion 900 of the regulator 930 can sit flush against the distal portion 996 of the support member 928.

In some embodiments, the base member 924 can be formed without the hole 929, and the annular recess 923 can be filled with a compressible fluid, such as air or some other gas. Thus, when the body portion 900 flexes, the compressible fluid can expand or compress, as needed, to allow the volume of the annular recess 923 to increase or decrease accordingly.

FIG. 51 is a perspective view of an embodiment of a regulator 1030. The regulator 1030 can be similar in some regards to the regulator 30, or any other regulator or valve member disclosed herein. In some embodiments, the regulator 1030 includes a body portion 1000, a proximal end portion 1002, and a distal end portion 1008. The proximal end portion 1002 can include an annular raised lip 1003 and an opening 1004 therethrough. The distal end portion 1008 can be substantially dome shaped or hemispherically shaped, and can include a single slit 1010 therethrough. The single slit 1010 can be formed to various different sizes. In some embodiments, the width of the single slit 1010 can be equal to or smaller than the width of the opening 1004. The slit 1010 can be symmetrically or asymmetrically formed in the distal end portion 1008 of the regulator 1030.

FIG. 52 is a perspective view of an embodiment of a regulator 1130. The regulator 1130 can be similar in some regards to the regulator 30, or any other regulator or valve member disclosed herein. In some embodiments, the regulator 1130 includes a body portion 1100, a proximal end portion 1102, and a distal end portion 1108. The proximal end portion 1102 can include an annular raised lip 1103 and an opening 1104 therethrough. In some embodiments, the distal end portion 1108 can be substantially dome shaped or substantially hemispherically shaped, and can include a plurality of slits 1110 (e.g., five, as illustrated). Each of the slits 1110 can meet at a center point on the distal end portion 1108 of the regulator 1130 and extend radially outwardly along the distal end portion 1108. In some embodiments a different numbers of slits can be used, such as, but not limited to, three slits, six slits, seven slits, etc. The number of slits can be chosen depending on the desired cracking pressure of the regulator 1130. Generally, a greater number of slits will result in a lower cracking pressure and the regulator 1130 will open more easily to allow fluid flow therethrough.

Figure 54:
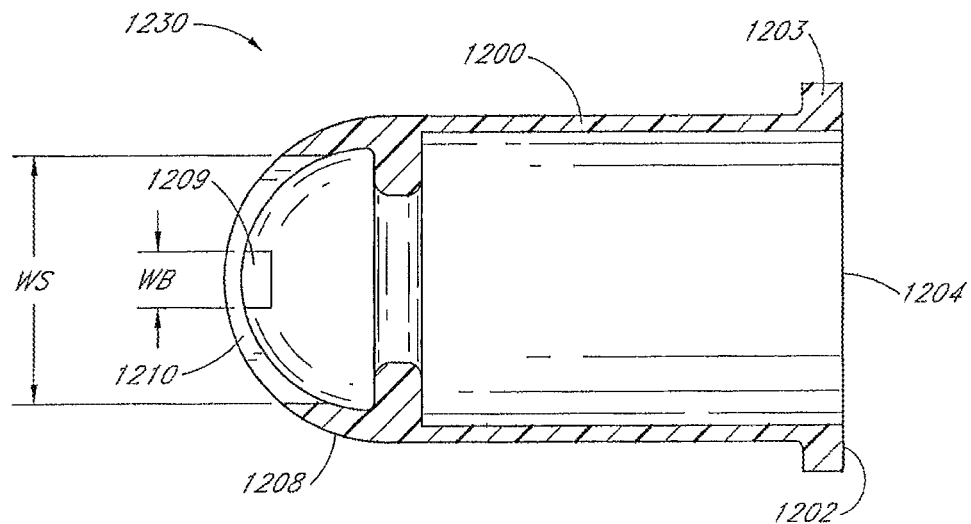
FIG. 54 is a section view of the regulator shown in FIG. 53 taken along the axial centerline of the regulator in a first direction.
Figure 55:
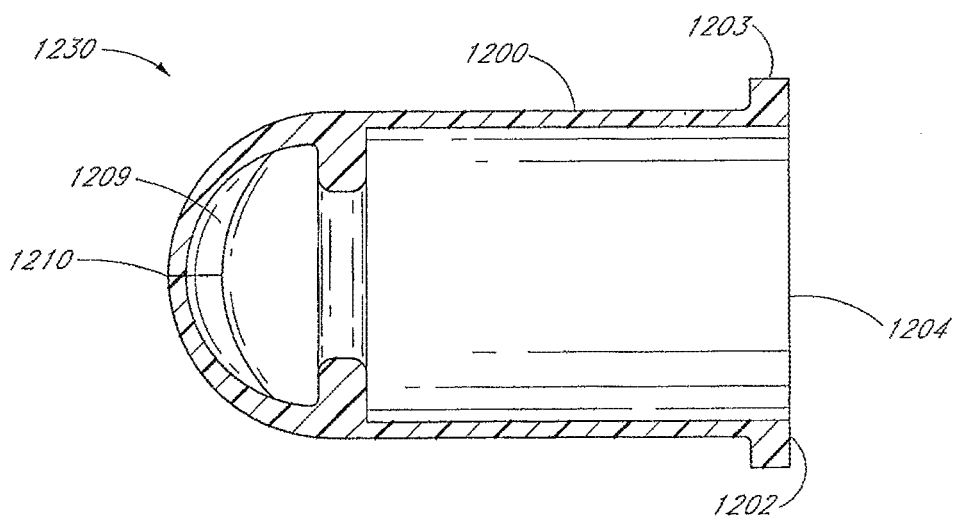
FIG. 55 is a section view of the regulator shown in FIG. 53 taken along the axial centerline of the regulator in a second direction.

FIG. 53 is a perspective view of an embodiment of a regulator 1230. FIG. 54 is a section view of the regulator 1230 taken along the axial centerline of the regulator 1230 on a first plane. FIG. 55 is a section view of the regulator 1230 taken along the axial centerline of the regulator on a second plane that is orthogonal to the first plane. The regulator 1230 can be similar in some regards to the regulator 30, or any other regulator or valve member disclosed herein. In some embodiments, the regulator 1230 includes a body portion 1200, a proximal end portion 1202, and a distal end portion 1208. The proximal end portion 1202 can include an annular raised lip 1203 and an opening 1204 therethrough. In some embodiments, the distal end portion 1208 can be substantially dome or hemispherically shaped, and can include a slit 1210. In some embodiments, a cross beam 1209 (shown in phantom in FIG. 53) is formed on either side of the slit 1209 with the slit 1209 passing therethrough. The cross beam 1209 can function to increase the thickness of the wall of the regulator across at least a portion of the width of the slit 1210, thereby increasing the cracking pressure required to open the regulator 1230.

In some embodiments, the cross beam 1209 can be centered on the axial centerline of the regulator 1230. With reference to FIG. 54, in some embodiments, the cross bar 1209 can have a width (represented by "WB" in FIG. 54) that is smaller than a width defined by the slit 1210 (represented by "WS" in FIG. 54). In some embodiments, the width WB of the cross bar can extend across the full length of the width WS of the slit 1210, or beyond the width WS of the slit 1210. In some embodiments, multiple cross bars can be used to achieve a desired cracking pressure for the regulator 1230.

Figure 56:
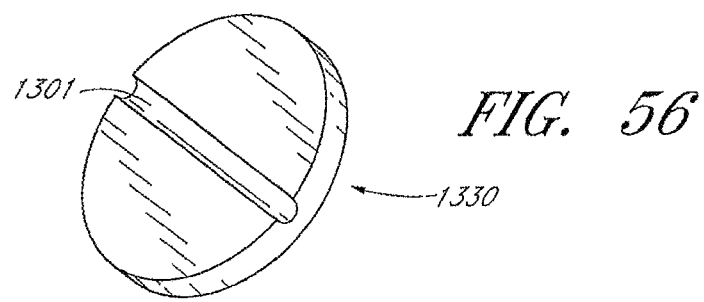
FIG. 56 is a distal perspective view of another embodiment of a valve member.

FIG. 56 is a perspective view of a one-way valve member 1330. In some embodiments, the valve member 1330 can be substantially disk shaped and can include a channel 1301 formed on one side thereof. The channel 1301 can pass through the center of the valve member 1330. The valve member 1330 can be constructed from a deformable, resilient material such as silicone-based deformable materials, rubbers, etc. The valve member 1330 can be constructed from a material capable of forming a fluid tight seal against a plastic or other rigid material.

Figure 57:
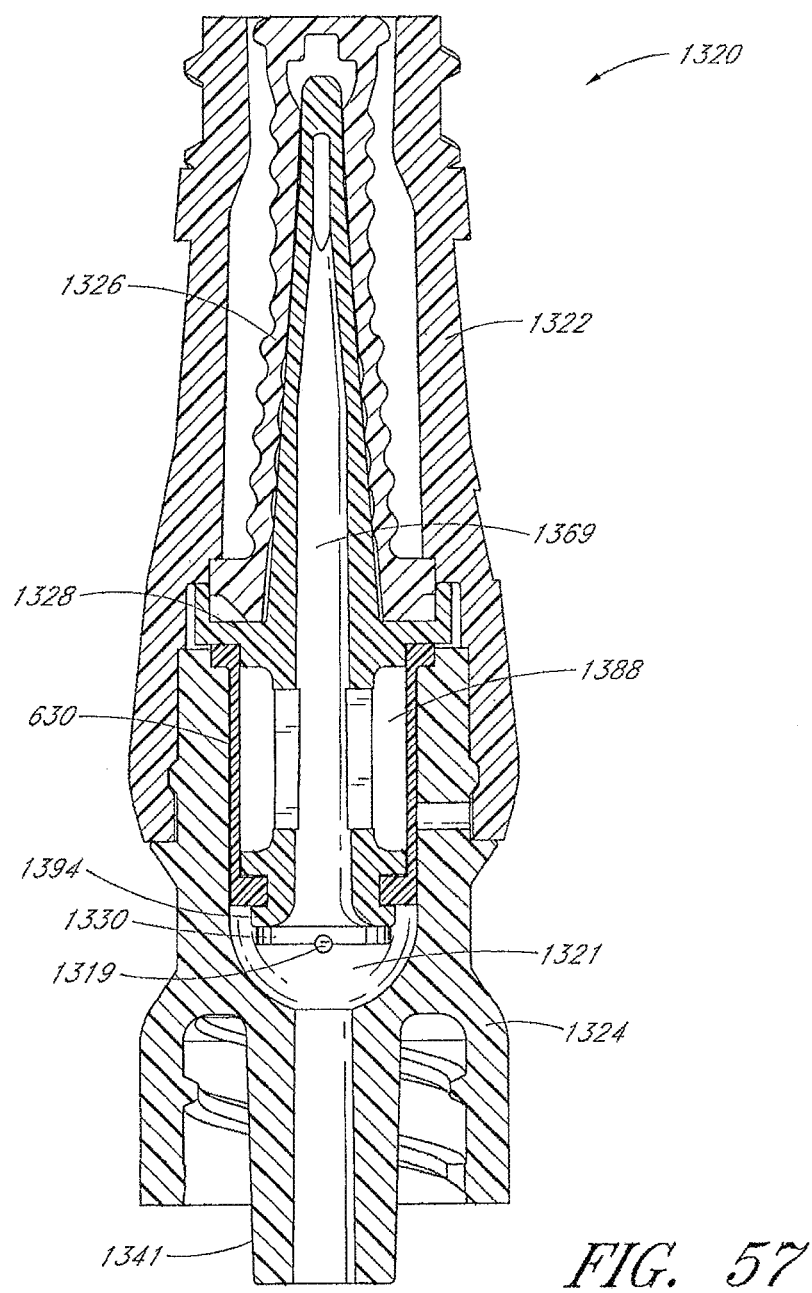
FIG. 57 is a section view of a valve or medical connector that includes the valve member shown in FIG. 56 in a closed configuration.

FIG. 57 is a section view of an embodiment of a valve or needleless connector 1320 configured to use the valve member 1330 shown in FIG. 56. In some embodiments, the connector 1320 can have any of the features or other details or configurations of any other connector described herein. In some embodiments, the connector 1320 can include a body member 1322, the base member 1324, a seal member 1326, a support member 1328, and a regulator 630, and the valve member 1330 which can be, for example, the same as, or similar to, the body member 22, base member 24, seal member 26, support member 28, and regulator 30 in connection with the connector 20.

The base member 1324 can include a cavity 1329 therein, and a bar 1319 can extend across at least a portion of the cavity 1329. The valve member 1330 can be positioned on the bar 1319 so that the bar 1319 fits into the channel 1301 on the valve member 1330. The support member 1328 can be positioned so that the distal surface of the annular protrusion 1394 contacts the proximal surface of the valve member 1330. In some embodiments, the support member 1328 can force the valve member 1330 to flex slightly so that the resilient force of the valve member 1330 forms an annular seal against the distal surface of the annular protrusion 1394.

Figure 58:
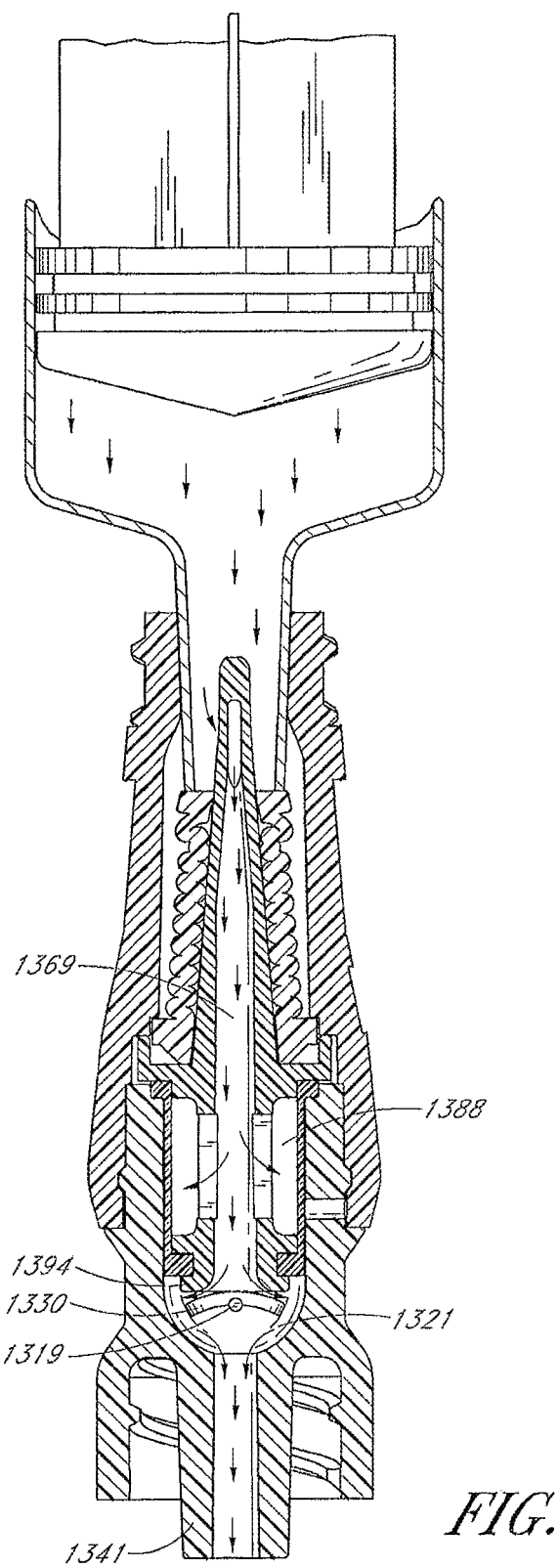
FIG. 58 is another section view of the connector shown in FIG. 57, with the valve member in an open configuration.

FIG. 58 shows a section view of the connector 1320 shown in FIG. 57 with the valve member 1330 in an open configuration while fluid is infused through the connector 1320. Fluid can be infused into the connector 1320 from a syringe 120 or other medical implement. The fluid can travel through a fluid passageway 1369 in the support member 1328 to the valve member 1330. When the pressure in the fluid passageway 1369 is sufficient greater than the pressure in the cavity 1321, the valve member 1330 flexes away from the support member 1328, breaking the seal and allowing fluid to flow into the cavity 1321 and out of the connector 1320 through the male tip protrusion 1341. When the pressure subsides (e.g., when fluid is no longer being infused), the valve member 1330 resiliently returns to its closed position (as shown in FIG. 57), forming a seal against the support member 1328.

If a syringe rebound, or other backflow inducing event, occurs, the pressure differential can cause the valve member 1330 to press more tightly against the support member 1328, and backflow can be prevented. In some embodiments, the connector 1320 can include a regulator 630 (as discussed in connection with FIGS. 43-45). The regulator 630 can be configured to flex inwardly to reduce the volume of the annular cavity 1388 to alleviate the pressure differential caused by the syringe rebound or other backflow-inducing event. In some embodiments, the valve member 1330 can be a check valve or one-way valve that substantially prevents fluid flow in the proximal direction. Therefore, in some embodiments, no regulator 630 providing a variable volume chamber is required to prevent backflow. However; in some embodiments, such as the embodiment shown in FIGS. 57 and 58, the regulator 630 can be included so that the variable volume chamber can reduce in volume to alleviate the pressure caused by a syringe rebound, or other backflow inducing event.

Figure 60:
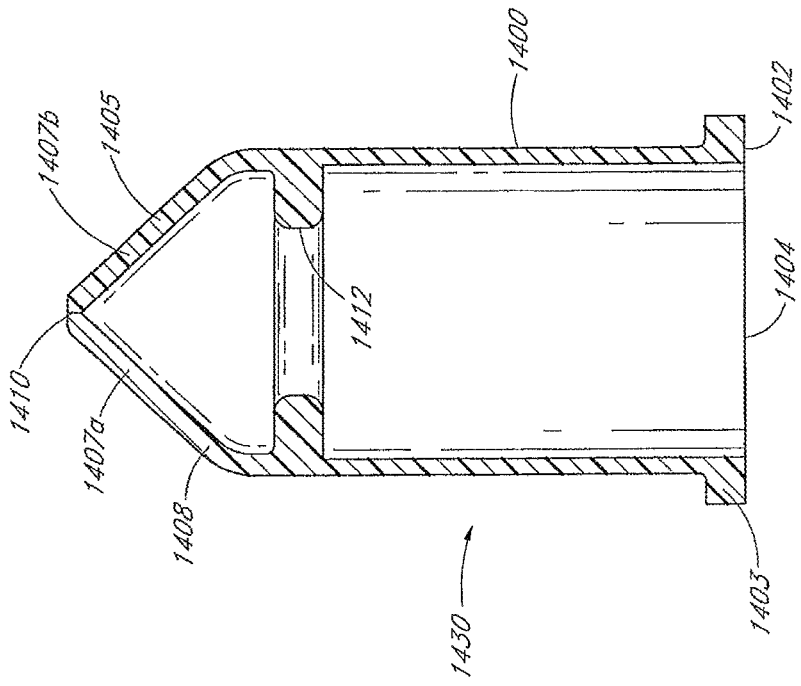
FIG. 60 is a section view of the regulator shown in FIG. 59 taken along the axial centerline of the regulator.
Figure 59:
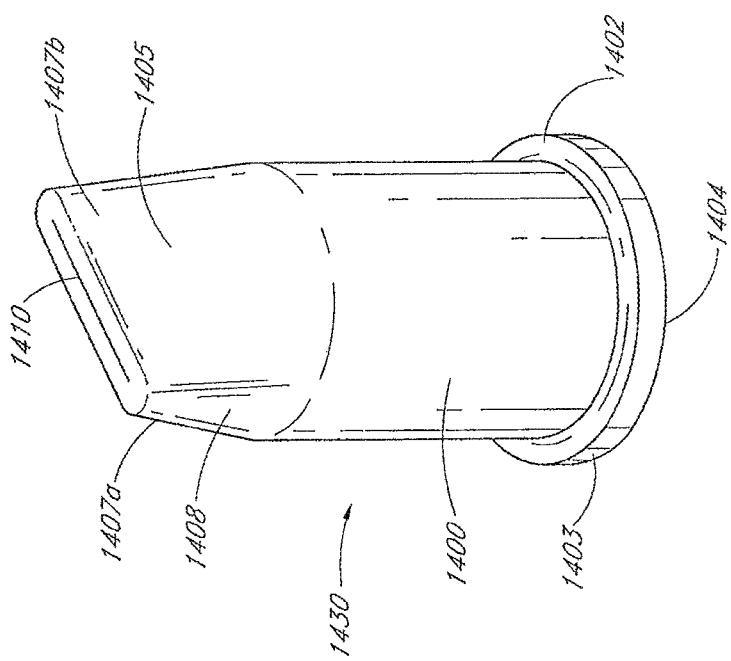
FIG. 59 is a distal perspective view of another embodiment of a regulator.

Various other types of check valves can be used to prevent backflow. For example, FIG. 59 is a perspective view of a regulator 1430 that includes a generally flat, tapering closure valve such as a duckbill check valve 1405. FIG. 60 is a section view of the regulator 1430 shown in FIG. 59. The regulator 1430 can be similar to the regulator 30, or to any other regulator or valve member disclosed herein. In some embodiments, the regulator 1430 can include a body portion 1400, a proximal end portion 1402, and a distal end portion 1408. The proximal end portion 1402 can include an annular raised lip 1403 and an opening 1404 therethrough. The distal end portion 1408 can include a duckbill check valve 1405 formed by two resilient generally flat, tapering surfaces or bills 1407a, 1407b that meet to form an elongate slit 1410 extending in a generally transverse direction across all or nearly all of the distal end thereof. The regulator 1430 can also include an inner annular protrusion 1412. Many variations are possible. For example, in some embodiments, the check valve 1405 and body portion 1400 of the regulator can be formed separately.

Figure 61:
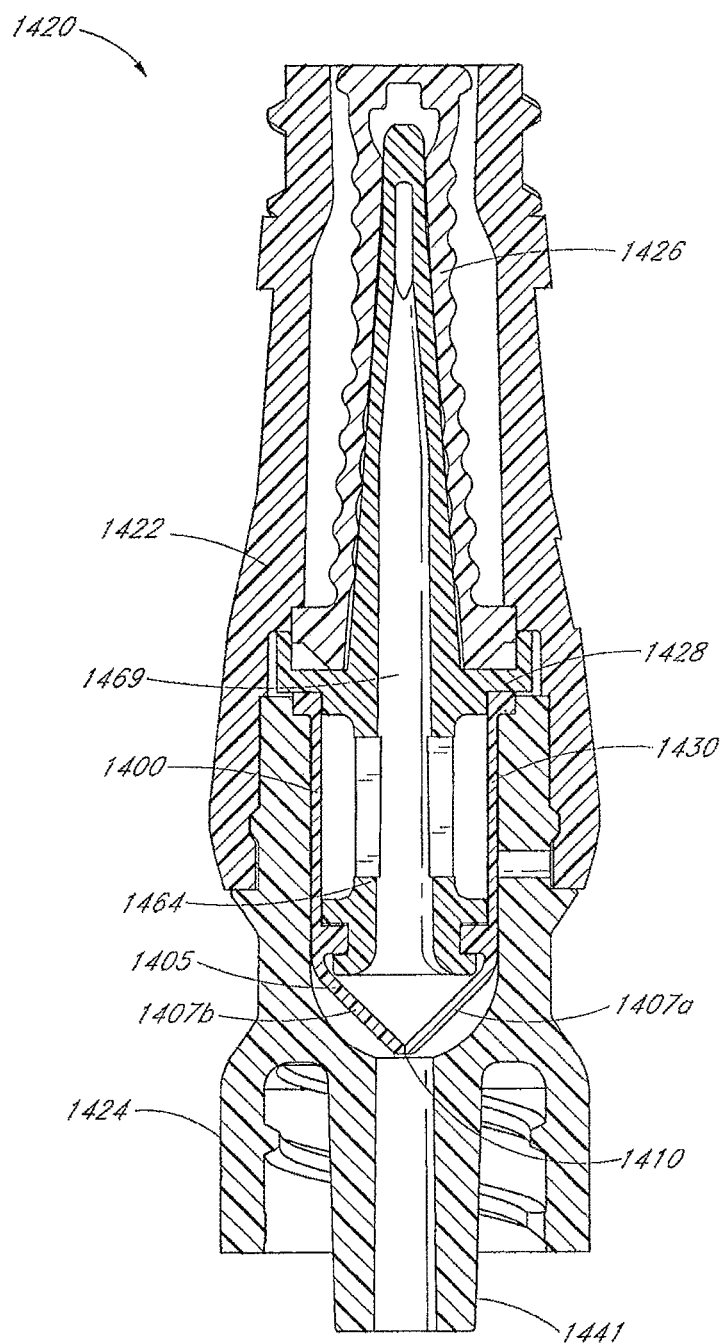
FIG. 61 is a section view of a valve or needleless connector that includes the regulator shown in FIG. 59 in a closed configuration.
Figure 62:
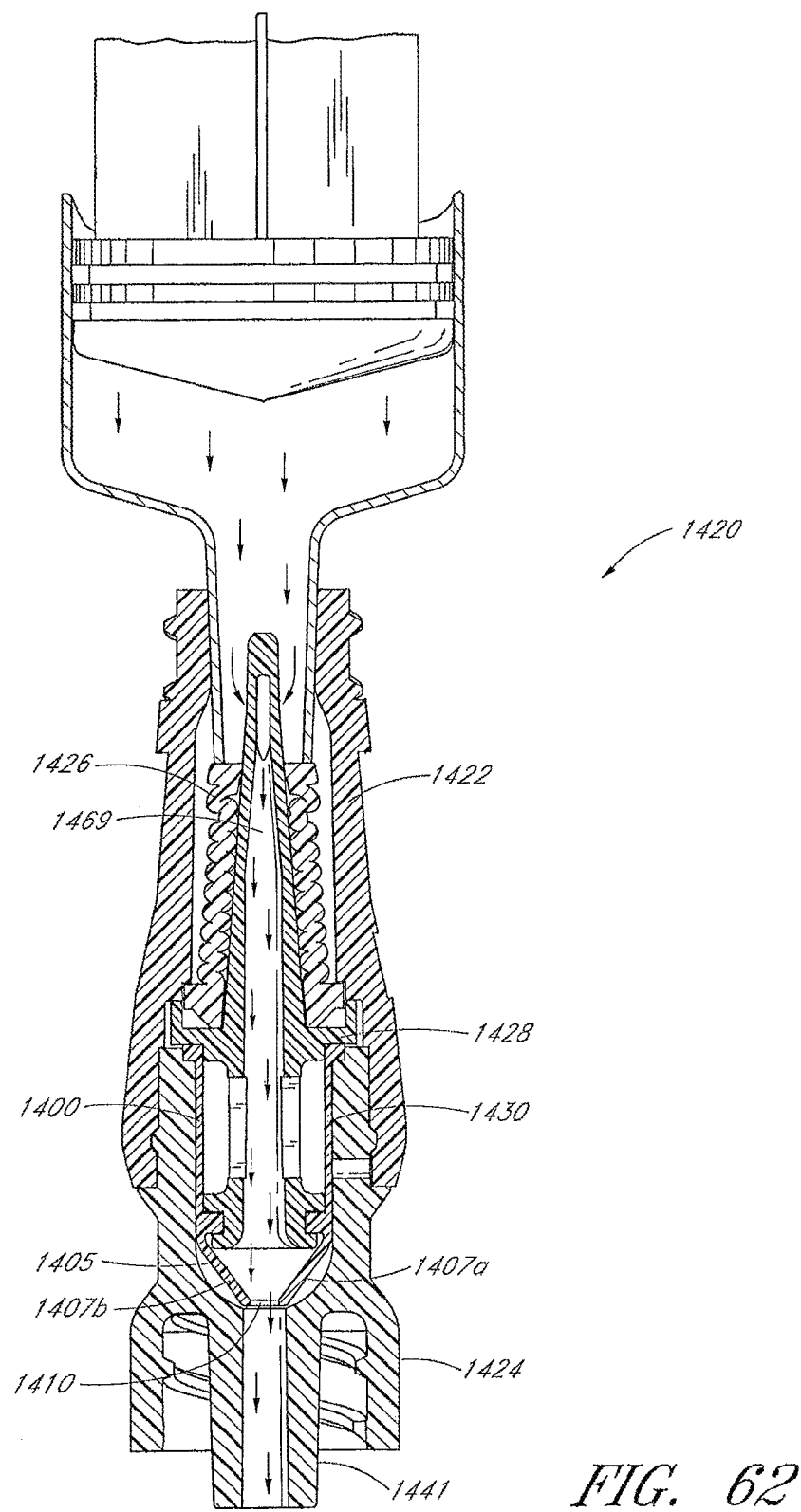
FIG. 62 is another section view of the connector shown in FIG. 61, with the regulator in an open configuration.

FIG. 61 is a section view of a valve or needleless connector 1420 that includes the regulator 1430 in a closed configuration. FIG. 62 is a section view of the connector 1420 with the regulator 1430 in an open configuration as fluid is infused through the connector 1420. In some embodiments, the connector 1420 can have any of the features or other details or configurations of any other connector described herein. In some embodiments, the connector 1420 can include a body member 1422, a base member 1424, a seal member 1426, a support member 1428, and a regulator 1430 which can be, for example, the same as, or similar to, the body member 22, base member 24, seal member 26, support member 28, and regulator 30 of the connector 20. The regulator 1430 can be positioned over the distal portion 1464 of the support member 1428, similarly to the regulator 30.

As fluid is infused into the connector 1420 from a medical implement (e.g., a syringe 120), the fluid can travel through the fluid passageway 1469 to the duckbill check valve 1405. The pressure differential caused by the influx of fluid can cause the bills 1407a, 1407b on the duckbill check valve 1405 to separate, thereby opening the slit 1410 and allowing fluid to flow through the duckbill check valve 1405 and out the connector 1420 through the male tip protrusion 1441.

If a syringe rebound, or other backflow inducing event, occurs, the resulting pressure differential can cause the bills 1407a, 1407b of the duckbill check valve 1405 to press against each other more tightly, preventing backflow of fluid. In some embodiments, the body portion 1400 of the regulator 1430 can flex inwardly to reduce the volume in the connector and alleviate some of the pressure caused by the syringe rebound or other retrograde-inducing event. In some embodiments, the duckbill check valve 1405 can be configured to substantially prevent flow of fluid in the distal direction. Accordingly, in some embodiments, the connector 1420 can include the duckbill check valve 1405, but can omit the body portion 1400 that provides the variable volume chamber.

In some embodiments, the backflow resist valve is not a check valve or one-way valve that substantially prevents backflow altogether. Rather, the backflow resist valve can prevent backflow until a certain threshold pressure differential is reached, at which point the backflow resist valve opens to allow baokflow to occur. In some embodiments, the backflow resist valve can be configured such that the threshold pressure differential is high enough to prevent unintentional backflow such as that caused by syringe rebound or withdrawal of a medical implement, but low enough to allow intentional backflow such as when fluid (e.g., blood) is intended to be drawn through the connector into the syringe. In some embodiments, the regulator 30 can provide a two-way backflow resist valve, as discussed in greater detail elsewhere herein. Other two-way backflow resist valves can be used.

Figure 63:
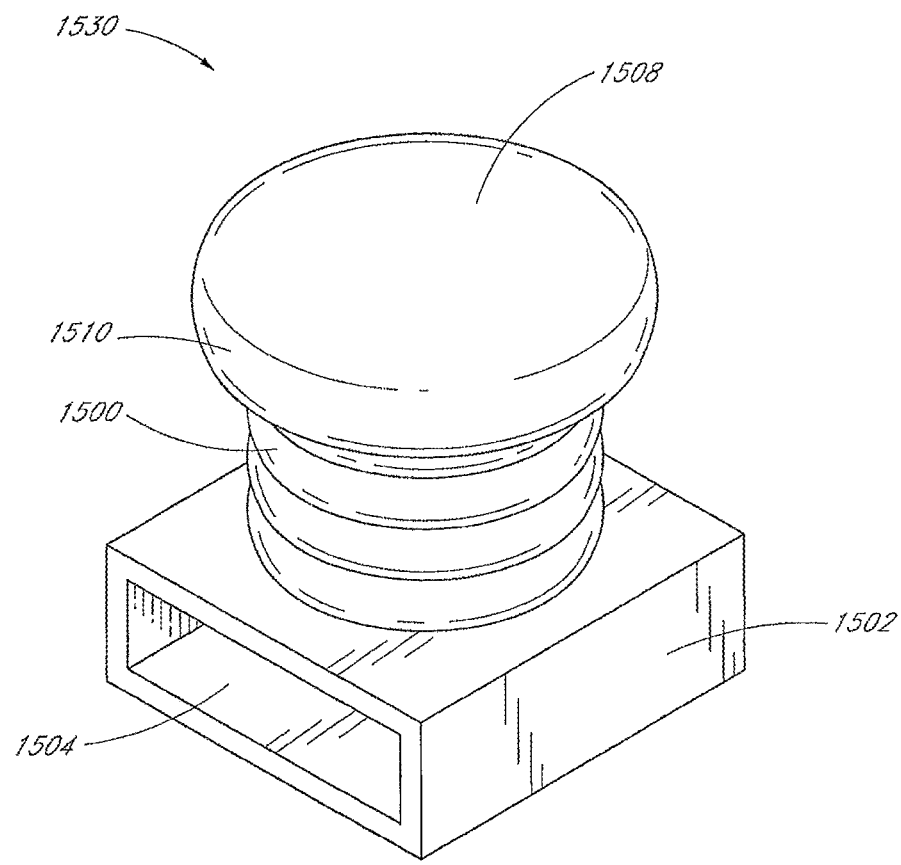
FIG. 63 is a proximal perspective view of another embodiment of a regulator.

FIG. 63 is a perspective view of an embodiment of a regulator 1530 that can function to control fluid flow and/or mitigate the effects of pressure differentials using a moving wall portion. In some embodiments, the moving wall portion can be generally flat and generally horizontal as illustrated. In some embodiments, the regulator 1530 can function as a two-way backflow resist valve, as will be described in more detail below. The regulator 1530 can include a resilient body portion 1500, a proximal moving wall or plug portion 1508, and a distal connector portion 1502. The distal connector portion 1502 can include a hole 1504 therethrough. The proximal wall or plug portion 1508 can be substantially disk shaped, and can include an annular tapered or rounded edge 1510 extending around the circumference of the plug portion 1508. In some embodiments, the wall or plug portion 1508 can be made of a resilient material, as illustrated, and in some embodiments, it can be rigid or substantially rigid. The resilient body portion 1500 can connect the plug portion 1508 to the connector portion 1502. In some embodiments, the resilient body portion 1500 can include one or more generally transverse or generally horizontal grooves, such as are created by a series of stacked o-rings, to assist in compression. In some embodiments, the resilient body portion 1500 can include a spring or other element that causes the resilient body portion 1500 to return to its original state after being stretched or compressed. The regulator 1530 can be constructed from a number of different suitable materials, including silicone-based deformable materials, rubbers, or other suitable materials. In some embodiments, the regulator 1530, or portions thereof, can be formed from a material that can form a fluid tight seal against a plastic or other rigid material.

Figure 64:
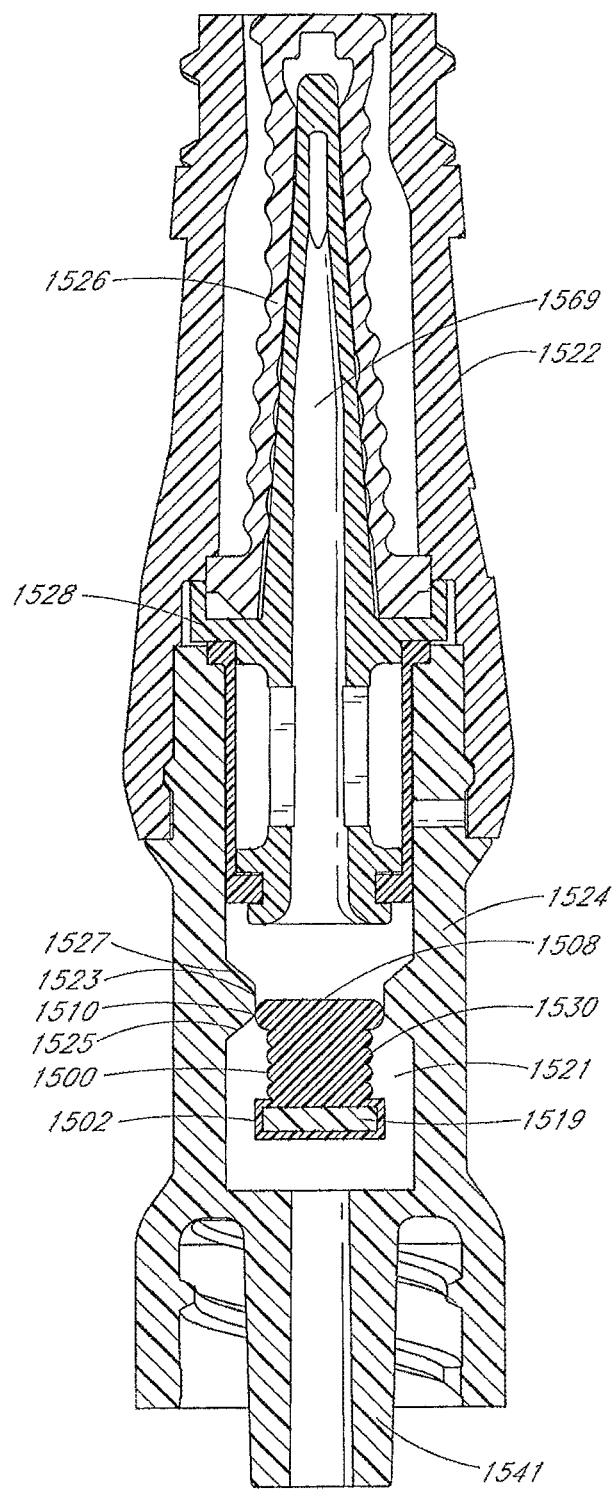
FIG. 64 is a section view of a valve or needleless connector that includes the regulator shown in FIG. 63 in a closed configuration.

FIG. 64 is a section view of a valve or needleless connector 1520 that includes the regulator 1530 in a relaxed position. In some embodiments, the connector 1520 can have any of the features or other details or configurations of any other connector described herein. In some embodiments, the connector 1520 can include a body member 1522, a base member 1524, a seal member 1526, a support member 1528, the regulator 630, and the regulator 1530 which can be, for example, the same as, or similar to, the body member 22, base member 24, seal member 26, support member 28, and regulator 30 of the connector 20.

In some embodiments, the base member 1524 includes a cavity 1521 therein, and a support bar 1519 extends within or through the cavity 1521. The connector portion 1502 can be configured to secure the regulator 1530 to the support bar 1519 with the support bar 1519 extending through the opening 1504 in the connector portion 1502. For example, in some embodiments, the base member 1524 can be constructed of two pieces, split down the axial centerline of the base member 1524. The regulator 1530 can be attached to one side piece of the base member 1524 and then the two base member pieces can be coupled via a snap fit, plastic welding, sonic welding, etc., to form the base member 1524 with the regulator 1530 secured thereto. The regulator 1530 can be secured to the connector in various other manners. For example, in some embodiments, a portion of the regulator 1530 can be positioned between two other components (e.g., the base member 1524 and the support member 1528) of the connector 1520, providing a friction or pressure fit that holds the regulator 1530 in place.

The cavity 1521 can include an annular ridge 1523 having a lower tapered surface 1525 and an upper tapered surface 1527. In some embodiments, the surface between the upper and lower tapered surfaces 1527, 1525 can be substantially cylindrical. The plug portion 1508 of the regulator 1530 can be seated against the annular ridge 1523 when the resilient body portion 1500 is in a relaxed or initial state. In some embodiments, the annular tapered edge of the plug portion 1508 is compressed slightly by the annular ridge 1523 so as to form a generally fluid tight annular seal between the plug portion 1508 and the ridge 1523.

Figure 65:
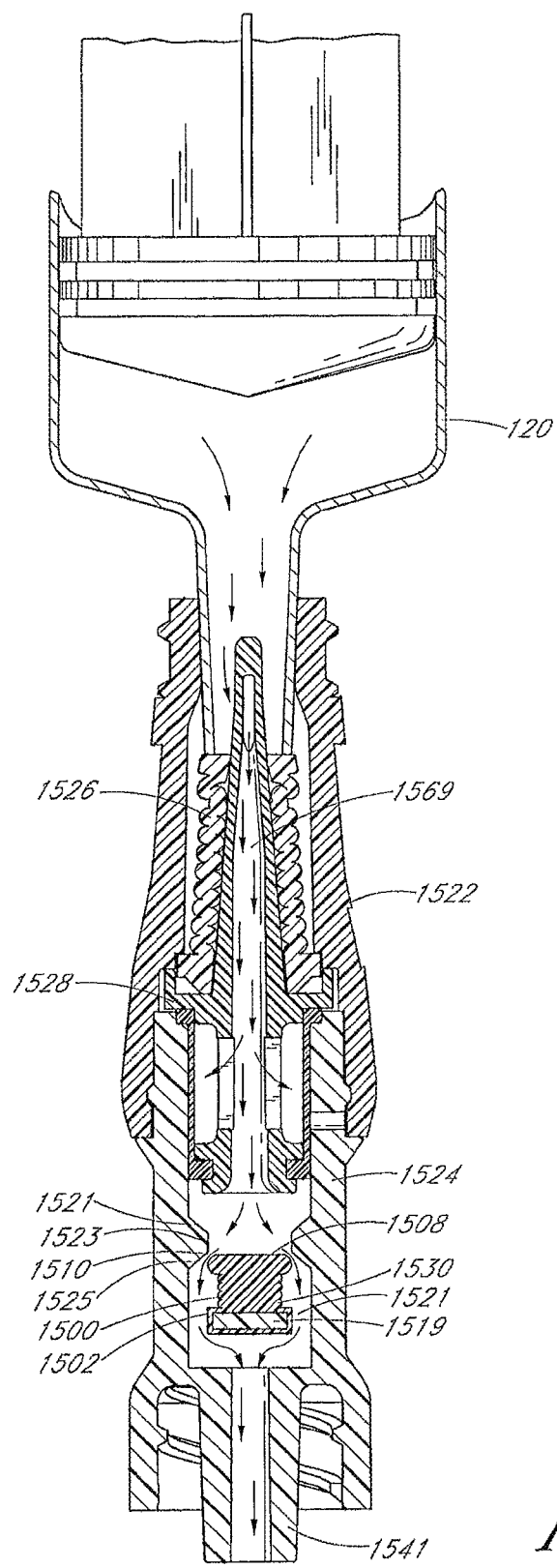
FIG. 65 is another section view of the connector shown in FIG. 64, with the regulator in a first open configuration.

FIG. 65 is a section view of the connector 1520 in which the regulator 1530 is in an open position as fluid is being infused through the connector 1520 in the distal direction. As fluid is infused into the connector 1520 from a medical implement (e.g., syringe 120), the fluid can travel through the fluid passageway 1569 formed in the support member 1528 and into the upper portion of the cavity 1521 until the fluid contacts the top surface of the plug portion 1508 of the regulator 1530. The pressure differential can cause the resilient body portion 1500 to compress, lowering the plug portion 1508 until the plug portion 1508 disengages from the annular ridge 1523, thereby breaking the annular seal and allowing the fluid to flow around the regulator 1530 and out the male tip protrusion 1541 of the connector 1520. When the pressure subsides (e.g., when fluid is no longer being infused into the connector 1520), the resilient body portion 1500 of the regulator 1530 can return to its relaxed state (shown in FIG. 64) and reengage the annular seal between the plug portion 1508 and the annular ridge 1523.

Figure 66:
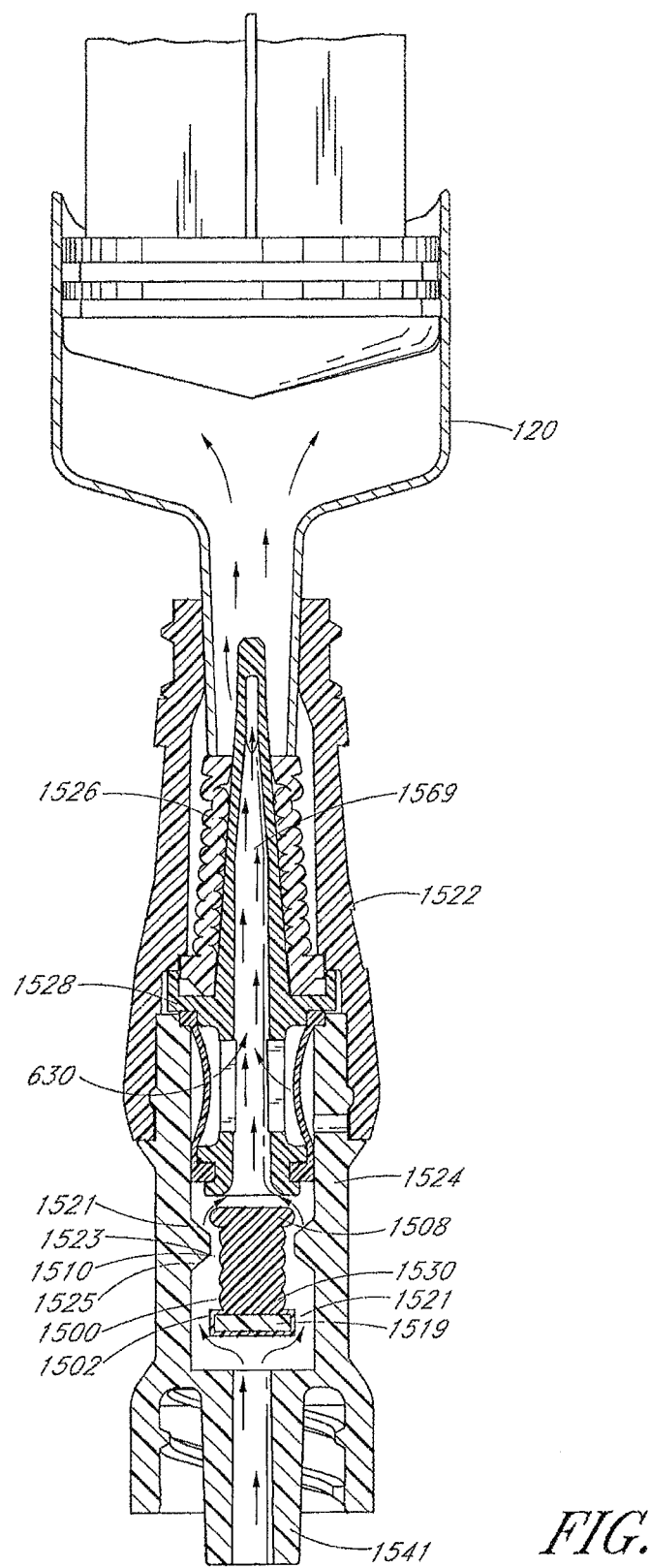
FIG. 66 is another section view of the connector shown in FIG. 64, with the regulator in a second open configuration.

FIG. 66 is a section view of the connector 1520 in which the regulator 630 is in an open position as fluid is drawn through the connector 1520 in the proximal direction. If a syringe rebound or other backflow-inducing event occurs, the resulting pressure differential can cause the regulator 630 to collapse (as shown in FIG. 66), thereby reducing the volume of the variable volume chamber and alleviating the pressure caused by the backflow-inducing event. In some embodiments, the regulator 1530 can be hollow or otherwise rendered sufficiently flexible so that it can both provide a valving function and a pressure-compensating function by changing its volume in response to pressure changes. In some embodiments, the force required to collapse the regulator 630 is less than the force required to stretch the resilient body member 1500 of the regulator 1530. Thus, the plug portion 1508 of the regulator 1530 can remain substantially and substantially non-deforming as the regulator 630 collapses so that the fluid located distal of the plug portion 1508 is generally not influenced by the vacuum created by the backflow-inducing event thereby generally entirely preventing fluid backflow.

In some embodiments, additional pressure can be applied after the regulator 630 has collapsed (e.g., by intentionally drawing back the plunger of the syringe 120). The additional pressure can cause the resilient body portion 1500 of the regulator 1530 to expand so that the plug portion 1508 slides axially up the annular ridge 1523. If enough pressure is applied, the plug portion 1508 can disengage from the annular ridge 1523 and allow fluid to flow in the proximal direction through the connector 1520, as shown in FIG. 66. In some embodiments, the regulator 1530 can be configured so that the force required to stretch the resilient body portion 1500 far enough to open the regulator 1530 for fluid flow in the proximal direction is greater than the force required to compress the resilient body portion 1500 far enough to open the regulator 1530 for fluid flow in the distal direction. In some embodiments, when the resilient body portion 1500 is in the relaxed state, the plug portion 1508 is located closer to the lower tapered surface 1525 than the upper tapered surface 1527.

In some embodiments, the thickness of the annular ridge 1523 (e.g., in the vertical direction) can be substantially larger than in the illustrated embodiment, thereby allowing the plug portion or wall 1508 to move a larger distance in either direction before opening the valve to fluid flow. For example, in some embodiments, the annular ridge 1523 or other interfacing structure can be at least about twice or three times as thick as the plug portion or wall 1508 that moves along it. The annular ridge 1523 or other interfacing structure can include a ledge, catch, or other impeding structure (not shown) to limit the movement of the wall or plug portion in the distal and/or proximal directions. In some embodiments, this arrangement can create a one-way valve.

Figure 67:
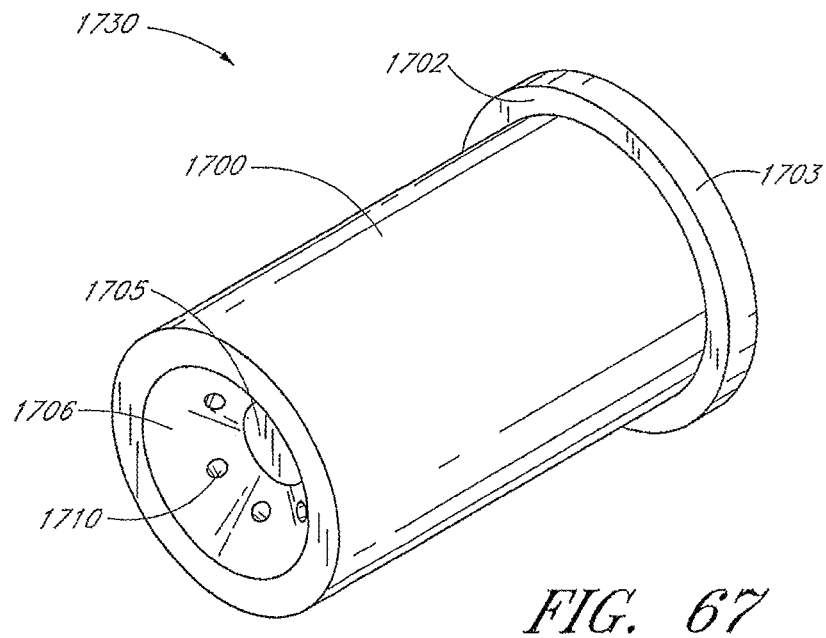
FIG. 67 is a distal perspective view of another embodiment of a regulator.
Figure 68:
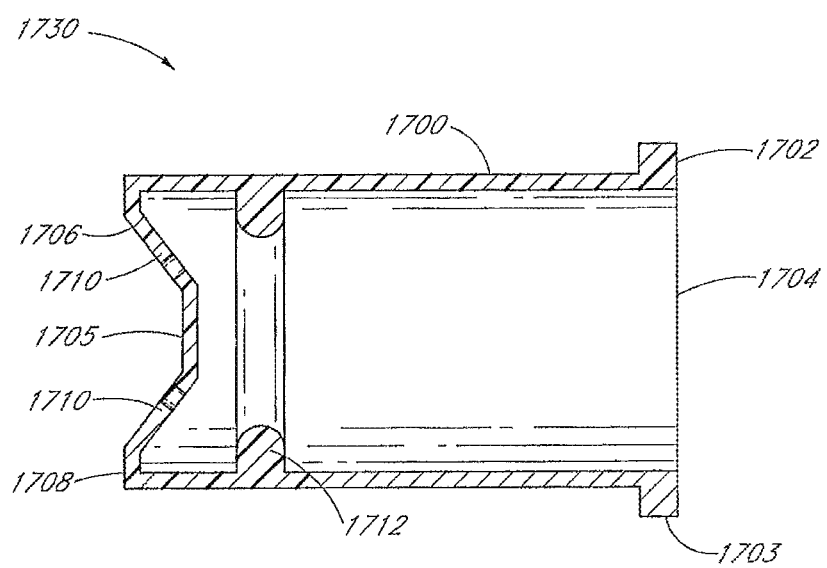
FIG. 68 is a section view of the regulator shown in FIG. 67, taken along the axial centerline of the regulator.

FIG. 67 is a perspective view of a regulator 1730. FIG. 68 is a section view of the regulator 1730 shown in FIG. 67 taken along the axial centerline of the regulator 1730. With reference to FIGS. 67 and 68, the regulator 1730 can include a body portion 1700, a proximal end portion 1702, and a distal end portion 1708. The proximal end portion can include an annular raised lip 1703 and an opening 1704 therethrough. The distal end portion 1708 can include a recessed central portion 1705 and a tapered annular wall 1706. One or more holes 1710 can be formed through the tapered annular wall. The regulator 1730 can also include an inner annular protrusion 1712. The regulator 1730 can be constructed from a number of different suitable materials, including silicone-based deformable materials, rubbers, or other suitable materials. In some embodiments, the regulator 1730, or portions thereof, can be formed from a material that can form a fluid tight seal against a plastic or other rigid material.

Figure 69:
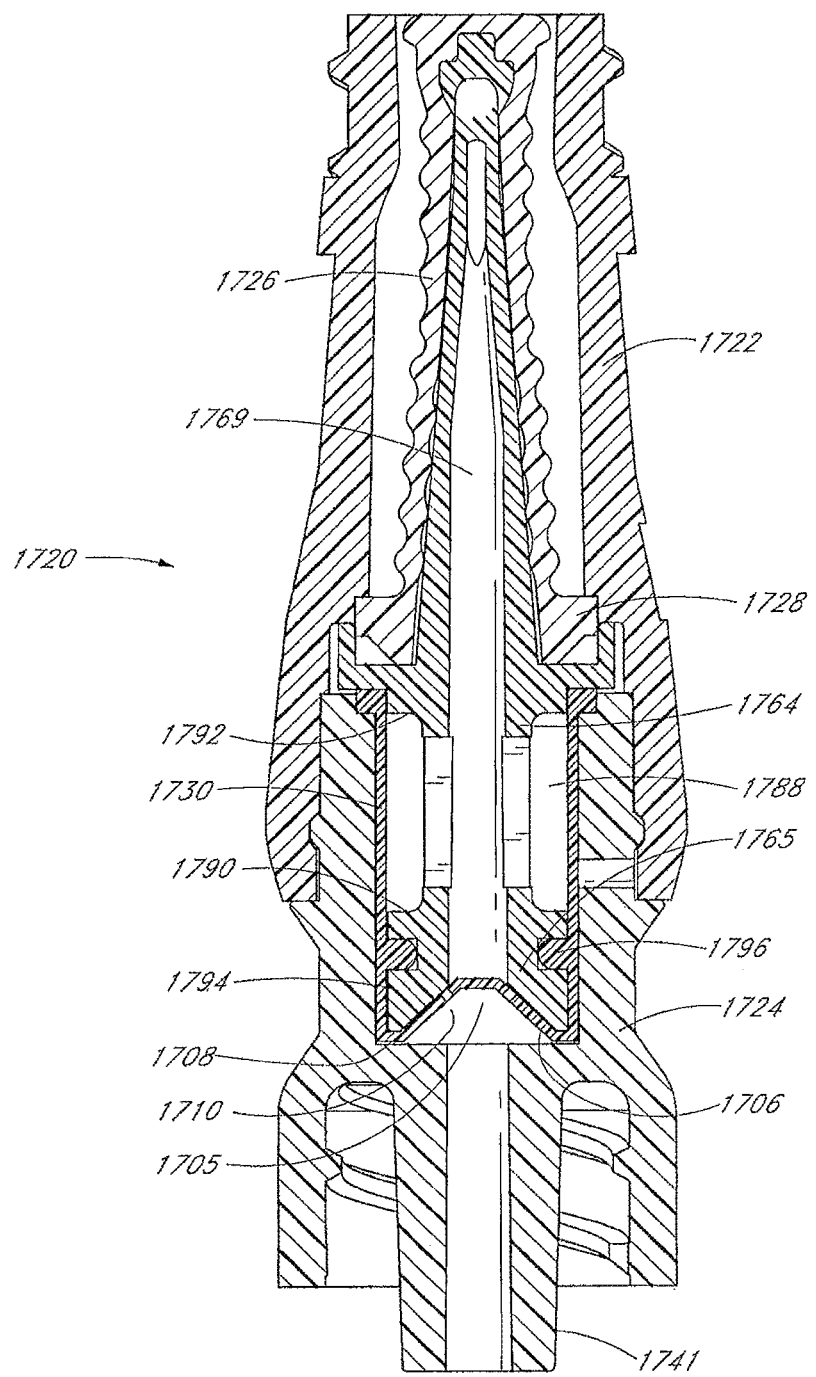
FIG. 69 is a valve or needleless connector that includes the regulator shown in FIG. 67 in a closed configuration.

FIG. 69 is a section view of a valve or needleless connector 1720 that includes the valve 1730 shown in FIGS. 67 and 68. The regulator 1730 is shown in an initial or relaxed (closed) state in FIG. 69. In some embodiments, the connector 1720 can have any of the features or other details or configurations of any other connector described herein. In some embodiments, the connector 1720 can include a body member 1722, a base member 1724, a seal member 1726, a support member 1728, and a regulator 1730 which can be, for example, the same as, or similar to, the body member 22, base member 24, seal member 26, support member 28, and regulator 30 of the connector 20.

The regulator 1730 can be positioned over the distal portion 1764 of the support member 1728, defining an annular cavity 1788 between two annular protrusions 1790, 1792 on the support member 1728. The inner annular protrusion 1712 of the regulator 1730 can be received within the channel 1796 formed between the annular protrusions 1790, 1794 to secure the regulator 1730 to the support member 1728. In some embodiments, the distal portion 1764 of the support member 1728 can be configured to receive the distal end portion 1708 of the regulator 1730. The support ember 1728 can include a tapered inner surface 1765 near the distal opening 1766 that is configured to receive the tapered annular wall 1706 so as to form a fluid tight seal therebetween when the distal end portion 1708 of the regulator 1730 is in the relaxed position. When the regulator 1730 is in the relaxed position shown in FIG. 69, the holes 1710 formed in the tapered annular wall 1706 can be covered by the tapered inner surface 1765 of the support member 1728 so that fluid does not flow through the holes 1765.

Figure 70:
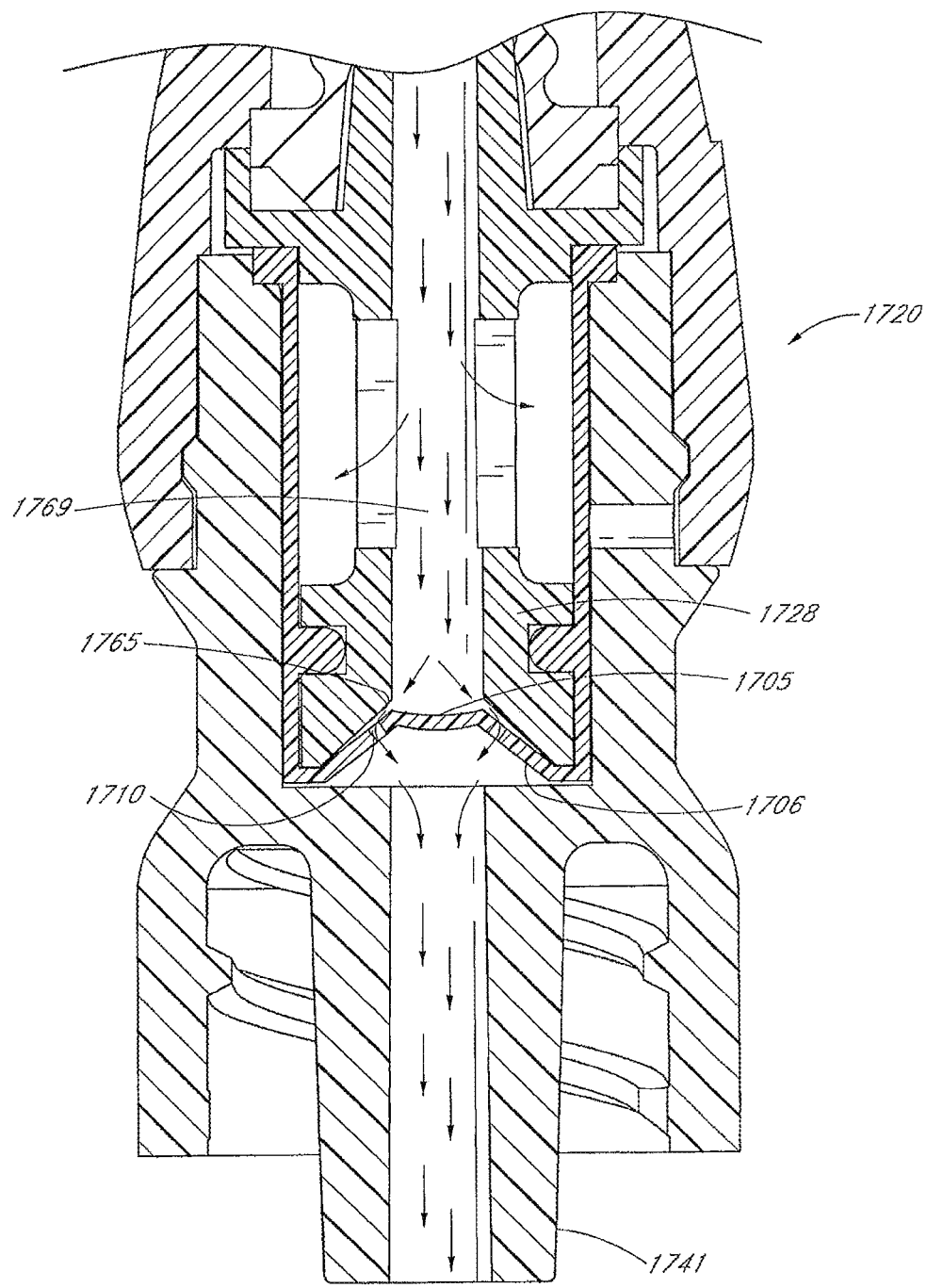
FIG. 70 is a partial section view of the connector shown in FIG. 69, with the regulator in a first open configuration.

FIG. 70 is a partial section view of the connector 1720 in which the regulator 1730 is in an open position as fluid is being infused through the connector 1720 in the distal direction. As fluid is infused into the connector 1720 from a medical implement (e.g., syringe), the fluid can travel through the fluid passageway 1769 formed in the support member 1728 until the fluid contacts the surface of the recessed center portion 1705 of the regulator 1730. The pressure differential can cause the distal end portion 1708 of the regulator 1730 to flex distally away from the support member 1728 until the tapered annular wall 1706 of the regulator 1730 disengages from the inner tapered wall 1765 of the support member 1728, thereby breaking the annular seal and allowing the fluid to flow through the holes 1710 in the regulator 1730 and out the male tip protrusion 1741 of the connector 1720. When the pressure subsides (e.g., when fluid is no longer being infused into the connector 1720), the resilient distal end portion 1708 of the regulator 1730 can return to its initial or relaxed state (shown in FIG. 69) so that the tapered annular wall 1706 reengages with, and seals against, the inner tapered surface 1765 of the support member 1728.

Figure 71:
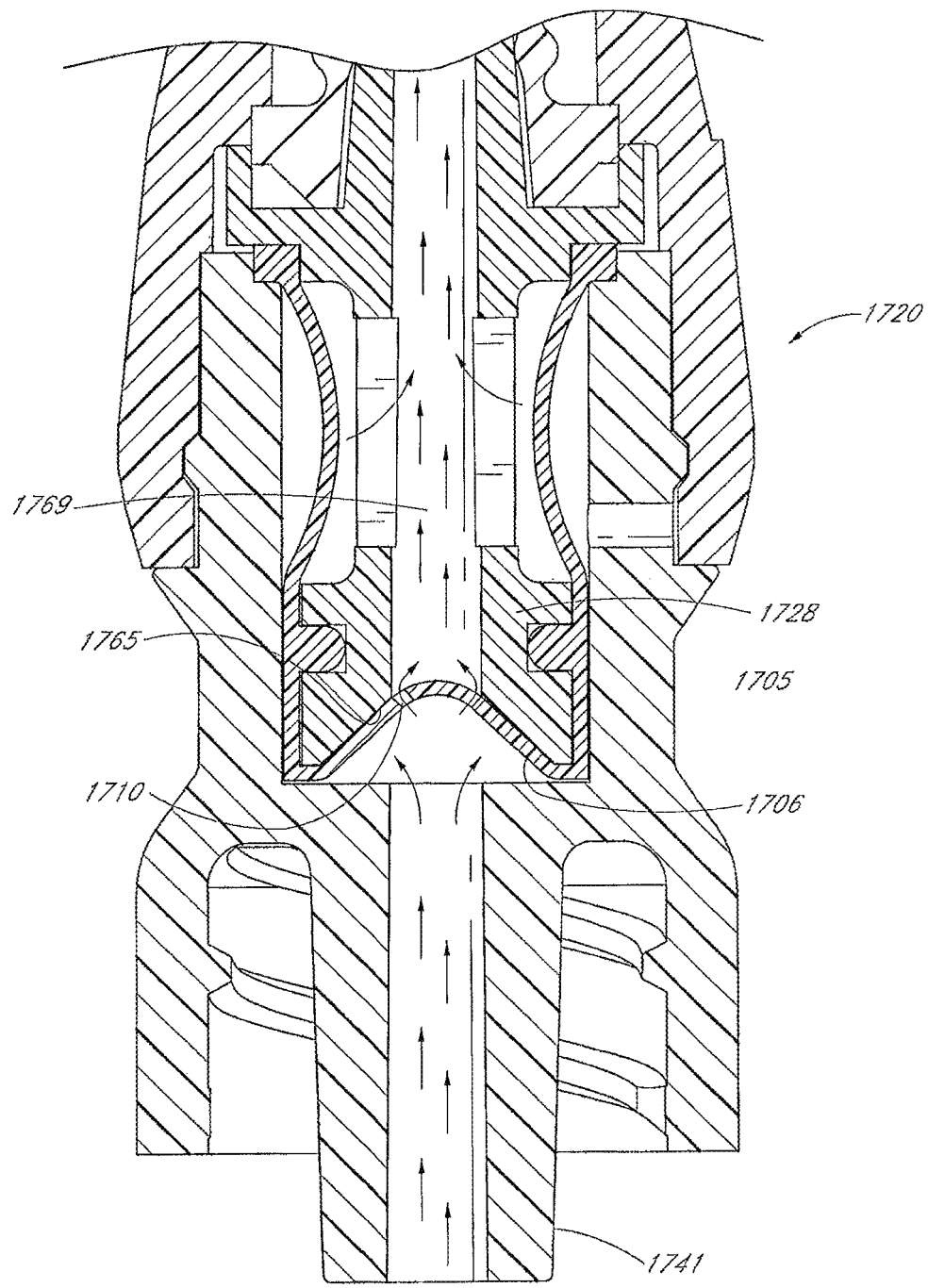
FIG. 71 is another partial section view of the connector shown in FIG. 69, with the regulator in a second open configuration.

FIG. 71 is a partial section view of the connector 1720 in which the regulator 1730 is in an open position as fluid is drawn through the connector 1720 in the proximal direction. If a backflow-inducing event occurs, the resulting pressure differential can cause the body portion 1700 of the regulator 1730 to collapse (as shown in FIG. 71), thereby reducing the volume of the annular cavity 1788 and alleviating the pressure caused by the syringe rebound or another backflow-inducing event. In some embodiments, the force required to collapse the body portion 1700 of the regulator 1730 is less than the force required to stretch the annular tapered wall 1706 of the regulator 1730. Thus, the recessed central portion 1705 of the regulator 1730 can remain substantially unaffected as the body portion 1700 of the regulator 1730 collapses or otherwise changes volume so that the fluid located distal of the regulator 1730 is generally not influenced by the vacuum created by the syringe rebound or any other retrograde-inducing event, thereby preventing fluid backflow.

In some embodiments, additional pressure can be applied after the body portion 1700 of the regulator 1730 has collapsed (e.g., by intentionally drawing back the plunger of the syringe). The additional pressure differential can cause the recessed central portion 1705 to be drawn proximally into the fluid passageway 1769 of the support member 1728 so that the tapered annular wall 1706 stretches. If enough pressure is applied, the holes 1710 formed in the tapered annular wall 1706 can be exposed, allowing fluid to flow in the proximal direction through the holes 1710 in the regulator 1730, as shown in FIG. 71. In some embodiments, the regulator 1730 can be configured so that the force required to stretch the tapered annular wall 1706 far enough to expose the holes 1710 and allow fluid flow in the proximal direction is greater than the force required disengage the tapered annular wall 1706 from the inner tapered wall 1765 of the support member 1728 to allow fluid flow in the distal direction.

Figure 72:
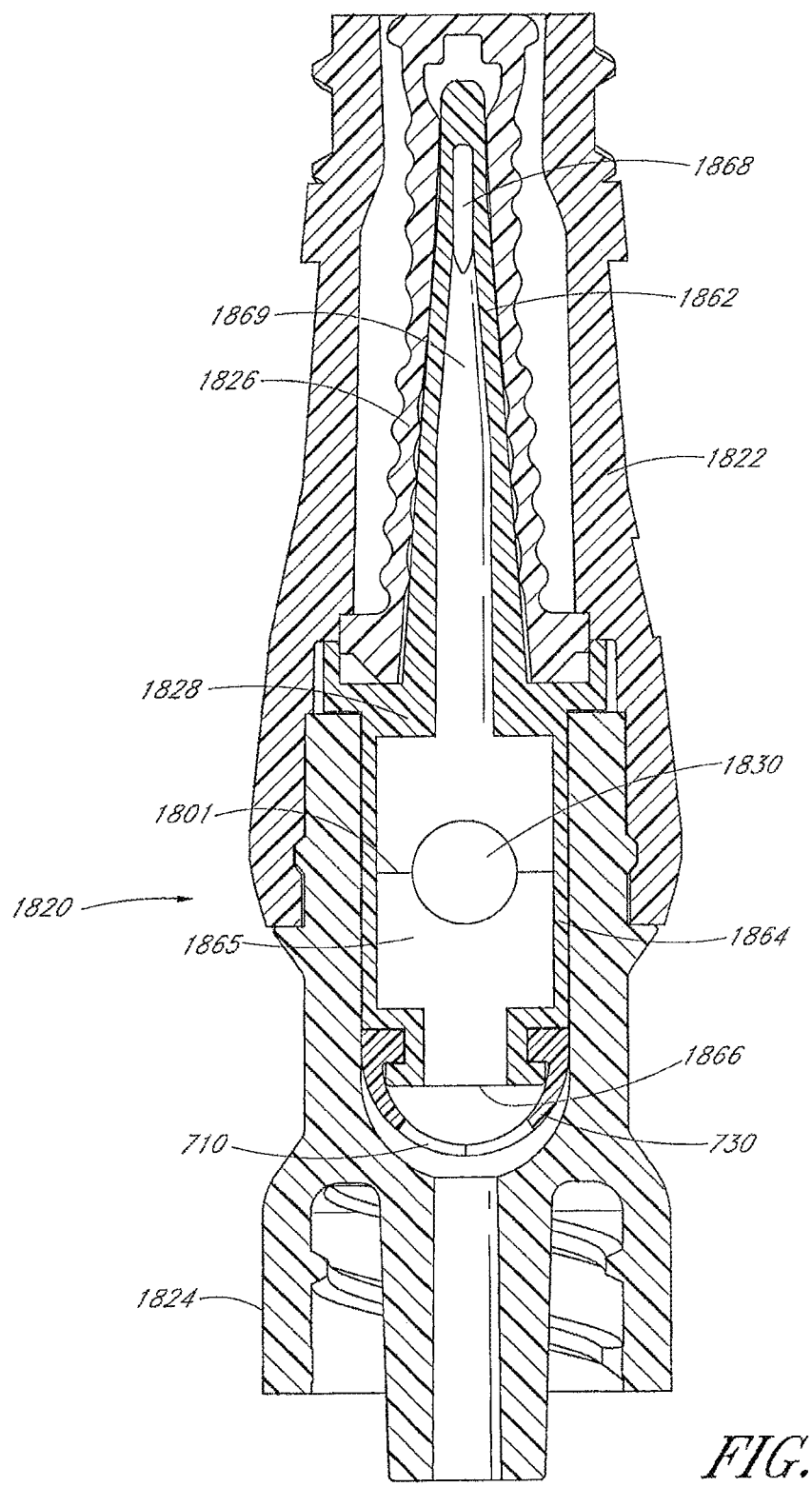
FIG. 72 is a section view of another embodiment of a valve or needleless connector support member.

FIG. 72 is a section view of a valve or needleless connector 1820. In some embodiments, the connector 1820 can have any of the features or other details or configurations of any other connector described herein. In some embodiments, the connector 1820 can include a body member 1822, a base member 1824, a seal member 1826, a support member 1828, a valve member 730, and a balloon member 1830, which can be, for example, the same as, or similar to, the body member 22, base member 24, seal member 26, support member 28, and regulator 30 of the connector 20.

In some embodiments, the distal portion 1864 of the support member 1828 can include an internal cavity 1865 in fluid communication with the distal opening 1866, the fluid passageway 1869, and the one or more holes 1868 formed in the elongate portion 1862. In some embodiments, the support member 1828 can be formed without the one or more openings formed laterally or radially through the distal portion. In some embodiments, the variable volume chamber can be contained within the internal cavity 1865 of the support member 1865 rather than by an annular channel formed on the outside of the support member. In some embodiments, a variable volume chamber 1830, such as a balloon member 1830, can be contained within the internal cavity 1865 of the support member 1828. The balloon member 1830 can be secured to the support member 1828 in many ways, such as by one or more tethers 1801, adhesive, etc. The variable volume chamber 1830 can have many different shapes and can be positioned in many different places. In some embodiments, the variable volume chamber 1830 is positioned in contact with or abutting against one or more interior surfaces of the internal cavity 1865 (e.g., in a corner thereof). The balloon member 1830 can be filled with a compressible/expandable fluid, such as air or other gas. The balloon member 1830 can expand when the volume of fluid contained within the internal cavity 1865 is reduced, thereby alleviating the pressure differential created by a backflow-inducing event.

In some embodiments, the valve member 730 can be positioned over the distal end portion 1864 of the support member 1828 in a manner similar to that described in connection with FIG. 48. In some embodiments, the force required to further expand the balloon member 1830 increases as the balloon member 1830 expands. Therefore, if sufficient pressure is applied (e.g., when intentionally drawing fluid into the syringe), at some point the force required to further expand the balloon member 1830 is greater than the force required to open the valve member 730 for fluid flow in the proximal direction. When this threshold pressure is reached, the one or more slits 710 on the valve member 730 open to allow fluid to flow through the valve member 730 in the proximal direction. In some embodiments, the balloon member 1830 can be configured such that its expanded volume at the threshold pressure is not large enough to interfere with the flow of fluid (e.g., by sealing off either opening into the cavity 1865, or by filling a portion of the cavity 1865). In some embodiments, the one or more tethers 1801 can be configured to maintain the balloon member 1830 at a position that does not interfere with fluid flow even when in the expanded state. In some embodiments, one or more retaining structures such as bars or walls (not shown) can prevent the balloon member 1830 from interfering with the flow of fluid when in the expanded state.

Figure 73:
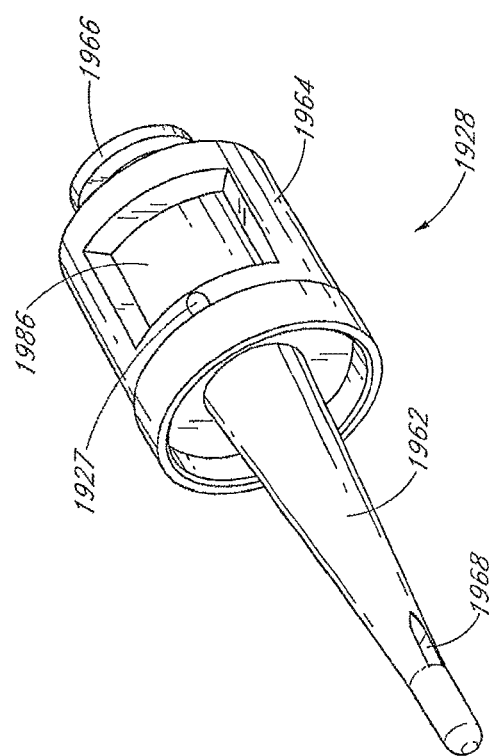
FIG. 73 is a proximal perspective view of another embodiment of a support member.
Figure 74:
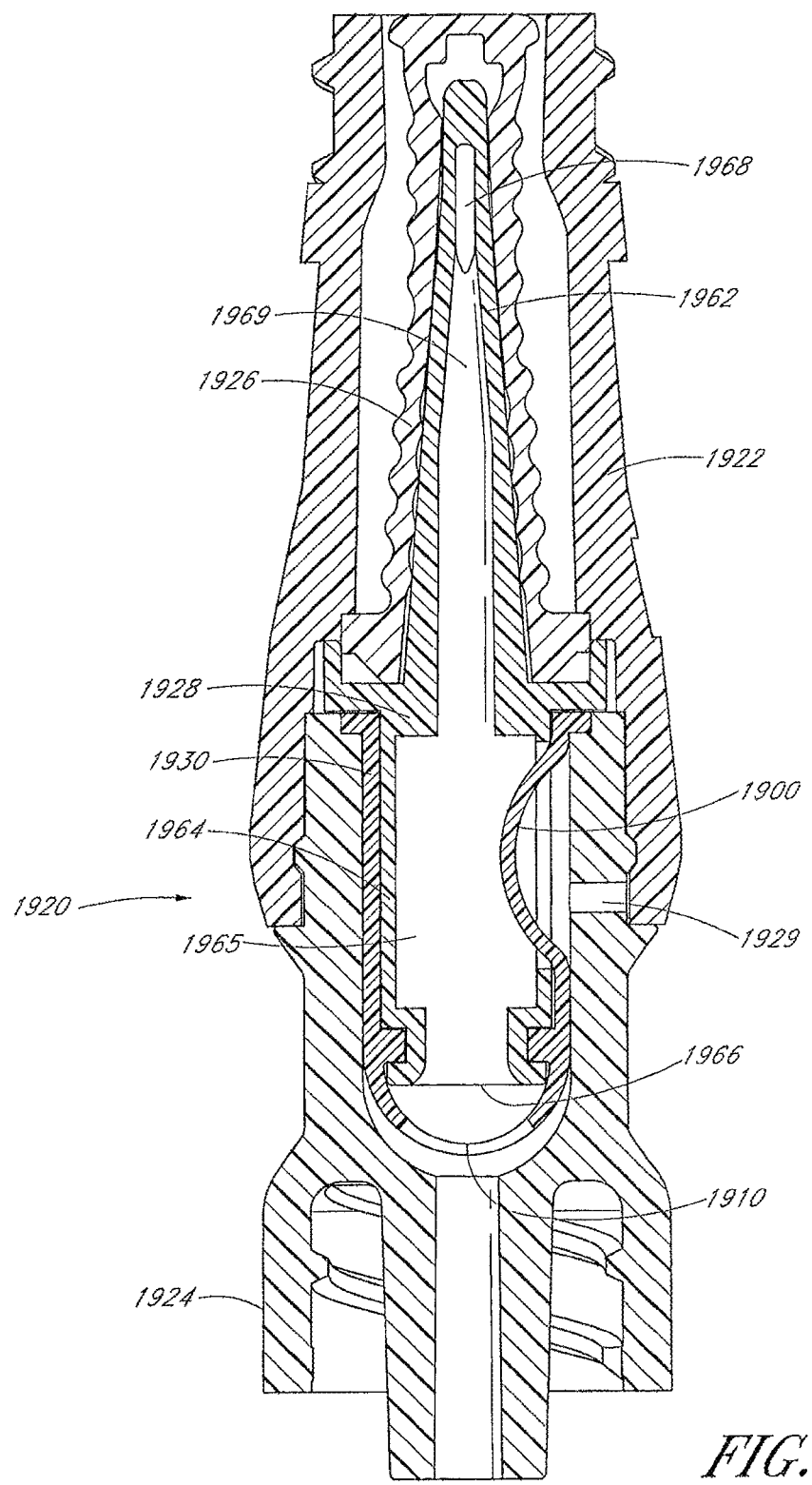
FIG. 74 is a section view of a valve or needleless connector that includes the support member shown in FIG. 73.

FIG. 73 is a perspective view of a support member 1928. FIG. 74 is a section view of a valve or needleless connector 1920 that includes the support member 1928. In some embodiments, the connector 1920 can have any of the features or other details or configurations of any other connector described herein. In some embodiments, the connector 1920 can include a body member 1922, a base member 1924, a seal member 1926, the support member 1928, a regulator 1930 which can be, for example, the same as, or similar to, the body member 22, base member 24, seal member 26, support member 28, and regulator 30 of the connector 20.

In some embodiments, the distal portion 1964 of the support member 1928 can comprise an internal cavity 1965 in fluid communication with the distal opening 1966, the fluid passageway 1969, and the one or more holes 1968 formed in the elongate portion 1962. The support member 1928 can include one or more openings 1986 formed laterally or radially through the distal portion 1964 thereof.

In some embodiments, the regulator 1930 can be positioned over the distal portion 1964 of the support member 1928 in a manner similar to that discussed in connection with the connector 20. In some embodiments, at least a portion of the body portion 1900 can be configured to stretch and expand, or otherwise move, through the opening 1968 formed in the distal portion 1964 of the support member 1928 and into the internal cavity 1965. If a backflow-inducing event occurs, air from outside the connector 1920 can pass through the hole 1929 and cause the body portion 1900 of the regulator 1930 to expand into the internal cavity 1965, thereby reducing the volume of fluid in the internal cavity 1965 and alleviating the pressure differential caused by the syringe rebound, withdrawal of a medical implement, or other backflow-inducing event. In some embodiments, the force required to cause the body portion 1900 to expand into the internal cavity 1965 is less than the force required to open the one or more slits 1910 on the regulator for fluid flow in the proximal direction. In some embodiments, if additional pressure is applied, such as when intentionally drawing fluid from the connector 1920 into a syringe, the slits 1910 on the regulator 1930 can open to allow fluid to flow in the proximal direction.

In some embodiments, the support member 1928 can include a protrusion 1927 or other feature configured to be received by a notch (not shown) in the base member 1924 so as to align the opening 1986 in the distal portion 1964 of the support member 1928 with the hole 1929 in the base member 1924. In some embodiments, the base member 1924 can include an annular air channel (not shown) in communication with the hole 1929 that allows air to reach the area of the body portion 1900 of the regulator 1930 that expands through the open 1986 even when the opening 1986 is not aligned with the hole 1929. In some embodiments, the support member 1928 can include multiple openings 1986 so that the body portion 1900 of the regulator 1930 can expand into the internal cavity 1965 from multiple locations. The annular air channel can allow air to reach each expanding location from a single air hole 1929, or multiple air holes 1929 can be formed in the base member 1924.

FIG. 75 is a section view of a support member 2028. FIG. 76 is a partial section view of a portion of the support member 2028. With reference to FIGS. 75 and 76, in some embodiments, the distal portion 2064 of the support member 2028 can include an internal cavity 2065 in fluid communication with the distal opening 2066, the fluid passageway 2069, and the one or more holes 2068 formed in the elongate portion 2062. The support member 2028 can include an opening 2086 formed laterally or radially through the distal portion 2064 thereof. In some embodiments, an inflatable member, such as bag member 2030 can be positioned in the opening 2086. The bag member 2030 can include a generally circular connection region 2002 that forms an airtight seal with the walls of the opening 2086 in a seat formed therein so that air cannot move past the connection region 2002 unless it enters the inner volume 2006 of the bag 2030. The connection region 2002 can be secured to the walls of the opening 2086 on exterior and/or interior surface of the support member 2028. The bag member 2030 can be folded, compressed, flattened, or otherwise made smaller in an initial position before fluid pressure differentials cause it to change its shape and volume.

FIG. 76 is a partial section view of the support member 2028 showing the bag member in a smaller-volume state. If a backflow-inducing event occurs, the bag member 2030 can inflate, expand, or otherwise move to increase its effective volume within the internal cavity 2065 as the inner volume 2006 fills with air from outside. As the volume of the inner volume 2006 of the bag member 2030 increases, the remaining volume of fluid in the internal cavity 2065 of the support member 2028 decreases, thereby alleviating the pressure differential created by the backflow event. In some embodiments, a backflow resist valve (e.g., the valve member 730) can be coupled to the distal end of the support member 2028 to cooperate with the variable volume chamber formed by the bag member 2030 to prevent backflow in a manner similar to those discussed elsewhere herein.

In some embodiments, the bag member 2030 can be constructed from a flaccid material (e.g., polyethylene) that can allow the bag member 2030 to inflate without substantial (or, in some cases, without any) expansion or stretching, or the bag member 2030 can be constructed from an elastomeric material (e.g., rubber or silicone) that allows the bag member 2030 to expand and contract. In some embodiments, the bag member 2030 can be constructed from a material that is relatively non-expandable, but is flexible enough to allow the bag member 2030 to unfold. In some embodiments, the bag member 2030 can be secured to the inside surface or outside surface of the support member 2028 rather than inside the opening 2086 itself.

In some embodiments, the support member 2028 can include a protrusion or other feature (not shown) that is received by a notch in another component (e.g. a base member) to align the opening 2086 with an air hole. In some embodiments, an annular air channel can provide fluid communication between the opening 2086 and the air hole in a similar manner to that discussed in connection with the connector 1920.

Figure 78:
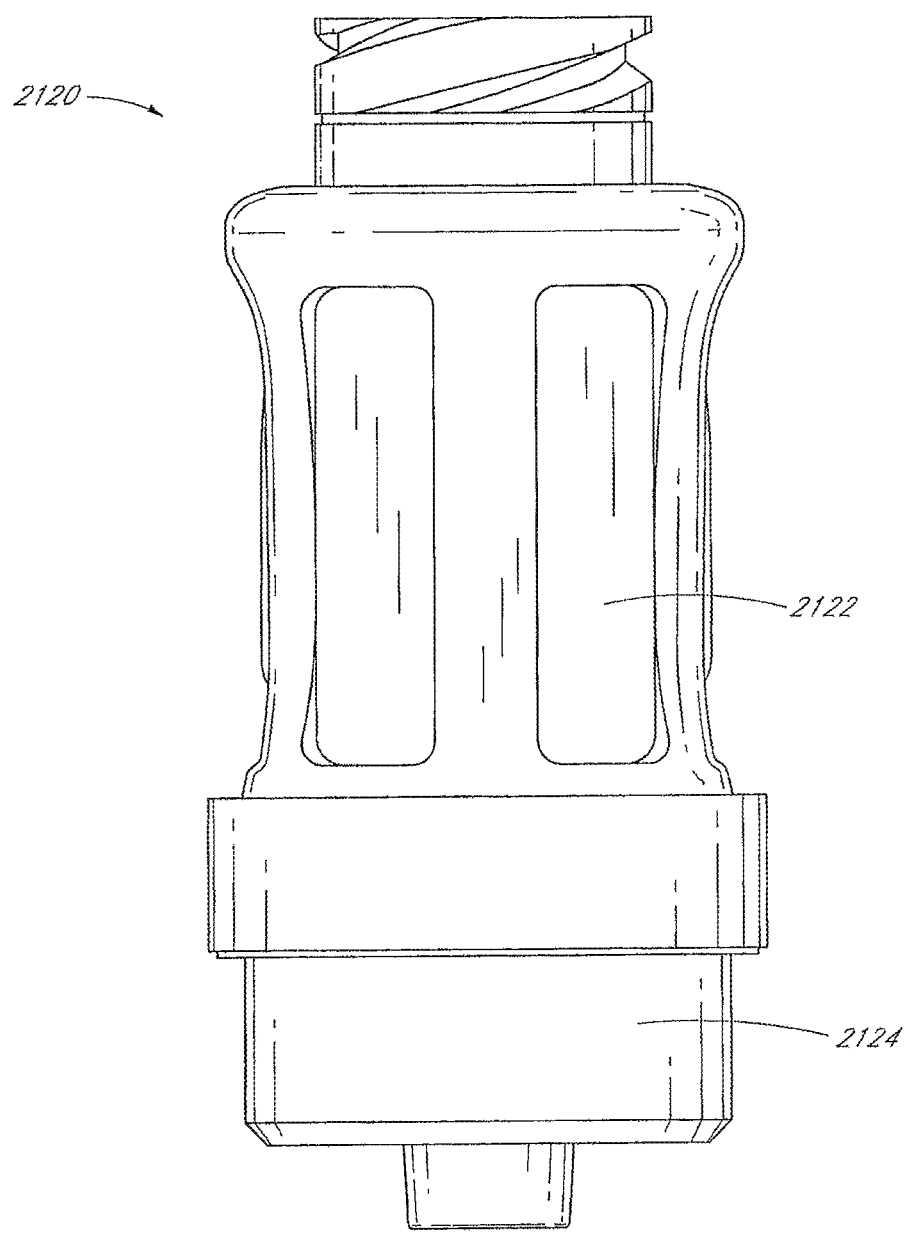
FIG. 78 is a side view of another embodiment of a valve or needleless connector.
Figure 79:
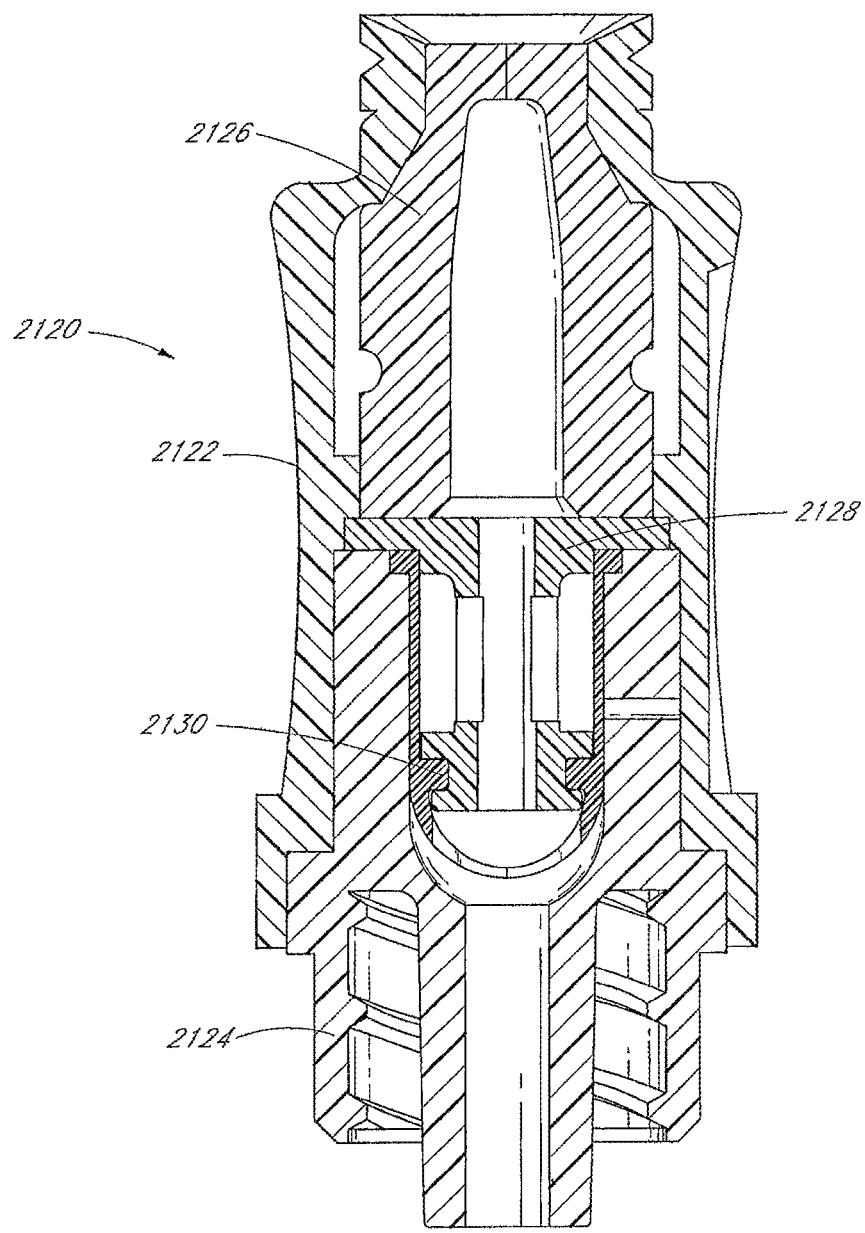
FIG. 79 is a section view of the connector shown in FIG. 78 taken along the axial centerline of the connector.

Many types of needleless connectors can include a backflow resistance module, such as any of those described herein. For example, FIG. 78 is a side view of a valve or needleless connector 2120, which can have some features or characteristics similar in some regards to the 2452040xx Swabable Valve available from Halkey-Roberts Corporation of St. Petersburg, Fla. FIG. 79 is a section view of the connector 2120 shown in FIG. 78. Some features and characteristics of the connector 2120 are described in U.S. Pat. No. 6,651,956, the entirety of which is hereby incorporated by reference herein for all that it discloses. In some embodiments, the connector 2120 can include a body member 2122, a base member 2124, a seal member 2126, a support member 2128 and a regulator 2130. In some embodiments, the support member 2128 can be formed without an elongate portion. The regulator 2130 and support member 2128, as well as other components of the connector 2120, can provide a backflow resistance module that includes a variable volume chamber and/or a backflow resist valve. The backflow resistance module of the illustrated embodiment of the connector 2120 can operate in a manner similar to that described herein in connection with the connector 20 to prevent backflow. In some embodiments, the connector 2120 can include any other backflow resistance module, such as those that are similar to the other backflow resistant modules disclosed herein.

Figure 80:
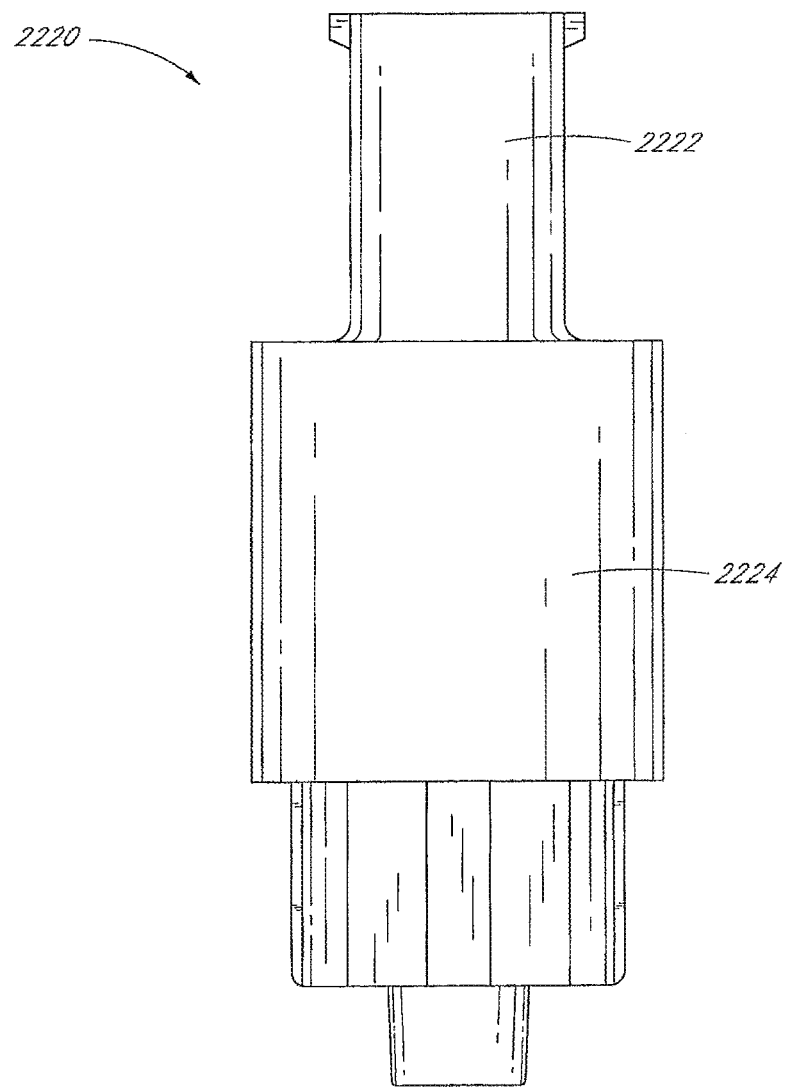
FIG. 80 is a side view of another embodiment of a valve or needleless connector.
Figure 81:
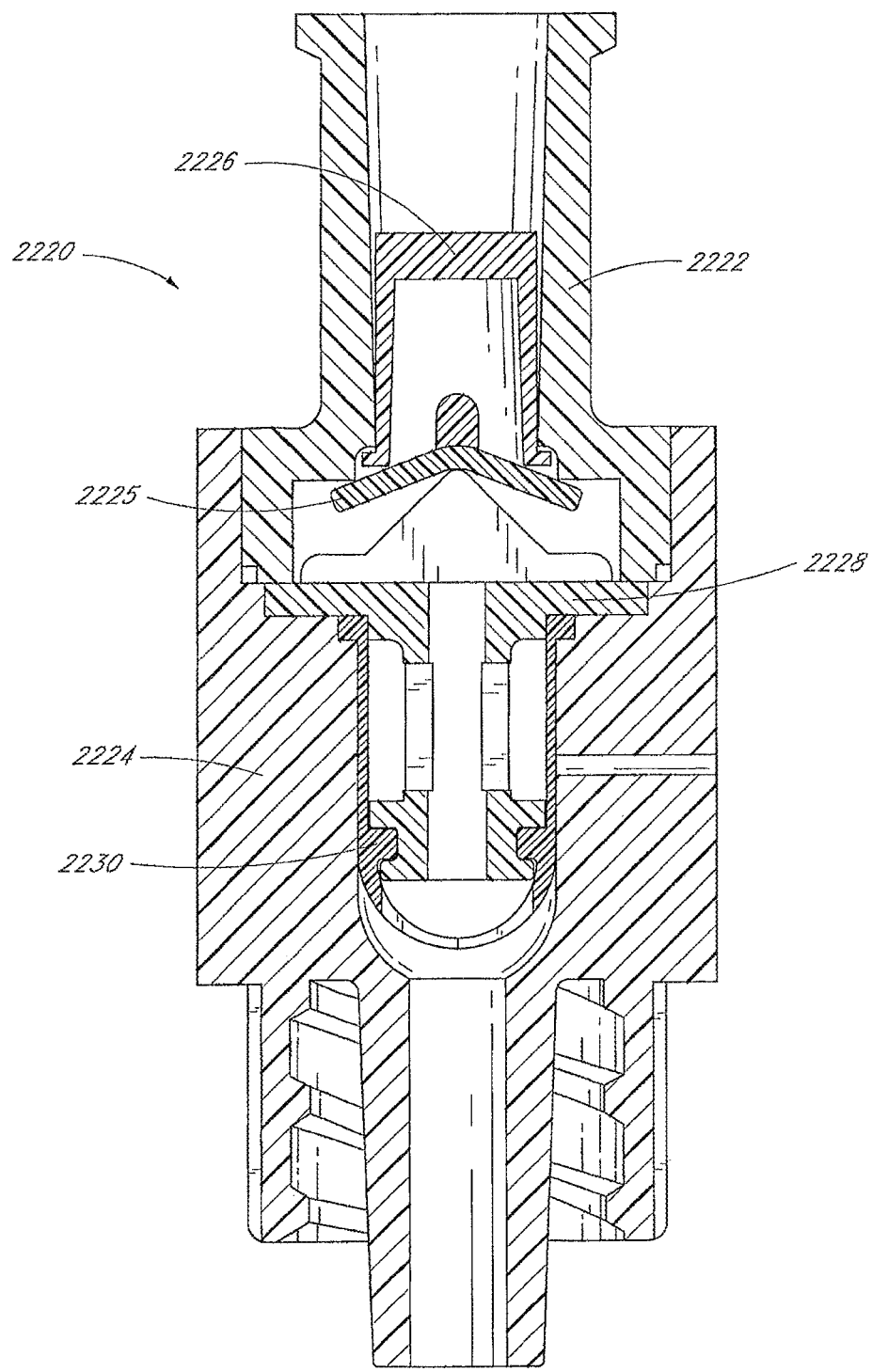
FIG. 81 is a section view of the connector shown in FIG. 80 taken along the axial centerline of the connector.

FIG. 80 is a side view of a valve or needleless connector 2220, which can have some features or characteristics similar in some regards to the SafeSite connector available from B. Braun Medical, Inc. FIG. 81 is a section view of the connector 2220. Some features and characteristics of the connector 2220 are described in U.S. Pat. No. 4,683,916, the entirety of which is hereby incorporated by reference herein for all that it discloses. In some embodiments, the connector 2220 can include a body member 2222, a base member 2224, a disk valve 2225, an actuator 2226 configured to open the disk valve 2225 when a medical implement attached to the connector 2220, a support member 2228, and a regulator 2230. In some embodiments, the support member 2228 can be formed without an elongate portion. The regulator 2230 and support member 2228, as well as other components of the connector 2220, can provide a backflow resistance module that includes a variable volume chamber and/or a backflow resist valve. The backflow resistance module of the illustrated embodiment of the connector 2220 can operate in a manner similar to that described herein in connection with the connector 20 to prevent backflow. In some embodiments, the connector 2220 can include any other backflow resistance module, such as those that are similar to the other backflow resistance modules disclosed herein.

Although the connector disk valve 2225 can be configured to seal the connector against fluid flow in the proximal direction as the medical implement is removed from the connector 2220, a small amount of backflow can occur as the medical implement is withdrawn before the disk valve 2225 closes. Also, some sources of backflow, such as syringe rebound, can occur while the connector 2220 is attached to a medical implement and the disk valve 2225 is open. The backflow resistance module of the connector 2220 can be configured to eliminate or reduce the effects of these backflow inducing events.

Figure 82:
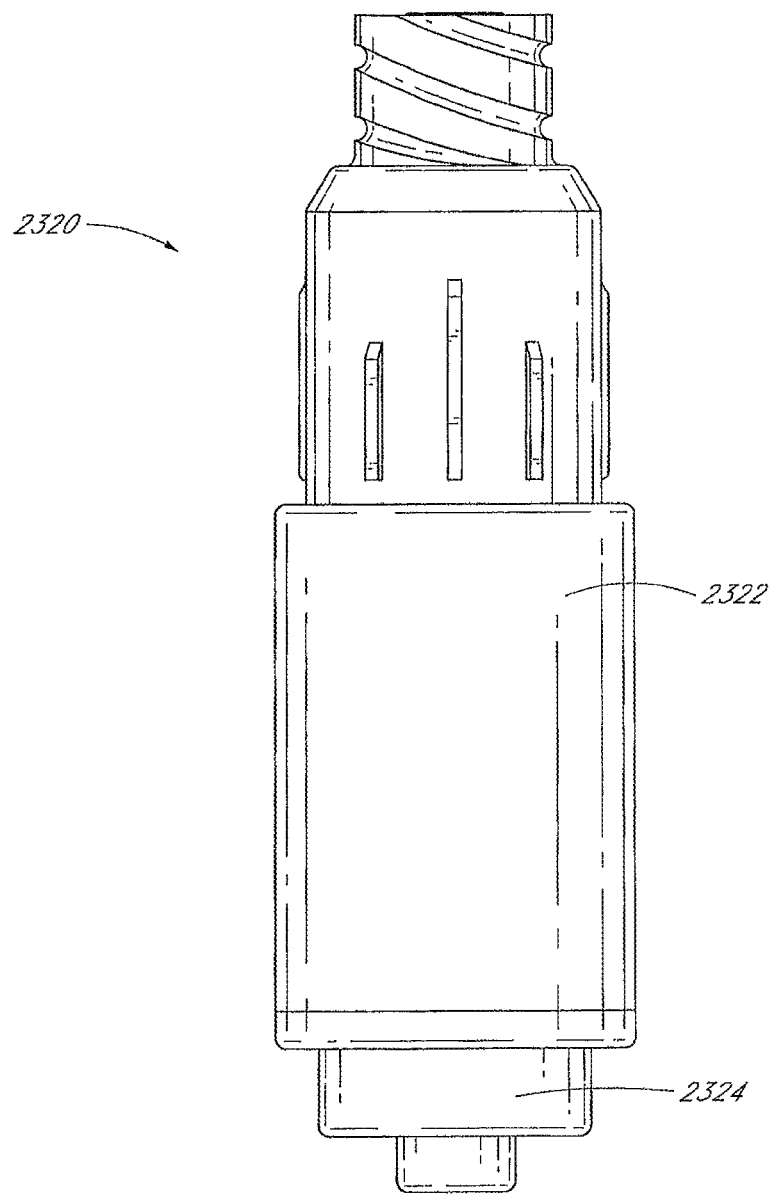
FIG. 82 is a side view of another embodiment of a valve or needleless connector.
Figure 83:
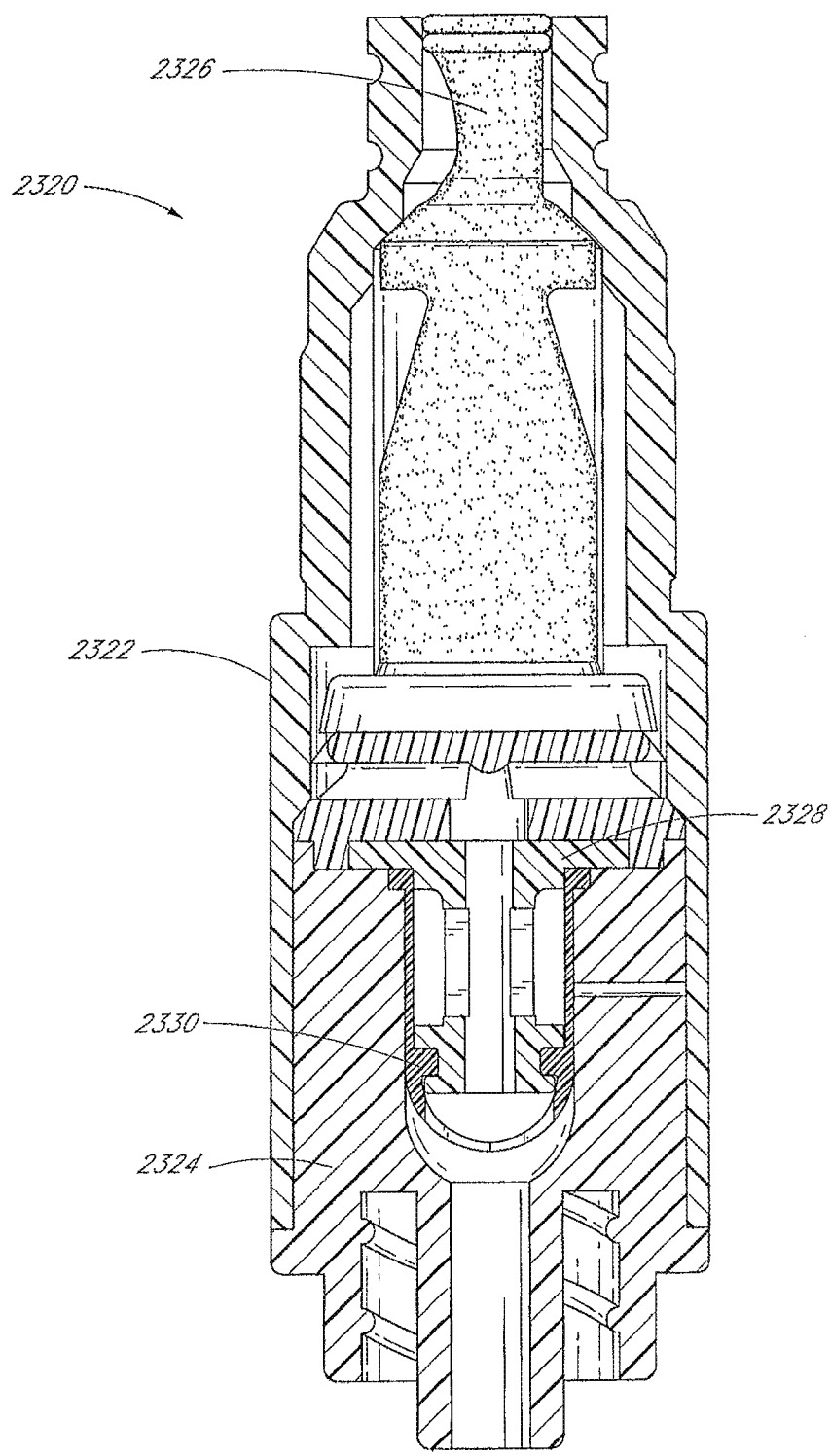
FIG. 83 is a section view of the connector shown in FIG. 82 taken along the axial centerline of the connector.

FIG. 82 is a side view of a valve or needleless connector 2320, which can have some features or characteristics similar in some regards to the MaxPlus connector available from Medegen, Inc. of Ontario, Calif. FIG. 83 is a section view of the connector 2320. Some features and characteristics of the connector 2320 are described in U.S. Pat. No. 5,782,816 and U.S. Patent Publication No. 2005/0059952, the entireties of each of which are both hereby incorporated by reference herein for all that they disclose. In some embodiments, the connector 2320 can include a body member 2322, a base member 2324, a resilient plug seal 2326, a support member 2328, and a regulator 2330. The regulator 2330 and support member 2328, as well as other components of the connector 2320, can provide a backflow resistance module that includes a variable volume chamber and a backflow resist valve. The backflow resistance module of the illustrated embodiment of the connector 2320 can operate in a manner similar to that described herein in connection with the connector 20 to prevent backflow. In some embodiments, the connector 2320 can include any other backflow resistance module, such as those that are similar to the other backflow resistance modules disclosed herein.

In some embodiments, the connector 2320 can be configured to produce a positive flow of fluid in the distal direction as a medical implement is disconnected from the connector 2320. For example, as a medical implement is connected to the connector 2320, the resilient plug seal 2326 can collapse and increase the volume of fluid inside the connector 2320. Then, as the medical implement is later removed, the resilient plug seal 2326 can expand reducing the volume of fluid in the connector 2320 and alleviating the pressure caused by removal of the medical implement. However, some sources of backflow, such as syringe rebound, can occur while the connector 2320 is attached to the medical implement and the resilient plug member 2326 is maintained in the compressed state. The backflow resistance module of the connector 2320 can be configured to eliminate or reduce the effects of the backflow inducing events not resolved by the resilient plug seal 2326. In some embodiments, the variable volume chamber formed at least in part by the regulator 2330 can change in volume independent of movement of the resilient plug seal 2326. In some embodiments, as a medical implement is attached to the connector, the variable volume chamber formed at least in part by the regulator 2330 can reduce in volume as fluid flows into the increasing volume around the resilient plug seal 2326, preventing or resisting backflow of fluid that would otherwise be drawn into the distal end of the connector 2320 (e.g., from a catheter). The variable volume chamber formed at least in part by the regulator 2330 can increase in volume as fluid is infused through the connector 2320 in the distal direction so that the backflow resistance module can be prepared to handle later backflow inducing events.

Figure 84:
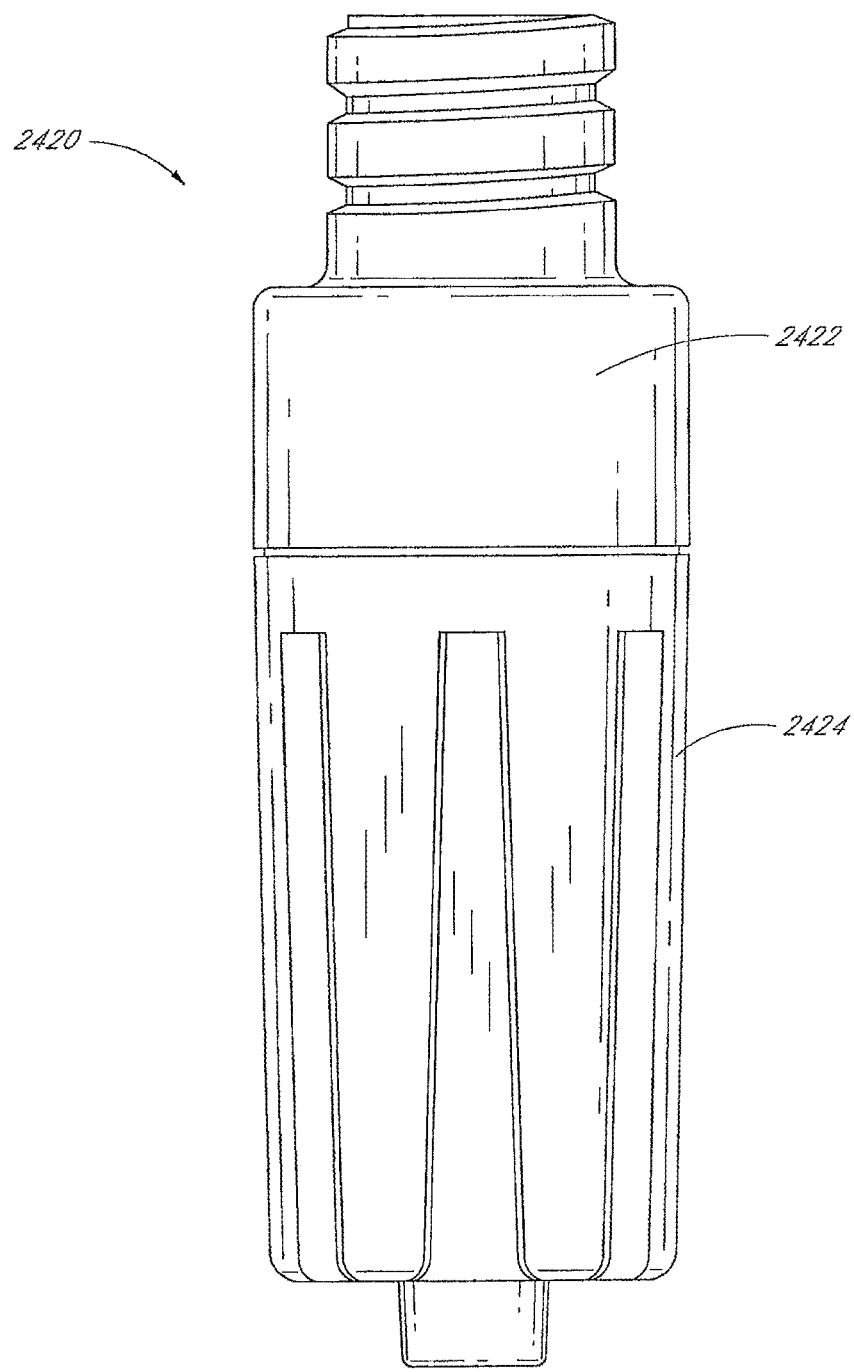
FIG. 84 is a side view of another embodiment of a valve or needleless connector.
Figure 85:
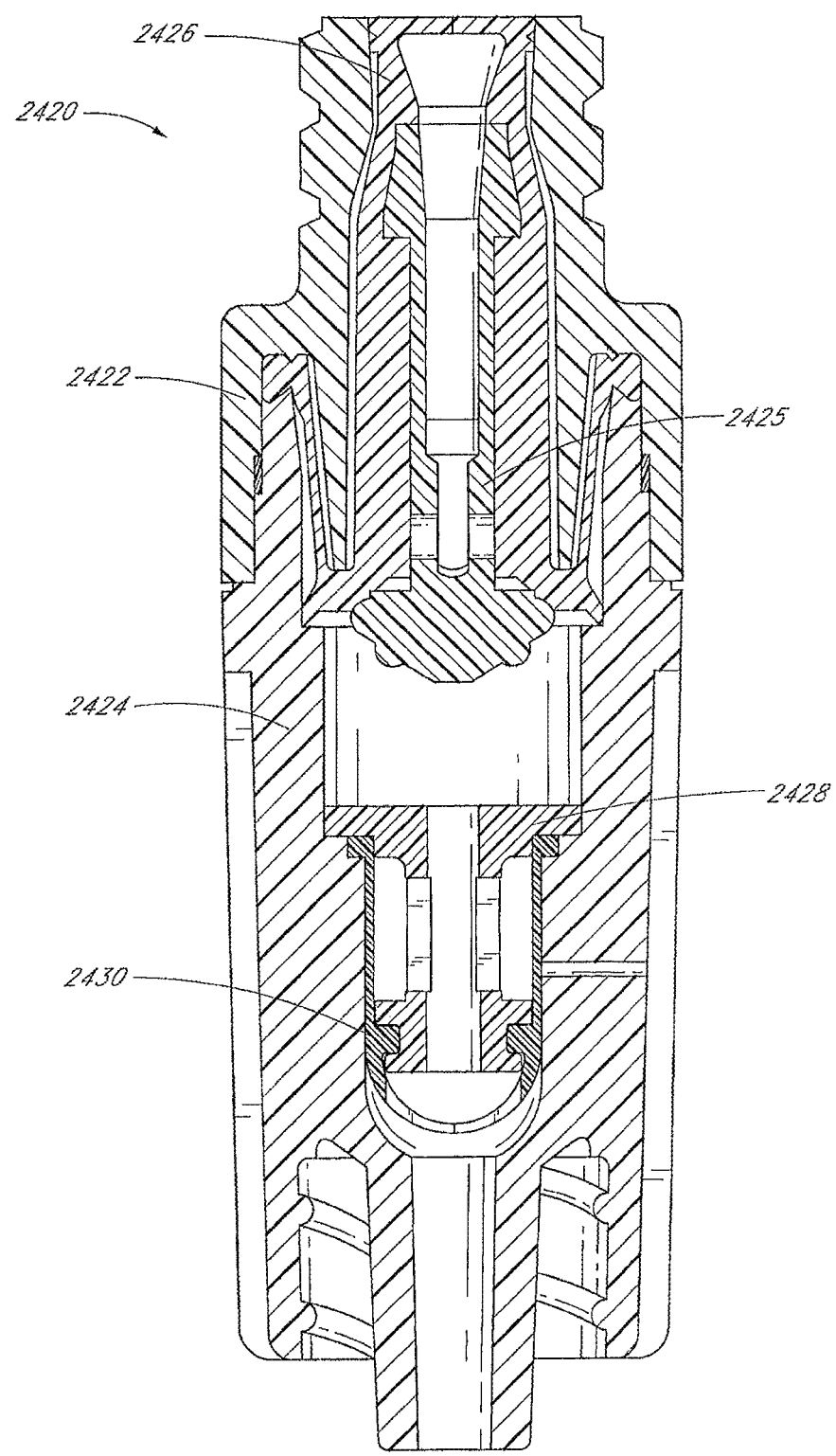
FIG. 85 is a section view of the connector shown in FIG. 84 taken along the axial centerline of the connector.

FIG. 84 is a side view of a valve or needleless connector 2420, which can have some features or characteristics similar in some regards to the CLEARLINK connector available from Baxter International, Inc., of Deerfield, Ill. FIG. 85 is a section view of the connector 2420. Some features and characteristics of the connector 2420 are described in U.S. Pat. No. 6,585,229, the entirety of which is hereby incorporated by reference herein for all that it discloses. In some embodiments, the connector 2420 can include a body member 2422, a base member 2424, a seal member 2426, a plug member 2425 slidably received inside the seal member 2426, a support member 2428, and a regulator 2430. The regulator 2430 and support member 2428, as well as other components of the connector 2420, can provide a backflow resistance module that includes a variable volume chamber and/or a backflow resist valve. The backflow resistance module of the illustrated embodiment of the connector 2420 can operate in a manner similar to that described herein in connection with the connector 20 to prevent backflow. In some embodiments, the connector 2420 can include any other backflow resistance module, such as those that are similar to the other backflow resistance modules disclosed herein.

Figure 86A:
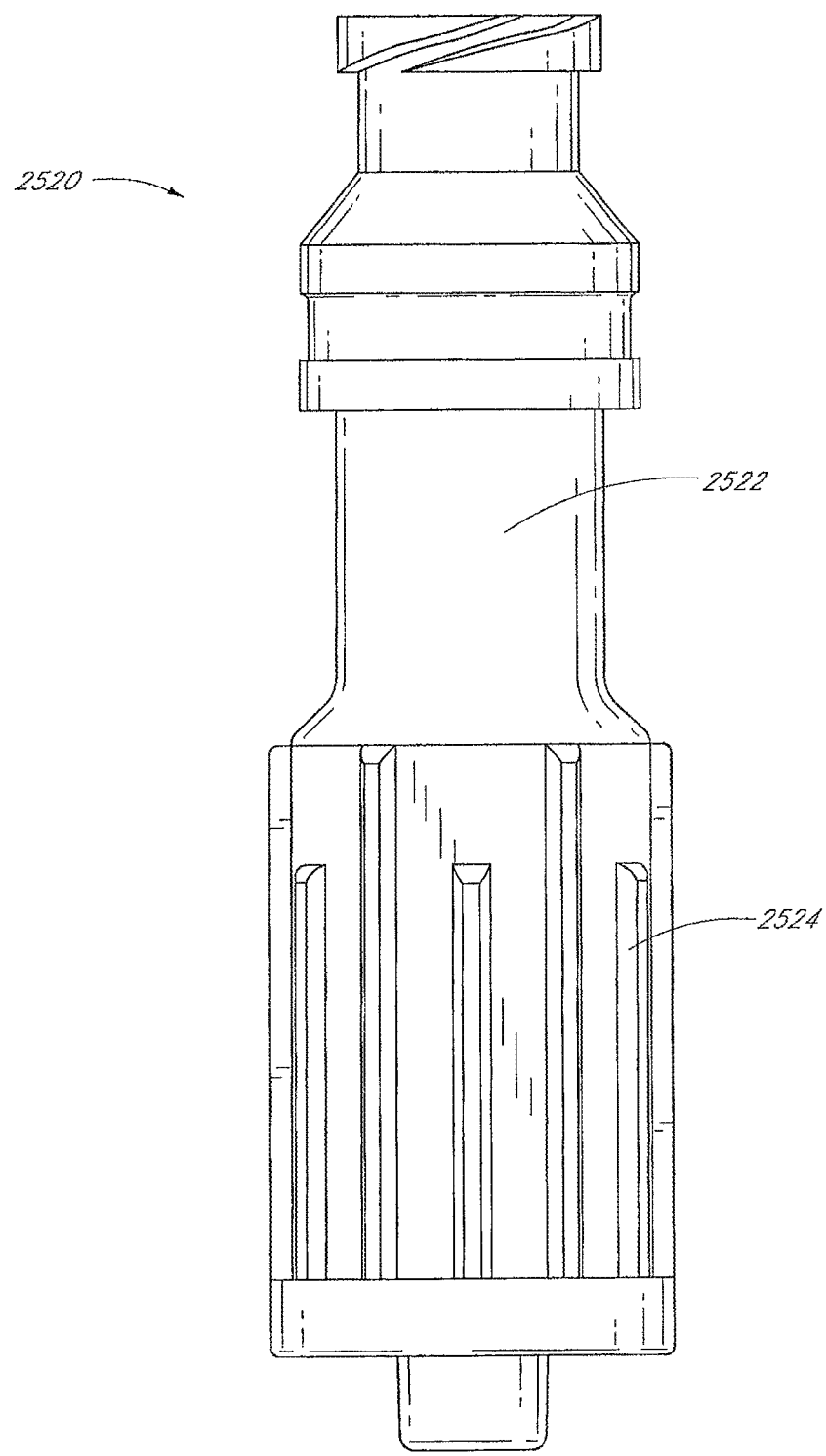
FIG. 86A is a side view of another embodiment of a valve or needleless connector.
Figure 86B:
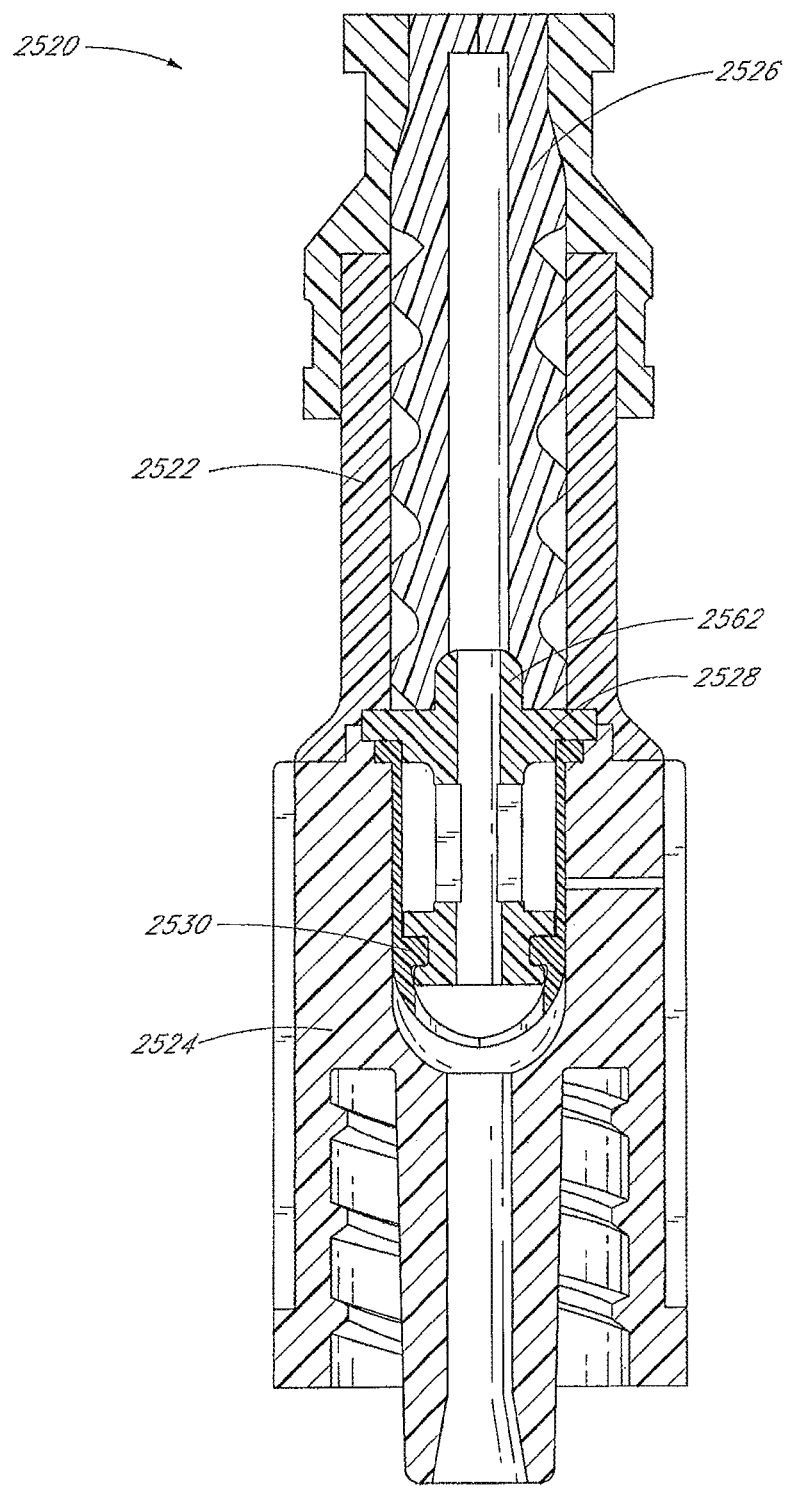
FIG. 86B is a section view of the connector shown in FIG. 86A taken along the axial centerline of the connector.

FIG. 86A is a side view of a valve or needleless connector 2520, which can have some features or characteristics similar in some regards to the SmartSite connector available from Cardinal Health, Inc. of Dublin, Ohio. FIG. 86B is a section view of the connector 2520. Some features and characteristics of the connector 2520 are described in U.S. Pat. No. 5,676,346, the entirety of which is hereby incorporated by reference herein for all that it discloses. In some embodiments, the connector 2520 can include a body member 2522, a base member 2524, a seal member 2526, a support member 2528, and a regulator 2530. In some embodiments, the support member 2528 does not include an elongate portion but instead includes a proximally extending projection 2562 that can be substantially shorter and does not extend through the proximal end of the seal member 2526. The regulator 2530 and support member 2528, as well as other components of the connector 2520, can provide a backflow resistance module that includes a variable volume chamber and/or a backflow resist valve. The backflow resistance module of the illustrated embodiment of the connector 2520 can operate in a manner similar to that described herein in connection with the connector 20 to prevent backflow. In some embodiments, the connector 2520 can include any other backflow resistance module, such as those that are similar to the other backflow resistance modules disclosed herein.

Figure 87A:
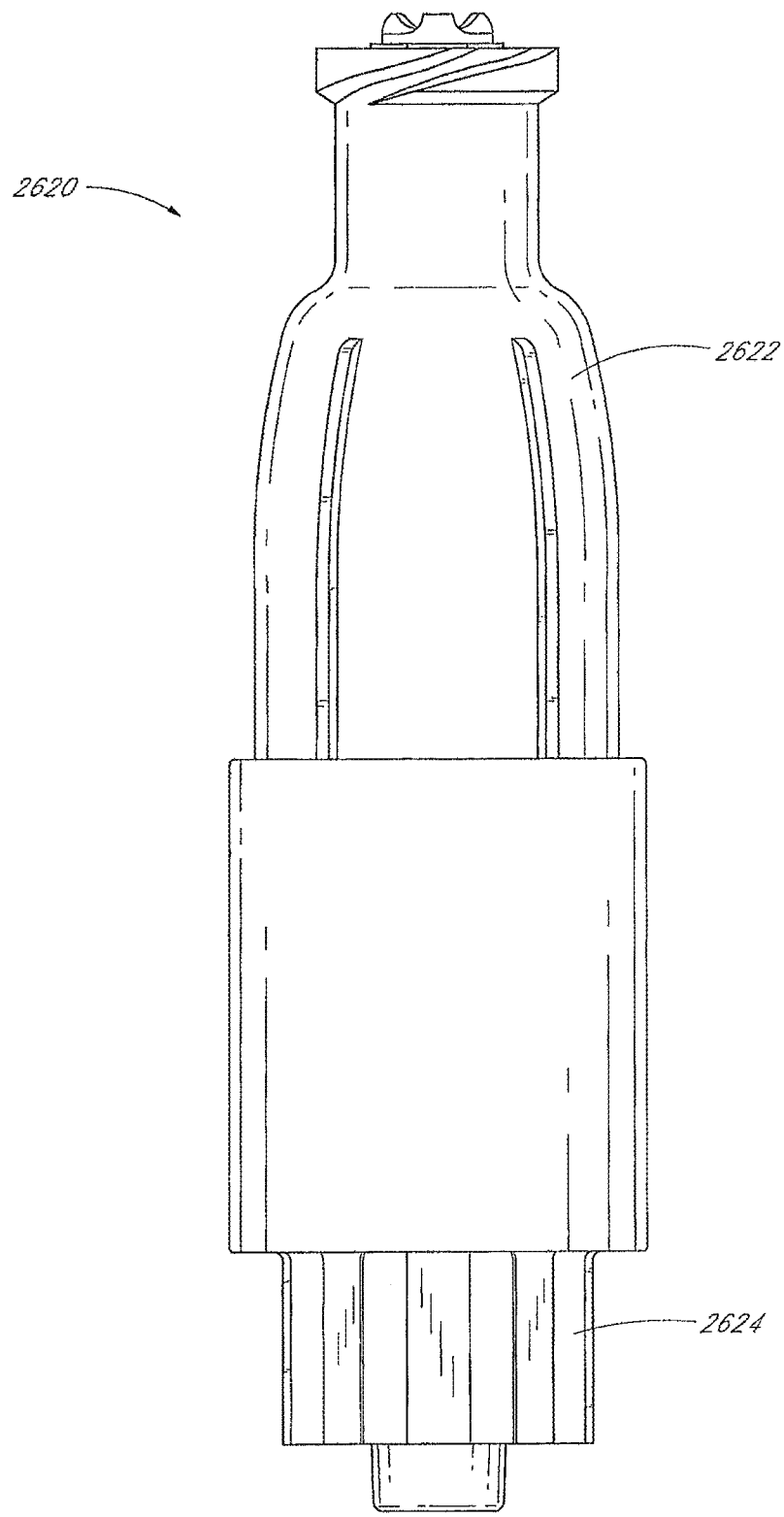
FIG. 87A is a side view of another embodiment of a valve or needleless connector.
Figure 87B:
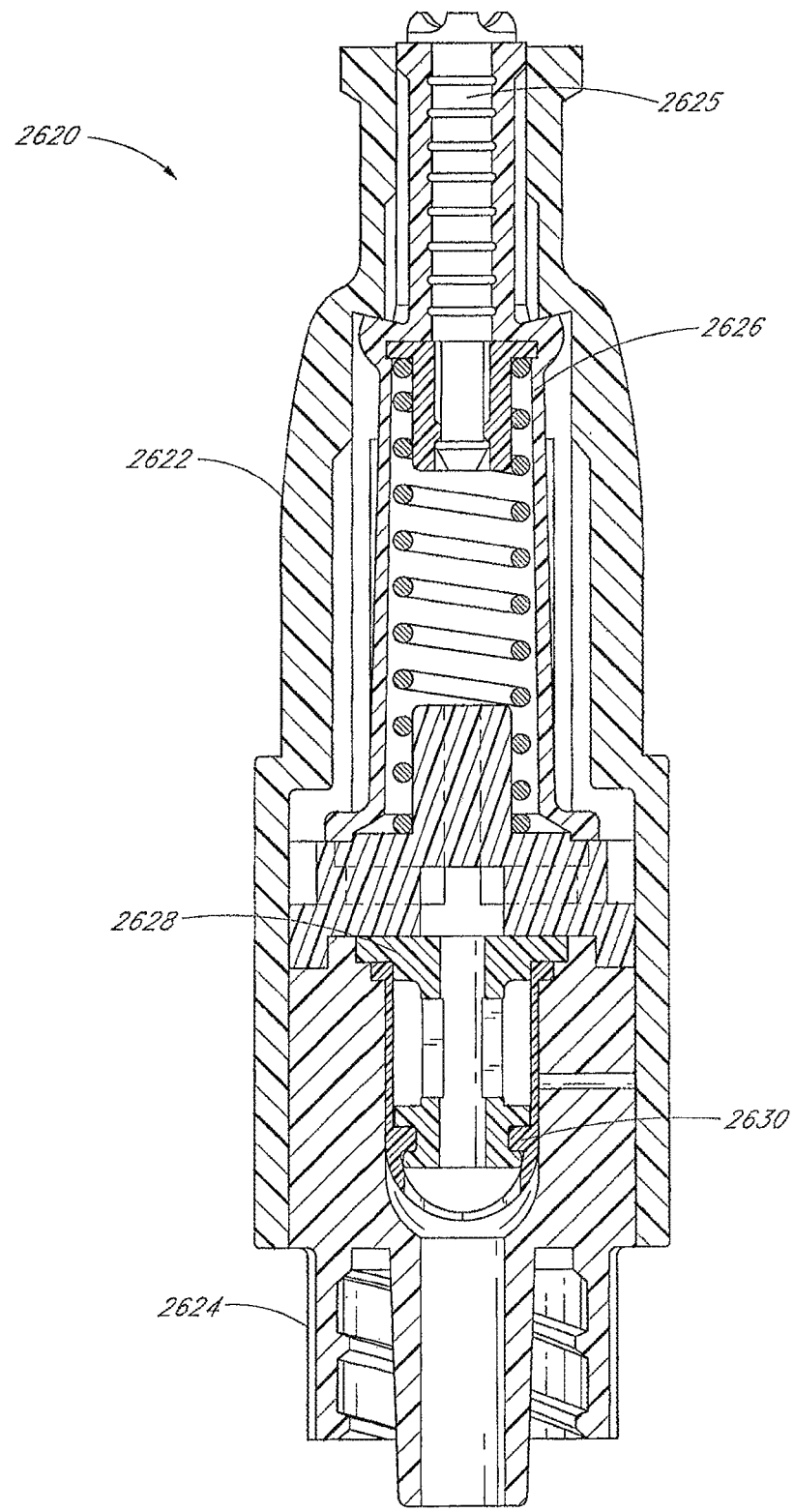
FIG. 87B is a section view of the connector shown in FIG. 87A taken along the axial centerline of the connector.

FIG. 87A is a side view of a valve or needleless connector 2620, which can have some features or characteristics similar in some regards to the UltraSite connector available from B. Braun Medical, Inc. FIG. 87B is a section view of the connector 2620. Some features and characteristics of the connector 2620 are described in U.S. Pat. No. 5,439,451, the entirety of which is hereby incorporated by reference herein for all that it discloses. In some embodiments, the connector 2620 can include a body member 2622, a base member 2624, a plug member 2625, a resilient seal member 2626, a support member 2628, and a regulator 2630. The regulator 2630 and support member 2628, as well as other components of the connector 2620, can provide a backflow resistance module that includes a variable volume chamber and a backflow resist valve. The backflow resistance module of the illustrated embodiment of the connector 2620 can operate in a manner similar to that described herein in connection with the connector 20 to prevent backflow. In some embodiments, the connector 2620 can include any other backflow resistance module, such as those that are similar to the other backflow resistance modules disclosed herein.

Figure 88A:
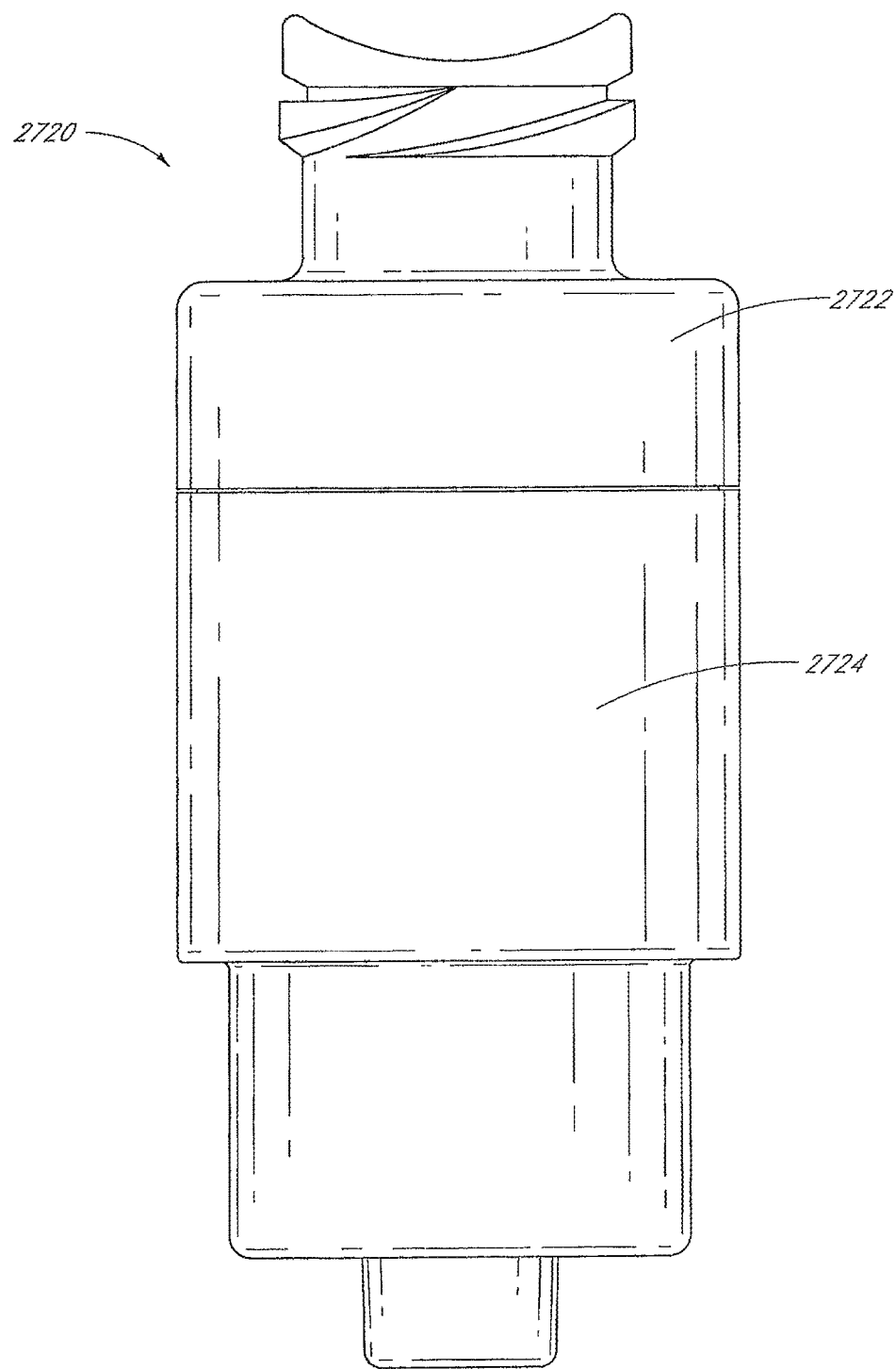
FIG. 88A is a side view of another embodiment of a valve or needleless connector.
Figure 88B:
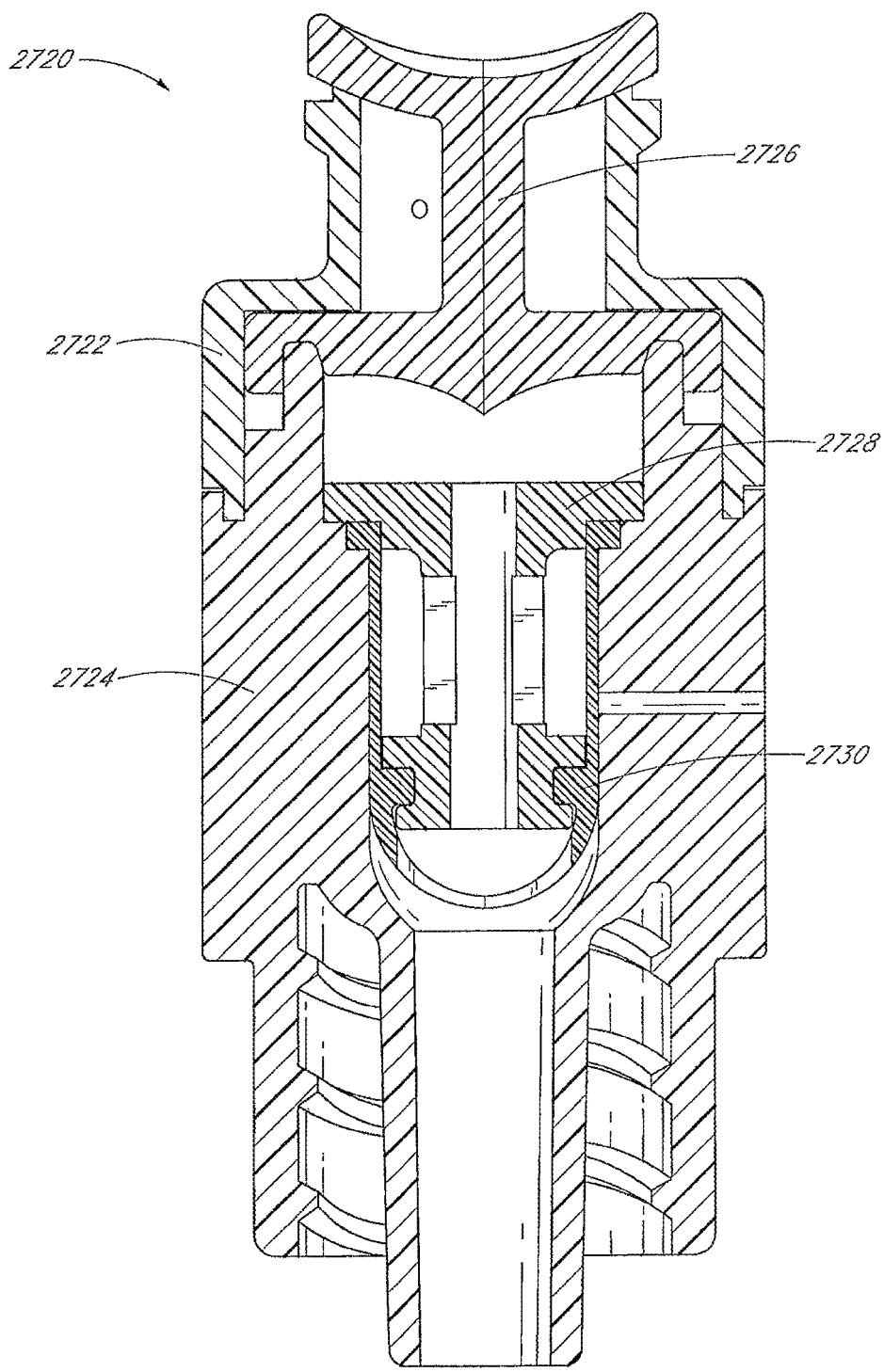
FIG. 88B is a section view of the connector shown in FIG. 88A taken along the axial centerline of the connector.

FIG. 88A is a side view of a valve or needleless connector 2720, which can have some features or characteristics similar in some regards to the Q-Syte connector available from Becton, Dickinson and Company, of Franklin Lakes, N.J. FIG. 88B is a section view of the connector 2720. Some features and characteristics of the connector 2720 are described in U.S. Pat. No. 6,908,459, the entirety of which is hereby incorporated by reference herein for all that it discloses. In some embodiments, the connector 2720 can include a body member 2722, a base member 2724, a seal member 2726, a support member 2728, and a regulator 2730. The regulator 2730 and support member 2728, as well as other components of the connector 2720, can provide a backflow resistance module that includes a variable volume chamber and/or a backflow resist valve. The backflow resistance module of the illustrated embodiment of the connector 2720 can operate in a manner similar to that described herein in connection with the connector 20 to prevent backflow. In some embodiments, the connector 2720 can include any other backflow resistance module, such as those that are similar to the other backflow resistance modules disclosed herein.

Figure 89A:
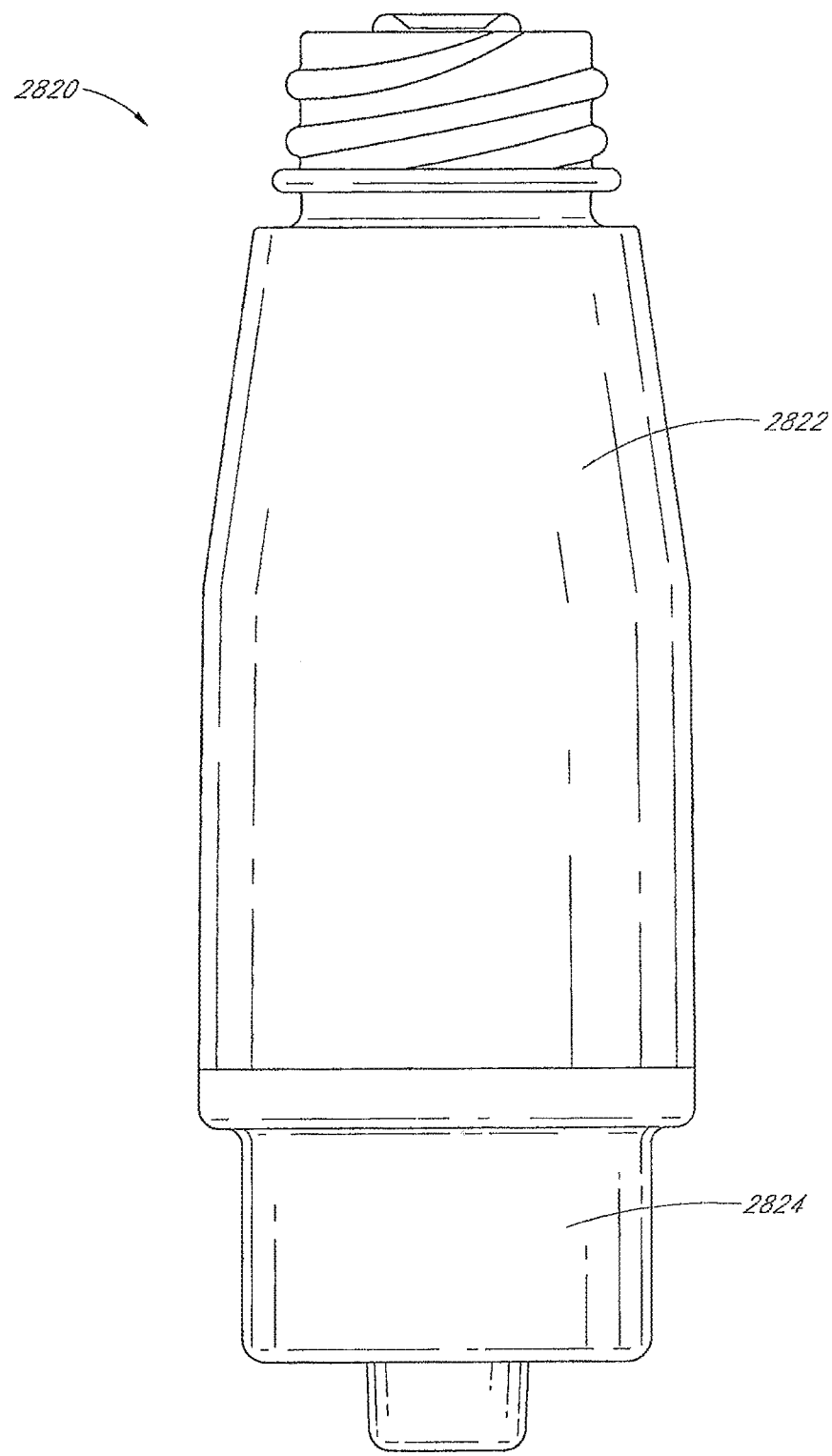
FIG. 89A is a side view of another embodiment of a valve or needleless connector.
Figure 89B:
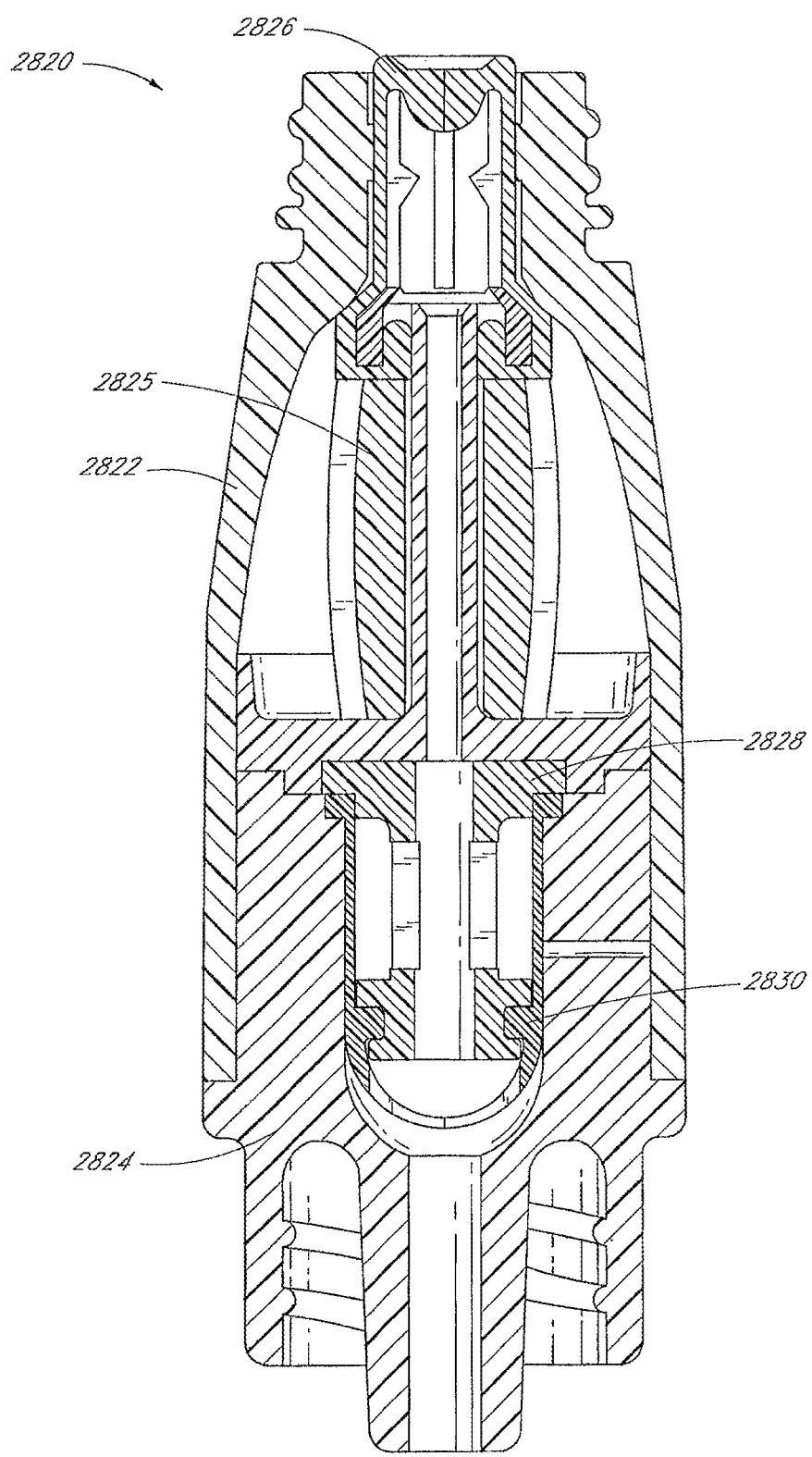
FIG. 89B is a section view of the connector shown in FIG. 89A taken along the axial centerline of the connector.

FIG. 89A is a side view of a valve or needleless connector 2820, which can have some features or characteristics similar in some regards to the Posiflow connector available from Becton, Dickinson and Company, of Franklin Lakes, N.J. FIG. 89B is a section view of the connector 2820. Some features and characteristics of the connector 2820 are described in U.S. Pat. No. 6,152,900, the entirety of which is hereby incorporated by reference herein for all that it discloses. In some embodiments, the connector 2820 can include a body member 2822, a base member 2824, a seal member 2826, a resilient member 2825, a support member 2828, and a regulator 2830. The regulator 2830 and support member 2828, as well as other components of the connector 2820, can provide a backflow resistance module that includes a variable volume chamber and/or a backflow resist valve. The backflow resistance module of the illustrated embodiment of the connector 2820 can operate in a manner similar to that described herein in connection with the connector 20 to prevent backflow. In some embodiments, the connector 2820 can include any other backflow resistance module, such as those that are similar to the other backflow resistance modules disclosed herein.

In some embodiments, the connector 2820 can be configured to produce a positive flow of fluid in the distal direction as a medical implement is disconnected from the connector 2820 to alleviate the pressure caused by removal of the medical implement. However, some sources of backflow, such as syringe rebound, can occur while the connector 2820 is attached to the medical implement. The backflow resistance module of the connector 2820 can be configured to eliminate or reduce the effects of the backflow inducing events not otherwise resolved. In some embodiments, the variable volume chamber formed at least in part by the regulator 2830 can change in volume independent of movement of the seal member 2826 and resilient member 2825 caused by attachment or removal of a medical implement. In some embodiments, as a medical implement is attached to the connector 2820, the variable volume chamber formed at least in part by the regulator 2830 can reduce in volume as fluid flows into the increasing volume in the seal member 2826, preventing backflow of fluid that would otherwise be drawn into the distal end of the connector 2820 (e.g., from a catheter). The variable volume chamber formed at least in part by the regulator 2830 can increase in volume as fluid is infused through the connector 2820 in the distal direction so that the backflow resistance module can be prepared to handle later backflow inducing events.

Figure 90A:
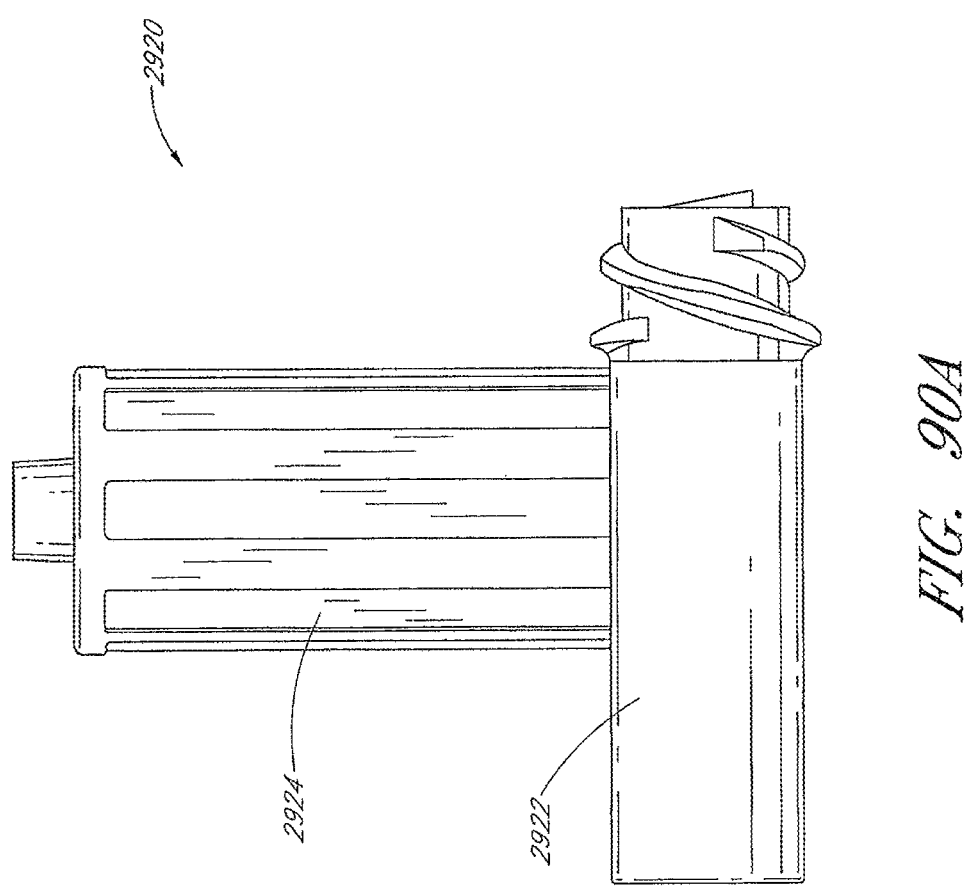
FIG. 90A is a side view of another embodiment of a valve or needleless connector.
Figure 90B:
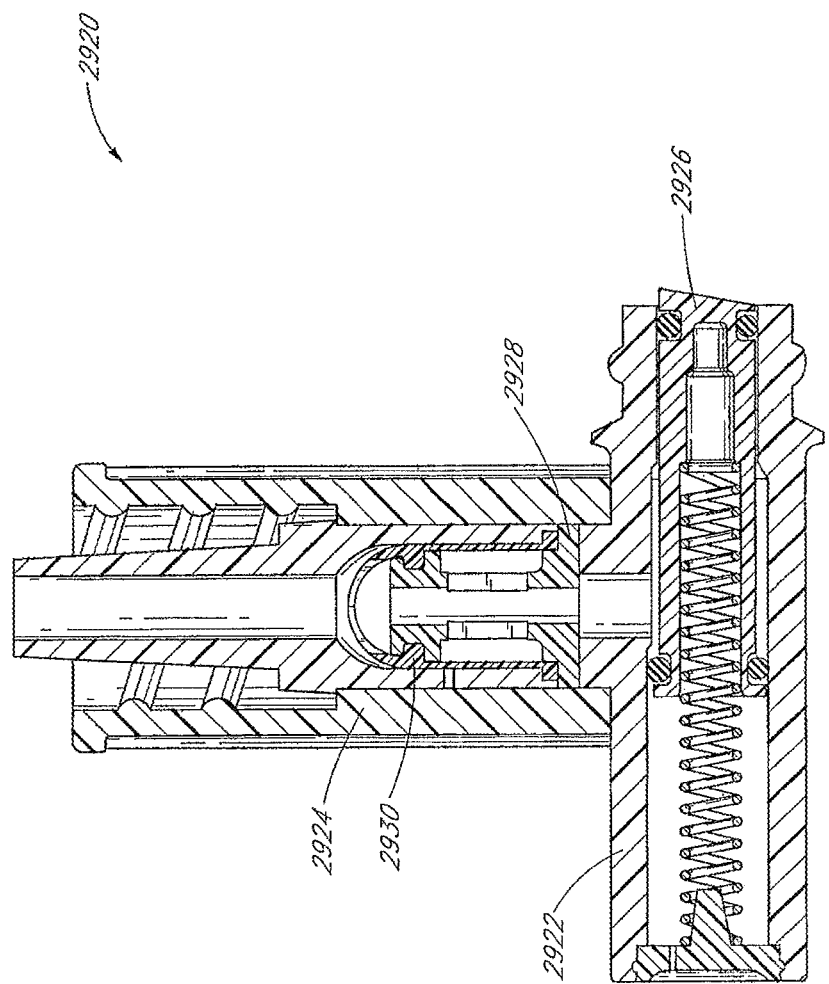
FIG. 90B is a section view of the connector shown in FIG. 90A taken along the axial centerline of the connector.

FIG. 90A is a side view of a valve or needleless connector 2920, which can have some features or characteristics similar in some regards to the CLC2000 connector available from ICU Medical, Inc., of San Clemente, Calif. FIG. 90B is a section view of the connector 2920. Some features and characteristics of the connector 2920 are described in U.S. Pat. No. 6,245,048, the entirety of which is hereby incorporated by reference herein for all that it discloses. In some embodiments, the connector 2920 can include a body member 2922, a base member 2924, a piston 2926 slidably positioned in the body member 2922, a support member 2928, and a regulator 2930. The regulator 2930 and support member 2928, as well as other components of the connector 2920, can provide a backflow resistance module that includes a variable volume chamber and a backflow resist valve. The backflow resistance module of the illustrated embodiment of the connector 2920 can operate in a manner similar to that described herein in connection with the connector 20 to prevent backflow. In some embodiments, the connector 2920 can include any other backflow resistance module, such as those that are similar to the other backflow resistance modules disclosed herein.

In some embodiments, the connector 2920 can be configured to produce a positive flow of fluid in the distal direction as a medical implement is disconnected from the connector 2920. The piston 1926 can be configured to slide down the body portion 1922 of the connector 2920 as the medical implement is attached, so that the volume of fluid around the plug 1926 increases. Then, as the medical implement is detached, the piston 2926 can slide up the body portion 1922, reducing the volume of fluid around the piston 2926 and alleviating the pressure caused by removal of the medical implement. However, some sources of backflow, such as syringe rebound, can occur while the connector 2920 is attached to the medical implement. The backflow resistance module of the connector 2920 can be configured to eliminate or reduce the effects of the backflow inducing events not resolved by the piston 2926. In some embodiments, the variable volume chamber formed at least in part by the regulator 2930 can change in volume independent of movement of the piston 2926 caused by attachment or removal of a medical implement. In some embodiments, as a medical implement is attached to the connector 2920, the variable volume chamber formed at least in part by the regulator 2930 can reduce in volume as fluid flows into the increasing volume around the piston 2926, preventing backflow of fluid that would otherwise be drawn into the distal end of the connector 2920 (e.g., from a catheter). The variable volume chamber formed at least in part by the regulator 2930 can increase in volume as fluid is infused through the connector 2920 in the distal direction so that the backflow resistance module can be prepared to handle later backflow inducing events.

Figure 91A:
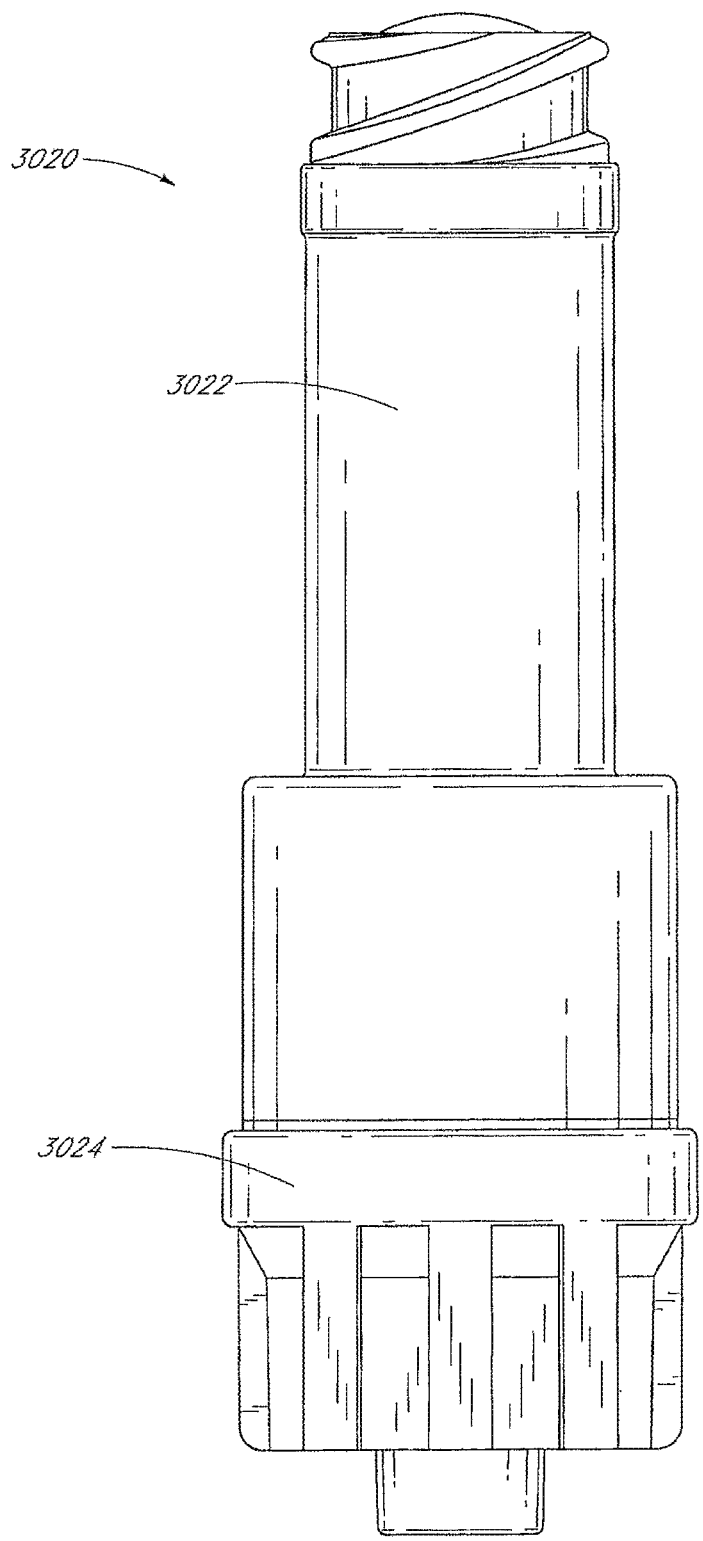
FIG. 91A is a side view of another embodiment of a valve or needleless connector.
Figure 91B:
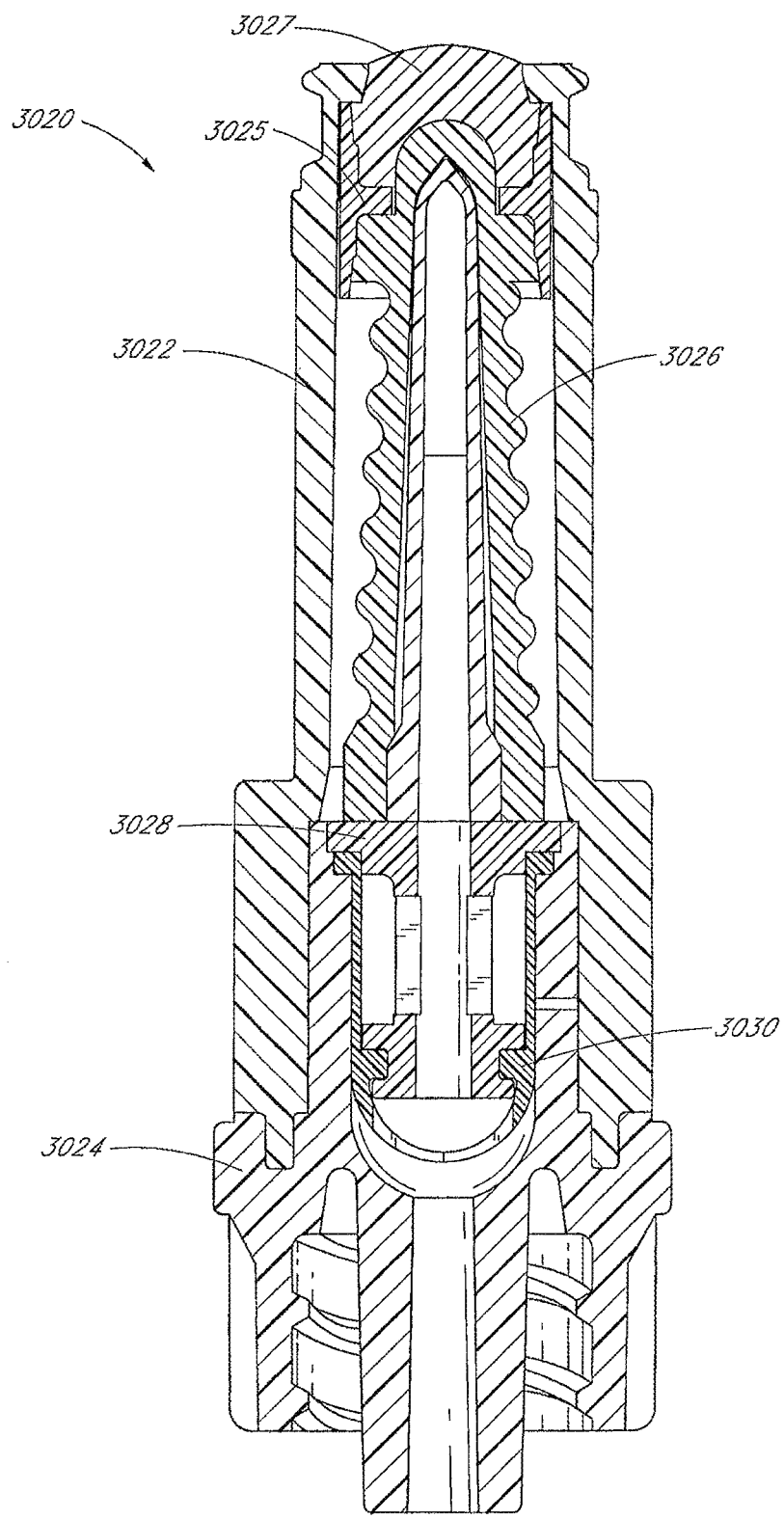
FIG. 91B is a section view of the connector shown in FIG. 91A taken along the axial centerline of the connector.

FIG. 91A is a side view of a valve or needleless connector 3020, which can have some features or characteristics similar in some regards to the InVision-Plus connector available from RyMed Technologies, Inc., of Franklin, Tenn. FIG. 91B is a section view of the connector 3020. Some features and characteristics of the connector 3020 are described in U.S. Pat. No. 6,994,315, the entirety of which is hereby incorporated by reference herein for all that it discloses. In some embodiments, the connector 3020 can include a body member 3022, a base member 3024, a seal member 3026, a guide member 3025, a septum member 3027, a support member 3028, and a regulator 3030. The regulator 3030 and support member 3028, as well as other components of the connector 3020, can provide a backflow resistance module that includes a variable volume chamber and/or a backflow resist valve. The backflow resistance module of the illustrated embodiment of the connector 3020 can operate in a manner similar to that described herein in connection with the connector 20 to prevent backflow. In some embodiments, the connector 3020 can include any other backflow resistance module, such as those that are similar to the other backflow resistance modules disclosed herein.

In some embodiments, the seal member 3026 can include a series of o-rings, arcuate segments, or other structures that facilitate the resilient return of the valve member 3026 to the uncompressed position after being compressed. In some embodiments, the o-rings, arcuate segments, or other structures can be joined end-to-end to generally form a helical pattern down the body of the seal member 3026, as shown, for example in FIG. 91B.

Although the embodiments shown in FIGS. 78-91B are illustrated as having a backflow resistance module provided by a support member and a regulator similar in some regards to the support member 28 and regulator 30, it will be understood that any other backflow resistance modules can be incorporated into the connectors shown in FIGS. 81A-91B, including those described herein.

Although some specific examples have been provided herein, it should be understood that a backflow resistance module can be incorporated into many other types of connectors than those specifically disclosed herein. For example, a backflow resistance module can be incorporated into a y-site connector, or into a connector providing access to an IV bag or other medication container, or into a catheter line.

Any features of the embodiments shown and/or described in the figures that have not been expressly described in this text, such as distances, proportions of components, etc. are also intended to form part of this disclosure. Additionally, although these inventions have been disclosed in the context of various embodiments, features, aspects, and examples, it will be understood by those skilled in the art that the present inventions extend beyond the specifically disclosed embodiments to other alternative embodiments and/or uses of the inventions and obvious modifications and equivalents thereof. Accordingly, it should be understood that various features and aspects of the disclosed embodiments can be combined with, or substituted for, one another in order to perform varying modes of the disclosed inventions. Thus, it is intended that the scope of the present inventions disclosed herein should not be limited by the particular disclosed embodiments described herein.

Although this invention has been disclosed in the context of a certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above.

The following is claimed:

1. A needleless medical connector configured to resist retrograde fluid flow caused by syringe rebound, proximal-end luer withdrawal, or externally-induced negative pressure, the medical connector comprising:

a housing comprising a first region formed of a single piece of material, and a second region that contacts the first region and is partially inserted within and extends distally from the first region, the first region comprising a threaded female end and the second region comprising a shroud and a male luer comprising an internal conduit with proximal and distal ends;

a proximal closure system comprising a seal member with a proximal surface, the seal member being positioned at least partially within the housing;

a plug member formed separately from the first region of the housing and the second region of the housing, a portion of the plug member being positioned within the seal member when the proximal closure system is in a closed position and a portion of the plug member being positioned outside of the seal member when the proximal closure system is in the closed position, the plug member being moveable with respect to the seal member; and an internal closure system comprising a dome valve positioned distal from where the second region contacts the first region, such that the dome valve does not contact the first region of the housing, and a distal end of the dome valve is proximate to the proximal end of the internal conduit of the male luer, the dome valve comprising a protrusion configured to help secure the dome valve within the second region;

wherein the dome valve is configured to open to permit fluid to flow from a proximal side of the dome valve to a distal side of the dome valve under a first fluid pressure differential between a proximal portion of the medical connector and a distal portion of the medical connector, and the dome valve is configured to open to permit fluid flow from the distal side of the dome valve to the proximal side of the dome valve under a second fluid pressure differential between the distal portion of the medical connector and the proximal portion of the medical connector that is higher than the first fluid pressure differential; and wherein the proximal closure system and the internal closure system are configured to open and close independently from each other.

2. The medical connector of claim 1, wherein the second region is formed of a single piece of material.

3. The medical connector of claim 1, wherein a proximal end face of the plug member is open.

4. The medical connector of claim 3, wherein a distal region of the plug member comprises a plurality of openings to permit fluid to flow through the connector in the open position.

5. The medical connector of claim 1, wherein a distal head near a distal end of the plug member is the widest portion of the plug member.

6. The medical connector of claim 5, wherein the distal head of the plug member contacts a distal end of the seal member in the closed position.

7. The medical connector of claim 5, wherein the dome valve is positioned in a curved recess within the housing.

8. The medical connector of claim 7, wherein a distal opening in the curved recess leads into the proximal end of the internal conduit of the male luer.

9. The medical connector of claim 1, wherein a tubular support member is positioned axially between the proximal seal member and the dome valve.

10. The medical connector of claim 1, further comprising a pressure regulator.

11. A medical connector configured to resist negative flow, the medical connector comprising:

a housing comprising a first portion and a second portion, and a contact region where the first portion contacts the second portion, the first portion comprising a threaded female end and the second portion comprising a threaded shroud and a male luer;

a proximal seal member positioned within the housing, the seal member comprising an open position and a closed position;

a plug member positioned in the closed position partly within the seal member and partly outside of the seal member, the plug member configured to move when the seal member transitions between the open and closed positions; and a dome valve positioned distal from the contact region, such that the dome valve does not contact the first portion of the housing;

wherein the dome valve is configured to open to permit fluid to flow from a proximal side of the dome valve to a distal side of the dome valve under a first fluid pressure differential between a proximal region of the medical connector and a distal region of the medical connector, and the dome valve is configured to open to permit fluid flow from the distal side of the dome valve to the proximal side of the dome valve under a second fluid pressure differential between the distal region of the medical connector and the proximal region of the medical connector that is higher than the first fluid pressure differential; and wherein the proximal seal member and the dome valve are configured to open and close independently from each other.

12. The medical connector of claim 11, wherein the first portion is formed of a single piece of material.

13. The medical connector of claim 12, wherein a proximal end face of the plug member is open.

14. The medical connector of claim 13, wherein a distal region of the plug member comprises a plurality of openings to permit fluid to flow through the connector in the open position.

15. The medical connector of claim 13, wherein a distal head near a distal end of the plug member is the widest portion of the plug member.

16. The medical connector of claim 15, wherein the distal head of the plug member contacts a distal end of the seal member in the closed position.

17. The medical connector of claim 12, wherein the dome valve is positioned within a curved recess within the housing.

18. The medical connector of claim 17, wherein a protrusion on the dome valve helps to retain the dome valve in place.

19. The medical connector of claim 17, wherein a tubular support member is positioned axially between the proximal seal member and the dome valve.

20. The medical connector of claim 17, wherein a distal opening in the curved recess leads into the proximal end of the internal conduit of the male luer.

21. The medical connector of claim 11, wherein the second portion is formed of a single piece of material.

22. The medical connector of claim 11, further comprising a pressure regulator.

* * * * *